(12) United States Patent
Ly et al.

(10) Patent No.: US 11,603,530 B2
(45) Date of Patent: Mar. 14, 2023

(54) MODIFIED PEPTIDE NUCLEIC ACID COMPOSITIONS

(71) Applicant: NeuBase Therapeutics, Inc., Pittsburgh, PA (US)

(72) Inventors: Danith H. Ly, Pittsburgh, PA (US); Shivaji A. Thadke, Pittsburgh, PA (US); Ramesh U. Batwal, Pittsburgh, PA (US); Dietrich A. Stephan, Pittsburgh, PA (US)

(73) Assignee: NEUBASE THERAPEUTICS, INC., Pittsburgh, PA (US)

( * ) Notice: Subject to any disclaimer, the term of this patent is extended or adjusted under 35 U.S.C. 154(b) by 0 days.

(21) Appl. No.: 17/232,001

(22) Filed: Apr. 15, 2021

(65) Prior Publication Data

US 2022/0324914 A1     Oct. 13, 2022

Related U.S. Application Data

(63) Continuation of application No. 17/218,145, filed on Mar. 30, 2021.

(60) Provisional application No. 63/002,326, filed on Mar. 30, 2020.

(51) Int. Cl.

| C07K 14/00 | (2006.01) |
|---|---|
| C12N 15/113 | (2010.01) |
| A61K 51/04 | (2006.01) |
| A61P 25/28 | (2006.01) |
| A61K 9/00 | (2006.01) |
| G01N 33/68 | (2006.01) |
| G01N 30/72 | (2006.01) |
| C07K 5/097 | (2006.01) |
| A61K 38/00 | (2006.01) |

(52) U.S. Cl.
CPC .......... *C12N 15/113* (2013.01); *A61K 9/0019* (2013.01); *A61K 9/0053* (2013.01); *A61K 9/0085* (2013.01); *A61K 51/0491* (2013.01); *A61P 25/28* (2018.01); *C07K 5/0821* (2013.01); *C07K 14/003* (2013.01); *G01N 30/7233* (2013.01); *G01N 33/6896* (2013.01); *A61K 38/00* (2013.01); *C12N 2310/3181* (2013.01)

(58) Field of Classification Search
None
See application file for complete search history.

(56) References Cited

U.S. PATENT DOCUMENTS

| 7,960,360 B2 | 6/2011 | Grandis et al. |
|---|---|---|
| 9,334,496 B2 | 5/2016 | Grandis et al. |
| 10,851,407 B2 | 12/2020 | Ly et al. |
| 2020/0318195 A1 | 10/2020 | Ly et al. |
| 2021/0309700 A1 | 10/2021 | Ly et al. |
| 2021/0309997 A1 | 10/2021 | Ly et al. |
| 2021/0324012 A1 | 10/2021 | Ly et al. |
| 2022/0112238 A1 | 4/2022 | Ly et al. |

FOREIGN PATENT DOCUMENTS

| WO | WO-2008018795 A1 | 2/2008 |
|---|---|---|
| WO | WO-2010014592 A1 | 2/2010 |

OTHER PUBLICATIONS

Schneggenburger et al. "Molecular Recognition at the Membrane-Water Interface: Controlling Integral Peptide Helices by Off-Membrane Nucleobase Pairing," J. Am. Chem. Soc., 2010, 132, 8020-8028 (Year: 2010).*

Chowdhury et al., Solid-phase N-terminal peptide enrichment study by optimizing trypsin proteolysis on homoarginine-modified proteins by mass spectrometry. Rapid Commun Mass Spectrom. Mar. 30, 2014;28(6):635-44.

Dragulescu-Andrasi et al. A simple gamma-backbone modification preorganizes peptide nucleic acid into a helical structure. J Am Chem Soc. Aug. 9, 2006;128(31):10258-67.

Dragulescu-Andrasi et al. Cell-permeable GPNA with appropriate backbone stereochemistry and spacing binds sequence-specifically to RNA. Chem Commun (Camb). Jan. 14, 2005;(2):244-6.

International Search Report and Written Opinion issued in PCT/US2021/025019 on Oct. 7, 2021.

Lee et al., "Controlling the Specificity of Modularly Assembled Small Molecules for RNA via Ligand Module Spacing: Targeting RNAs that Cause Myotonic Muscular Dystrophy", J Am Chem Soc. Dec. 2, 2009;131 (47):17464-17472.

Meloni, Bruno P et al. "Cationic Arginine-Rich Peptides (CARPs): A Novel Class of Neuroprotective Agents With a Multimodal Mechanism of Action." Frontiers in neurology vol. 11 108. Feb. 25, 2020.

Ray A, Nordén B. Peptide nucleic acid (PNA): its medical and biotechnical applications and promise for the future. FASEB J. Jun. 2000;14(9):1041-60.

Zhou et al. Novel binding and efficient cellular uptake of guanidine-based peptide nucleic acids (GPNA). J Am Chem Soc. Jun. 11, 2003;125(23):6878-9.

Manicardi et al., Cellular uptakes, biostabilities and anti-miR-210 activities of chiral arginine-PNAs in leukaemic K562 cells. Chembiochem. Jun. 18, 2012;13(9):1327-37. doi: 10.1002/cbic.201100745. Epub May 25, 2012. PMID: 22639449; PMCID: PMC3401907.

(Continued)

*Primary Examiner* — Christina Bradley
(74) *Attorney, Agent, or Firm* — Wilson Sonsini Goodrich & Rosati

(57) ABSTRACT

The present disclosure relates to compounds useful for the detection or modulation of target nucleic acids, including DNA and RNA. The present disclosure further relates to methods for treatment of trinucleotide repeat disorders, which can include administration of oligonucleotide analogues that can bind pathogenic nucleotide repeats in DNA or RNA.

1 Claim, 33 Drawing Sheets

(56) References Cited

OTHER PUBLICATIONS

Moccia et al., "Insights on chiral, backbone modified peptide nucleic acids: Properties and biological activity." Artificial DNA, PNA & XNA vol. 5,3 (2014): e1107176. doi:10.1080/1949095X.2015.1107176.

Sahu et al., Synthesis of conformationally preorganized and cell-permeable guanidine-based gamma-peptide nucleic acids (gammaGPNAs). J Org Chem. Feb. 20, 2009;74(4):1509-16. doi: 10.1021/jo802211n. PMID: 19161276; PMCID: PMC2650244.

Stanzl et al., Fifteen years of cell-penetrating, guanidinium-rich molecular transporters: basic science, research tools, and clinical applications. Acc Chem Res. Dec. 17, 2013;46(12):2944-54. doi: 10.1021/ar4000554. Epub May 22, 2013. PMID: 23697862; PMCID: PMC3796152.

Lu, X. W., Synthesis and properties of amino- and guanidino-peptoid peptide nucleic acids. Doctoral thesis, Nanyang Technological University, (2010) Singapore.

\* cited by examiner

Compound 1

[$^{14}$C]-Compound 1

Compound 2

Compound 4

Compound 3

MODIFIED PEPTIDE NUCLEIC ACID COMPOSITIONS

CROSS REFERENCE

This application is a continuation of U.S. patent application Ser. No. 17/218,145, filed Mar. 30, 2021, which claims the benefit of U.S. Provisional Application No. 63/002,326, filed Mar. 30, 2020, each of which is hereby incorporated by reference in its entirety.

BACKGROUND

Huntington's disease (HD) is a neurodegenerative genetic disease caused by a mutation in the huntingtin (HTT) gene, which is thought to be important for many essential cell activities. Those with HD experience a loss of neurons in the brain over time mostly due to the toxic accumulation of faulty HTT protein in their cells. Current treatment options work to lessen individual movement and psychiatric symptoms, but there is no treatment for HD that can slow or stop the progression of the disease.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

In some embodiments, the present disclosure provides a compound comprising a chain, wherein the chain comprises a series of atoms concatenated to form the chain, wherein a plurality of the atoms that are concatenated to form the chain are each independently substituted with a substituent that bears a guanidino group, wherein the chain has a pattern of one atom that is independently substituted with a substituent that bears a guanidino group, followed by five consecutive atoms that are not substituted by a substituent that bears a guanidino group, followed by a second atom that is independently substituted with a substituent that bears a guanidino group, followed by another five consecutive atoms that are not substituted by a substituent that bears a guanidino group, followed by a third atom that is independently substituted with a substituent that bears a guanidino group, wherein a first end of the chain or a second end of the chain is substituted with a peptide.

In some embodiments, the present disclosure provides a compound comprising a peptide nucleic acid sequence and a cell permeabilizing group attached to the peptide nucleic acid sequence, wherein if a radiolabeled analogue of the compound is subjected to an assay, wherein the assay comprises:
  (a) a first component, wherein the first component comprises:
    (i) administering a 5 mg/kg intravenous bolus dose of the radiolabeled analogue to a caudal vein of a monkey, wherein the monkey is a male Cynomolgus monkey;
    (ii) euthanizing the monkey 4 hours after the administering;
    (iii) after (ii), freezing the monkey in a mixture of hexane and solid carbon dioxide for at least two hours to provide a frozen carcass;
    (iv) embedding the frozen carcass, left lateral side uppermost, in 2% w/v aqueous sodium carboxymethylcellulose to provide an embedded carcass;
    (v) sectioning the embedded carcass into 40 µm sagittal whole body sections with a cryomacrotome;
    (vi) mounting the 40 µm sagittal whole body sections on pressure sensitive tape;
    (vii) after (vi), dehydrating the whole body sections in the cryomacrotome at about −20° C. for about 60 hours;
    (viii) after (vii), placing the whole body sections against an image plate sensitive to carbon-14 for no longer than four days;
    (ix) after (viii), scanning the image plate with a phosphor imager system; and
    (x) after (ix), determining a concentration of the radiolabeled analogue in brain tissue of the whole body sections; and
  (b) a second component, wherein the second component is analogous to the first component except that the second component uses another monkey that is euthanized 168 hours after the administering, wherein the radiolabeled analogue comprises an N-terminus that is substituted with a $^{14}$C-enriched glycine residue, and the radiolabeled analogue consists of a structure that differs from the compound solely in that the compound lacks the $^{14}$C-enriched glycine residue of the radiolabeled analogue,
then in the assay, the concentration of the radiolabeled analogue in brain tissue determined in the second component is equivalent to at least about 80% of the concentration of the radiolabeled analogue in brain tissue determined in the first component.

In some embodiments, the present disclosure provides a compound comprising a peptide nucleic acid sequence, wherein the peptide nucleic acid sequence comprises: (i) a series of peptide nucleic acid residues having a repeating triad of nucleobase side chains; and (ii) a cell permeabilizing group attached to the series of peptide nucleic acid residues, wherein if the compound is subjected to an assay, and the assay comprises:
  (a) administering by intracerebroventricular administration a dose amount of about 0.1 mg/kg to about 2 mg/kg of the compound to mice;
  (b) euthanizing the mice at a time point between about 1 hour and 28 days post intracerebroventricular administration;
  (c) collecting brain tissues from the mice after the euthanizing; and
  (d) using liquid chromatography-tandem mass spectrometry to determine concentrations of the brain tissues in the mice,
then in the assay, a mean maximum brain concentration is observed in the mice at a time to maximum brain concentration of about 1 hour to about 50 hours post administration and the mean maximum brain concentration of the mice is observed to be about 3000 ng/mL to about 22000 ng/mL.

In some embodiments, the present disclosure provides a compound comprising a peptide nucleic acid sequence, wherein the peptide nucleic acid sequence comprises: (i) a series of peptide nucleic acid residues having a repeating triad of nucleobase side chains; and (ii) a cell permeabilizing group attached to the series of peptide nucleic acid residues, wherein if the compound is subjected to an assay, and the assay comprises:

(a) administering by intracerebroventricular administration a dose amount of about 0.1 mg/kg to about 1.5 mg/kg of the compound to mice;
(b) collecting blood samples from cava veins of the mice at a time point between about 1 hour and 28 days post intracerebroventricular administration;
(c) after the collecting the blood samples, euthanizing the mice at a time point between about 1 hour and 28 days post intracerebroventricular administration;
(d) after the euthanizing, collecting brain, intestine, liver, lung, kidney, or muscle tissues from the mice; and
(e) using liquid chromatography-tandem mass spectrometry to determine concentrations of the compound in the brain, intestine, liver, lung, kidney, or muscle tissues that were collected; and
(f) using the liquid chromatography-tandem mass spectrometry to determine concentrations of the compound in plasma from the blood samples that were collected from the mice,
then, in the assay, the compound is observed to accumulate in the brain of the mice for at most about a month after the administering and the compound is not observed at a detectable level during the month in the plasma, intestine, liver, lung, kidney, or muscle of the mice.

In some embodiments, the present disclosure provides a compound comprising a peptide nucleic acid sequence, wherein the peptide nucleic acid sequence comprises: (i) a series of peptide nucleic acid residues having a repeating triad of nucleobase side chains; and (ii) a cell permeabilizing group attached to the series of peptide nucleic acid residues, wherein if the compound is subjected to a plasma protein binding assay, and the plasma protein binding assay comprises:
(a) performing a human component of the plasma protein binding assay, wherein the human component of the plasma protein binding assay comprises (1) spiking single aliquots of human plasma with a 10 mg/mL of a first solution of the compound to obtain at least a second solution of the compound with concentrations of about 1 µg/mL to about 50 µg/mL; (2) using ultracentrifugation on the at least the second solution of the compound to separate a mixture comprising the compounds that are bound to plasma proteins; (3) using liquid chromatography-tandem mass spectrometry to determine a plasma protein binding percentage in the human plasma;
(b) performing a mouse component of the plasma protein binding assay, wherein the mouse component of the plasma protein binding assay differs from the human component of the plasma protein binding assay only in that mouse plasma is used instead of the human plasma;
(c) performing a dog component of the plasma protein binding assay, wherein the dog component of the plasma protein binding assay differs from the human component of the plasma protein binding assay only in that dog plasma is used instead of the human plasma;
(d) performing a minipig component of the plasma protein binding assay, wherein the minipig component of the plasma protein binding assay differs from the human component of the plasma protein binding assay only in that minipig plasma is used instead of the human plasma;
(e) performing a sheep component of the plasma protein binding assay, wherein the sheep component of the plasma protein binding assay differs from the human component of the plasma protein binding assay only in that sheep plasma is used instead of the human plasma; and
(f) performing a monkey component of the plasma protein binding assay, wherein the monkey component of the plasma protein binding assay differs from the human component of the plasma protein binding assay only in that monkey plasma is used instead of the human plasma,
then in the plasma protein binding assay, the plasma protein binding percentage is at least about 85% in the human, mouse, dog, minipig, sheep, or monkey.

In some embodiments, the present disclosure provides a compound having the formula (I):

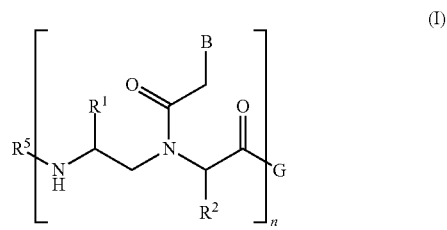

wherein:
each B is independently a nucleobase;
each $R^1$ is independently a side chain of a natural amino acid, a guanidino($C_1$-$C_4$)alkyl, or hydrogen;
each $R^2$ is independently a side chain of a natural amino acid, a guanidino($C_1$-$C_4$)alkyl, or hydrogen;
$R^5$ is a sequence comprising at least one alpha amino acid residue, beta amino acid residue, gamma amino acid residue, or a combination thereof; hydrogen; or a water solubilizing group;
n is an integer from 3-30; and
G is OH, $NH_2$, or

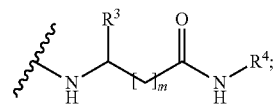

wherein:
$R^3$ is hydrogen or an amino($C_1$-$C_4$)alkyl;
$R^4$ is a sequence comprising at least one alpha amino acid residue, beta amino acid residue, gamma amino acid residue, or a combination thereof; or hydrogen; and
m is 0 or 1;
wherein the compound comprises at least one guanine-cytosine-thymine sequence;
or a pharmaceutically-acceptable salt thereof.

In some embodiments, the present disclosure provides a method of treating a condition in a subject, the method comprising administering to the subject a therapeutically-effective amount of any compound of the disclosure.

DETAILED DESCRIPTION

Figure 1:
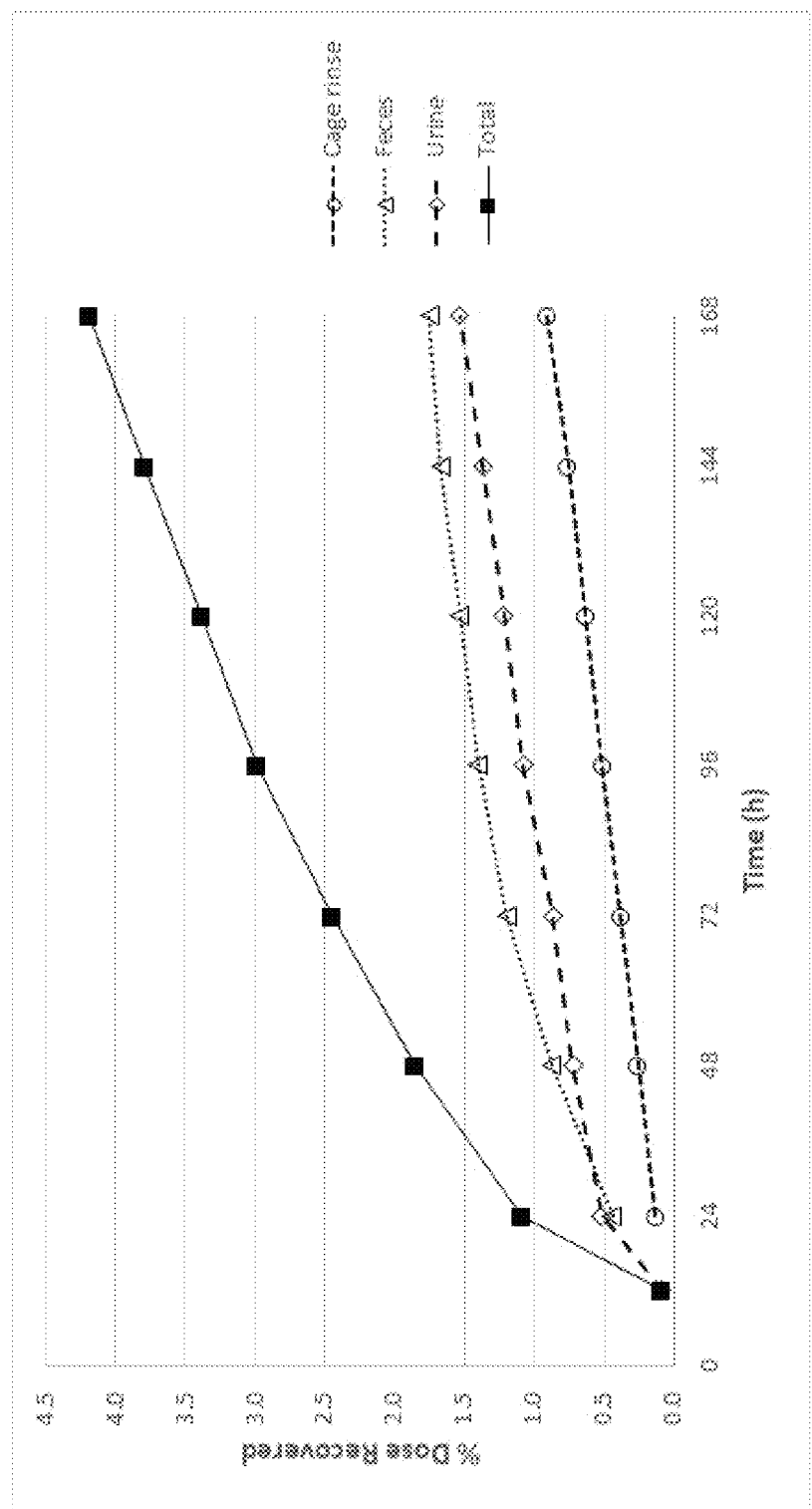
FIG. 1 illustrates cumulative excretion of radioactivity following a single intravenous bolus of [$^{14}$C]-Compound 1 to a male cynomolgus monkeys at 5 mg/kg (Animal 103).

Huntington's disease (HD) is a genetic disease associated with an abnormally long CAG repeat expansion in the huntingtin gene (HTT), which codes for the huntingtin protein (HTT). HTT genes that contain repeat lengths beyond a certain threshold produce mutant huntingtin protein (mHTT), which can induce pathological changes in the central nervous system. The risk, penetrance, and age of disease onset can be correlated with length of the HTT repeat expansion. Repeat counts of less than 27 CAG triads are associated with normal phenotype, while repeat counts from 27 to 35 generally confer normal phenotype but enhanced risk of disease in offspring. 36 to 39 repeats are associated with incomplete or reduced penetrance, with disease symptoms manifesting later in adult life, if at all. Repeat lengths greater than 40 confer full penetrance, while repeat counts of greater than 60 produce disease that can manifest as early as childhood.

Compounds of the Disclosure

The present disclosure relates to compounds useful for the detection or modulation of target nucleic acids, including DNA and RNA. The present disclosure further relates to methods for treatment of trinucleotide repeat disorders, which can include administration of oligonucleotide analogues that can bind pathogenic nucleotide repeats in DNA or RNA. In some embodiments, compounds of the disclosure bind CAG repeats within the mutant mHTT transcript present in Huntington's disease, thereby modulating expression of mHTT protein.

In some embodiments, the disclosure provides a compound comprising a chain. The chain can comprise a series of atoms concatenated to form the chain. A plurality of the atoms that are concatenated to form the chain can be independently substituted with a substituent that bears a polar group, which can be, for example, a guanidino group. The chain can have a pattern of one atom that is independently substituted with a substituent that bears a polar group, followed by five consecutive atoms that are not substituted by a substituent that bears a polar group, followed by a second atom that is independently substituted with a substituent that bears a polar group, followed by another five consecutive atoms that are not substituted by a substituent that bears a polar group, followed by a third atom that is independently substituted with a substituent that bears a polar group.

In some embodiments, the chain has a pattern of one atom that is independently substituted with a substituent that bears a polar group (e.g., guanidino group), followed by seventeen consecutive atoms that are not substituted by a substituent that bears a polar group, followed by a second atom that is independently substituted with a substituent that bears a polar group, followed by another seventeen consecutive atoms that are not substituted by a substituent that bears a polar group, followed by a third atom that is independently substituted with a substituent that bears a polar group. In some embodiments, the third atom that is independently substituted with a substituent that bears a polar group (e.g., guanidino group) is followed by eleven consecutive atoms that are not substituted by a substituent that bears a polar group, followed by a fourth atom that is independently substituted with a substituent that bears a polar group. In some embodiments, the fourth atom that is independently substituted with a substituent that bears a polar group is followed by another eleven consecutive atoms that are not substituted by a substituent that bears a polar group. In some embodiments, the first atom, the second atom, and the third atom are each gamma carbons of a peptide nucleic acid oligomer. In some embodiments, the first atom, the second atom, and the third atom are each alpha carbons of a peptide nucleic acid oligomer.

In some embodiments, the chain can have a pattern of one atom that is independently substituted with a substituent that bears a polar group (e.g., guanidino group), followed by eleven consecutive atoms that are not substituted by a substituent that bears a polar group, followed by a second atom that is independently substituted with a substituent that bears a polar group, followed by another eleven consecutive atoms that are not substituted by a substituent that bears a polar group, followed by a third atom that is independently substituted with a substituent that bears a polar group.

Suitable polar groups can include groups that bear a formal charge at physiological pH, such as a guanidino group. In some embodiments, each substituent that bears a guanidino group is independently guanidinoalkyl. In some embodiments, each substituent that bears a guanidino group is independently guanidino($C_1$-$C_4$)alkyl. In some embodiments, each substituent that bears a guanidino group is 2-guanidino-eth-1-yl. In some embodiments, each substituent that bears a guanidino group is 3-guanidino-prop-1-yl. In some embodiments, each substituent that bears a guanidino group is 4-guanidino-but-1-yl.

Compounds of the disclosure can comprise nucleobases or nucleobase analogs. In some embodiments, the pattern can further comprise one atom that is independently substituted with a substituent that bears a first nucleobase, followed by five consecutive atoms that are not substituted by a substituent that bears a nucleobase, followed by a second atom that is independently substituted with a substituent that bears a second nucleobase, followed by another five consecutive atoms that are not substituted by a substituent that bears a nucleobase, followed by a third atom that is independently substituted with a substituent that bears a third nucleobase.

In some embodiments, the substituent that bears the first nucleobase, the substituent that bears the second nucleobase, and the substituent that bears the third nucleobase are each independently purinylacyl, purinylalkylene, pyrimidinylacyl, or pyrimidinylalkylene. In some embodiments, the substituent that bears the first nucleobase, the substituent that bears the second nucleobase, and the substituent that bears the third nucleobase are each independently guaninylacyl, adeninylacyl, cytosinylacyl, thyminylacyl, or uracilylacyl. In some embodiments, the first nucleobase, the second nucleobase, and the third nucleobase form a sequence that is CTG, TGC, or GCT.

In some embodiments, a compound of the disclosure can be resistant to degradation by enzymes (e.g. nucleases or proteases). In some embodiments, the compound can be stable in a subject. In some embodiments, a compound of the disclosure can be water-soluble. In some embodiments, the compound can be endocytosed by a cell comprising a target sequence of the compound. In some embodiments, the compound is endocytosed, pinocytosed, phagocytosed in a cell that does not contain the target sequence. In some embodiments, the compound is transcytosed across the endothelia lining of the cerebral vasculature, or "blood-brain barrier."

Peptide Nucleic Acids

The present disclosure peptide nucleic acid analogs and pharmaceutically-acceptable salts thereof. In some embodiments, the compound comprises a peptide nucleic acid domain. Peptide nucleic acids are oligonucleotide analogues that comprise a chain of repeating N-(2-aminoethyl)-glycine units linked by peptide bonds, where the glycyl nitrogen of one or more units is functionalized with an alkylene or acyl group bearing a nucleobase. Peptide nucleic acids can optionally comprise substitution on the N-(2-aminoethyl)-glycine backbone, for example:

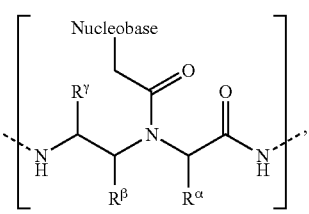

where substituents $R^\alpha$, $R^\beta$, $R^\gamma$, are alpha, beta, and gamma substituents, respectively. In some embodiments, the peptide nucleic acid chain is substituted with a polar group, such as a group that comprises a guanidino moiety. The polar group can be bound to the alpha or gamma position of at least one peptide nucleic acid subunit.

A compound of the disclosure (e.g., a peptide nucleic acid) can comprise a chain of atoms with termini that are substituted or unsubstituted. For example, a first end of the chain and a second end of the chain can be each independently unsubstituted or substituted with an amino acid. For example, a first end of the chain and a second end of the chain can be each independently unsubstituted or substituted with a peptide. In some embodiments, the compound is a peptide nucleic acid oligomer, wherein the first end of the chain is an N-terminus of the peptide nucleic acid oligomer, and the second end of the chain is a C-terminus of the peptide nucleic acid oligomer. In some embodiments, the C-terminus of the peptide nucleic acid oligomer is bound by a peptide bond to a peptide, which can be for example, a sequence comprising alpha amino acid residues, beta amino acid residues, gamma amino acid residues, or a combination thereof. In some embodiments, the C-terminus of the peptide nucleic acid oligomer is bound by a peptide bond to amidated lysine. In some embodiments, the C-terminus of the peptide nucleic acid oligomer is bound by a peptide bond to amidated beta-lysine.

In some embodiments, the C-terminus or N-terminus of the peptide nucleic acid is substituted with a cell-permeabilizing group. In some embodiments, the cell permeabilizing group is a polypeptide comprising 3 to 8 lysine residues. In some embodiments, the polypeptide is linked to the peptide nucleic acid via an amide bond. In some embodiments, the polypeptide is linked to the peptide nucleic acid via a peptide bond, a disulfide bond, or a linker comprising two penicillamine residues bound by a disulfide bond.

In some embodiments, the compound can comprise from 4 to 10 guanidino groups. In some embodiments, the compound can comprise from 6 to 8 guanidino groups. In some embodiments, the compound can comprise from 7 to 9 guanidino groups. In some embodiments, the compound can comprise 1, 2, 3, 4, 5, 6, 7, 8, 9, 10, 11, 12, 13, 14, 15, or more guanidino groups. Each of the three guanidino groups can be independently bound to the peptide nucleic acid chain. In some embodiments, the group that comprises a guanidino moiety is a 4-guanidino-but-1-yl group, a 3-guanidino-prop-1-yl group, or a 2-guanidino-eth-1-yl group. In some embodiments, a sequence of the peptide nucleic acid domain comprises $(GCT)_n$, wherein n is 1-10. In some embodiments, a sequence of the peptide nucleic acid domain is domain $(GCT)_6G$. In In some embodiments, a sequence of the peptide nucleic acid domain is GCTGCT. In some embodiments, a sequence of the peptide nucleic acid domain is CTGCTG.

In some embodiments, a compound of the disclosure can comprise a moiety that improves cell-permeability of the compound relative to a molecule without the moiety that is otherwise identical to the compound. For example, a compound of the disclosure can reach an intracellular target within the cytoplasm or nucleus.

In some embodiments, the disclosure provides a compound comprising a pharmacophore region attached to a multiply-positively charged region, wherein:
a) the pharmacophore region comprises a number of peptide nucleic acid residues, wherein the number of peptide nucleic acid residues is at least 7 and is not a multiple of 3;
b) each peptide nucleic acid residue of the pharmacophore region independently comprises a backbone part and a side chain part attached to the backbone part;
c) none of the backbone parts of the peptide nucleic acid residues of the pharmacophore region bears a positive formal charge at neutral pH;
d) each side chain part independently bears a nucleobase;
e) the nucleobases of each of the side chain parts collectively form a sequence;
f) the sequence is complementary to a native, human nucleic acid sequence associated with Huntington's Disease;
g) the sequence comprises a subsequence that is cytosine-thymine-guanine-cytosine-thymine-guanine; and
h) the multiply-positively charged region comprises at least six consecutive building blocks, wherein each of the consecutive building blocks independently comprises a side chain that carries a positive formal charge at neutral pH.

In some embodiments, the present disclosure provides a compound represented by the structure of formula (I):

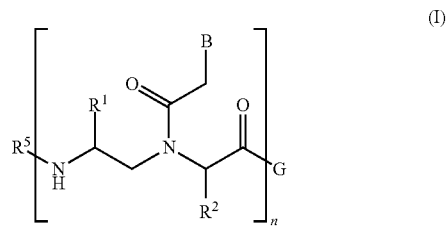

wherein
each B is independently a nucleobase;
each $R^1$ is independently a side chain of a natural amino acid, a guanidino($C_1$-$C_4$)alkyl, or hydrogen;
each $R^2$ is independently a side chain of a natural amino acid, a guanidino($C_1$-$C_4$)alkyl, or hydrogen;
$R^5$ is a sequence comprising at least one alpha amino acid residue, beta amino acid residue, gamma amino acid residue, or a combination thereof; hydrogen; or a water solubilizing group;
n is an integer from 3-30;
G is OH, $NH_2$, or

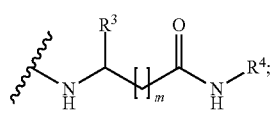

wherein
R³ is hydrogen or an amino($C_1$-$C_4$)alkyl;
R⁴ is a sequence comprising at least one alpha amino acid residue, beta amino acid residue, gamma amino acid residue, or a combination thereof; or hydrogen; and
m is 0 or 1;
wherein the compound comprises at least one guanine-cytosine-thymine sequence; or a pharmaceutically-acceptable salt thereof or a radiolabeled derivative thereof.

In some embodiments, each nucleobase B is independently guanine, thymine, or cytosine. In some embodiments, B is guanine. In some embodiments, B is thymine. In some embodiments, B is cytosine. In some embodiments, B is adenine. In some embodiments, B is uracil. In some embodiments, each nucleobase B is an analog of a naturally occurring nucleobase.

In some embodiments, at least one R¹ is guanidino($C_1$-$C_4$)alkyl. In some embodiments, more than one R¹ is guanidino($C_1$-$C_4$)alkyl. In some embodiments, at least one every other R¹ is guanidino($C_1$-$C_4$)alkyl. In some embodiments, at least one every third R¹ is guanidino($C_1$-$C_4$)alkyl. In some embodiments, at least one every second or third R¹ is guanidino($C_1$-$C_4$)alkyl. In some embodiments, each R¹ is guanidino($C_1$-$C_4$)alkyl. In some embodiments, at least one R¹ is 4-guanidinobut-1-yl. In some embodiments, at least one R¹ is 3-guanidinoprop-1-yl. In some embodiments at least one R¹ is 2-guanidino-eth-1-yl. In some embodiments, at least one R¹ is hydrogen. In some embodiments, each R¹ is hydrogen.

In some embodiments, at least one R² is guanidino($C_1$-$C_4$)alkyl. In some embodiments, more than one R² is guanidino($C_1$-$C_4$)alkyl. In some embodiments, at least one every other R² is guanidino($C_1$-$C_4$)alkyl. In some embodiments, at least one every third R² is guanidino($C_1$-$C_4$)alkyl. In some embodiments, at least one every second or third R² is guanidino($C_1$-$C_4$)alkyl. In some embodiments, each R² is guanidino($C_1$-$C_4$)alkyl. In some embodiments, at least one R² is 4-guanidinobut-1-yl. In some embodiments, at least one R² is 3-guanidinoprop-1-yl. In some embodiments at least one R² is 2-guanidino-eth-1-yl. In some embodiments, at least one R² is hydrogen. In some embodiments, each R² is hydrogen.

In some embodiments, G is

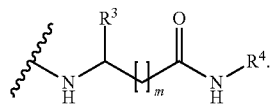

In some embodiments, R⁵ is the water-solubilizing group. In some embodiments, the water-solubilizing group is a multiply-positively charged region that comprises at least six consecutive building blocks. In some embodiments, each of the consecutive building blocks independently comprises a side chain that carries a positive formal charge at neutral pH.

In some embodiments, R³ is hydrogen. In some embodiments, R³ is an amino($C_1$-$C_4$)alkyl. In some embodiments, R³ is 4-aminobut-1-yl. In some embodiments, R³ is 3-aminoprop-1-yl. In some embodiments, m is 0. In some embodiments, m is 1.

In some embodiments, R⁴ is hydrogen. In some embodiments, R⁴ is a sequence comprising at least one alpha amino acid residue. In some embodiments, R⁴ is a sequence comprising at least one beta amino acid residue. In some embodiments, R⁴ is a sequence comprising at least one gamma amino acid residue. In some embodiments, R⁴ is

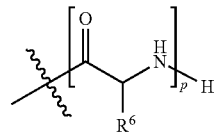

wherein
p is 1, 2, 3, 4, 5, 6, 7, 8, 9, or 10; and
each R⁶ is independently hydrogen or an amino($C_1$-$C_4$)alkyl.

In some embodiments, R⁴ is

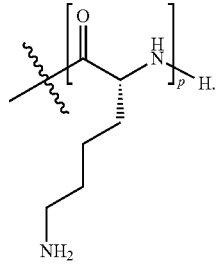

In some embodiments, p is 3, 4, 5, 6, 7, or 8. In some embodiments, p is 3. In some embodiments, p is 4. In some embodiments, p is 5. In some embodiments, p is 6. In some embodiments, p is 7. In some embodiments, p is 8.

In some embodiments, R⁵ is hydrogen.

In some embodiments, R⁵ is

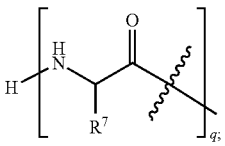

wherein
each R⁷ is independently a side chain of a natural amino acid; and
q is 0 or 1

In some embodiments, R⁷ is a side chain of an alpha amino acid. In some embodiments, R⁷ is a side chain of an beta amino acid. In some embodiments, R⁷ is a side chain of a gamma amino acid. In some embodiments, q is 0. In some embodiments, q is 1.

In some embodiments, R⁵ is

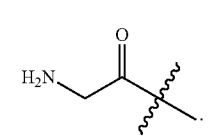

In some embodiments, $R^5$ is

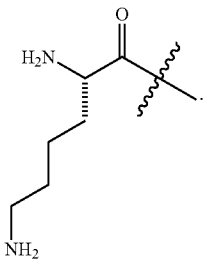

In some embodiments, the water solubilizing group comprises a structure that has multiple formal charges at physiological pH. In some embodiments, $R^5$ is the multiple formal charges are positive charges.

In some embodiments, when G is OH or $NH_2$, at least one of $R^1$ and $R^2$ is a side chain of a natural amino acid or a guanidino($C_1$-$C_4$)alkyl, and $R^5$ is not hydrogen.

In some embodiments, when $R^1$ and $R^2$ are both hydrogen, G is

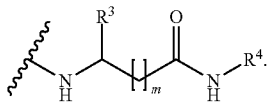

In some embodiments, when $R^1$ and $R^2$ are both hydrogen, G is

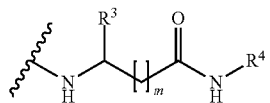

and $R^5$ is the sequence comprising at least one alpha amino acid residue.

In some embodiments, the compound has the formula:

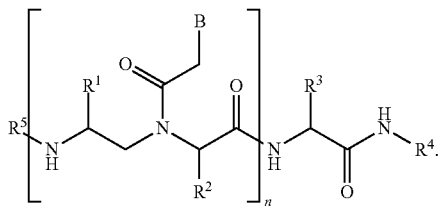

In some embodiments, n is 6. In some embodiments, at least one $R^1$ is 4-guanidinobut-1-yl. In some embodiments, each $R^1$ is 4-guanidinobut-1-yl. In some embodiments, at least one $R^2$ is hydrogen. In some embodiments, each $R^2$ is hydrogen. In some embodiments, $R^3$ is 4-aminobut-1-yl. In some embodiments, $R^3$ is 3-aminoprop-1-yl. In some embodiments, $R^4$ is hydrogen. In some embodiments, $R^5$ is hydrogen. In some embodiments, $R^5$ is

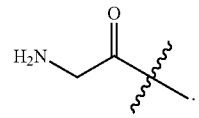

In some embodiments, the compound has the formula:

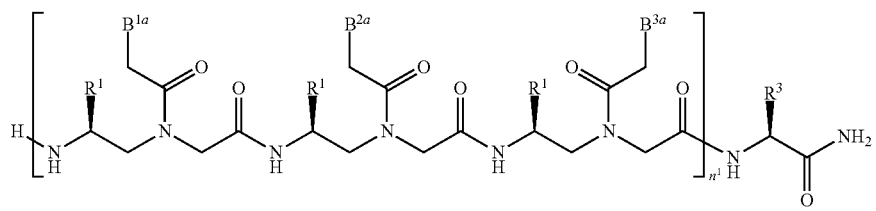

wherein
each $B^{1a}$, $B^{2a}$ and $B^{3a}$ is independently cytosine, guanine, or thymine; and
$n^1$ is 1, 2, 3, 4, 5, 6, 7, 8, 9, or 10.

In some embodiments, $n^1$ is 2. In some embodiments, the compound comprises the sequence $(CTG)_2$. In some embodiments, at least one $R^1$ is 4-guanidinobut-1-yl. In some embodiments, each $R^1$ is 4-guanidinobut-1-yl. In some embodiments, at least one $R^1$ is hydrogen. In some embodiments, $R^3$ is 4-aminobut-1-yl. In some embodiments, $R^3$ is 3-aminoprop-1-yl.

In some embodiments, the compound has the formula:

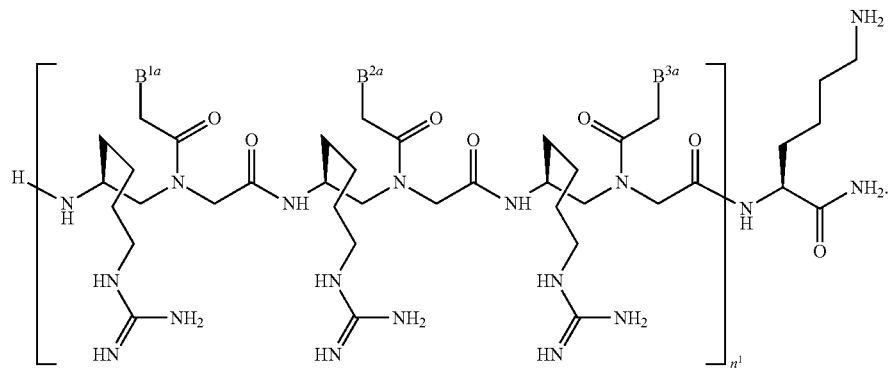

In some embodiments, $B^{1a}$ is cytosine, $B^{2a}$ is thymine and $B^{3a}$ is guanine. In some embodiments, $n^1$ is 2.

In some embodiments, the compound has the formula:

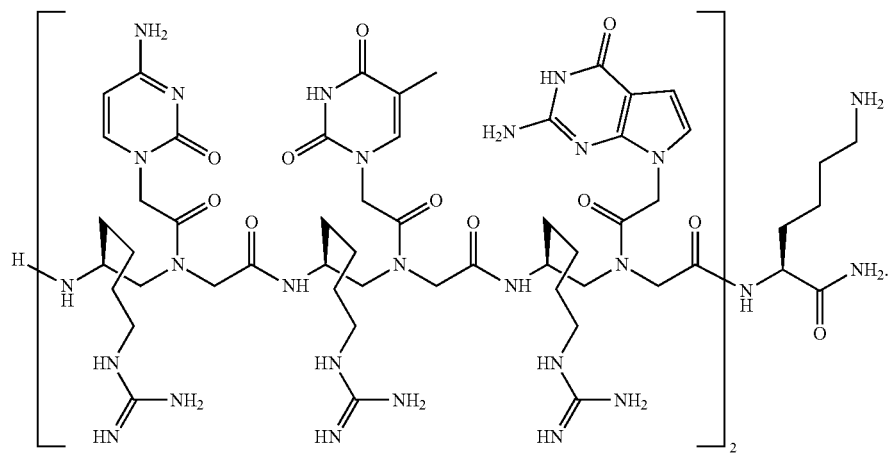

In some embodiments, the compound has the formula:

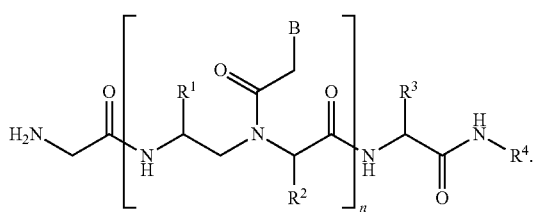

In some embodiments, n is 6. In some embodiments, the compound comprises the sequence $(CTG)_2$. In some embodiments, at least one $R^1$ is 4-guanidinobut-1-yl. In some embodiments, each $R^1$ is 4-guanidinobut-1-yl. In some embodiments, at least one $R^1$ is hydrogen. In some embodiments, $R^3$ is 4-aminobut-1-yl. In some embodiments, $R^3$ is 3-aminoprop-1-yl.

In some embodiments, the compound has the formula:

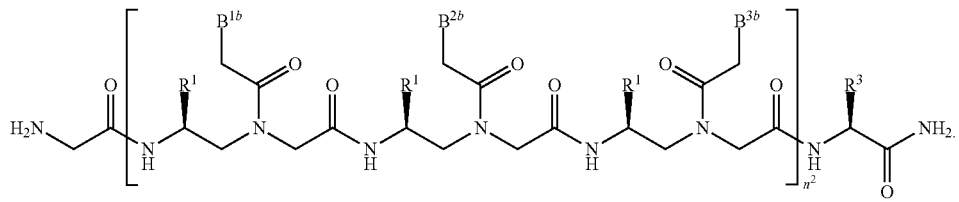

wherein
each $B^{1b}$, $B^{2b}$ and $B^{3b}$ is independently cytosine, guanine or thymine; and
$n^2$ is 1, 2, 3, 4, 5, 6, 7, 8, 9, or 10.

In some embodiments, $n^2$ is 2. In some embodiments, $R^1$ is 4-guanidinobut-1-yl. In some embodiments, $R^3$ is 4-aminobut-1-yl. In some embodiments, $R^3$ is 3-aminoprop-1-yl.

In some embodiments, the compound has the formula:

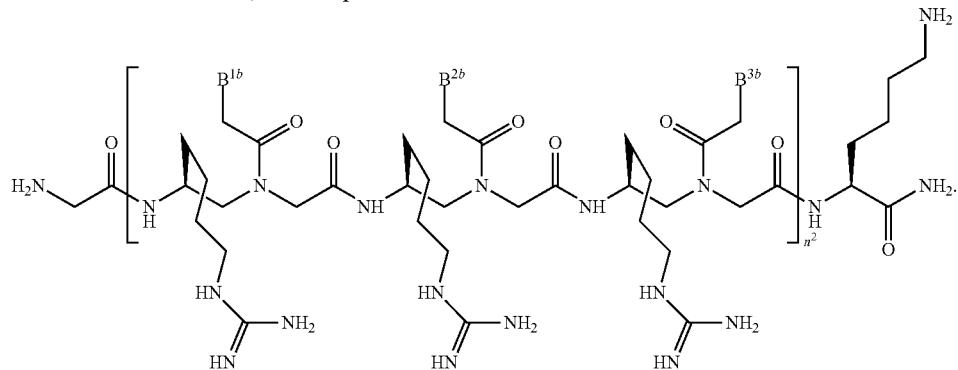

In some embodiments, $B^{1b}$ is cytosine, $B^{2b}$ is thymine and $B^{3b}$ is guanine. In some embodiments, $n^2$ is 2.

In some embodiments, the compound has the formula:

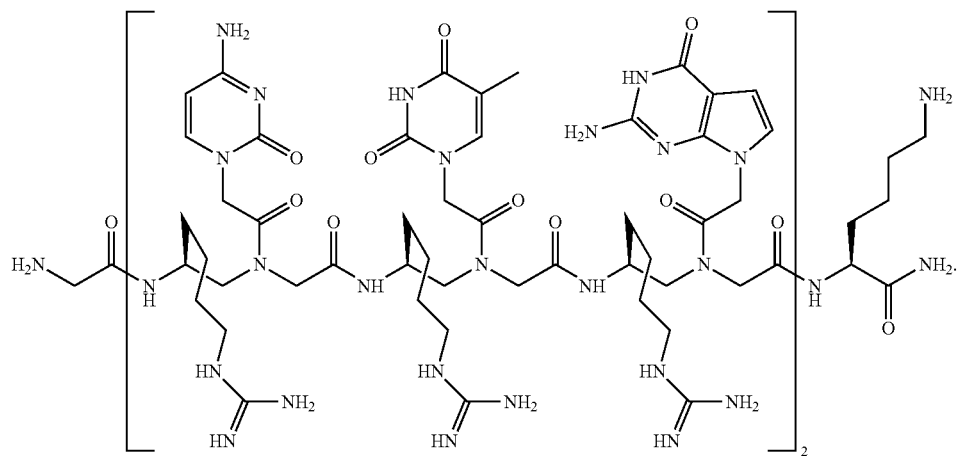

In some embodiments, the compound has the formula:

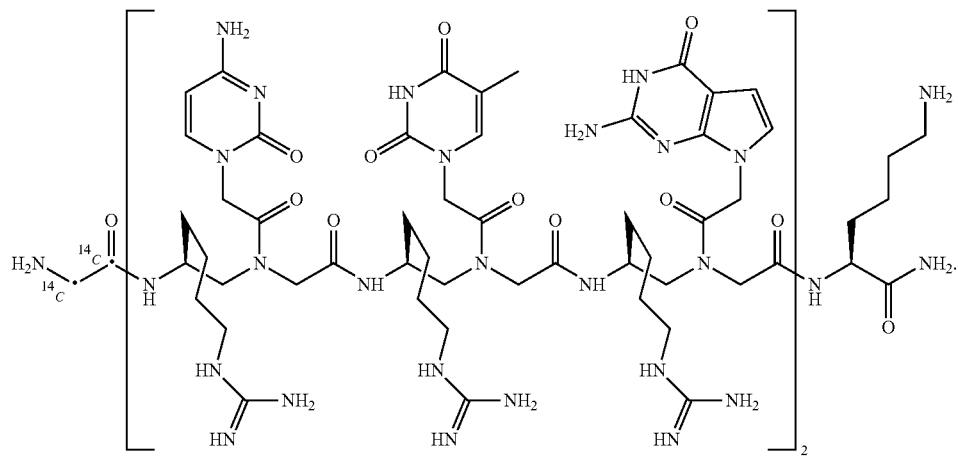

In some embodiments, the compound has the formula:

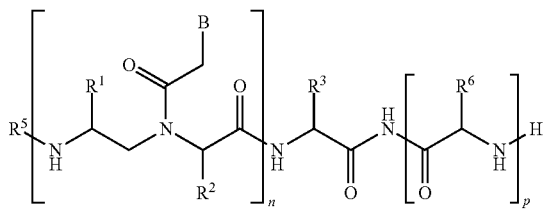

wherein
p is 1, 2, 3, 4, 5, 6, 7, 8, 9, or 10; and
each $R^6$ is independently hydrogen or an amino($C_1$-$C_4$) alkyl.

In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 19. In some embodiments, n is 20.

In some embodiments, at least one $R^1$ is hydrogen. In some embodiments, n is greater than 1, and every other $R^1$ is hydrogen. In some embodiments, at least one $R^1$ is 4-guanidinobut-1-yl. In some embodiments, n is greater than 1, and every other $R^1$ is 4-guanidinobut-1-yl.

In some embodiments, at least one $R^2$ is hydrogen. In some embodiments, each $R^2$ is hydrogen. In some embodiments, at least one $R^2$ is 4-guanidinobut-1-yl. In some embodiments, every other $R^2$ is 4-guanidinobut-1-yl.

In some embodiments, $R^3$ is 4-aminobut-1-yl. In some embodiments, $R^3$ is 3-aminoprop-1-yl.

In some embodiments, $R^4$ is hydrogen. In some embodiments, $R^4$ is

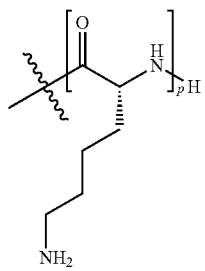

wherein p is 1, 2, 3, 4, 5, 6, 7, 8, 9, or 10.

In some embodiments, p is 3. In some embodiments, p is 4. In some embodiments, p is 5. In some embodiments, p is 6. In some embodiments, p is 7. In some embodiments, p is 8.

In some embodiments, $R^5$ is hydrogen. In some embodiments, $R^5$ is

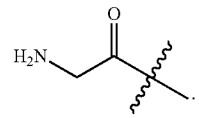

In some embodiments, $R^5$ is

In some embodiments, $R^6$ is 4-aminobut-1-yl. In some embodiments, $R^6$ is 3-aminoprop-1-yl.

In some embodiments, the compound has the formula:

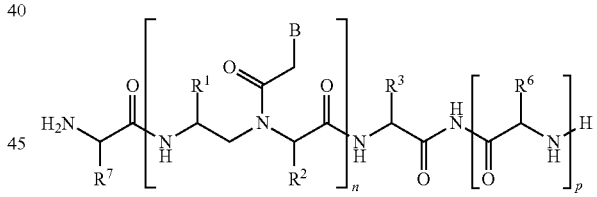

wherein
$R^7$ is a side chain of a natural amino acid.

In some embodiments, $R^7$ is 4-aminobut-1-yl. In some embodiments, $R^7$ is 3-aminoprop-1-yl.

In some embodiments, the compound has the structure

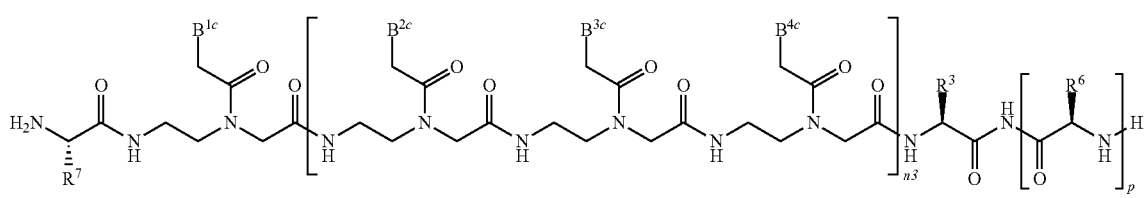

wherein
each $B^{1c}$, $B^{2c}$, $B^{3c}$ and $B^{4c}$ is independently cytosine, guanine or thymine; and
$n^3$ is 1, 2, 3, 4, 5, 6, 7, 8, 9, or 10.

In some embodiments, $B^{1c}$ is guanine. In some embodiments, $B^{2c}$ is cytosine. In some embodiments, $B^{3c}$ is thymine. In some embodiments, $B^{4c}$ is guanine.

In some embodiments, $n^3$ is 6.

In some embodiments, p is 7.

In some embodiments, $R^3$ is 4-aminobut-1-yl. In some embodiments, $R^3$ is 3-aminoprop-1-yl.

In some embodiments, $R^6$ is 4-aminobut-1-yl. In some embodiments, $R^6$ is 3-aminoprop-1-yl.

In some embodiments, $R^7$ is 4-aminobut-1-yl. In some embodiments, $R^7$ is 3-aminoprop-1-yl.

In some embodiments, the compound comprises a sequence comprising $G(CTG)_6$.

In some embodiments, the compound has the structure

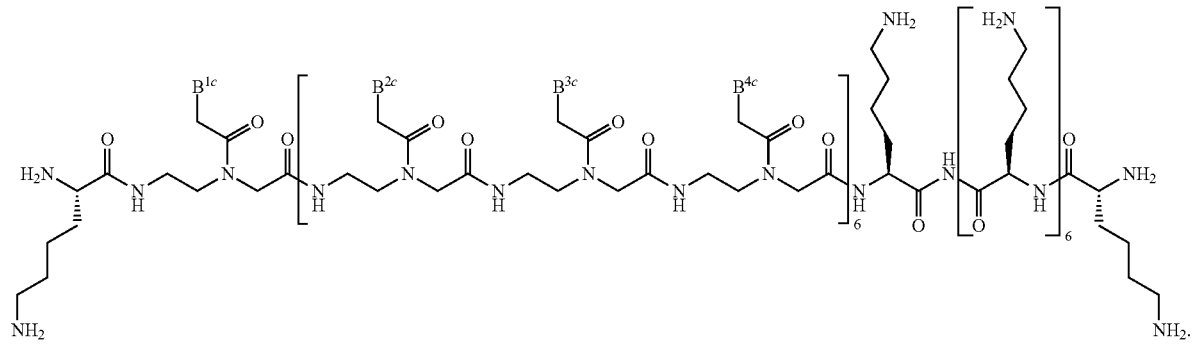

In some embodiments, the compound has the structure

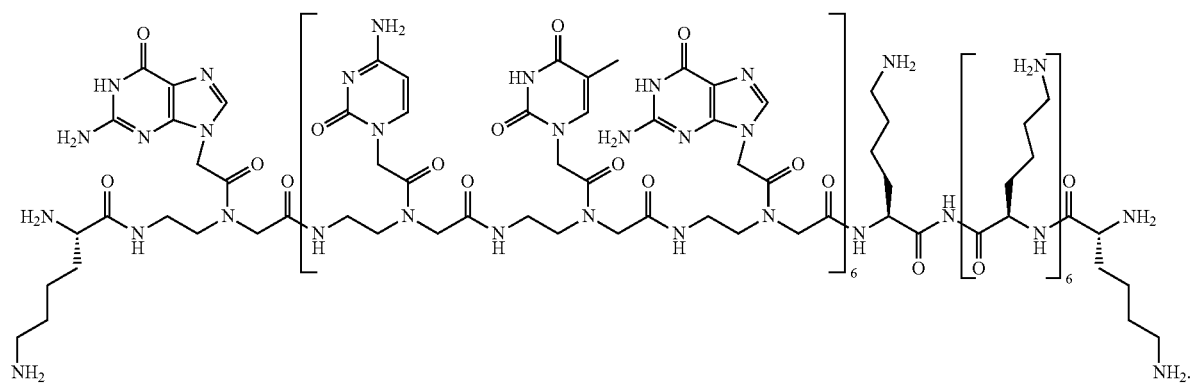

In some embodiments, the compound has the structure

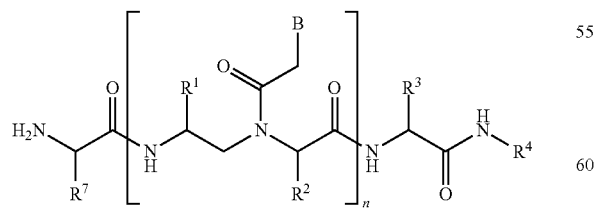

wherein
$R^7$ is a side chain of a natural amino acid.

In some embodiments, $R^7$ is 4-aminobut-1-yl. In some embodiments, $R^7$ is 3-aminoprop-1-yl.

In some embodiments, the compound has the structure

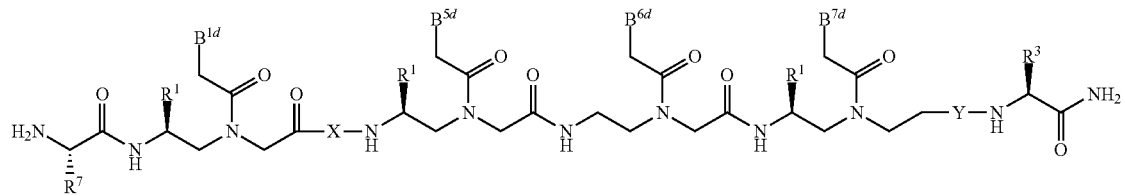

wherein
X is

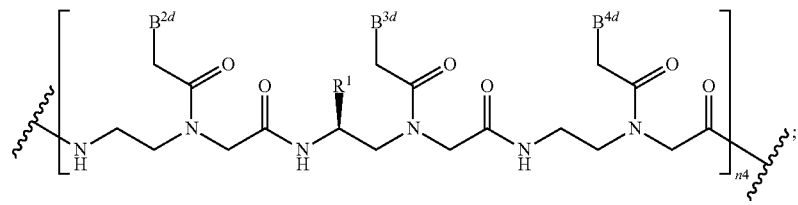

Y is

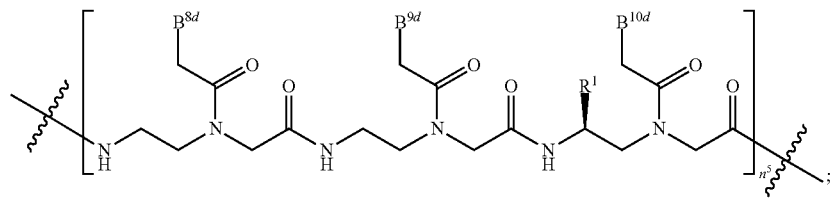

each $B^{1d}$, $B^{2d}$, $B^{3d}$, $B^{4d}$, $B^{5d}$, $B^{6d}$, $B^{7d}$, $B^{8d}$, $B^{9d}$, and $B^{10d}$ is independently cytosine, guanine or thymine;
$n^4$ is 1, 2, 3, 4, 5, 6, 7, 8, 9, or 10; and
$n^5$ is 1, 2, 3, 4, 5, 6, 7, 8, 9, or 10.

In some embodiments, $B^{1d}$ is guanine. In some embodiments, $B^{2d}$ is cytosine. In some embodiments, $B^{3d}$ is thymine. In some embodiments, $B^{4d}$ is guanine. In some embodiments, $B^{5d}$ is cytosine. In some embodiments, $B^{6d}$ is thymine. In some embodiments, $B^{7d}$ is guanine. In some embodiments, $B^{8d}$ is cytosine. In some embodiments, $B^{9d}$ is thymine. In some embodiments, $B^{10d}$ is guanine.

In some embodiments, $n^4$ is 3. In some embodiments, $n^5$ is 2.

In some embodiments, $R^3$ is 4-aminobut-1-yl. In some embodiments, at least one $R^1$ is 4-guanidinobut-1-yl. In some embodiments, each $R^1$ is 4-guanidinobut-1-yl.

In some embodiments, $R^3$ is 4-aminobut-1-yl. In some embodiments, $R^3$ is 3-aminoprop-1-yl. In some embodiments, In some embodiments, $R^7$ is 4-aminobut-1-yl. In some embodiments, $R^7$ is 3-aminoprop-1-yl.

In some embodiments, the compound has the structure:

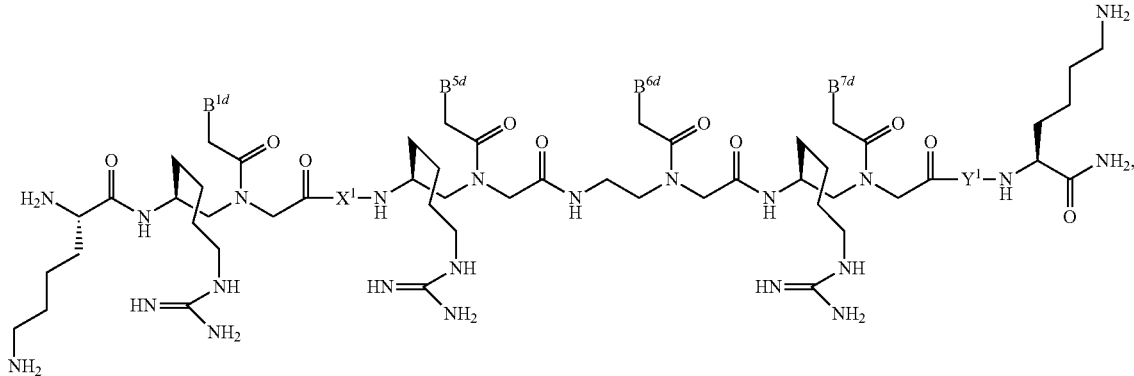

wherein
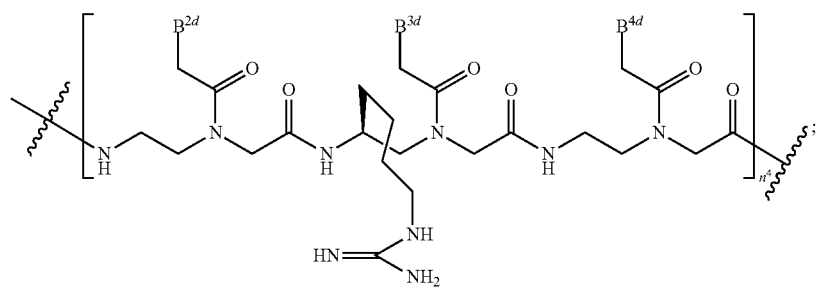
and
Y¹ is
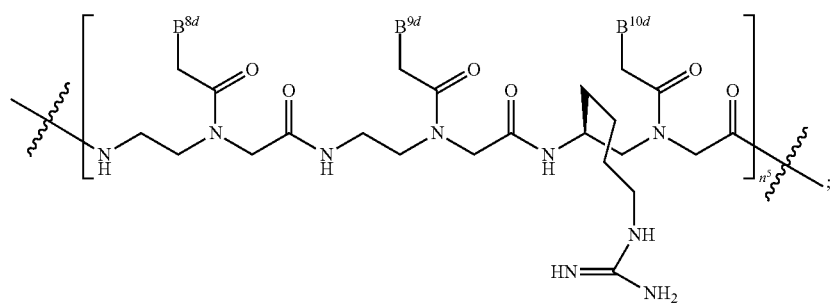
In some embodiments, the compound has the structure:
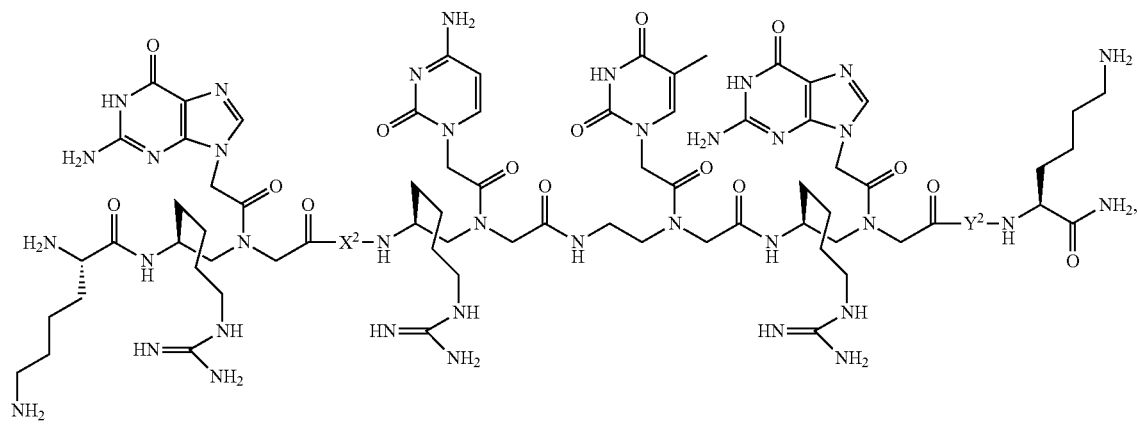

wherein X² is
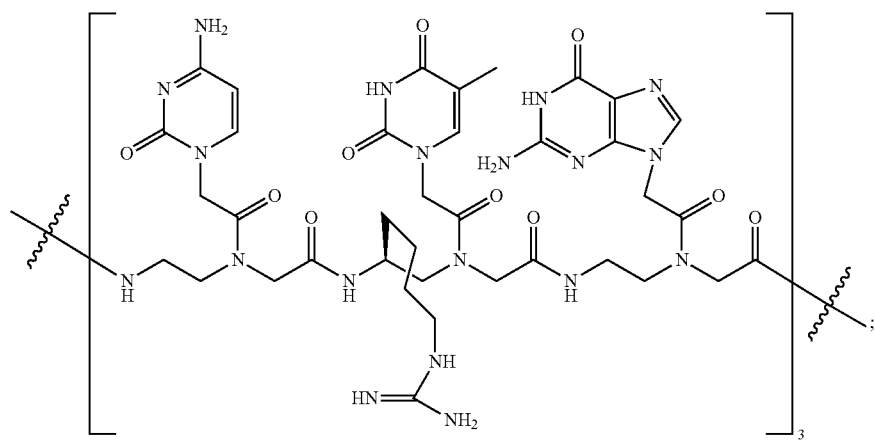
and
Y² is
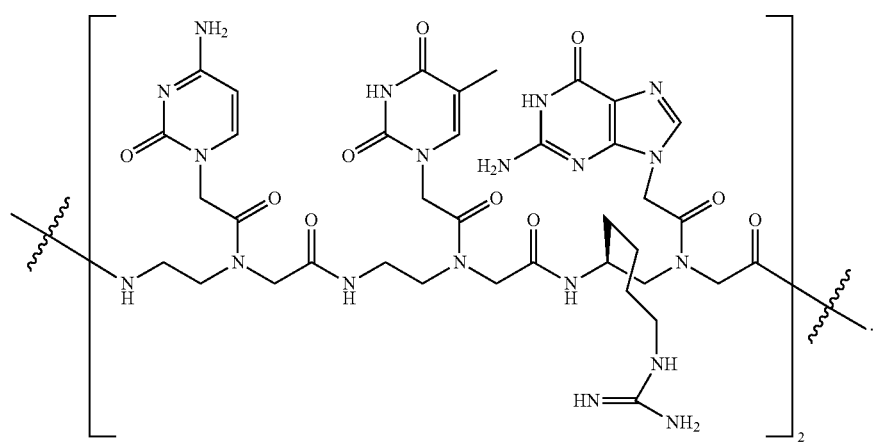
In some embodiments, the compound has the structure:
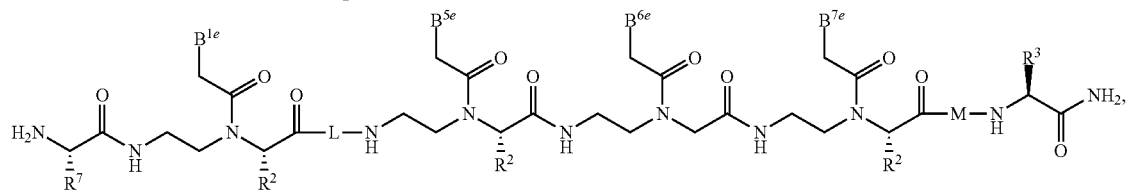
wherein
L is
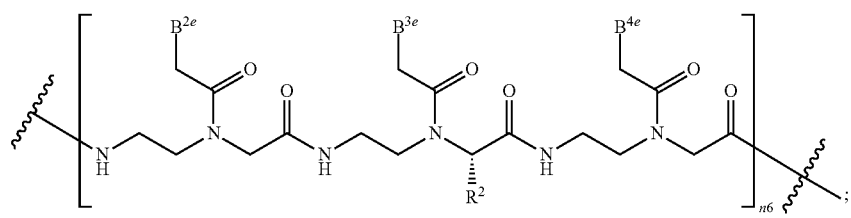

M is

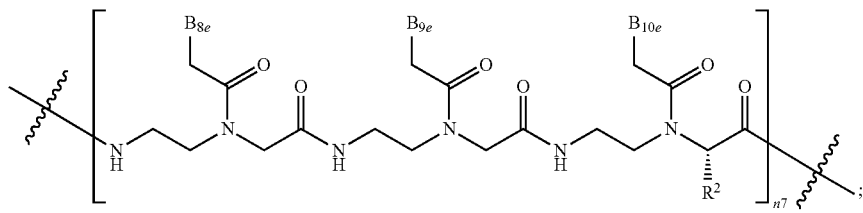

each $B^{1e}, B^{2e}, B^{3e}, B^{4e}, B^{5e}, B^{6e}, B^{7e}, B^{8e}, B^{9e}$ and $B^{10e}$ is independently cytosine, guanine or thymine;
$n^6$ is 1, 2, 3, 4, 5, 6, 7, 8, 9, or 10; and
$n^7$ is 1, 2, 3, 4, 5, 6, 7, 8, 9, or 10.

In some embodiments, We is guanine. In some embodiments, $B^{2e}$ is cytosine. In some embodiments, $B^{3e}$ is thymine. In some embodiments, $B^{4e}$ is guanine. In some embodiments, $B^{5e}$ is cytosine. In some embodiments, $B^{6e}$ is thymine. In some embodiments, $B^{7e}$ is guanine. In some embodiments, $B^{8e}$ is cytosine. In some embodiments, $B^{9e}$ is thymine. In some embodiments, $B^{10e}$ is guanine.

In some embodiments, $n^6$ is 3. In some embodiments, $n^7$ is 2.

In some embodiments, at least one $R^2$ is 3-guanidinoprop-1-yl. In some embodiments, each $R^2$ is 3-guanidinoprop-1-yl. In some embodiments, at least one $R^2$ is 4-guanidinobut-1-yl. In some embodiments, each $R^2$ is 4-guanidinobut-1-yl.

In some embodiments, $R^3$ is 4-aminobut-1-yl. In some embodiments, $R^3$ is 3-aminoprop-1-yl.

In some embodiments, $R^7$ is 4-aminobut-1-yl. In some embodiments, $R^7$ is 3-aminoprop-1-yl.

In some embodiments, the compound has the structure:

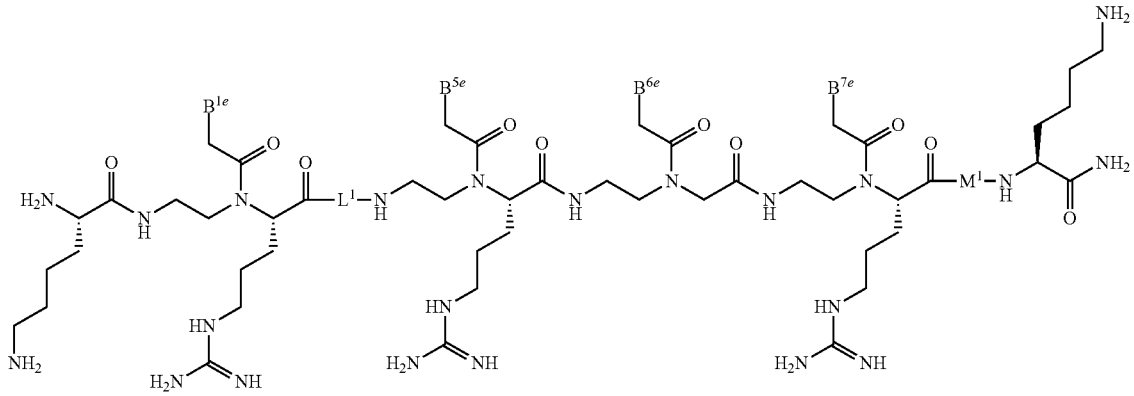

wherein
$L^1$ is

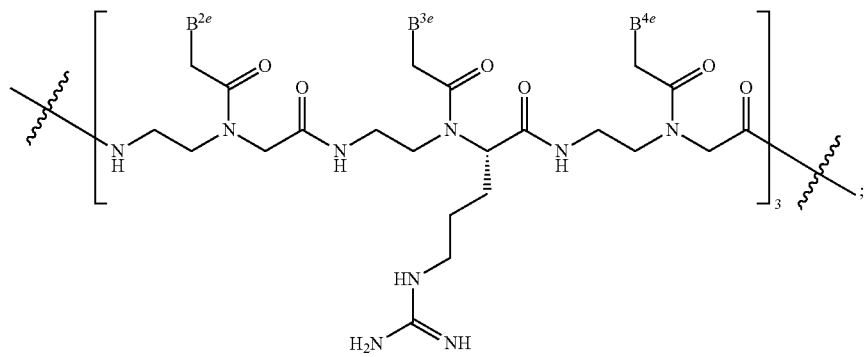

and M¹ is
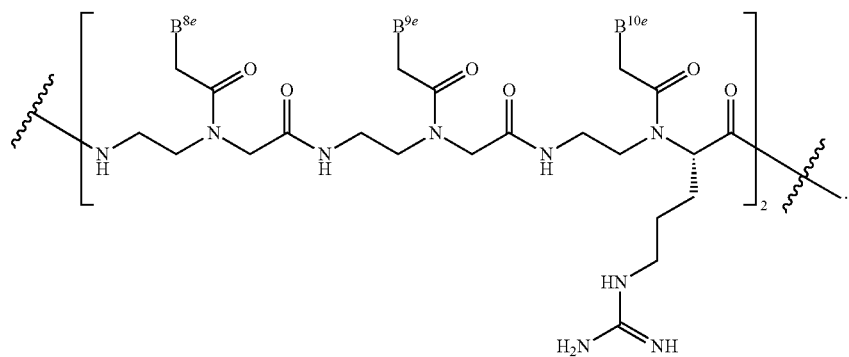
In some embodiments, the compound has the structure:
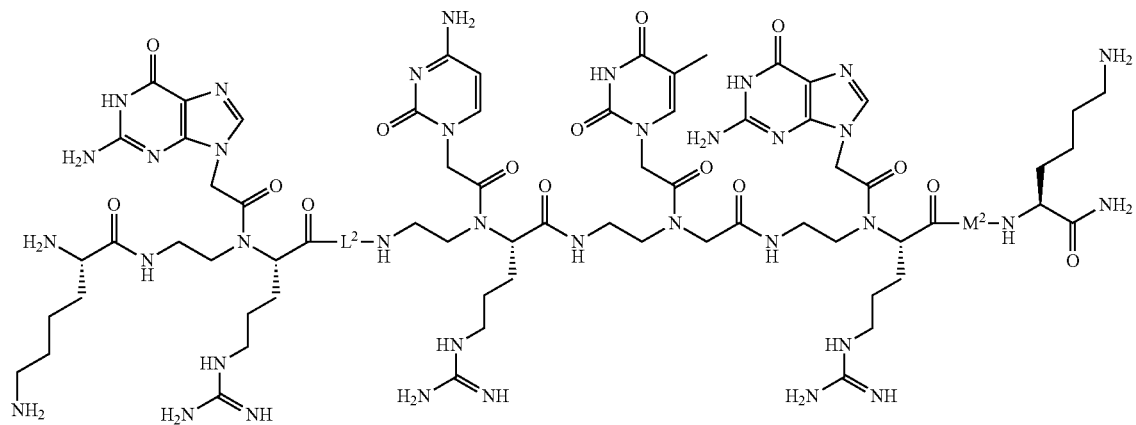
wherein
L²
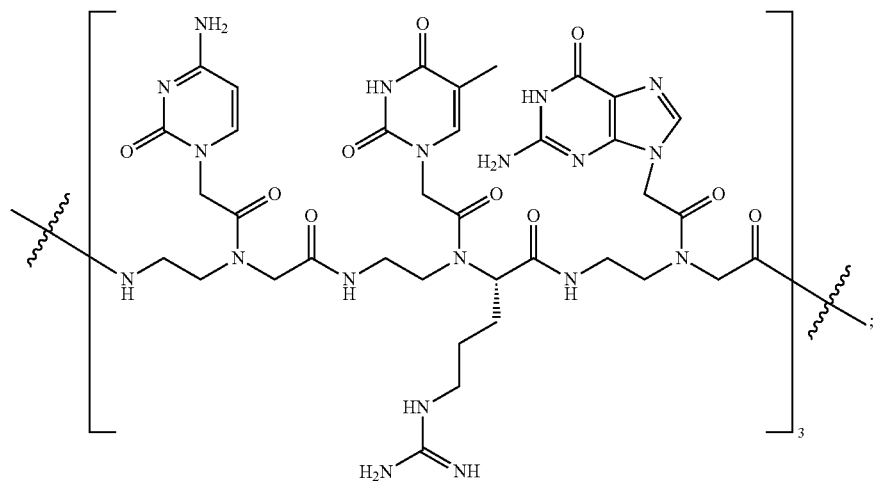

and
M² is

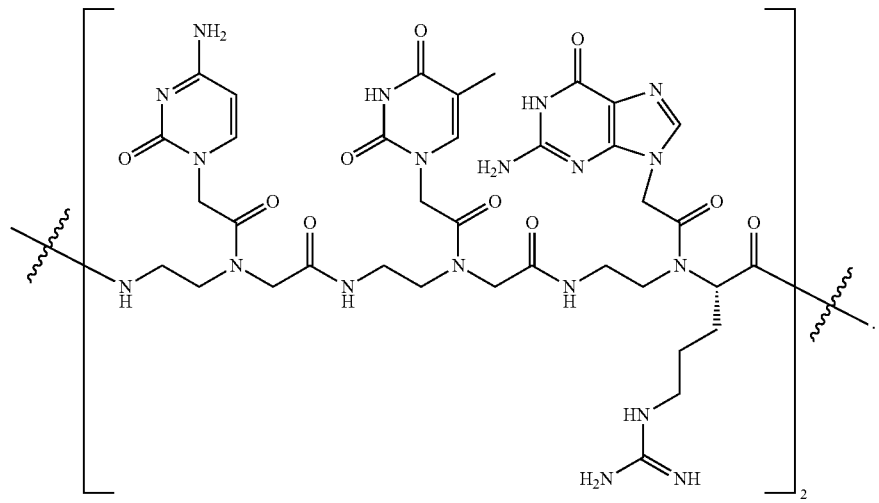

Chemical Groups

Each chemical group disclosed herein may be unsubstituted or substituted. Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, haloalkynyl groups, alkoxy groups, aryl groups, aryloxy groups, aralkyl groups, arylalkoxy groups, heterocyclyl groups, acyl groups, hydrocarbyl groups, acyloxy groups, carbamate groups, amide groups, and ester groups.

Non-limiting examples of alkyl and alkylene groups include straight, branched, and cyclic alkyl and alkylene groups. An alkyl group can be, for example, a $C_1, C_2, C_3, C_4, C_5, C_6, C_7, C_8, C_9, C_{10}, C_{11}, C_{12}, C_{13}, C_{14}, C_{15}, C_{16}, C_{17}, C_{18}, C_{19}, C_{20}, C_{21}, C_{22}, C_{23}, C_{24}, C_{25}, C_{26}, C_{27}, C_{28}, C_{29}, C_{30}, C_{31}, C_{32}, C_{33}, C_{34}, C_{35}, C_{36}, C_{37}, C_{38}, C_{39}, C_{40}, C_{41}, C_{42}, C_{43}, C_{44}, C_{45}, C_{46}, C_{47}, C_{48}, C_{49}$, or $C_{50}$ group that is substituted or unsubstituted. A $(C_1-C_4)$ alkyl groups is an alkyl group comprising between one and four carbon atoms.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2, C_3, C_4, C_5, C_6, C_7, C_8, C_9, C_{10}, C_{11}, C_{12}, C_{13}, C_{14}, C_{15}, C_{16}, C_{17}, C_{18}, C_{19}, C_{20}, C_{21}, C_{22}, C_{23}, C_{24}, C_{25}, C_{26}, C_{27}, C_{28}, C_{29}, C_{30}, C_{31}, C_{32}, C_{33}, C_{34}, C_{35}, C_{36}, C_{37}, C_{38}, C_{39}, C_{40}, C_{41}, C_{42}, C_{43}, C_{44}, C_{45}, C_{46}, C_{47}, C_{48}, C_{49}$, or $C_{50}$ group that is substituted or unsubstituted.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2, C_3, C_4, C_5, C_6, C_7, C_8, C_9, C_{10}, C_{11}, C_{12}, C_{13}, C_{14}, C_{15}, C_{16}, C_{17}, C_{18}, C_{19}, C_{20}, C_{21}, C_{22}, C_{23}, C_{24}, C_{25}, C_{26}, C_{27}, C_{28}, C_{29}, C_{30}, C_{31}, C_{32}, C_{33}, C_{34}, C_{35}, C_{36}, C_{37}, C_{38}, C_{39}, C_{40}, C_{41}, C_{42}, C_{43}, C_{44}, C_{45}, C_{46}, C_{47}, C_{48}, C_{49}$, or $C_{50}$ group that is substituted or unsubstituted.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

A hydrocarbyl group can be any group consisting of carbon and hydrogen atoms, and can include alkyl groups, alkenyl groups, alkynyl groups, and aryl groups. A hydrocarbyl group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group.

A hydrocarbylcarbonyl group can be a carbonyl group substituted with a hydrocarbyl group, which can be, for example, benzoyl, acetyl, propanoyl, butanoyl, pentanoyl, hexanoyl, heptanoyl, octanoyl, nonanoyl, decanoyl, undencanoyl, dodecanoyl, tridencanoyl, myristoyl, pentadecenoyl, palmitoyl, heptadecanoyl, stearoyl, nondecanoyl, arachidoyl, as well as acyl groups derived from saturated, mono-unsaturated, and polyunsaturated fatty acids, such as myristoleoyl, palmitoleoyl, sapienoyl, oleoyl, elaidoyl, vaccenoyl, linoleoyl, linoelaidoyl, α-linolenoyl, or arachidonoyl. A hydrocarbylcarbonyl group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group.

An aminoalkylene group can be an alkyl group substituted with an amino group, such as, for example, aminomethyl, 2-aminoeth-1-yl, 3-aminoprop-1-yl, 2-aminoprop-1-yl, 4-aminobut-1-yl, 3-aminobut-1-yl, 2-aminobut-1-yl, 5-aminopen-1-yl, 4-aminopent-1-yl, 4-aminopent-1-yl, 3-aminopent-1-yl, 2-aminopent-1-yl, a lysine side chain, or an ornithine side chain.

A guanidinoalkylene group can be an alkyl group substituted with a guanidino group, such as, for example, guanidinomethyl, 2-guanidinoeth-1-yl, 3-guanidinoprop-1-yl, 2-guanidinoprop-1-yl, 4-guanidinobut-1-yl, 3-guanidinobut-1-yl, 2-guanidinobut-1-yl, 5-guanidinopent-1-yl, 4-guanidinopent-1-yl, 4-guanidinopent-1-yl, 3-guanidinopent-1-yl, 2-guanidinopent-1-yl, an arginine side chain, or a homoarginine side chain.

"Polypeptide", "peptide" and their grammatical equivalents as used herein refer to a polymer of amino acid residues. Polypeptides and proteins disclosed herein (including functional portions and functional variants thereof) can comprise synthetic amino acids in place of one or more naturally-occurring amino acids. The disclosure contemplates both L- and D-forms of amino acid residues.

A compound of the disclosure may be radiolabeled. One or more of the atoms of the compound of the disclosure may be substituted with a radioactive or non-radioactive isotope, for example of $^2H$, $^3H$, $^{11}C$, $^{13}C$, $^{14}C$, 13N, $^{15}N$, $^{15}O$, $^{17}O$, $^{18}O$, or combinations thereof. In one embodiment, at least one carbon of the compound of the disclosure may be substituted with $^{14}C$.

Therapeutic Methods

The present disclosure describes the use of a compound and methods to treat conditions or genetic disease, including trinucleotide repeat disorders. The method can comprise administering to the subject a therapeutically-effective amount of a compound of the disclosure. In some embodiments, the genetic disease is a polyglutamine (polyQ) disease. Polyglutamine diseases include trinucleotide repeat disorders involving genes that comprise an abnormally high number of CAG repeats. In some embodiments, the polyglutamine disease is SCAT (Spinocerebellar ataxia Type 1), SCA2 (Spinocerebellar ataxia Type 2), SCA3 (Spinocerebellar ataxia Type 3 or Machado-Joseph disease), SCA6 (Spinocerebellar ataxia Type 6), SCAT (Spinocerebellar ataxia Type 7), SCA12 (Spinocerebellar ataxia Type 12), SCA17 (Spinocerebellar ataxia Type 17), DRPLA (Dentatorubropallidoluysian atrophy), SBMA (Spinal and bulbar muscular atrophy), or Huntington's disease.

In some embodiments, the condition is a neurological condition. In some embodiments, the neurological condition is Huntington's disease. In some embodiments, the condition is a central nervous system condition. In some embodiments, the condition is associated with aging. In some embodiments, the condition is associated with cognitive impairment. In some embodiments, the condition is associated with memory loss. In some embodiments, the condition is associated with deterioration of motor skills.

In some embodiments, the polyglutamine disease is Huntington's disease. Treatment can be administered on the basis of number of CAG repeats in the HTT gene of a subject. For example, a subject administered a compound of the disclosure can comprise a HTT gene that contains more than 27 CAG repeats. In some embodiments, the HTT gene of the subject contains at least 36 repeats, at least 40 repeats, at least 50 repeats, or at least 60 repeats. In some embodiments, the HTT gene of the subject contains from 27 to 36 repeats, from 27 to 36 repeats, from 27 to 40 repeats, from 27 to 60 repeats, from 27 to 80 repeats, from 27 to 90 repeats, from 36 to 40 repeats, from 36 to 60 repeats, from 36 to 80 repeats, from 36 to 90 repeats, from 40 to 60 repeats, from 40 to 80 repeats, from 40 to 90 repeats, or from 60 to 90 repeats.

In some embodiments, administration of a compound of the disclosure does not exhibit immunogenicity. In some embodiments, administration of a compound of the disclosure does not promote generation of neutralizing antibodies, complement factors, pro-inflammatory cytokines, or type 1 interferons upon or after administration of the compound to a subject. In some embodiments, the compounds do not activate the TLR9 receptor and are not presented in MHCI or MHCII complexes to the immune system.

Compounds of the disclosure can be systemically administered to a subject in need thereof as a therapeutically-effective amount of a compound that binds to a repeat codon. The subject can comprise a bloodstream, a brain, and a blood-brain-barrier. The compound that binds to the repeat codon can enter the brain by passing from the bloodstream through the blood-brain-barrier into the brain.

Modes of Administration

A compound of the disclosure or a composition comprising a compound of the disclosure (for example, a pharmaceutical composition) can be administered to a subject in various forms and by various suitable routes of administration.

A compound of the disclosure or a composition comprising a compound of the disclosure (for example, a pharmaceutical composition) can be administered in a local manner, for example, via injection of the compound directly into an organ, optionally in a depot or sustained release formulation or implant. A compound of the disclosure or a composition comprising a compound of the disclosure (for example, a pharmaceutical composition) can be administered in a systemic manner.

In some embodiments, a compound of the disclosure or a composition comprising a compound of the disclosure (for example, a pharmaceutical composition) is administered parenterally. Parenteral administration can be, for example, by bolus injection or by gradual infusion or perfusion over time. Administration can also be by surgical deposition of a bolus, or positioning of a medical device.

In some embodiments, a compound of the disclosure or a composition comprising a compound of the disclosure (for example, a pharmaceutical composition) is administered orally. In some embodiments, a compound of the disclosure or a composition comprising a compound of the disclosure (for example, a pharmaceutical composition) is administered by an intravenous, intratumoral, subcutaneous, intramuscular, intracerebral, intracerebroventricular, intra-articular, intraperitoneal, intracranial, intrathecal, intranasal, buccal, sublingual, oral, or rectal administration route. In some embodiments, a compound of the disclosure or a composition comprising a compound of the disclosure (for example, a pharmaceutical composition) is administered by intravenous administration. In some embodiments, a compound of the disclosure or a composition comprising a compound of the disclosure (for example, a pharmaceutical composition) is administered by subcutaneous administration. In some embodiments, a compound of the disclosure or a composition comprising a compound of the disclosure (for example, a pharmaceutical composition) is administered by intracerebroventricular administration. In some embodiments, a compound of the disclosure or a composition comprising a compound of the disclosure (for example, a pharmaceutical composition) is administered by oral administration. In some embodiments, a compound of the disclosure or a composition comprising a compound of the disclosure (for example, a pharmaceutical composition) is administered by intrathecal administration.

Any aforementioned route of administration can be combined with another route of administration. For example, a compound of the disclosure can be delivered by a first route of administration, and one or more subsequent maintenance doses of the compound can be delivered by the same or a different route of administration. In some embodiments, a compound of the disclosure or a composition comprising a compound of the disclosure (for example, a pharmaceutical composition) is administered by intrathecal administration, and one or more subsequent maintenance doses of the compound or the composition comprising the compound are delivered by subcutaneous administration or intravenous administration.

Non-limiting examples of suitable modes and routes of administration include oral, topical, parenteral, intravenous injection, intravenous infusion, subcutaneous injection, subcutaneous infusion, intramuscular injection, intramuscular infusion, intradermal injection, intradermal infusion, intraperitoneal injection, intraperitoneal infusion, intracerebral injection, intracerebral infusion, subarachnoid injection, subarachnoid infusion, intraocular injection, intraspinal injection, intrasternal injection, ophthalmic administration, endothelial administration, local administration, intranasal administration, intrapulmonary administration, rectal administration, intraarterial administration, intrathecal administration, inhalation, intralesional administration, intradermal administration, epidural administration, absorption through epithelial or mucocutaneous linings (e.g., oral mucosa, rectal and intestinal mucosa), intracapsular administration, subcapsular administration, intracardiac administration, transtracheal administration, subcuticular administration, subarachnoid administration, subcapsular administration, intraspinal administration, and intrasternal administration.

A compound of the disclosure or a composition comprising a compound of the disclosure (for example, a pharmaceutical composition) can be administered via a non-invasive method. Examples of non-invasive modes of administering can include using a needleless injection device, and topical administration, for example, eye drops. Multiple administration routes can be employed for efficient delivery.

Depending on the intended mode of administration, the compositions can be in the form of solid, semi solid or liquid dosage forms, such as, for example, tablets, suppositories, pills, capsules, powders, liquids, suspensions, lotions, creams, or gels, for example, in unit dosage form suitable for single administration of a precise dosage. The composition can be formulated into any suitable dosage form for administration, for example, aqueous dispersions, liquids, gels, syrups, elixirs, slurries, and suspensions, for administration to a subject or a patient.

Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semisolid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

In some embodiments, the composition is formulated into solutions (for example, for IV administration). In some cases, the pharmaceutical composition is formulated as an infusion. In some cases, the pharmaceutical composition is formulated as an injection.

A compound of the disclosure or a composition comprising a compound of the disclosure (for example, a pharmaceutical composition) can be administered in the form of a rapid release formulation, in the form of an extended release formulation, or in the form of an intermediate release formulation. A rapid release form can provide an immediate release. An extended release formulation can provide a controlled release or a sustained delayed release.

A composition comprising a compound of the disclosure can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements, or has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some embodiments, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours. A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16, or about 24 hours.

A pharmaceutical composition disclosed herein can be targeted to any suitable tissue or cell type. Modes, routes, and compositions of the disclosure can be suitable to target a compound of the disclosure to a particular tissue, or a subset of tissues. Non-limiting examples of tissues that can be targeted include kidney (e.g., kidney cortex), joints, cartilage, liver, salivary glands, bone (e.g., bone surface), skin, lung, muscle, pancreas, hair follicles, large intestine mucosa, aortic wall, small intestine mucosa, adrenal gland, stomach mucosa, spleen, bone marrow, lymph nodes, thymus, brain, cerebellum, olfactory bulb, thalamus, caudate putamen, cerebral cortex, substantia nigra, lateral ventricle, choroid plexus, and combinations thereof.

Dosing

Pharmaceutical compositions described herein can be in unit dosage forms suitable for single administration of precise dosages. In unit dosage form, the formulation is divided into unit doses containing appropriate quantities of one or more compound. The dosage (e.g., therapeutically-effective amount) for a compound described herein can be in any amount necessary.

A compound described herein can be present in a composition or a unit dose in a range of from about 1 mg to about 2000 mg; from about 5 mg to about 1000 mg, from about 10 mg to about 25 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition or a unit dose in a range of from about 1 µg to about 2000 µg; from about 5 µg to about 1000 µg, from about 10 µg to about 25 µg, from about 50 µg to about 250 µg, from about 100 µg to about 200 µg, from about 1 µg to about 50 µg, from about 50 µg to about 100 µg, from about 100 µg to about 150 µg, from about 150 µg to about 200 µg, from about 200 µg to about 250 µg, from about 250 µg to about 300 µg, from about 300 µg to about 350 µg, from about 350 µg to about 400 µg, from about 400 µg to about 450 µg, from about 450 µg to about 500 µg, from about 500 µg to about 550 µg, from about 550 µg to about 600 µg, from about 600 µg to about 650 µg, from about 650 µg to about 700 µg, from about 700 µg to about 750 µg, from about 750 µg to about 800 µg, from about 800 µg to about 850 µg, from about 850 µg to about 900 µg, from about 900 µg to about 950 µg, or from about 950 µg to about 1000 µg.

A compound described herein can be present in a composition or a unit dose in an amount of about 0.001 mg, about 0.002 mg, about 0.003 mg, about 0.004 mg, about 0.005 mg, about 0.006 mg, about 0.007 mg, about 0.008 mg, about 0.009 mg, about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a composition is present in a composition or a unit dose in an amount that is at least about 0.001 mg, at least about 0.002 mg, at least about 0.003 mg, at least about 0.004 mg, at least about 0.005 mg, at least about 0.006 mg, at least about 0.007 mg, at least about 0.008 mg, at least about 0.009 mg, at least about 0.01 mg, at least about 0.02 mg, at least about 0.03 mg, at least about 0.04 mg, at least about 0.05 mg, at least about 0.06 mg, at least about 0.07 mg, at least about 0.08 mg, at least about 0.09 mg, at least about 0.1 mg, at least about 0.2 mg, at least about 0.3 mg, at least about 0.4 mg, at least about 0.5 mg, at least about 0.6 mg, at least about 0.7 mg, at least about 0.8 mg, at least about 0.9 mg, at least about 1 mg, at least about 2 mg, at least about 3 mg, at least about 4 mg, at least about 5 mg, at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 125 mg, at least about 150 mg, at least about 175 mg, at least about 200 mg, at least about 250 mg, at least about 300 mg, at least about 350 mg, at least about 400 mg, at least about 450 mg, at least about 500 mg, at least about 550 mg, at least about 600 mg, at least about 650 mg, at least about 700 mg, at least about 750 mg, at least about 800 mg, at least about 850 mg, at least about 900 mg, at least about 950 mg, at least about 1000 mg, at least about 1050 mg, at least about 1100 mg, at least about 1150 mg, at least about 1200 mg, at least about 1250 mg, at least about 1300 mg, at least about 1350 mg, at least about 1400 mg, at least about 1450 mg, at least about 1500 mg, at least about 1550 mg, at least about 1600 mg, at least about 1650 mg, at least about 1700 mg, at least about 1750 mg, at least about 1800 mg, at least about 1850 mg, at least about 1900 mg, at least about 1950 mg, or at least about 2000 mg.

In some embodiments, a composition is present in a composition or a unit dose in an amount that is at most about 0.001 mg, at most about 0.002 mg, at most about 0.003 mg, at most about 0.004 mg, at most about 0.005 mg, at most about 0.006 mg, at most about 0.007 mg, at most about 0.008 mg, at most about 0.009 mg, at most about 0.01 mg, at most about 0.02 mg, at most about 0.03 mg, at most about 0.04 mg, at most about 0.05 mg, at most about 0.06 mg, at most about 0.07 mg, at most about 0.08 mg, at most about 0.09 mg, at most about 0.1 mg, at most about 0.2 mg, at most about 0.3 mg, at most about 0.4 mg, at most about 0.5 mg, at most about 0.6 mg, at most about 0.7 mg, at most about 0.8 mg, at most about 0.9 mg, at most about 1 mg, at most about 2 mg, at most about 3 mg, at most about 4 mg, at most about 5 mg, at most about 10 mg, at most about 15 mg, at most about 20 mg, at most about 25 mg, at most about 30 mg, at most about 35 mg, at most about 40 mg, at most about 45 mg, at most about 50 mg, at most about 55 mg, at most about 60 mg, at most about 65 mg, at most about 70 mg, at most about 75 mg, at most about 80 mg, at most about 85 mg, at most about 90 mg, at most about 95 mg, at most about 100 mg, at most about 125 mg, at most about 150 mg, at most about 175 mg, at most about 200 mg, at most about 250 mg, at most about 300 mg, at most about 350 mg, at most about 400 mg, at most about 450 mg, at most about 500 mg, at most about 550 mg, at most about 600 mg, at most about 650 mg, at most about 700 mg, at most about 750 mg, at most about 800 mg, at most about 850 mg, at most about 900 mg, at most about 950 mg, at most about 1000 mg, at most about 1050 mg, at most about 1100 mg, at most about 1150 mg, at most about 1200 mg, at most about 1250 mg, at most about 1300 mg, at most about 1350 mg, at most about 1400 mg, at most about 1450 mg, at most about 1500 mg, at most about 1550 mg, at most about 1600 mg, at most about 1650 mg, at most about 1700 mg, at most about 1750 mg, at most about 1800 mg, at most about 1850 mg, at most about 1900 mg, at most about 1950 mg, or at most about 2000 mg.

In some embodiments, a dose (e.g., a unit dose) is about 0.001 mg/kg, about 0.002 mg/kg, about 0.003 mg/kg, about 0.004 mg/kg, about 0.005 mg/kg, about 0.006 mg/kg, about 0.007 mg/kg, about 0.008 mg/kg, about 0.009 mg/kg, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 2 mg/kg, about 3 mg/kg, about 4 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 125 mg/kg, about 150 mg/kg, about 175 mg/kg, about 200 mg/kg, about 250 mg/kg, about 300 mg/kg, about 350 mg/kg, about 400 mg/kg, about 450 mg/kg, about 500 mg/kg, about 550 mg/kg, about 600 mg/kg, about 650 mg/kg, about 700 mg/kg, about 750 mg/kg, about 800 mg/kg, about 850 mg/kg, about 900 mg/kg, about 950 mg/kg, about 1000 mg/kg, about 1050 mg/kg, about 1100 mg/kg, about 1150 mg/kg, about 1200 mg/kg, about 1250 mg/kg, about 1300 mg/kg, about 1350 mg/kg, about 1400 mg/kg, about 1450 mg/kg, about 1500 mg/kg, about 1550 mg/kg, about 1600 mg/kg, about 1650 mg/kg, about 1700 mg/kg, about 1750 mg/kg, about 1800 mg/kg, about 1850 mg/kg, about 1900 mg/kg, about 1950 mg/kg, or about 2000 mg/kg based on body mass of a subject or a patient.

In some embodiments, a dose (e.g., a unit dose) is at least about 0.001 mg/kg, at least about 0.002 mg/kg, at least about 0.003 mg/kg, at least about 0.004 mg/kg, at least about 0.005 mg/kg, at least about 0.006 mg/kg, at least about 0.007 mg/kg, at least about 0.008 mg/kg, at least about 0.009 mg/kg, at least about 0.01 mg/kg, at least about 0.02 mg/kg, at least about 0.03 mg/kg, at least about 0.04 mg/kg, at least about 0.05 mg/kg, at least about 0.06 mg/kg, at least about 0.07 mg/kg, at least about 0.08 mg/kg, at least about 0.09 mg/kg, at least about 0.1 mg/kg, at least about 0.2 mg/kg, at least about 0.3 mg/kg, at least about 0.4 mg/kg, at least about 0.5 mg/kg, at least about 0.6 mg/kg, at least about 0.7 mg/kg, at least about 0.8 mg/kg, at least about 0.9 mg/kg, at least about 1 mg/kg, at least about 2 mg/kg, at least about 3 mg/kg, at least about 4 mg/kg, at least about 5 mg/kg, at least about 10 mg/kg, at least about 15 mg/kg, at least about 20 mg/kg, at least about 25 mg/kg, at least about 30 mg/kg, at least about 35 mg/kg, at least about 40 mg/kg, at least about 45 mg/kg, at least about 50 mg/kg, at least about 55 mg/kg, at least about 60 mg/kg, at least about 65 mg/kg, at least about 70 mg/kg, at least about 75 mg/kg, at least about 80 mg/kg, at least about 85 mg/kg, at least about 90 mg/kg, at least about 95 mg/kg, at least about 100 mg/kg, at least about 125 mg/kg, at least about 150 mg/kg, at least about 175 mg/kg, at least about 200 mg/kg, at least about 250 mg/kg, at least about 300 mg/kg, at least about 350 mg/kg, at least about 400 mg/kg, at least about 450 mg/kg, at least about 500 mg/kg, at least about 550 mg/kg, at least about 600 mg/kg, at least about 650 mg/kg, at least about 700 mg/kg, at least about 750 mg/kg, at least about 800 mg/kg, at least about 850 mg/kg, at least about 900 mg/kg, at least about 950 mg/kg, at least about 1000 mg/kg, at least about 1050 mg/kg, at least about 1100 mg/kg, at least about 1150 mg/kg, at least about 1200 mg/kg, at least about 1250 mg/kg, at least about 1300 mg/kg, at least about 1350 mg/kg, at least about 1400 mg/kg, at least about 1450 mg/kg, at least about 1500 mg/kg, at least about 1550 mg/kg, at least about 1600 mg/kg, at least about 1650 mg/kg, at least about 1700 mg/kg, at least about 1750 mg/kg, at least about 1800 mg/kg, at least about 1850 mg/kg, at least about 1900 mg/kg, at least about 1950 mg/kg, or at least about 2000 mg/kg based on body mass of a subject or a patient.

In some embodiments, a dose (e.g., a unit dose) is at most about 0.001 mg/kg, at most about 0.002 mg/kg, at most about 0.003 mg/kg, at most about 0.004 mg/kg, at most about 0.005 mg/kg, at most about 0.006 mg/kg, at most about 0.007 mg/kg, at most about 0.008 mg/kg, at most about 0.009 mg/kg, at most about 0.01 mg/kg, at most about 0.02 mg/kg, at most about 0.03 mg/kg, at most about 0.04 mg/kg, at most about 0.05 mg/kg, at most about 0.06 mg/kg, at most about 0.07 mg/kg, at most about 0.08 mg/kg, at most about 0.09 mg/kg, at most about 0.1 mg/kg, at most about 0.2 mg/kg, at most about 0.3 mg/kg, at most about 0.4 mg/kg, at most about 0.5 mg/kg, at most about 0.6 mg/kg, at most about 0.7 mg/kg, at most about 0.8 mg/kg, at most about 0.9 mg/kg, at most about 1 mg/kg, at most about 2 mg/kg, at most about 3 mg/kg, at most about 4 mg/kg, at most about 5 mg/kg, at most about 10 mg/kg, at most about 15 mg/kg, at most about 20 mg/kg, at most about 25 mg/kg, at most about 30 mg/kg, at most about 35 mg/kg, at most about 40 mg/kg, at most about 45 mg/kg, at most about 50 mg/kg, at most about 55 mg/kg, at most about 60 mg/kg, at most about 65 mg/kg, at most about 70 mg/kg, at most about 75 mg/kg, at most about 80 mg/kg, at most about 85 mg/kg, at most about 90 mg/kg, at most about 95 mg/kg, at most about 100 mg/kg, at most about 125 mg/kg, at most about 150 mg/kg, at most about 175 mg/kg, at most about 200 mg/kg, at most about 250 mg/kg, at most about 300 mg/kg, at most about 350 mg/kg, at most about 400 mg/kg, at most about 450 mg/kg, at most about 500 mg/kg, at most about 550 mg/kg, at most about 600 mg/kg, at most about 650 mg/kg, at most about 700 mg/kg, at most about 750 mg/kg, at most about 800 mg/kg, at most about 850 mg/kg, at most about 900 mg/kg, at most about 950 mg/kg, at most about 1000 mg/kg, at most about 1050 mg/kg, at most about 1100 mg/kg, at most about 1150 mg/kg, at most about 1200 mg/kg, at most about 1250 mg/kg, at most about 1300 mg/kg, at most about 1350 mg/kg, at most about 1400 mg/kg, at most about 1450 mg/kg, at most about 1500 mg/kg, at most about 1550 mg/kg, at most about 1600 mg/kg, at most about 1650 mg/kg, at most about 1700 mg/kg, at most about 1750 mg/kg, at most about 1800 mg/kg, at most about 1850 mg/kg, at most about 1900 mg/kg, at most about 1950 mg/kg, or at most about 2000 mg/kg based on body mass of a subject or a patient.

In some embodiments, a dose (e.g., a unit dose) is about 1 mg/kg to about 2000 mg/kg; from about 5 mg/kg to about 1000 mg/kg, from about 10 mg/kg to about 25 mg/kg, from about 50 mg/kg to about 250 mg/kg, from about 100 mg/kg to about 200 mg/kg, from about 1 mg/kg to about 50 mg/kg, from about 50 mg/kg to about 100 mg/kg, from about 100 mg/kg to about 150 mg/kg, from about 150 mg/kg to about 200 mg/kg, from about 200 mg/kg to about 250 mg/kg, from about 250 mg/kg to about 300 mg/kg, from about 300 mg/kg to about 350 mg/kg, from about 350 mg/kg to about 400 mg/kg, from about 400 mg/kg to about 450 mg/kg, from about 450 mg/kg to about 500 mg/kg, from about 500 mg/kg to about 550 mg/kg, from about 550 mg/kg to about 600 mg/kg, from about 600 mg/kg to about 650 mg/kg, from about 650 mg/kg to about 700 mg/kg, from about 700 mg/kg to about 750 mg/kg, from about 750 mg/kg to about 800 mg/kg, from about 800 mg/kg to about 850 mg/kg, from about 850 mg/kg to about 900 mg/kg, from about 900 mg/kg to about 950 mg/kg, from about 950 mg/kg to about 1000 mg/kg, about 1 µg/kg to about 2000 µg/kg; from about 5 µg/kg to about 1000 µg/kg, from about 10 µg/kg to about 25 µg/kg, from about 50 µg/kg to about 250 µg/kg, from about 100 µg/kg to about 200 µg/kg, from about 1 µg/kg to about 50 µg/kg, from about 50 µg/kg to about 100 µg/kg, from about 100 µg/kg to about 150 µg/kg, from about 150 µg/kg to about 200 µg/kg, from about 200 µg/kg to about 250 µg/kg, from about 250 µg/kg to about 300 µg/kg, from about 300 µg/kg to about 350 µg/kg, from about 350 µg/kg to about 400 µg/kg, from about 400 µg/kg to about 450 µg/kg, from about 450 µg/kg to about 500 µg/kg, from about 500 µg/kg to about 550 µg/kg, from about 550 µg/kg to about 600 µg/kg, from about 600 µg/kg to about 650 µg/kg, from about 650 µg/kg to about 700 µg/kg, from about 700 µg/kg to about 750 µg/kg, from about 750 µg/kg to about 800 µg/kg, from about 800 µg/kg to about 850 µg/kg, from about 850 µg/kg to about 900 µg/kg, from about 900 µg/kg to about 950 µg/kg, or from about 950 µg/kg to about 1000 µg/kg based on body mass of a subject or a patient.

Pharmaceutical compositions and formulations described herein can comprise, for example, a compound of the disclosure at any suitable concentration. A formulation can comprise a composition of the disclosure at a concentration of, for example, about 0.001 mg/mL, about 0.002 mg/mL, about 0.003 mg/mL, about 0.004 mg/mL, about 0.005 mg/mL, about 0.006 mg/mL, about 0.007 mg/mL, about 0.008 mg/mL, about 0.009 mg/mL, about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 125 mg/mL, about 150 mg/mL, about 175 mg/mL, about 200 mg/mL, about 250 mg/mL, about 300 mg/mL, about 350 mg/mL, about 400 mg/mL, about 450 mg/mL, about 500 mg/mL, about 550 mg/mL, about 600 mg/mL, about 650 mg/mL, about 700 mg/mL, about 750 mg/mL, about 800 mg/mL, about 850 mg/mL, about 900 mg/mL, about 950 mg/mL, about 1000 mg/mL, about 1050 mg/mL, about 1100 mg/mL, about 1150 mg/mL, about 1200 mg/mL, about 1250 mg/mL, about 1300 mg/mL, about 1350 mg/mL, about 1400 mg/mL, about 1450 mg/mL, about 1500 mg/mL, about 1550 mg/mL, about 1600 mg/mL, about 1650 mg/mL, about 1700 mg/mL, about 1750 mg/mL, about 1800 mg/mL, about 1850 mg/mL, about 1900 mg/mL, about 1950 mg/mL, or about 2000 mg/mL.

In some embodiments, a formulation of the disclosure comprises a compound of the disclosure at a concentration of at least about 0.001 mg/mL, at least about 0.002 mg/mL, at least about 0.003 mg/mL, at least about 0.004 mg/mL, at least about 0.005 mg/mL, at least about 0.006 mg/mL, at least about 0.007 mg/mL, at least about 0.008 mg/mL, at least about 0.009 mg/mL, at least about 0.01 mg/mL, at least about 0.02 mg/mL, at least about 0.03 mg/mL, at least about 0.04 mg/mL, at least about 0.05 mg/mL, at least about 0.06 mg/mL, at least about 0.07 mg/mL, at least about 0.08 mg/mL, at least about 0.09 mg/mL, at least about 0.1 mg/mL, at least about 0.2 mg/mL, at least about 0.3 mg/mL, at least about 0.4 mg/mL, at least about 0.5 mg/mL, at least about 0.6 mg/mL, at least about 0.7 mg/mL, at least about 0.8 mg/mL, at least about 0.9 mg/mL, at least about 1 mg/mL, at least about 2 mg/mL, at least about 3 mg/mL, at least about 4 mg/mL, at least about 5 mg/mL, at least about 10 mg/mL, at least about 15 mg/mL, at least about 20 mg/mL, at least about 25 mg/mL, at least about 30 mg/mL, at least about 35 mg/mL, at least about 40 mg/mL, at least about 45 mg/mL, at least about 50 mg/mL, at least about 55 mg/mL, at least about 60 mg/mL, at least about 65 mg/mL, at least about 70 mg/mL, at least about 75 mg/mL, at least about 80 mg/mL, at least about 85 mg/mL, at least about 90 mg/mL, at least about 95 mg/mL, at least about 100 mg/mL, at least about 125 mg/mL, at least about 150 mg/mL, at least about 175 mg/mL, at least about 200 mg/mL, at least about 250 mg/mL, at least about 300 mg/mL, at least about 350 mg/mL, at least about 400 mg/mL, at least about 450 mg/mL, at least about 500 mg/mL, at least about 550 mg/mL, at least about 600 mg/mL, at least about 650 mg/mL, at least about 700 mg/mL, at least about 750 mg/mL, at least about 800 mg/mL, at least about 850 mg/mL, at least about 900 mg/mL, at least about 950 mg/mL, at least about 1000 mg/mL, at least about 1050 mg/mL, at least about 1100 mg/mL, at least about 1150 mg/mL, at least about 1200 mg/mL, at least about 1250 mg/mL, at least about 1300 mg/mL, at least about 1350 mg/mL, at least about 1400 mg/mL, at least about 1450 mg/mL, at least about 1500 mg/mL, at least about 1550 mg/mL, at least about 1600 mg/mL, at least about 1650 mg/mL, at least about 1700 mg/mL, at least about 1750 mg/mL, at least about 1800 mg/mL, at least about 1850 mg/mL, at least about 1900 mg/mL, at least about 1950 mg/mL, or at least about 2000 mg/mL.

In some embodiments, a formulation of the disclosure comprises a compound of the disclosure at a concentration of at most about 0.002 mg/mL, at most about 0.003 mg/mL, at most about 0.004 mg/mL, at most about 0.005 mg/mL, at most about 0.006 mg/mL, at most about 0.007 mg/mL, at most about 0.008 mg/mL, at most about 0.009 mg/mL, at most about 0.01 mg/mL, at most about 0.02 mg/mL, at most about 0.03 mg/mL, at most about 0.04 mg/mL, at most about 0.05 mg/mL, at most about 0.06 mg/mL, at most about 0.07 mg/mL, at most about 0.08 mg/mL, at most about 0.09 mg/mL, at most about 0.1 mg/mL, at most about 0.2 mg/mL, at most about 0.3 mg/mL, at most about 0.4 mg/mL, at most about 0.5 mg/mL, at most about 0.6 mg/mL, at most about 0.7 mg/mL, at most about 0.8 mg/mL, at most about 0.9 mg/mL, at most about 1 mg/mL, at most about 2 mg/mL, at most about 3 mg/mL, at most about 4 mg/mL, at most about 5 mg/mL, at most about 10 mg/mL, at most about 15 mg/mL, at most about 20 mg/mL, at most about 25 mg/mL, at most about 30 mg/mL, at most about 35 mg/mL, at most about 40 mg/mL, at most about 45 mg/mL, at most about 50 mg/mL, at most about 55 mg/mL, at most about 60 mg/mL, at most about 65 mg/mL, at most about 70 mg/mL, at most about 75 mg/mL, at most about 80 mg/mL, at most about 85 mg/mL, at most about 90 mg/mL, at most about 95 mg/mL, at most about 100 mg/mL, at most about 125 mg/mL, at most about 150 mg/mL, at most about 175 mg/mL, at most about 200 mg/mL, at most about 250 mg/mL, at most about 300 mg/mL, at most about 350 mg/mL, at most about 400 mg/mL, at most about 450 mg/mL, at most about 500 mg/mL, at most about 550 mg/mL, at most about 600 mg/mL, at most about 650 mg/mL, at most about 700 mg/mL, at most about 750 mg/mL, at most about 800 mg/mL, at most about 850 mg/mL, at most about 900 mg/mL, at most about 950 mg/mL, at most about 1000 mg/mL, at most about 1050 mg/mL, at most about 1100 mg/mL, at most about 1150 mg/mL, at most about 1200 mg/mL, at most about 1250 mg/mL, at most about 1300 mg/mL, at most about 1350 mg/mL, at most about 1400 mg/mL, at most about 1450 mg/mL, at most about 1500 mg/mL, at most about 1550 mg/mL, at most about 1600 mg/mL, at most about 1650 mg/mL, at most about 1700 mg/mL, at most about 1750 mg/mL, at most about 1800 mg/mL, at most about 1850 mg/mL, at most about 1900 mg/mL, at most about 1950 mg/mL, or at most about 2000 mg/mL.

In some embodiments, a formulation of the disclosure comprises a compound of the disclosure at a concentration of about 1 mg/mL to about 2000 mg/mL; from about 5 mg/mL to about 1000 mg/mL, from about 10 mg/mL to about 25 mg/mL, from about 50 mg/mL to about 250 mg/mL, from about 100 mg/mL to about 200 mg/mL, from about 1 mg/mL to about 50 mg/mL, from about 50 mg/mL to about 100 mg/mL, from about 100 mg/mL to about 150 mg/mL, from about 150 mg/mL to about 200 mg/mL, from about 200 mg/mL to about 250 mg/mL, from about 250 mg/mL to about 300 mg/mL, from about 300 mg/mL to about 350 mg/mL, from about 350 mg/mL to about 400 mg/mL, from about 400 mg/mL to about 450 mg/mL, from about 450 mg/mL to about 500 mg/mL, from about 500 mg/mL to about 550 mg/mL, from about 550 mg/mL to about 600 mg/mL, from about 600 mg/mL to about 650 mg/mL, from about 650 mg/mL to about 700 mg/mL, from about 700 mg/mL to about 750 mg/mL, from about 750 mg/mL to about 800 mg/mL, from about 800 mg/mL to about 850 mg/mL, from about 850 mg/mL to about 900 mg/mL, from about 900 mg/mL to about 950 mg/mL, from about 950 mg/mL to about 1000 mg/mL, about 1 µg/mL to about 2000 µg/mL; from about 5 µg/mL to about 1000 µg/mL, from about 10 µg/mL to about 25 µg/mL, from about 50 µg/mL to about 250 µg/mL, from about 100 µg/mL to about 200 µg/mL, from about 1 µg/mL to about 50 µg/mL, from about 50 µg/mL to about 100 µg/mL, from about 100 µg/mL to about 150 µg/mL, from about 150 µg/mL to about 200 µg/mL, from about 200 µg/mL to about 250 µg/mL, from about 250 µg/mL to about 300 µg/mL, from about 300 µg/mL to about 350 µg/mL, from about 350 µg/mL to about 400 µg/mL, from about 400 µg/mL to about 450 µg/mL, from about 450 µg/mL to about 500 µg/mL, from about 500 µg/mL to about 550 µg/mL, from about 550 µg/mL to about 600 µg/mL, from about 600 µg/mL to about 650 µg/mL, from about 650 µg/mL to about 700 µg/mL, from about 700 µg/mL to about 750 µg/mL, from about 750 µg/mL to about 800 µg/mL, from about 800 µg/mL to about 850 µg/mL, from about 850 µg/mL to about 900 µg/mL, from about 900 µg/mL to about 950 µg/mL, or from about 950 µg/mL to about 1000 µg/mL.

Therapeutic Effects
Tissue Distribution and Pharmacokinetics

Compounds disclosed herein can have favorable properties for administration to subjects or patients, for example, favorable pharmacokinetic or tissue distribution parameters.

In some embodiments, if a study or assay (e.g., tissue distribution study) is conducted, wherein the study or assay comprises administering (e.g., intracerebroventricular administration) a compound of the disclosure (e.g., Compound 1) to a study patient or subject at a dose amount of about 0.1 mg/kg to about 1.5 mg/kg, then the compound accumulates in the study patient's brain for at most about 1 month after dosing. In some embodiments, the compound is not observed or is rarely observed at a detectable level during the month in the study patient's plasma, intestine, liver, lung, kidney, and/or muscle.

In some embodiments, the compound can be subjected to an assay or a study (e.g., a tissue distribution study) and in the study, the compound can be observed to accumulate in the brain of a study patient (e.g., mice) for a time period (e.g., most about a month) after the administering. In some embodiments, the compound is not observed at a detectable level during the time period in the plasma, intestine, liver, lung, kidney, and/or muscle of the study patient. In some embodiments, the assay can comprise administering (e.g., intracerebroventricular administration) a dose amount (e.g., about 0.1 mg/kg to about 1.5 mg/kg) of the compound to a study patient (e.g., mice). Blood samples can be collected (e.g., from cava veins) of the study patient at a time point (e.g., between about 1 hour and 28 days) post administration. After collecting the blood samples, the study patients can be euthanized at a time point between (e.g., about 1 hour and 28 days) post administration. After the euthanasia, various tissues (e.g., brain, intestine, liver, lung, kidney, and/or muscle tissues) can be collected from the study patients.

Various analytical techniques can be used to determine concentrations of the compound in tissues and/or other samples collected from study patients (for example, blood, plasma, urine, feces, etc). Non-limiting examples of techniques that can be used to determine concentrations of the compound include mass spectrometry, for example, liquid chromatography mass spectrometry (LC-MS), gas chromatography mass spectrometry (GC-MS), tandem MS (MS/MS, e.g, LC-MS/MS or GC-MS/MS), Matrix-assisted laser desorption ionization-time of flight mass spectrometry (MALDI-TOF MS), triple quadrupole mass spectrometry (TQMS), Quadrupole Trap MS, hybrid linear trap orbitrap MS, quadrupole-Orbitrap mass spectrometry, High performance or ultra-high performance liquid chromatography (HPLC or UHPLC, e.g., with MS or ultraviolet detection), time of flight (TOF) MS, Selected reaction monitoring (SRM), Multiple reaction monitoring (MRM) nuclear magnetic resonance (NMR, for example, continuous-wave (cw), pulsed or Fourier-Transform, 1H, 13C, 19F, 31P, or other nuclei), variations thereof, or combinations thereof.

In some embodiments, if an assay or study is conducted, wherein the study or assay comprises administering (e.g., via intracerebroventricular administration) a compound of the disclosure (e.g., Compound 1) to a study patient (e.g., mouse) or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the compound accumulates in the study patient's or subject's brain for a time period of at most about 1 month (for example, at most about 3 days, at most about 7 days, at most about 14 days, at most about 21 days, at most about 27 days, or at most about 28 days) after dosing. In some embodiments, the compound is not observed or is rarely observed during this time period at a detectable level in the study patient's or subject's plasma, intestine, liver, lung, kidney, and/or muscle.

In some embodiments, if an assay or study is conducted, wherein the study or assay comprises administering (e.g., via intracerebroventricular administration) a compound of the disclosure (e.g., Compound 1) to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the compound accumulates in the study patient's or subject's brain for a time period of at least about 1 day (for example, at least about 1 day, at least about 3 days, at least about 7 days, at least about 14 days, at least about 21 days, at least about 27 days, at least about 28 days, at least about 1 month, at least about 2 months, or at least about 3 months) after dosing. In some embodiments, the compound is not observed or is rarely observed during this time period at a detectable level in the study patient's or subject's plasma, intestine, liver, lung, kidney, and/or muscle.

In some embodiments, if an assay or study is conducted, wherein the study or assay comprises administering (e.g., via intracerebroventricular administration) a compound of the disclosure (e.g., Compound 1) to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the compound accumulates in the study patient's or subject's spleen for a time period of at most about 1 month (for example, at most about 3 days, at most about 7 days, at most about 14 days, at most about 21 days, at most about 27 days, or at most about 28 days) after dosing. In some embodiments, the compound is not observed or is rarely observed at a detectable level during this time period in the study patient's or subject's plasma, intestine, liver, lung, kidney, and/or muscle.

In some embodiments, if an assay or study is conducted, wherein the study or assay comprises administering (e.g., via intracerebroventricular administration) a compound of the disclosure (e.g., Compound 1) to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the compound accumulates in the study patient's or subject's spleen for a time period of at least about 1 day (for example, at least about 1 day, at least about 3 days, at least about 7 days, at least about 14 days, at least about 21 days, at least about 27 days, at least about 28 days, at least about 1 month, at least about 2 months, or at least about 3 months) after dosing. In some embodiments, the compound is not observed or is rarely observed at a detectable level during this time period in the study patient's or subject's plasma, intestine, liver, lung, kidney, and/or muscle.

In some embodiments, if an assay or study is conducted, wherein the study or assay comprises administering (e.g., via intracerebroventricular administration) a compound of the disclosure (e.g., Compound 1) to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the compound accumulates in the study patient's or subject's heart for a timer period of at most about 1 month (for example, at most about 3 days, at most about 7 days, at most about 14 days, at most about 21 days, at most about 27 days, or at most about 28 days) after dosing. In some embodiments, the compound is not observed or is rarely observed at a detectable level during this time period in the study patient's or subject's plasma, intestine, liver, lung, kidney, and/or muscle.

In some embodiments, if an assay or study is conducted, wherein the study or assay comprises administering (e.g., via intracerebroventricular administration) a compound of the disclosure (e.g., Compound 1) to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the compound accumulates in the study patient's or subject's heart for a time period of at least about 1 day (for example, at least about 1 day, at least about 3 days, at least about 7 days, at least about 14 days, at least about 21 days, at least about 27 days, at least about 28 days, at least about 1 month, at least about 2 months, or at least about 3 months) after dosing. In some embodiments, the compound is not observed or is rarely observed at a detectable level during this period in the study patient's or subject's plasma, intestine, liver, lung, kidney, and/or muscle.

In some embodiments, if an assay or study is conducted, wherein the study or assay comprises administering (e.g., via intracerebroventricular administration) a compound of the disclosure (e.g., Compound 1) to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the compound accumulates in the study patient's or subject's brain for a time period of at most about 1 month (for example, at most about 3 days, at most about 7 days, at most about 14 days, at most about 21 days, at most about 27 days, or at most about 28 days) after dosing. In some embodiments, the compound is not observed or is rarely observed at a detectable level during this time period in the study patient's or subject's plasma, intestine, liver, lung, kidney, and/or muscle.

In some embodiments, if an assay or study is conducted, wherein the study or assay comprises administering (e.g., via intracerebroventricular administration) a compound of the disclosure (e.g., Compound 1) to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the compound accumulates in the study patient's or subject's brain at a time period for at least about 1 day (for example, at least about 1 day, at least about 3 days, at least about 7 days, at least about 14 days, at least about 21 days, at least about 27 days, at least about 28 days, at least about 1 month, at least about 2 months, or at least about 3 months) after dosing. In some embodiments, the compound is not observed or is rarely observed at a detectable level during this time period in the study patient's or subject's plasma, intestine, liver, lung, kidney, and/or muscle.

In some embodiments, if an assay or study is conducted, wherein the study or assay comprises administering (e.g., via intracerebroventricular administration) a compound of the disclosure (e.g., Compound 1) to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the compound accumulates in the study patient's or subject's spleen for a time period of at most about 1 month (for example, at most about 3 days, at most about 7 days, at most about 14 days, at most about 21 days, at most about 27 days, or at most about 28 days) after dosing. In some embodiments, the compound is not observed or is rarely observed during this time period at a detectable level in the study patient's or subject's plasma, intestine, liver, lung, kidney, and/or muscle.

In some embodiments, if an assay or study is conducted, wherein the study or assay comprises administering (e.g., via intracerebroventricular administration) a compound of the disclosure (e.g., Compound 1) to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the compound accumulates in the study patient's or subject's spleen for a time period of at least about 1 day (for example, at least about 1 day, at least about 3 days, at least about 7 days, at least about 14 days, at least about 21 days, at least about 27 days, at least about 28 days, at least about 1 month, at least about 2 months, or at least about 3 months) after dosing. In some embodiments, the compound is not observed or is rarely observed at a detectable level during this time period in the study patient's or subject's plasma, intestine, liver, lung, kidney, and/or muscle.

In some embodiments, if an assay or study is conducted, wherein the study or assay comprises administering (e.g., via intracerebroventricular administration) a compound of the disclosure (e.g., Compound 1) to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the compound accumulates in the study patient's or subject's heart for a time period of at most about 1 month (for example, at most about 3 days, at most about 7 days, at most about 14 days, at most about 21 days, at most about 27 days, or at most about 28 days) after dosing. In some embodiments, the compound is not observed or is rarely observed at a detectable level during this time period in the study patient's or subject's plasma, intestine, liver, lung, kidney, and/or muscle.

In some embodiments, if an assay or study is conducted, wherein the study or assay comprises administering (e.g., via intracerebroventricular administration) a compound of the disclosure (e.g., Compound 1) to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the compound accumulates in the study patient's or subject's heart for a time period of at least about 1 day (for example, at least about 1 day, at least about 3 days, at least about 7 days, at least about 14 days, at least about 21 days, at least about 27 days, at least about 28 days, at least about 1 month, at least about 2 months, or at least about 3 months) after dosing. In some embodiments, the compound is not observed or is rarely observed at a detectable level during this time period in the study patient's or subject's plasma, intestine, liver, lung, kidney, and/or muscle.

In some embodiments, a dose can be modulated to achieve a desired pharmacokinetic or pharmacodynamics profile, such as a desired or effective blood profile, as described herein.

Pharmacokinetic and pharmacodynamic data can be obtained by various experimental techniques. Appropriate pharmacokinetic and pharmacodynamic profile components describing a particular composition can vary due to variations in drug metabolism in human subjects. Pharmacokinetic and pharmacodynamic profiles can be based on the determination of the mean parameters of a group of subjects. The group of subjects includes any reasonable number of subjects suitable for determining a representative mean, e.g., 5 subjects, 10 subjects, 15 subjects, 20 subjects, 25 subjects, 30 subjects, 35 subjects, or more. The mean is determined, for example, by calculating the average of all subject's measurements for each parameter measured. A dose can be modulated to achieve a desired pharmacokinetic or pharmacodynamics profile, such as a desired or effective blood profile, as described herein.

In some embodiments, the subject is a vertebrate. In some embodiments, the subject is a mammal. In some embodiments, the subject is a human. In some embodiments, the subject is a primate, ape, monkey, sheep, equine, bovine, porcine, minipig, canine, feline, goat, camelid, rodent, rabbit, mouse, rat, hamster, gerbil, hamster, chinchilla, fancy rat, guinea pig, C57BL6J mouse, Beagle dog, Göttingen minipig, or Cynomolgus monkey. In some embodiments, a subject is a non-human subject. In some embodiments, a subject is a veterinary subject.

In some embodiments, the patient is a vertebrate. In some embodiments, the patient is a mammal. In some embodiments, the patient is a human. In some embodiments, the patient is a primate, ape, monkey, sheep, equine, bovine, porcine, minipig, canine, feline, goat, camelid, rodent, rabbit, mouse, rat, hamster, gerbil, hamster, chinchilla, fancy rat, guinea pig, C57BL6J mouse, Beagle dog, Göttingen minipig, or Cynomolgus monkey. In some embodiments, a patient is a non-human patient. In some embodiments, a patient is a veterinary patient.

In some embodiments, a patient and a subject are the same species. In some embodiments, a subject and a patient are human.

In some embodiments, a patient and a subject are different species. In some embodiments, a subject is human and a patient is a non-human, for example, a non-human vertebrate, non-human mammal, non-human primate, ape, monkey, sheep, equine, bovine, porcine, minipig, canine, feline, goat, camelid, rodent, rabbit, mouse, rat, hamster, gerbil, hamster, chinchilla, fancy rat, or guinea pig. In some embodiments, a patient is human and a subject is a non-human, for example, a non-human vertebrate, non-human mammal, non-human primate, ape, monkey, sheep, equine, bovine, porcine, minipig, canine, feline, goat, camelid, rodent, rabbit, mouse, rat, hamster, gerbil, hamster, chinchilla, fancy rat, or guinea pig.

A pharmacokinetic parameter can be any parameter suitable for describing a compound. Non-limiting examples of pharmacodynamic and pharmacokinetic parameters that can be calculated for a compound that is administered with the methods of the invention include:

a) the amount of drug administered, which can be represented as a dose D;
b) the dosing interval, which can be represented as $\tau$;
c) the apparent volume in which a drug is distributed, which can be represented as a volume of distribution $V_d$, where $V_d = D/C_0$;
d) the amount of drug in a given volume of plasma, which can be represented as concentration $C_0$ or $C_{ss}$, where $C_0$ or $C_{ss} = D/Vd$ and can be represented as a mean plasma concentration over a plurality of samples;
e) the half-life of a drug $t_{1/2}$, where $t_{1/2} = \ln(2)/k_e$;
f) the rate at which a drug is removed from the body $k_e$, where $k_e = \ln(2)/t_{1/2} = CL/V_d$; g) the rate of infusion required to balance the equation $K_{in}$, where $K_{in} = C_{ss} \cdot CL$;
h) the integral of the concentration-time curve after administration of a single dose, which can be represented as $AUC_{0-\infty}$, wherein $$\int_0^\infty C\, dt,$$

or in steady-state, which can be represented as $AUC_{\tau,ss}$, wherein $$\int_t^{t+\tau} C\, dt;$$

i) the volume of plasma cleared of the drug per unit time, which can be represented as CL (clearance), wherein $$CL = V_d \cdot k_e = D/AUC;$$

j) the systemically available fraction of a drug, which can be represented as f, where $$f = \frac{AUCpo \cdot Div}{AUCiv \cdot Dpo};$$

k) the peak plasma concentration of a drug after administration, $C_{max}$;
l) the time taken by a drug to reach $C_{max}$, $t_{max}$;
m) the lowest concentration that a drug reaches before the next dose is administered $C_{min}$; and
n) the peak trough fluctuation within one dosing interval at steady state, which can be represented as $$\% \; PTF = 100 \cdot \frac{(Cmax, ss - Cmin, ss)}{Cav, ss} \text{ where } C_{av,ss} = \frac{AUC\tau, ss}{\tau}$$

In some embodiments, if the compound is subjected to a study or an assay (e.g., a pharmacokinetic study), then a mean maximum brain concentration (e.g., 3000 ng/mL to about 22000 ng/mL) can be observed in a study patient (e.g., mice) at a time to maximum brain concentration (e.g., about 1 hour to about 50 hours post administration). In some embodiments, the assay can comprise administering by administering (e.g., intracerebroventricular administration) a dose amount of about 0.1 mg/kg to about 2 mg/kg of the compound to the study patient (e.g., mice). The mice can be euthanized at a time point (e.g., between about 1 hour and 28 days) post administration. Various tissues (e.g., brain tissues) can be collected from the study patients after the euthanizing. Concentrations of the tissues in the study patients can be determined using various techniques, disclosed herein, such as liquid chromatography-tandem mass spectrometry.

Brain Pharmacokinetics

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $T_{max}$ of the compound in brain is at least 0.5, at least 1, at least 2, at least 4, at least 8, at least 12, at least 16, at least 20, at least 24, at least 28, at least 32, at least 36, at least 40, at least 44, or at least 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $T_{max}$ of the compound in brain is at most 6, at most 12, at most 16, at most 20, at most 24, at most 28, at most 32, at most 36, at most 40, at most 44, at most 48, at most 72, at most 96, or at most 120 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $T_{max}$ of the compound in brain is about 0.5 to about 120, about 1 to about 24, about 1 to about 36, about 1 to about 48, about 2 to about 36, about 6 to about 24, about 1 to about 6, about 6 to about 12, about 12 to about 24, about 12 to about 18, about 18 to about 48, about 18 to about 36, or about 24 to about 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $C_{max}$ of the compound in brain is at least about 1, at least about 1000, at least about 2000, at least about 3000, at least about 4000, at least about 5000, at least about 6000, at least about 7000, at least about 8000, at least about 9000, at least about 10000, at least about 12000, at least about 14000, at least about 16000, at least about 18000, at least about 20000, at least about 22000, or at least about 25000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $C_{max}$ of the compound in brain is at most about 3000, at most about 4000, at most about 5000, at most about 6000, at most about 7000, at most about 8000, at most about 9000, at most about 10000, at most about 12000, at most about 14000, at most about 16000, at most about 18000, at most about 20000, at most about 22000, at most about 25000, at most about 30000 or at most about 50000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Cmax of the compound in brain is about 1000 to about 50000, about 2000 to about 25000, about 3000 to about 22000, about 2000 to about 5000, about 5000 to about 15000, or about 10000 to about 25000 ng/mL.

In some embodiments, at a dose amount of 0.3 mg/kg, the mean maximum brain concentration is from about 3000 ng/mL to about 4000 ng/mL. In some embodiments, at a dose amount of 0.6 mg/kg, the mean maximum brain concentration is from about 6000 ng/mL to about 12000 ng/mL. In some embodiments, at a dose amount of 1 mg/kg, the mean maximum brain concentration is from about 15000 ng/mL to about 22000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $AUC_{last}$ of the compound for brain is at least about 0.5×10^6, at least about 1×10^6, at least about 1.5×10^6, at least about 2×10^6, at least about 2.5×10^6, at least about 3×10^6, at least about 4×10^6, at least about 5×10^6, at least about 6×10^6, at least about 7×10^6, at least about 8×10^6, or at least about 10×10^6 ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean AUClast of the compound for brain is at most about 1.5×10^6, at most about 2×10^6, at most about 2.5×10^6, at most about 3×10^6, at most about 4×10^6, at most about 5×10^6, at most about 6×10^6, at most about 7×10^6, at most about 8×10^6, at most about 10×10^6, at most about 15×10^6, or at most about 20×10^6 ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean AUClast of the compound for brain is about 0.5×10^6 to about 20×10^6, about 1×10^6 to about 15×10^6, about 1×10^6 to about 10×10^6, about 1.5×10^6 to about 8×10^6, about 1×10^6 to about 5×10^6, about 5×10^6 to about 10×10^6, about 1×10^6 to about 3×10^6, or about 2×10^6 to about 5×10^6 ng·h/mL. In some embodiments, the AUClast of the study patient or subject (e.g., mice) is observed to be about 1400000 h*ng/mL to about 7500000 h*ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Tlast for brain is at least about 1, at least about 2, at least about 3, at least about 4, at least about 5, at least about 6, at least about 7, at least about 10, at least about 12, at least about 14, at least about 21, at least about 28, at least about 35, at least about 42, at least about 49, or at least about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Tlast for brain is at most about 1, at most about 2, at most about 3, at most about 4, at most about 5, at most about 6, at most about 7, at most about 10, at most about 12, at most about 14, at most about 21, at most about 28, at most about 35, at most about 42, at most about 49, at most about 100 days, at most about 200, or at most about 300 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Tlast for brain is about 1 to about 300, about 2 to about 100, about 5 to about 50, about 10 to about 30, about 1 to about 20, about 20 to about 40, about 40 to about 60, about 60 to about 80, or about 80 to about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $T_{1/2}$ for brain is at least 6, at least 24, at least 48, at least 100, at least 200, at least 500, at least 1000, at least 1500, at least 2000, at least 2500, at least 3000, or at least 5000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean T½ for brain is at most 24, at most 48, at most 100, at most 200, at most 500, at most 1000, at most 1500, at most 2000, at most 2500, at most 3000, at most 5000, at most 10000, or at most 20000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean T½ for brain is about 24 to about 20000, about 100 to about 15000, about 500 to about 10000, about 500 to about 5000, about 100 to about 1000, about 1000 to about 2000, or about 3000 to about 5000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $T_{max}$ of the compound in brain is at least 0.5, at least 1, at least 2, at least 4, at least 8, at least 12, at least 16, at least 20, at least 24, at least 28, at least 32, at least 36, at least 40, at least 44, or at least 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $T_{max}$ of the compound in brain is at most 6, at most 12, at most 16, at most 20, at most 24, at most 28, at most 32, at most 36, at most 40, at most 44, at most 48, at most 72, at most 96, or at most 120 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $T_{max}$ of the compound in brain is about 0.5 to about 120, about 1 to about 24, about 1 to about 36, about 1 to about 48, about 2 to about 36, about 6 to about 24, about 1 to about 6, about 6 to about 12, about 12 to about 24, about 12 to about 18, about 18 to about 48, about 18 to about 36, or about 24 to about 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $C_{max}$ of the compound in brain is at least about 1, at least about 1000, at least about 2000, at least about 3000, at least about 4000, at least about 5000, at least about 6000, at least about 7000, at least about 8000, at least about 9000, at least about 10000, at least about 12000, at least about 14000, at least about 16000, at least about 18000, at least about 20000, at least about 22000, or at least about 25000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Cmax of the compound in brain is at most about 3000, at most about 4000, at most about 5000, at most about 6000, at most about 7000, at most about 8000, at most about 9000, at most about 10000, at most about 12000, at most about 14000, at most about 16000, at most about 18000, at most about 20000, at most about 22000, at most about 25000, at most about 30000 or at most about 50000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Cmax of the compound in brain is about 1000 to about 50000, about 2000 to about 25000, about 3000 to about 22000, about 2000 to about 5000, about 5000 to about 15000, or about 10000 to about 25000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $AUC_{last}$ of the compound for brain is at least about $0.5 \times 10^{\wedge}6$, at least about $1 \times 10^{\wedge}6$, at least about $1.5 \times 10^{\wedge}6$, at least about $2 \times 10^{\wedge}6$, at least about $2.5 \times 10^{\wedge}6$, at least about $3 \times 10^{\wedge}6$, at least about $4 \times 10^{\wedge}6$, at least about $5 \times 10^{\wedge}6$, at least about $6 \times 10^{\wedge}6$, at least about $7 \times 10^{\wedge}6$, at least about $8 \times 10^{\wedge}6$, or at least about $10 \times 10^{\wedge}6$ ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $AUC_{last}$ of the compound for brain is at most about $1.5 \times 10^{\wedge}6$, at most about $2 \times 10^{\wedge}6$, at most about $2.5 \times 10^{\wedge}6$, at most about $3 \times 10^{\wedge}6$, at most about $4 \times 10^{\wedge}6$, at most about $5 \times 10^{\wedge}6$, at most about $6 \times 10^{\wedge}6$, at most about $7 \times 10^{\wedge}6$, at most about $8 \times 10^{\wedge}6$, at most about $10 \times 10^{\wedge}6$, at most about $15 \times 10^{\wedge}6$, or at most about $20 \times 10^{\wedge}6$ ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean AUClast of the compound for brain is about $0.5 \times 10^{\wedge}6$ to about $20 \times 10^{\wedge}6$, about $1 \times 10^{\wedge}6$ to about $15 \times 10^{\wedge}6$, about $1 \times 10^{\wedge}6$ to about $10 \times 10^{\wedge}6$, about $1.5 \times 10^{\wedge}6$ to about $8 \times 10^{\wedge}6$, about $1 \times 10^{\wedge}6$ to about $5 \times 10^{\wedge}6$, about $5 \times 10^{\wedge}6$ to about $10 \times 10^{\wedge}6$, about $1 \times 10^{\wedge}6$ to about $3 \times 10^{\wedge}6$, or about $2 \times 10^{\wedge}6$ to about $5 \times 10^{\wedge}6$ ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Tlast for brain is at least about 1, at least about 2, at least about 3, at least about 4, at least about 5, at least about 6, at least about 7, at least about 10, at least about 12, at least about 14, at least about 21, at least about 28, at least about 35, at least about 42, at least about 49, or at least about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Tlast for brain is at most about 1, at most about 2, at most about 3, at most about 4, at most about 5, at most about 6, at most about 7, at most about 10, at most about 12, at most about 14, at most about 21, at most about 28, at most about 35, at most about 42, at most about 49, at most about 100 days, at most about 200, or at most about 300 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Tlast for brain is about 1 to about 300, about 2 to about 100, about 5 to about 50, about 10 to about 30, about 1 to about 20, about 20 to about 40, about 40 to about 60, about 60 to about 80, or about 80 to about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean T½ for brain is at least 6, at least 24, at least 48, at least 100, at least 200, at least 500, at least 1000, at least 1500, at least 2000, at least 2500, at least 3000, or at least 5000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean T½ for brain is at most 24, at most 48, at most 100, at most 200, at most 500, at most 1000, at most 1500, at most 2000, at most 2500, at most 3000, at most 5000, at most 10000, or at most 20000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean T½ for brain is about 24 to about 20000, about 100 to about 15000, about 500 to about 10000, about 500 to about 5000, about 100 to about 1000, about 1000 to about 2000, or about 3000 to about 5000 hours.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 1.5 hour at 0.3 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 48 hour at 0.3 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 4 hour at 0.6 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 1.5 hour at 0.6 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 24 hour at 1 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 8 hour at 1 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 3110 ng/mL at 0.3 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 3930 ng/mL at 0.3 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 6490 ng/mL at 0.6 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 11400 ng/mL at 0.6 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 15500 ng/mL at 1 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 21500 ng/mL at 1 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 1440000 ng·h/mL at 0.3 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 1800000 ng·h/mL at 0.3 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 2470000 ng·h/mL at 0.6 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 2360000 ng·h/mL at 0.6 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 5530000 ng·h/mL at 1 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 7150000 ng·h/mL at 1 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $T_{last}$ of the compound is within 70% to 130% of a $T_{last}$ of 648 hours, after administration of a single dose to a subject.

Spleen Pharmacokinetics

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $T_{max}$ of the compound in spleen is at least 0.5, at least 1, at least 2, at least 4, at least 8, at least 12, at least 16, at least 20, at least 24, at least 28, at least 32, at least 36, at least 40, at least 44, or at least 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $T_{max}$ of the compound in spleen is at most 6, at most 12, at most 16, at most 20, at most 24, at most 28, at most 32, at most 36, at most 40, at most 44, at most 48, at most 72, at most 96, or at most 120 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $T_{max}$ of the compound in spleen is about 0.5 to about 120, about 1 to about 24, about 1 to about 36, about 1 to about 48, about 2 to about 36, about 6 to about 24, about 1 to about 6, about 6 to about 12, about 12 to about 24, about 12 to about 18, about 18 to about 48, about 18 to about 36, or about 24 to about 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $C_{max}$ of the compound in spleen is at least about 1, at least about 50, at least about 100, at least about 250, at least about 500, at least about 750, at least about 1250, at least about 1500, at least about 2000, at least about 2500, at least about 3000, at least about 5000, or at least about 10000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Cmax of the compound in spleen is at most about 1000, at most about 1500, at most about 2000, at most about 2500, at most about 3000, at most about 4000, at most about 5000, or at most about 10000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Cmax of the compound in spleen is about 100 to about 50000, about 200 to about 5000, about 300 to about 4000, about 500 to about 3000, about 500 to about 1000, about 1000 to about 2000, about 1000 to about 3000, or about 2000 to about 4000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $AUC_{last}$ of the compound for spleen is at least about $0.01 \times 10^6$, at least about $0.05 \times 10^6$, at least about $0.08 \times 10^6$, at least about $0.1 \times 10^6$, at least about $0.2 \times 10^6$, at least about $0.3 \times 10^6$, at least about $0.4 \times 10^6$, at least about $0.5 \times 10^6$, at least about $0.75 \times 10^6$, at least about $1 \times 10^6$, at least about $3 \times 10^6$, or at least about $5 \times 10^6$ ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean AUClast of the compound for spleen is at most about $0.08 \times 10^6$, at most about $0.1 \times 10^6$, at most about $0.2 \times 10^6$, at most about $0.3 \times 10^6$, at most about $0.4 \times 10^6$, at most about $0.5 \times 10^6$, at most about $0.75 \times 10^6$, at most about $1 \times 10^6$, at most about $1.5 \times 10^6$, at most about $2 \times 10^6$, or at most about $5 \times 10^6$ ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean AUClast of the compound for spleen is about $0.01 \times 10^6$ to about $5 \times 10^6$, about $0.05 \times 10^6$ to about $3 \times 10^6$, about $0.075 \times 10^6$ to about $2 \times 10^6$, about $0.09 \times 10^6$ to about $1.1 \times 10^6$, about $0.1 \times 10^6$ to about $0.8 \times 10^6$, about $0.1 \times 10^6$ to about $0.5 \times 10^6$, about $0.1 \times 10^6$ to about $0.3 \times 10^6$, about $0.3 \times 10^6$ to about $1 \times 10^6$, about $0.5 \times 10^6$ to about $1 \times 10^6$, about $0.1 \times 10^6$ to about $0.2 \times 10^6$, about $0.2 \times 10^6$ to about $0.3 \times 10^6$, or about $0.3 \times 10^6$ to about $0.5 \times 10^6$ ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Tlast for spleen is at least about 1, at least about 2, at least about 3, at least about 4, at least about 5, at least about 6, at least about 7, at least about 10, at least about 12, at least about 14, at least about 21, at least about 28, at least about 35, at least about 42, at least about 49, or at least about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Tlast for spleen is at most about 1, at most about 2, at most about 3, at most about 4, at most about 5, at most about 6, at most about 7, at most about 10, at most about 12, at most about 14, at most about 21, at most about 28, at most about 35, at most about 42, at most about 49, at most about 100 days, at most about 200, or at most about 300 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Tlast for spleen is about 1 to about 300, about 2 to about 100, about 5 to about 50, about 10 to about 30, about 1 to about 20, about 20 to about 40, about 40 to about 60, about 60 to about 80, or about 80 to about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean T½ for spleen is at least 6, at least 24, at least 48, at least 100, at least 150, at least 200, at least 250, at least 300, at least 400, at least 500, or at least 1000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean T½ for spleen is at most 24, at most 48, at most 100, at most 200, at most 300, at most 400, at most 500, at most 600, at most 750, at most 1000, or at most 5000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean T½ for spleen is about 24 to about 20000, about 50 to about 15000, about 50 to about 1000, about 100 to about 500, about 100 to about 300, about 100 to about 200, about 200 to about 300, about 300 to about 400, about 400 to about 500, or about 3000 to about 5000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $T_{max}$ of the compound in spleen is at least 0.5, at least 1, at least 2, at least 4, at least 8, at least 12, at least 16, at least 20, at least 24, at least 28, at least 32, at least 36, at least 40, at least 44, or at least 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $T_{max}$ of the compound in spleen is at most 6, at most 12, at most 16, at most 20, at most 24, at most 28, at most 32, at most 36, at most 40, at most 44, at most 48, at most 72, at most 96, or at most 120 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $T_{max}$ of the compound in spleen is about 0.5 to about 120, about 1 to about 24, about 1 to about 36, about 1 to about 48, about 2 to about 36, about 6 to about 24, about 1 to about 6, about 6 to about 12, about 12 to about 24, about 12 to about 18, about 18 to about 48, about 18 to about 36, or about 24 to about 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $C_{max}$ of the compound in spleen is at least about 1, at least about 50, at least about 100, at least about 250, at least about 500, at least about 750, at least about 1250, at least about 1500, at least about 2000, at least about 2500, at least about 3000, at least about 5000, or at least about 10000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $C_{max}$ of the compound in spleen is at most about 1000, at most about 1500, at most about 2000, at most about 2500, at most about 3000, at most about 4000, at most about 5000, or at most about 10000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Cmax of the compound in spleen is about 100 to about 50000, about 200 to about 5000, about 300 to about 4000, about 500 to about 3000, about 500 to about 1000, about 1000 to about 2000, about 1000 to about 3000, or about 2000 to about 4000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $AUC_{last}$ of the compound for spleen is at least about $0.01\times10^6$, at least about $0.05\times10^6$, at least about $0.08\times10^6$, at least about $0.1\times10^6$, at least about $0.2\times10^6$, at least about $0.3\times10^6$, at least about $0.4\times10^6$, at least about $0.5\times10^6$, at least about $0.75\times10^6$, at least about $1\times10^6$, at least about $3\times10^6$, or at least about $5\times10^6$ ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $AUC_{last}$ of the compound for spleen is at most about $0.08\times10^6$, at most about $0.1\times10^6$, at most about $0.2\times10^6$, at most about $0.3\times10^6$, at most about $0.4\times10^6$, at most about $0.5\times10^6$, at most about $0.75\times10^6$, at most about $1\times10^6$, at most about $1.5\times10^6$, at most about $2\times10^6$, or at most about $5\times10^6$ ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean AUClast of the compound for spleen is about $0.01\times10^6$ to about $5\times10^6$, about $0.05\times10^6$ to about $3\times10^6$, about $0.075\times10^6$ to about $2\times10^6$, about $0.09\times10^6$ to about $1.1\times10^6$, about $0.1\times10^6$ to about $0.8\times10^6$, about $0.1\times10^6$ to about $0.5\times10^6$, about $0.1\times10^6$ to about $0.3\times10^6$, about $0.3\times10^6$ to about $1\times10^6$, about $0.5\times10^6$ to about $1\times10^6$, about $0.1\times10^6$ to about $0.2\times10^6$, about $0.2\times10^6$ to about $0.3\times10^6$, or about $0.3\times10^6$ to about $0.5\times10^6$ ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Tlast for spleen is at least about 1, at least about 2, at least about 3, at least about 4, at least about 5, at least about 6, at least about 7, at least about 10, at least about 12, at least about 14, at least about 21, at least about 28, at least about 35, at least about 42, at least about 49, or at least about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Tlast for spleen is at most about 1, at most about 2, at most about 3, at most about 4, at most about 5, at most about 6, at most about 7, at most about 10, at most about 12, at most about 14, at most about 21, at most about 28, at most about 35, at most about 42, at most about 49, at most about 100 days, at most about 200, or at most about 300 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Tlast for spleen is about 1 to about 300, about 2 to about 100, about 5 to about 50, about 10 to about 30, about 1 to about 20, about 20 to about 40, about 40 to about 60, about 60 to about 80, or about 80 to about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $T_{1/2}$ for spleen is at least 6, at least 24, at least 48, at least 100, at least 150, at least 200, at least 250, at least 300, at least 400, at least 500, or at least 1000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean T½ for spleen is at most 24, at most 48, at most 100, at most 200, at most 300, at most 400, at most 500, at most 600, at most 750, at most 1000, or at most 5000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean T½ for spleen is about 24 to about 20000, about 50 to about 15000, about 50 to about 1000, about 100 to about 500, about 100 to about 300, about 100 to about 200, about 200 to about 300, about 300 to about 400, about 400 to about 500, or about 3000 to about 5000 hours.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 4 hour at 0.3 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 8 hour at 0.3 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 24 hour at 0.6 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 24 hour at 0.6 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 48 hour at 1 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 48 hour at 1 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 756 ng/mL at 0.3 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 586 ng/mL at 0.3 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 1530 ng/mL at 0.6 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 984 ng/mL at 0.6 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 2940 ng/mL at 1 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 2270 ng/mL at 1 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 48300 ng·h/mL at 0.3 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 96500 ng·h/mL at 0.3 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 166000 ng·h/mL at 0.6 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 98300 ng·h/mL at 0.6 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 1010000 ng·h/mL at 1 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 449000 ng·h/mL at 1 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $T_{last}$ of the compound is within 70% to 130% of a $T_{last}$ of 144 hours at 0.3 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $T_{last}$ of the compound is within 70% to 130% of a $T_{last}$ of 648 hours at 0.3 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $T_{last}$ of the compound is within 70% to 130% of a $T_{last}$ of 312 hours at 0.6 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $T_{last}$ of the compound is within 70% to 130% of a $T_{last}$ of 648 hours at 0.6 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $T_{last}$ of the compound is within 70% to 130% of a $T_{last}$ of 648 hours at 1 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $T_{last}$ of the compound is within 70% to 130% of a $T_{last}$ of 312 hours at 1 mg/kg, after administration of a single dose to a female subject.

Heart Pharmacokinetics

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $T_{max}$ of the compound in heart is at least 0.5, at least 1, at least 2, at least 4, at least 8, at least 12, at least 16, at least 20, at least 24, at least 28, at least 32, at least 36, at least 40, at least 44, or at least 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $T_{max}$ of the compound in heart is at most 6, at most 12, at most 16, at most 20, at most 24, at most 28, at most 32, at most 36, at most 40, at most 44, at most 48, at most 72, at most 96, or at most 120 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $T_{max}$ of the compound in heart is about 0.5 to about 120, about 1 to about 24, about 1 to about 36, about 1 to about 48, about 2 to about 36, about 6 to about 24, about 1 to about 6, about 6 to about 12, about 12 to about 24, about 12 to about 18, about 18 to about 48, about 18 to about 36, or about 24 to about 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $C_{max}$ of the compound in heart is at least about 1, at least about 50, at least about 100, at least about 250, at least about 500, at least about 750, at least about 1250, at least about 1500, at least about 2000, at least about 2500, at least about 3000, at least about 5000, or at least about 10000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Cmax of the compound in heart is at most about 750, at most about 1000, at most about 1500, at most about 2000, at most about 2500, at most about 3000, at most about 4000, at most about 5000, or at most about 10000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Cmax of the compound in heart is about 100 to about 50000, about 200 to about 5000, about 300 to about 4000, about 300 to about 3000, about 300 to about 1000, about 100 to about 2000, about 1000 to about 3000, or about 2000 to about 4000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $AUC_{last}$ of the compound for heart is at least about $0.01 \times 10^6$, at least about $0.05 \times 10^6$, at least about $0.08 \times 10^6$, at least about $0.1 \times 10^6$, at least about $0.2 \times 10^6$, at least about $0.3 \times 10^6$, at least about $0.4 \times 10^6$, at least about $0.5 \times 10^6$, at least about $0.75 \times 10^6$, at least about $1 \times 10^6$, at least about $3 \times 10^6$, or at least about $5 \times 10^6$ ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $AUC_{last}$ of the compound for heart is at most about $0.08 \times 10^6$, at most about $0.1 \times 10^6$, at most about $0.2 \times 10^6$, at most about $0.3 \times 10^6$, at most about $0.4 \times 10^6$, at most about $0.5 \times 10^6$, at most about 0.75×10^6, at most about 1×10^6, at most about 1.5×10^6, at most about 2×10^6, or at most about 5×10^6 ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean AUClast of the compound for heart is about 0.01×10^6 to about 5×10^6, about 0.05×10^6 to about 3×10^6, about 0.075×10^6 to about 2×10^6, about 0.09×10^6 to about 1.1×10^6, about 0.1×10^6 to about 0.8×10^6, about 0.1×10^6 to about 0.5×10^6, about 0.1×10^6 to about 0.3×10^6, about 0.3×10^6 to about 1×10^6, about 0.5×10^6 to about 1×10^6, about 0.1×10^6 to about 0.2×10^6, about 0.2×10^6 to about 0.3×10^6, or about 0.3×10^6 to about 0.5×10^6 ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Tlast for heart is at least about 1, at least about 2, at least about 3, at least about 4, at least about 5, at least about 6, at least about 7, at least about 10, at least about 12, at least about 14, at least about 21, at least about 28, at least about 35, at least about 42, at least about 49, or at least about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Tlast for heart is at most about 1, at most about 2, at most about 3, at most about 4, at most about 5, at most about 6, at most about 7, at most about 10, at most about 12, at most about 14, at most about 21, at most about 28, at most about 35, at most about 42, at most about 49, at most about 100 days, at most about 200, or at most about 300 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean Tlast for heart is about 1 to about 300, about 2 to about 100, about 5 to about 50, about 10 to about 30, about 1 to about 20, about 20 to about 40, about 40 to about 60, about 60 to about 80, or about 80 to about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean $T_{1/2}$ for heart is at least 6, at least 24, at least 48, at least 100, at least 150, at least 200, at least 250, at least 300, at least 400, at least 500, or at least 1000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean T½ for heart is at most 24, at most 48, at most 100, at most 200, at most 300, at most 400, at most 500, at most 600, at most 750, at most 1000, or at most 5000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.01 mg/kg to about 5 mg/kg (for example, about 0.1 to about 2 mg/kg, about 0.2 to about 1.5 mg/kg, about 0.3 to about 1.2 mg/kg, about 0.3 to about 1 mg/kg, about 0.3 to about 0.6 mg/kg, or about 0.6 to about 1 mg/kg), then the mean T½ for heart is about 24 to about 20000, about 50 to about 15000, about 50 to about 1000, about 100 to about 500, about 100 to about 300, about 100 to about 200, about 200 to about 300, about 300 to about 400, about 400 to about 500, or about 3000 to about 5000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $T_{max}$ of the compound in heart is at least 0.5, at least 1, at least 2, at least 4, at least 8, at least 12, at least 16, at least 20, at least 24, at least 28, at least 32, at least 36, at least 40, at least 44, or at least 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $T_{max}$ of the compound in heart is at most 6, at most 12, at most 16, at most 20, at most 24, at most 28, at most 32, at most 36, at most 40, at most 44, at most 48, at most 72, at most 96, or at most 120 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $T_{max}$ of the compound in heart is about 0.5 to about 120, about 1 to about 24, about 1 to about 36, about 1 to about 48, about 2 to about 36, about 6 to about 24, about 1 to about 6, about 6 to about 12, about 12 to about 24, about 12 to about 18, about 18 to about 48, about 18 to about 36, or about 24 to about 48 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $C_{max}$ of the compound in heart is at least about 1, at least about 50, at least about 100, at least about 250, at least about 500, at least about 750, at least about 1250, at least about 1500, at least about 2000, at least about 2500, at least about 3000, at least about 5000, or at least about 10000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Cmax of the compound in heart is at most about 1000, at most about 1500, at most about 2000, at most about 2500, at most about 3000, at most about 4000, at most about 5000, or at most about 10000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Cmax of the compound in heart is about 100 to about 50000, about 200 to about 5000, about 300 to about 4000, about 500 to about 3000, about 500 to about 1000, about 1000 to about 2000, about 1000 to about 3000, or about 2000 to about 4000 ng/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean $AUC_{last}$ of the compound for heart is at least about 0.01×10^6, at least about 0.05×10^6, at least about 0.08×10^6, at least about 0.1×10^6, at least about 0.2×10^6, at least about 0.3×10^6, at least about 0.4×10^6, at least about 0.5×10^6, at least about 0.75×10^6, at least about 1×10^6, at least about 3×10^6, or at least about 5×10^6 ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean AUClast of the compound for heart is at most about 0.08×10^6, at most about 0.1×10^6, at most about 0.2×10^6, at most about 0.3×10^6, at most about 0.4×10^6, at most about 0.5×10^6, at most about 0.75×10^6, at most about 1×10^6, at most about 1.5×10^6, at most about 2×10^6, or at most about 5×10^6 ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean AUClast of the compound for heart is about 0.01×10^6 to about 5×10^6, about 0.05×10^6 to about 3×10^6, about 0.075×10^6 to about 2×10^6, about 0.09×10^6 to about 1.1×10^6, about 0.1×10^6 to about 0.8×10^6, about 0.1×10^6 to about 0.5×10^6, about 0.1×10^6 to about 0.3× 10^6, about 0.3×10^6 to about 1×10^6, about 0.5×10^6 to about 1×10^6, about 0.1×10^6 to about 0.2×10^6, about 0.2×10^6 to about 0.3×10^6, or about 0.3×10^6 to about 0.5×10^6 ng·h/mL.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Tlast for heart is at least about 1, at least about 2, at least about 3, at least about 4, at least about 5, at least about 6, at least about 7, at least about 10, at least about 12, at least about 14, at least about 21, at least about 28, at least about 35, at least about 42, at least about 49, or at least about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Tlast for heart is at most about 1, at most about 2, at most about 3, at most about 4, at most about 5, at most about 6, at most about 7, at most about 10, at most about 12, at most about 14, at most about 21, at most about 28, at most about 35, at most about 42, at most about 49, at most about 100 days, at most about 200, or at most about 300 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean Tlast for heart is about 1 to about 300, about 2 to about 100, about 5 to about 50, about 10 to about 30, about 1 to about 20, about 20 to about 40, about 40 to about 60, about 60 to about 80, or about 80 to about 100 days.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean T½ for heart is at least 6, at least 24, at least 48, at least 100, at least 150, at least 200, at least 250, at least 300, at least 400, at least 500, or at least 1000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean T½ for heart is at most 24, at most 48, at most 100, at most 200, at most 300, at most 400, at most 500, at most 600, at most 750, at most 1000, or at most 5000 hours.

In some embodiments, if a pharmacokinetic study is conducted, wherein the pharmacokinetic study comprises administering (e.g., via intracerebroventricular administration) a compound of the disclosure to a study patient or subject at a dose amount of about 0.001 mg/kg to about 0.5 mg/kg (for example, about 0.008 to about 0.163 mg/kg, about 0.016 to about 0.125 mg/kg, about 0.025 to about 0.1 mg/kg, about 0.025 to about 0.08 mg/kg, about 0.025 to about 0.05 mg/kg, or about 0.05 to about 0.08 mg/kg), then the mean T½ for heart is about 24 to about 20000, about 50 to about 15000, about 50 to about 1000, about 100 to about 500, about 100 to about 300, about 100 to about 200, about 200 to about 300, about 300 to about 400, about 400 to about 500, or about 3000 to about 5000 hours.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 48 hours at 0.3 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $T_{max}$ of the compound is within 70% to 130% of a $T_{max}$ of 24 hours at 0.3 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 416 ng/mL at 0.3 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $C_{max}$ of the compound is within 70% to 130% of a $C_{max}$ of 729 ng/mL at 0.3 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 160000 ng·h/mL at 0.3 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $AUC_{last}$ of the compound is within 70% to 130% of an $AUC_{last}$ of 184000 ng·h/mL at 0.3 mg/kg, after administration of a single dose to a female subject.

In some embodiments, provided herein is a pharmaceutical composition in unit dose form for intracerebroventricular delivery of a compound comprising a peptide nucleic acid sequence, wherein the mean $T_{last}$ of the compound is within 70% to 130% of a $T_{last}$ of 648 hours at 0.3 mg/kg, after administration of a single dose to a male subject.

In some embodiments, provided herein is a pharmaceutical composition in unit dose form for intracerebroventricular delivery of a compound comprising a peptide nucleic acid sequence, wherein the mean $T_{last}$ of the compound is within 70% to 130% of a $T_{last}$ of 648 hours at 0.3 mg/kg, after administration of a single dose to a female subject.

Biodistribution

Biodistribution of compounds of the disclosure can be evaluated via methods that can directly or indirectly detect the presence of compound in tissue. For example, tissue of a subject administered a compound of the disclosure can be evaluated by mass spectroscopic methods, such as tandem mass spectrometry, whereby presence of compound in tissue samples can be evaluated on the basis of intensity of a signal corresponding to the mass of ionized compound or compound fragments. Other methods suitable for determination of biodistribution include administration of a radiolabeled analogue of the compound, and evaluation of the radiographic signature of the analogue in the subject via imaging techniques such as autoradiography, positron emission tomography, or single-photon emission computed tomography.

In some embodiments, biodistribution of a radiolabeled analogue is evaluated via quantitative whole body autoradiography (QWBA). In quantitative whole body autoradiography, an animal subject is administered the radiolabeled analogue, euthanized at a specified timepoint subsequent to administration, frozen, and suspended in embedding media such as aqueous sodium carboxymethyl cellulose. The suspended carcass can be sectioned in a cryomacrotome, and the resulting sections can be mounted on an adhesive support and placed on an imaging plate sensitive to the specific radioisotope used in the radiolabeled analogue, such as carbon-14. The exposed imaging plates can then be converted to electronic form using a phosphor imager system, and selected areas of the image file can be electronically integrated to provide concentrations of analogue expressed in ng-equivalents of compound per gram of tissue (ng-eq/g).

The QWBA assay can be repeated on multiple animal subjects, or selected parameters of the assay can be varied from animal to animal, such as dosage, route of administration, or time from compound administration to euthanization. For example, a QWBA can comprise three components, where one animal is euthanized four hours after administration of a radiolabeled analogue, a second animal is euthanized 12 hours after administration of the radiolabeled analogue, and a third animal is euthanized 7 days after administration of the radiolabeled analogue. Concentrations of the analogue in various tissues of each animal can then be determined and compared across each animal, thereby providing insight into the timecourse of biodistribution of the radiolabeled analogue and compound. In each study component, urine and feces of each subject animal can be collected and evaluated for radiolabeled analogue content.

Upon systemic administration, a compound of the disclosure, or a radiolabeled analogue thereof can exhibit distribution into certain tissues, for example, as determined by quantitative whole-body autoradiography (QWBA).

In some embodiments, if an assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then the compound can be distributed to, for example, kidney cortex, joints, cartilage, liver, salivary glands, bone surface, pancreas, hair follicles, large intestine mucosa, aortic wall, small intestine mucosa, adrenal gland, stomach mucosa, spleen, bone marrow, lymph nodes, thymus, brain, cerebellum, olfactory bulb, thalamus, caudate putamen, cerebral cortex, substantia nigra, lateral ventricle, choroid plexus, or a combination thereof, for example, as determined by quantitative whole-body autoradiography (QWBA). In some embodiments, the compound is distributed in the tissue for at least 6, at least 24, at least 48, at least 100, at least 125, at least 150, at least 200, at least 250, at least 300, at least 400, at least 500, or at least 1000 hours.

In some embodiments, if in a study or assay (e.g., tissue distribution study), the compound is administered (e.g., via single dose intravenous administration) to a study patient or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then the compound can be distributed to, for example, Adrenal gland cortex, Adrenal gland medulla, Aortic wall, Bone inner, Bone surface, Bone marrow, Brain caudate, Brain cerebellum, Brain cortex, Brain lateral ventricle, Brain olfactory bulb, Brain putamen, Brain substantia nigra, Brain thalamus, Brown fat, Eye uveal tract (choroid+RPE), Hair follicles, Heart blood, Heart myocardium, Joints (cartilage), Kidney cortex, Kidney medulla, Large intestine content, Large intestine mucosa, Large intestine wall, Liver, Lung, Lymph nodes, Pancreas, Pituitary gland, Salivary glands—Parotid, Salivary glands—other, Skeletal muscle, Skin, Small intestine content, Small intestine mucosa, Small intestine wall, Spinal cord, Spleen, Stomach content, Stomach mucosa, Stomach wall, Testis, Thymus, Thyroid gland, Urinary Bladder, Urine, White fat, Whole blood, or a combination thereof, for example, as determined by quantitative whole-body autoradiography (QWBA). In some embodiments, the compound is distributed in the tissue for at least 6, at least 24, at least 48, at least 100, at least 125, at least 150, at least 200, at least 250, at least 300, at least 400, at least 500, or at least 1000 hours.

In some embodiments, the disclosure provides a compound comprising a peptide nucleic acid sequence and a cell permeabilizing group attached to the peptide nucleic acid sequence. In an assay of a retention of the compound in a brain of a subject following administration of the compound to the subject, an amount of the compound within the brain at seven, eight, nine, or ten days subsequent to the administration can be equivalent to at least 80% of an amount of the compound within the brain at 4 hours subsequent to the administration. In some embodiments, the amount of the compound within the brain at seven, eight, nine, or ten days subsequent to the administration is equivalent to at least 100% of the amount of the compound within the brain at 4 hours subsequent to the administration. In some embodiments, the amount of the compound within the brain at seven, eight, nine, or ten days subsequent to the administration is equivalent to at least 150% of the amount of the compound within the brain at 4 hours subsequent to the administration. In some embodiments, the amount of the compound within the brain at seven, eight, nine, or ten days subsequent to the administration is equivalent to at least 200% of the amount of the compound within the brain at 4 hours subsequent to the administration.

In some embodiments, the disclosure provides a compound comprising a peptide nucleic acid sequence and a cell permeabilizing group attached to the peptide nucleic acid sequence. In an assay of a retention of the compound in a brain of a subject following administration of the compound to the subject, least 80% of the compound present in the brain at 4 hours subsequent to the administration can remain in the brain for at least 7 days following the administration. In some embodiments, the assay is a quantitative whole body autoradiography assay.

In some embodiments, the disclosure provides a compound comprising a peptide nucleic acid sequence and a cell permeabilizing group attached to the peptide nucleic acid sequence. In an assay of a retention of the compound in a skeletal muscle of a subject following administration of the compound to the subject, an amount of the compound within the skeletal muscle at seven, eight, nine, or ten days subsequent to the administration may be equivalent to at least 40% of an amount of the compound within the skeletal muscle at 4 hours subsequent to the administration. In some embodiments, the amount of the compound within the skeletal muscle at seven, eight, nine, or ten days subsequent to the administration is equivalent to at least 60% of the amount of the compound within the skeletal muscle at 4 hours subsequent to the administration. In some embodiments, the amount of the compound within the skeletal muscle at seven, eight, nine, or ten days subsequent to the administration is equivalent to at least 80% of the amount of the compound within the skeletal muscle at 4 hours subsequent to the administration. In some embodiments, the amount of the compound within the skeletal muscle at seven, eight, nine, or ten days subsequent to the administration is equivalent to at least 90% of the amount of the compound within the skeletal muscle at 4 hours subsequent to the administration. In some embodiments, the assay is a quantitative whole body autoradiography assay.

In some embodiments, the disclosure provides a compound comprising a peptide nucleic acid sequence and a cell permeabilizing group attached to the peptide nucleic acid sequence. In an assay of a retention of the compound in skeletal muscle of a subject following administration of the compound to the subject, least 80% of the compound present in the skeletal muscle at 4 hours subsequent to the administration can remain in the skeletal muscle for at least 7 days following the administration. In some embodiments, the assay is a quantitative whole body autoradiography assay.

In some embodiments, a concentration of the compound in the brain of the subject is at least about 100 nanograms of the compound per gram of wet brain tissue, 200 nanograms of the compound per gram of wet brain tissue, 300 nanograms of the compound per gram of wet brain tissue, 400 nanograms of the compound per gram of wet brain tissue, 500 nanograms of the compound per gram of wet brain tissue, 600 nanograms of the compound per gram of wet brain tissue, 700 nanograms of the compound per gram of wet brain tissue, 800 nanograms of the compound per gram of wet brain tissue, 900 nanograms of the compound per gram of wet brain tissue, or 1000 nanograms of the compound per gram of wet brain tissue after about 4 hours subsequent to the administering.

In some embodiments, a concentration of the compound in the brain of the subject is at least about 100 nanograms of the compound per gram of wet brain tissue, 200 nanograms of the compound per gram of wet brain tissue, 300 nanograms of the compound per gram of wet brain tissue, 400 nanograms of the compound per gram of wet brain tissue, 500 nanograms of the compound per gram of wet brain tissue, 600 nanograms of the compound per gram of wet brain tissue, 700 nanograms of the compound per gram of wet brain tissue, 800 nanograms of the compound per gram of wet brain tissue, 900 nanograms of the compound per gram of wet brain tissue, or 1000 nanograms of the compound per gram of wet brain tissue after about 7 days subsequent to the administering.

In some embodiments, a concentration of the compound the brain of the subject is at least about 200 nanograms of the compound per gram of wet brain tissue after about 4 hours subsequent to the administering. In some embodiments, a concentration of the compound in the brain of the subject is at least about 200 nanograms of the compound per gram of wet brain tissue after about 7 days subsequent to the administering. In some embodiments, a concentration of the compound in the brain of the subject is at least about 100 nanomoles of the compound per liter after about 4 hours subsequent to the administering. In some embodiments, a concentration of the compound in the brain of the subject is at least about 100 nanomoles of the compound per liter after about 7 days subsequent to the administering.

Upon systemic administration, a compound of the disclosure or a radiolabeled analogue thereof can exhibit a low rate of excretion.

In some embodiments, if an assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then less than about 20%, less than about 15%, less than about 10%, less than about 9%, less than about 8%, less than about 7%, less than about 6%, less than about 5%, less than about 4%, less than about 3%, less than about 2.5%, less than about 2%, less than about 1.9%, less than about 1.8%, less than about 1.7%, less than about 1.6%, less than about 1.5%, less than about 1.4%, less than about 1.3%, less than about 1.2%, less than about 1.1%, or less than about 1% of the dose can be recovered from urine, for example, over about 168.

In some embodiments, if an assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$]C-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then less than about 20%, less than about 15%, less than about 10%, less than about 9%, less than about 8%, less than about 7%, less than about 6%, less than about 5%, less than about 4%, less than about 3%, less than about 2.5%, less than about 2%, less than about 1.9%, less than about 1.8%, less than about 1.7%, less than about 1.6%, less than about 1.5%, less than about 1.4%, less than about 1.3%, less than about 1.2%, less than about 1.1%, or less than about 1% of the dose can be recovered from feces, for example, over about 168 hours.

In some embodiments, if an assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then less than about 20%, less than about 15%, less than about 10%, less than about 9%, less than about 8%, less than about 7%, less than about 6%, less than about 5%, less than about 4%, less than about 3%, less than about 2.5%, less than about 2%, less than about 1.9%, less than about 1.8%, less than about 1.7%, less than about 1.6%, less than about 1.5%, less than about 1.4%, less than about 1.3%, less than about 1.2%, less than about 1.1%, or less than about 1% of the dose can be excreted, for example, over about 168 hours.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then the mean $T_{1/2}$ for plasma is at least 6, at least 24, at least 48, at least 100, at least 125, at least 150, at least 200, at least 250, at least 300, at least 400, at least 500, or at least 1000 hours.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then a mean $T_{1/2}$ for plasma is at most 24, at most 48, at most 100, at most 200, at most 300, at most 400, at most 500, at most 600, at most 750, at most 1000, or at most 5000 hours.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then a mean $T_{1/2}$ for plasma is about 24 to about 20000, about 50 to about 15000, about 50 to about 1000, about 100 to about 500, about 100 to about 300, about 100 to about 200, about 200 to about 300, about 300 to about 400, about 400 to about 500, or about 3000 to about 5000 hours.

In some embodiments, if a study or assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then the mean $C_{max}$ of the compound in plasma is at least about 1, at least about 1000, at least about 2000, at least about 3000, at least about 4000, at least about 5000, at least about 6000, at least about 7000, at least about 8000, at least about 9000, at least about 10000, at least about 12000, at least about 14000, at least about 16000, at least about 18000, at least about 20000, at least about 22000, or at least about 25000 ng-eq/g.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then the mean $C_{max}$ of the compound in plasma is at most about 3000, at most about 4000, at most about 5000, at most about 6000, at most about 7000, at most about 8000, at most about 9000, at most about 10000, at most about 12000, at most about 14000, at most about 16000, at most about 18000, at most about 20000, at most about 22000, at most about 25000, at most about 30000 or at most about 50000 ng-eq/g.

In some embodiments, if a study or assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then the mean $C_{max}$ of the compound in plasma is about 1000 to about 50000, about 2000 to about 25000, about 3000 to about 22000, about 2000 to about 5000, about 5000 to about 15000, or about 10000 to about 25000 ng-eq/g.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then the mean $T_{1/2}$ for plasma is at least 6, at least 24, at least 48, at least 100, at least 125, at least 150, at least 200, at least 250, at least 300, at least 400, at least 500, or at least 1000 hours.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then a mean $T_{1/2}$ for plasma is at most 24, at most 48, at most 100, at most 200, at most 300, at most 400, at most 500, at most 600, at most 750, at most 1000, or at most 5000 hours.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then a mean $T_{1/2}$ for plasma is about 24 to about 20000, about 50 to about 15000, about 50 to about 1000, about 100 to about 500, about 100 to about 300, about 100 to about 200, about 200 to about 300, about 300 to about 400, about 400 to about 500, or about 3000 to about 5000 hours.

In some embodiments, if a study or assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient (e.g., a monkey) or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then the mean $C_{max}$ of the compound in plasma is at least about 1, at least about 1000, at least about 2000, at least about 3000, at least about 4000, at least about 5000, at least about 6000, at least about 7000, at least about 8000, at least about 9000, at least about 10000, at least about 12000, at least about 14000, at least about 16000, at least about 18000, at least about 20000, at least about 22000, or at least about 25000 ng-eq/g.

In some embodiments, if a study or assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient (e.g., a monkey) or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then the mean $C_{max}$ of the compound in plasma is at most about 3000, at most about 4000, at most about 5000, at most about 6000, at most about 7000, at most about 8000, at most about 9000, at most about 10000, at most about 12000, at most about 14000, at most about 16000, at most about 18000, at most about 20000, at most about 22000, at most about 25000, at most about 30000 or at most about 50000 ng-eq/g.

In some embodiments, if a study or assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient (e.g., a monkey) or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then the mean $C_{max}$ of the compound in plasma is about 1000 to about 50000, about 2000 to about 25000, about 3000 to about 22000, about 2000 to about 5000, about 5000 to about 15000, or about 10000 to about 25000 ng-eq/g.

In some embodiments, provided herein is a pharmaceutical composition in unit dose form for intravenous delivery of a compound comprising a peptide nucleic acid sequence or a radiolabeled analogue thereof, wherein the mean $AUC_{0-t}$ of the compound is within 70% to 130% of an $AUC_{0-t}$ of 205000 h·ng-eq/g in plasma, after administration of a single dose to a subject.

In some embodiments, provided herein is a pharmaceutical composition in unit dose form for intravenous delivery of a compound comprising a peptide nucleic acid sequence or a radiolabeled analogue thereof, wherein the mean $C_{max}$ of the compound is within 70% to 130% of a $C_{max}$ of 11500 ng-eq/g in plasma, after administration of a single dose to a subject.

In some embodiments, provided herein is a pharmaceutical composition in unit dose form for intravenous delivery of a compound comprising a peptide nucleic acid sequence, wherein the mean $t_{1/2}$ of the compound is within 70% to 130% of a $t_{1/2}$ of 141 hours in plasma, after administration of a single dose to a subject.

In some embodiments, the subject is a primate, a monkey, or a human.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then the mean $T_{1/2}$ for blood is at least 6, at least 24, at least 48, at least 100, at least 125, at least 150, at least 200, at least 250, at least 300, at least 400, at least 500, or at least 1000 hours.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then a mean $T_{1/2}$ for blood is at most 24, at most 48, at most 100, at most 200, at most 300, at most 400, at most 500, at most 600, at most 750, at most 1000, or at most 5000 hours.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then a mean $T_{1/2}$ for blood is about 24 to about 20000, about 50 to about 15000, about 50 to about 1000, about 100 to about 500, about 100 to about 300, about 100 to about 200, about 200 to about 300, about 300 to about 400, about 400 to about 500, or about 3000 to about 5000 hours.

In some embodiments, if a study or assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient (e.g., monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then the mean $C_{max}$ of the compound in blood is at least about 1, at least about 1000, at least about 2000, at least about 3000, at least about 4000, at least about 5000, at least about 6000, at least about 7000, at least about 8000, at least about 9000, at least about 10000, at least about 12000, at least about 14000, at least about 16000, at least about 18000, at least about 20000, at least about 22000, or at least about 25000 ng-eq/g.

In some embodiments, if a study or assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then the mean $C_{max}$ of the compound in blood is at most about 3000, at most about 4000, at most about 5000, at most about 6000, at most about 7000, at most about 8000, at most about 9000, at most about 10000, at most about 12000, at most about 14000, at most about 16000, at most about 18000, at most about 20000, at most about 22000, at most about 25000, at most about 30000 or at most about 50000 ng-eq/g.

In some embodiments, if a study or assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient (e.g., a monkey) or subject at a dose amount of about 5 mg/kg (for example, about 0.05 to about 500 mg/kg, about 0.5 to about 50 mg/kg, about 1 to about 10 mg/kg, about 2 to about 8 mg/kg, about 3 to about 7 mg/kg, or about 4 to about 6 mg/kg), then the mean $C_{max}$ of the compound in blood is about 1000 to about 50000, about 2000 to about 25000, about 3000 to about 22000, about 2000 to about 5000, about 5000 to about 15000, or about 10000 to about 25000 ng-eq/g.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then the mean $T_{1/2}$ for blood is at least 6, at least 24, at least 48, at least 100, at least 125, at least 150, at least 200, at least 250, at least 300, at least 400, at least 500, or at least 1000 hours.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then a mean $T_{1/2}$ for blood is at most 24, at most 48, at most 100, at most 200, at most 300, at most 400, at most 500, at most 600, at most 750, at most 1000, or at most 5000 hours.

In some embodiments, if a study or assay is conducted (e.g., tissue distribution study), wherein the assay comprises administering (e.g., via single dose intravenous administration) a compound of the disclosure (e.g., Compound 1) or a radiolabeled analogue thereof (e.g., [$^{14}$C]-Compound 1) to a study patient or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then a mean $T_{1/2}$ for blood is about 24 to about 20000, about 50 to about 15000, about 50 to about 1000, about 100 to about 500, about 100 to about 300, about 100 to about 200, about 200 to about 300, about 300 to about 400, about 400 to about 500, or about 3000 to about 5000 hours.

In some embodiments, if a study or assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then the mean $C_{max}$ of the compound in blood is at least about 1, at least about 1000, at least about 2000, at least about 3000, at least about 4000, at least about 5000, at least about 6000, at least about 7000, at least about 8000, at least about 9000, at least about 10000, at least about 12000, at least about 14000, at least about 16000, at least about 18000, at least about 20000, at least about 22000, or at least about 25000 ng-eq/g.

In some embodiments, if a study or assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then the mean $C_{max}$ of the compound in blood is at most about 3000, at most about 4000, at most about 5000, at most about 6000, at most about 7000, at most about 8000, at most about 9000, at most about 10000, at most about 12000, at most about 14000, at most about 16000, at most about 18000, at most about 20000, at most about 22000, at most about 25000, at most about 30000 or at most about 50000 ng-eq/g.

In some embodiments, if a study or assay is conducted (e.g., tissue distribution study), wherein the assay comprises administering (e.g., via single dose intravenous administration) a radiolabeled analogue of a compound of the disclosure (e.g., [$^{14}$C]-Compound 1) to a study patient or subject at a dose amount of about 1.6 mg/kg (for example, about 0.015 to about 160 mg/kg, about 0.16 to about 16 mg/kg, about 0.3 to about 3.2 mg/kg, about 0.65 to about 2.6 mg/kg, about 1 to about 2.3 mg/kg, or about 1.3 to about 2 mg/kg), then the mean $C_{max}$ of the compound in blood is about 1000 to about 50000, about 2000 to about 25000, about 3000 to about 22000, about 2000 to about 5000, about 5000 to about 15000, or about 10000 to about 25000 ng-eq/g.

In some embodiments, provided herein is a pharmaceutical composition in unit dose form for intravenous delivery of a compound comprising a peptide nucleic acid sequence, wherein the mean $AUC_{0-t}$ of a radiolabeled analogue of the compound is within 70% to 130% of an $AUC_{0-t}$ of 231000 h·ng-eq/g in blood, after administration of a single dose to a subject.

In some embodiments, provided herein is a pharmaceutical composition in unit dose form for intravenous delivery of a compound comprising a peptide nucleic acid sequence, wherein the mean $C_{max}$ of a radiolabeled analogue of the compound is within 70% to 130% of a $C_{max}$ of 7510 ng-eq/g in blood, after administration of a single dose to a subject.

In some embodiments, provided herein is a pharmaceutical composition in unit dose form for intravenous delivery of a compound comprising a peptide nucleic acid sequence, wherein the mean $t_{1/2}$ of the compound is within 70% to 130% of a $t_{1/2}$ of 229 hours in blood, after administration of a single dose to a subject.

In some embodiments, the subject is a primate, a monkey, or a human.

In some embodiments, no more than 2% of the therapeutically-effective amount of the compound is excreted by the subject in urine over a 7 day period subsequent to the administering. In some embodiments, no more than 2% of the therapeutically-effective amount of the compound is excreted by the subject in feces over a 7 day period subsequent to the administering.

In some embodiments, a compound of the disclosure can achieve full biodistribution without lipid nanoparticles. For example, the backbone is covalently modified such that the compound exhibits cell permeability that does not differ across cell types. For example, the backbone can be covalently modified with functional groups (e.g., guanidino groups) such that the compound exhibits cell permeability that does not significantly differ across cell types.

In some embodiments, if the compound, disclosed herein, is subjected to a plasma protein binding assay, then, in the plasma protein binding assay, the plasma protein binding percentage is at least about 85% in one or more study patients. In some embodiments, the plasma protein binding percentage is at least about 85% in each of a human, mouse, dog, minipig, sheep, and/or monkey. In some embodiments, the plasma protein binding assay comprises performing the plasma protein binding assay on a study patient. In some embodiments, at a concentration of about 1 µg/mL, the plasma protein binding percentage is at least about 95% in the human, mouse, dog, minipig, sheep, and/or monkey. In some embodiments, at the concentration of about 1 µg/mL, the plasma protein binding percentage is at least about 95% in each of the human, mouse, dog, minipig, sheep, and monkey.

In some embodiments, the plasma protein binding assay comprises spiking single aliquots of a study patient's plasma with a first solution of the compound (e.g., 10 mg/mL of the first solution of the compound) to obtain at least a second solution of the compound (e.g., with concentrations of about 1 µg/mL to about 50 µg/mL). In some embodiments, a separation technique (e.g., ultracentrifugation) is used on the at least the second solution of the compound to separate a mixture comprising the compounds that are bound to plasma proteins. In some embodiments, plasma protein binding percentage in the study patient's plasma can be determined using various techniques, disclosed herein, such as liquid chromatography-tandem mass spectrometry.

In some embodiments, the plasma protein binding assay comprises performing a human component of the plasma protein binding assay. For example, the human component of the plasma protein binding assay comprises spiking single aliquots of human plasma with a first solution of the compound (e.g., 10 mg/mL of the first solution of the compound) to obtain at least a second solution of the compound (e.g., with concentrations of about 1 µg/mL to about 50 µg/mL). In some embodiments, a separation technique (e.g., ultracentrifugation) is used on the at least the second solution of the compound to separate a mixture comprising the compounds that are bound to plasma proteins. In some embodiments, a plasma protein binding percentage in the human plasma can be determine using various techniques, disclosed herein, such as liquid chromatography-tandem mass spectrometry. In some embodiments, a mouse component of the plasma protein binding assay is performed. In some embodiments, the mouse component of the plasma protein binding assay differs from the human component of the plasma protein binding assay only in that mouse plasma is used instead of the human plasma. In some embodiments, a dog component of the plasma protein binding assay is performed. In some embodiments, the dog component of the plasma protein binding assay differs from the human component of the plasma protein binding assay only in that dog plasma is used instead of the human plasma. In some embodiments, a minipig component of the plasma protein binding assay is performed. In some embodiments, the minipig component of the plasma protein binding assay differs from the human component of the plasma protein binding assay only in that minipig plasma is used instead of the human plasma. In some embodiments, a sheep component of the plasma protein binding assay is performed. In some embodiments, the sheep component of the plasma protein binding assay differs from the human component of the plasma protein binding assay only in that sheep plasma is used instead of the human plasma. In some embodiments, a monkey component of the plasma protein binding assay is performed. In some embodiments, the monkey component of the plasma protein binding assay differs from the human component of the plasma protein binding assay only in that monkey plasma is used instead of the human plasma.

In some embodiments, in a plasma binding protein assay (e.g., in vitro plasma binding protein assay), if the compound is assessed in plasma from a host species, (e.g., spiked into pooled plasma at a concentration of about 0.01, about 0.1, about 0.5, about 1, about 5, about 10, about 50, about 100, about 500, or about 1000 µg/mL), then the % binding of the compound to plasma proteins (PPB) is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 95.5%, about 96%, about 96.5%, about 97%, about 97.5%, about 98%, about 98.5%, about 99%, about 99.1%, about 99.1%, about 99.3%, about 99.4%, about 99.5%, about 99.6%, about 99.7%, about 99.8%, about 99.9%, about 99.95%, or about 99.99%. The host species can be, for example, mouse (e.g., C57BL6), dog (e.g., beagle), minipig (e.g., Gottingen minipig), sheep, monkey (e.g., Cynomolgus monkey), human, or any suitable animal disclosed herein.

In some embodiments, in a plasma binding protein assay (e.g., in vitro plasma binding protein assay), if the compound is assessed in plasma from a host species, (e.g., spiked into pooled plasma at a concentration of about 0.01, about 0.1, about 0.5, about 1, about 5, about 10, about 50, about 100, about 500, or about 1000 µg/mL), then the % binding of the compound to plasma proteins (PPB) is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 95.5%, at least about 96%, at least about 96.5%, at least about 97%, at least about 97.5%, at least about 98%, at least about 98.5%, at least about 99%, at least about 99.1%, at least about 99.1%, at least about 99.3%, at least about 99.4%, at least about 99.5%, at least about 99.6%, at least about 99.7%, at least about 99.8%, at least about 99.9%, at least about 99.95%, or at least about 99.99%. The host species can be, for example, mouse (e.g., C57BL6), dog (e.g., beagle), minipig (e.g., Gottingen minipig), sheep, monkey (e.g., Cynomolgus monkey), human, or any suitable animal disclosed herein.

In some embodiments, in a plasma binding protein assay (e.g., in vitro plasma binding protein assay), if the compound is assessed in plasma from a host species, (e.g., spiked into pooled plasma at a concentration of about 0.01, about 0.1, about 0.5, about 1, about 5, about 10, about 50, about 100, about 500, or about 1000 µg/mL), then the % binding of the compound to plasma proteins (PPB) is at most about 1%, at most about 2%, at most about 3%, at most about 4%, at most about 5%, at most about 6%, at most about 7%, at most about 8%, at most about 9%, at most about 10%, at most about 11%, at most about 12%, at most about 13%, at most about 14%, at most about 15%, at most about 16%, at most about 17%, at most about 18%, at most about 19%, at most about 20%, at most about 21%, at most about 22%, at most about 23%, at most about 24%, at most about 25%, at most about 26%, at most about 27%, at most about 28%, at most about 29%, at most about 30%, at most about 31%, at most about 32%, at most about 33%, at most about 34%, at most about 35%, at most about 36%, at most about 37%, at most about 38%, at most about 39%, at most about 40%, at most about 41%, at most about 42%, at most about 43%, at most about 44%, at most about 45%, at most about 46%, at most about 47%, at most about 48%, at most about 49%, at most about 50%, at most about 51%, at most about 52%, at most about 53%, at most about 54%, at most about 55%, at most about 56%, at most about 57%, at most about 58%, at most about 59%, at most about 60%, at most about 61%, at most about 62%, at most about 63%, at most about 64%, at most about 65%, at most about 66%, at most about 67%, at most about 68%, at most about 69%, at most about 70%, at most about 71%, at most about 72%, at most about 73%, at most about 74%, at most about 75%, at most about 76%, at most about 77%, at most about 78%, at most about 79%, at most about 80%, at most about 81%, at most about 82%, at most about 83%, at most about 84%, at most about 85%, at most about 86%, at most about 87%, at most about 88%, at most about 89%, at most about 90%, at most about 91%, at most about 92%, at most about 93%, at most about 94%, at most about 95%, at most about 95.5%, at most about 96%, at most about 96.5%, at most about 97%, at most about 97.5%, at most about 98%, at most about 98.5%, at most about 99%, at most about 99.1%, at most about 99.1%, at most about 99.3%, at most about 99.4%, at most about 99.5%, at most about 99.6%, at most about 99.7%, at most about 99.8%, at most about 99.9%, at most about 99.95%, or at most about 99.99%. The host species can be, for example, mouse (e.g., C57BL6), dog (e.g., beagle), minipig (e.g., Gottingen minipig), sheep, monkey (e.g., Cynomolgus monkey), human, or any suitable animal disclosed herein.

In some embodiments, in a plasma binding protein assay (e.g., in vitro plasma binding protein assay), if the compound is assessed in plasma from a host species, (e.g., spiked into pooled plasma at a concentration of about 0.01, about 0.1, about 0.5, about 1, about 5, about 10, about 50, about 100, about 500, or about 1000 µg/mL), then the % binding of the compound to plasma proteins (PPB) is about 0% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 0% to about 20%, about 0% to about 30%, about 0% to about 40%, about 0% to about 50%, about 0% to about 60%, about 0% to about 70%, about 0% to about 80%, about 0% to about 90%, about 10% to about 30%, about 10% to about 40%, about 10% to about 50%, about 10% to about 60%, about 10% to about 70%, about 10% to about 80%, about 10% to about 90%, about 10% to about 100%, about 20% to about 40%, about 20% to about 50%, about 20% to about 60%, about 20% to about 70%, about 20% to about 80%, about 20% to about 90%, about 20% to about 100%, about 30% to about 50%, about 30% to about 60%, about 30% to about 70%, about 30% to about 80%, about 30% to about 90%, about 30% to about 100%, about 40% to about 60%, about 40% to about 70%, about 40% to about 80%, about 40% to about 90%, about 40% to about 100%, about 50% to about 70%, about 50% to about 80%, about 50% to about 90%, about 50% to about 100%, about 60% to about 80%, about 60% to about 90%, about 60% to about 100%, about 70% to about 90%, about 70% to about 100%, or about 80% to about 100%, about 85% to about 99%, about 87% to about 99%, about 88% to about 99%, about 89% to about 99%, about 90% to about 99%, about 91% to about 99%, about 92% to about 99%, about 93% to about 99%, about 94% to about 99%, about 95% to about 99%, about 96% to about 99%, about 97% to about 99%, about 98% to about 99%, about 85% to about 98%, about 87% to about 98%, about 88% to about 98%, about 89% to about 98%, about 90% to about 98%, about 91% to about 98%, about 92% to about 98%, about 93% to about 98%, about 94% to about 98%, about 95% to about 98%, about 96% to about 98%, about 97% to about 98%, about 85% to about 97%, about 87% to about 97%, about 88% to about 97%, about 89% to about 97%, about 90% to about 97%, about 91% to about 97%, about 92% to about 97%, about 93% to about 97%, about 94% to about 97%, about 95% to about 97%, about 96% to about 97%, about 85% to about 96%, about 87% to about 96%, about 88% to about 96%, about 89% to about 96%, about 90% to about 96%, about 91% to about 96%, about 92% to about 96%, about 93% to about 96%, about 94% to about 96%, about 95% to about 96%, about 85% to about 95%, about 87% to about 95%, about 88% to about 95%, about 89% to about 95%, about 90% to about 95%, about 91% to about 95%, about 92% to about 95%, about 93% to about 95%, or about 94% to about 95%. The host species can be, for example, mouse (e.g., C57BL6), dog (e.g., beagle), minipig (e.g., Gottingen minipig), sheep, monkey (e.g., Cynomolgus monkey), human, or any suitable animal disclosed herein.

EXAMPLES

Example 1. In Vitro Plasma Protein Binding of Compound 1 in Mouse, Dog, Minipig, Sheep, Monkey, and Human This study was designed to determine the in vitro binding of Compound 1 to plasma proteins in C57BL6J mouse, Beagle dog, Gottingen minipig, sheep, Cynomolgus monkey, and human. Plasma Protein Binding (PPB) was assessed in pooled male plasma at nominal Compound 1 concentrations of 1, 10, and 50 µg/mL. The assay was performed using the ultrafiltration technique and the concentrations of Compound 1 were determined by LC MS/MS analysis. Warfarin was used as positive control to validate each ultrafiltration run.

Using Busher's classification, Compound 1 binding to plasma proteins was ranked as high-to-very high (PPB>85.0%) at 1 µg/mL and high (85.0%≤PPB≤98.0%) at both 10 and 50 µg/mL. A slight concentration dependence was observed over the concentration range investigated, suggesting the tendency of PPB to become non-linear with increasing Compound 1 concentration. This trend was more evidently in mouse, dog, minipig, and human.

PPB results of Compound 1 at various concentrations are summarized in TABLE 1.

TABLE 1

| Species | Compound 1 Nominal concentration (µg/mL) | % F | % PPB |
|---|---|---|---|
| Mouse | 1 | <4.6 ± 0.3[a] | >95.4 ± 0.3[a] |
|  | 10 | 8.4 ± 1.8 | 91.6 ± 1.8 |
|  | 50 | 10.0[b] | 90.0[b] |
| Dog | 1 | <4.4 ± 0.3[a] | >95.6 ± 0.3[a] |
|  | 10 | 7.0[b] | 93.0[b] |
|  | 50 | 6.5 ± 1.4 | 93.5 ± 1.4 |
| Minipig | 1 | <4.4 ± 0.3[a] | >95.6 ± 0.3[a] |
|  | 10 | 5.3 ± 0.3 | 94.7 ± 0.3 |
|  | 50 | 8.3[b] | 91.7[b] |
| Sheep | 1 | <2.8 ± 0.4[a] | >97.2 ± 0.4[a] |
|  | 10 | 4.2 ± 0.5 | 95.8 ± 0.5 |
|  | 50 | 3.8 ± 0.4 | 96.2 ± 0.4 |
| Monkey | 1 | <3.8 ± 0.5[a] | >96.2 ± 0.5[a] |
|  | 10 | 4.7 ± 0.2 | 95.3 ± 0.2 |
|  | 50 | 4.8[b] | 95.2[b] |
| Human | 1 | <3.1 ± 0.2[a] | >96.9 ± 0.2[a] |
|  | 10 | 6.2 ± 0.4 | 93.8 ± 0.4 |
|  | 50 | 6.4 ± 0.5 | 93.6 ± 0.5 |

[a]Since Compound 1 concentration in the ultrafiltrate sample was less than the lower quantification limit (LLOQ = 50 ng/mL), the fraction unbound is calculated as F % < [LLOQ/($C_0$ · R)]*100, and PPB expressed as PPB % > 100 − F %; $C_0$ is the Compound 1 initial concentration and R is the recovery
[b]SD not calculated since N ≤ 2

Test Systems

Male C57BL6J mouse, male Beagle dog, male Göttingen minipig, male sheep, male Cynomolgus Monkey, and male human plasma was purchased from BIOIVT (UK). Preclinical plasma was pooled from at least 3 different non-fasted animals, whereas human plasma was obtained from at least 3 healthy and fasted volunteers.

$K_3$EDTA was used as the anti-coagulant for both the species.

All plasma was stored at 20° C. and thawed only once on the day of the experiment. No pH correction was applied before the experiment.

Experimental Design

In this study the binding of Compound 1 to mouse, dog, minipig, sheep, monkey, and human plasma proteins was determined in triplicate at the nominal concentrations of 1, 10, and 50 µg/mL using the ultrafiltration technique.

The separation of unbound Compound 1 from plasma proteins was performed using Centrifree® ultrafiltration devices with a 30,000 NMWL regenerated cellulose membrane.

The suitability of ultrafiltration as method for protein binding determination of Compound 1 was assessed.

Warfarin was used as a control compound at the single concentration of 4.1 µM in male human plasma (n=3) and the control was tested in parallel with the test item on each ultrafiltration run to confirm the correct experimental performance.

Methods and Procedures
Preparation of Phosphate Buffered Saline (PBS).

Phosphate buffered saline (PBS) was prepared at the concentration of 0.146 M. The pH was measured and found to be 7.40. PBS was stored at 4° C.

Compound 1 Spiking Solutions.

The stock solution (SS) containing Compound 1 at 10 mg/mL was prepared on. SS was further diluted in PBS supplemented with 0.2% (v/v) formic acid to obtain the working solution WS1, 100 µg/mL. Compound 1 SS and Compound 1 WS were stored at −80° C.

Preparation of Warfarin Solutions.

A stock solution of warfarin (SS_W) was prepared in water:acetonitrile (50:50, v/v) at a nominal concentration of 3.24 mM (corresponding to 1 mg/mL). This solution was further diluted in the same solvent to obtain the working solution WS_W, 410 µM, which was used for plasma spiking.

Warfarin SS_W was stored at 4° C. (for not more than 21 days, as per method sheet). Warfarin WS_W was freshly prepared on each ultrafiltration occasion.

Plasma Samples Preparation.

An appropriate volume of single aliquots of mouse, dog, minipig, sheep, monkey, and human plasma was spiked with SS 10 mg/mL or WS 100 µg/mL to obtain the target concentrations of 1, 10, and 50 µg/mL. Each sample was then mixed by gentle rocking and rotating for approximately 10-15 minutes prior to being transferred to ultrafiltration tubes.

The same procedure was performed for the preparation of warfarin control sample 4.1 µM (corresponding to 1265 ng/mL) in male human plasma.

Method Suitability for Ultrafiltration.

To assess the suitability of the ultrafiltration technique, experiments to determine potential non-specific binding to the filter membrane and test item stability in plasma and PBS over the incubation time were conducted.

Assessment of Non-Specific Binding of Compound 1 to Ultrafiltration Equipment.

An appropriate amount of PBS was spiked at three test item concentrations (1, 10, and 50 µg/mL). The samples were mixed for 1-2 min at room temperature.

Triplicate aliquots of each spiked sample were transferred into ultrafiltration tubes and spun at 1500 g in a Biofuge centrifuge with a fixed angle rotor at room temperature, until all loaded volume has passed through the filter.

Prior to centrifugation ($t_0$), triplicate aliquots from each sample were collected and Compound 1 concentrations ($C_O$) were determined by LC-MS/MS analysis. After centrifugation, triplicate aliquots of the bottom ultrafiltrate ($C_u$) were retained and then analyzed by LC-MS/MS.

Assessment of Compound 1 Stability in Plasma and PBS.

The stability of Compound 1 was assessed at two test item concentrations (1 and 50 µg/mL) in all plasma species and in PBS by incubating each matrix for 15 min at 37° C. plus 4 hours at room temperature (time which covers incubation, ultrafiltration and sample treatment for analysis). Compound 1 concentrations were determined by LC-MS/MS analysis at both $t_0$ and $t_{4h}$.

Ultrafiltration Procedure.

The in vitro binding of Compound 1 to plasma proteins was determined at the three concentrations 1, 10, and 50 µg/mL.

To prevent the non-specific binding of Compound 1 to the ultrafiltration tubes, the inner wall was rinsed with 10% (v/v) Triton X-100 solution and left to dry for at least 1 hour before use.

Triplicate aliquots of each spiked plasma were transferred into ultrafiltration tubes. The ultrafiltration tubes were spun at room temperature for 20 min at 1500 g in a Biofuge centrifuge with a fixed angle rotor.

Prior to centrifugation, triplicate aliquots of spiked plasma were retained to give the concentration of Compound 1 in plasma ($C_O$) post-ultracentrifugation. After centrifugation, an appropriate aliquot of the top retentate ($C_r$) and bottom ultrafiltrate ($C_u$) was then removed for LC-MS/MS analysis.

The whole ultrafiltration devices, the ultrafiltrate reservoirs and the filtrate cups were weighed before adding the sample, after adding the sample (only for the whole ultrafiltration devices) and at the end of the centrifugation.

The same procedure was performed for warfarin control samples.

Determination of Protein Content in the Ultrafiltration Samples.

After collection, each ultrafiltration sample was checked for protein content to assess a possible protein contamination and then to confirm the filter integrity over ultrafiltration. The presence of proteins was assessed in the ultrafiltrate using the Bradford method.

A calibration standard curve of bovine serum albumin was prepared at the following concentrations: 0, 50, 100, 200, 400, 600, 800, and 1000 µg/mL.

Calibration standard samples and ultrafiltrate samples were dispensed in a 96-well plate (6 µL/well) and supplemented with Coomassie Brilliant Blue G Solution (300 µL). After 1 min at room temperature, the absorbance of each well was measured at λ=595 nm by an absorbance microplate reader Sample Treatment and Analysis.

Appropriate aliquots of spiked plasma (collected prior to and after ultrafiltration) and ultrafiltration samples (collected after ultrafiltration) were supplemented with an equal volume (matrix matching) of drug-free PBS or drug-free plasma, respectively.

After matrix matching, plasma and ultrafiltration samples were extracted and analysed by LC-MS/MS.

Storage of Samples.

All samples were collected into uniquely identifiable containers, labelled with the study number, sample type, nominal sample concentration and incubation time. Compound 1 samples and Warfarin samples were stored at −80° C.

Data Handling and Analysis

Plasma Protein Binding Calculations

Non-Specific Binding (NSB)

NSB to ultrafiltration tubes was determined from the Compound 1 concentrations in PBS samples prior to centrifugation ($C_0$) and in the collected ultrafiltration samples after centrifugation ($C_u$).

$$NSB\ \% = \frac{C_0 - C_u}{C_0} \cdot 100$$

where:

$C_0$=concentration of Compound 1 before the ultrafiltration, ng/mL $C_u$=concentration of Compound 1 after ultrafiltration, ng/mL Stability Assessment.

The extent of any potential loss of Compound 1 after incubation in plasma (or PBS) at room temperature as long as the duration of the experiment ($t_{4h}$) was calculated as follows:

$$\%\ \text{difference}(t_{4h} - t_0) = \frac{C_{4h} - C_0}{C_0} \cdot 100$$

Where:

$C_0$=concentration in matrix (plasma or PBS) at $t_0$, ng/mL $C_{4h}$=concentration in matrix (plasma or PBS) after $t_{4h}$, ng/mL Plasma Protein Binding.

The % binding of Compound 1 (B % or PPB %) to plasma proteins was determined using the following equations:

$$B\ \% = 100 - (F\ \%)$$

$$F = \frac{C_u}{R \cdot C_0}$$

Where:

F=free fraction

R=recovery

The same calculations were performed for warfarin control sample.

Total Recovery.

Comparing the concentration of Compound 1 in the ultrafiltrate and in the retentate samples (after ultrafiltration) with that of Compound 1 in the samples before the ultrafiltration, a recovery value was obtained, as described in the following formula:

$$R\ \% = \left(\frac{C_u \times V_u + C_r \times V_r}{C_0 \times V_0}\right) \cdot 100$$

Where:

$V_0$=initial volume of plasma sample, before ultrafiltration (mL)

$V_r$=volume of retentate, after ultrafiltration (mL)

$V_u$=volume of ultrafiltrate, after ultrafiltration (mL)

$C_0$=concentration in to plasma sample (ng/mL)

$C_r$=concentration in the retentate sample (ng/mL)

$C_u$=concentration in the ultrafiltrate sample (ng/mL)

The density of each matrix (plasma, retentate and ultrafiltration sample) was assumed 1.

The same calculations were performed for warfarin control sample.

Protein Binding Acceptance Criteria.

NSB≤20% is acceptable. Compound 1 was considered stable in plasma and PBS if the percentage difference between concentration after $t_{4h}$ and $t_0$ is within ±15%. Protein binding of the positive control warfarin should be ≥98.0%. The protein concentration measured after ultrafiltration should be ≤0.3 mg/mL.

Recovery (R) values (Range of Recovery, %) were assessed as detailed as follows: R≥200 or R≤50 means Experimental data not valid; 50≤R<80 or 120<R≤200 means Experimental data potentially unreliable; and 80≤R≤120 means Experimental data valid.

Results

Non-Specific Binding (NSB) Assessment.

On average, NSB to filter membrane represented 20.5%, 6.2%, and 2.2% at 1, 10, and 50 µg/mL Compound 1 concentrations, respectively, indicating an increase of NSB contribution with decreasing concentration (which is the typical trend for compounds showing NSB). Since the NSB was not greater than around 20% (in the worst-case scenario), the ultrafiltration technique was deemed fit for purpose.

The results of NSB assessment are presented in TABLE 2.

TABLE 2

| | Concentration of Compound 1 | | |
|---|---|---|---|
| $C_0$ Nominal Concentration (ng/mL) | $C_0$ Actual Concentration (ng/mL) | $C_u$ (ng/mL) | Average % NSB |
| 1000 | 950 | 761 | 20.5% |
| | 886 | 760 | |
| | 861 | 626 | |
| Mean ± SD | 899 ± 46 | 716 ± 78 | |
| 10000 | 9978 | 9450 | 6.2% |
| | 9479 | 9550 | |
| | 10442 | 8980 | |
| Mean ± SD | 9966 ± 482 | 9327 ± 305 | |
| 50000 | 49368 | 48269 | 2.2% |
| | 49917 | 50900 | |
| | 51746 | 48414 | |
| Mean ± SD | 50344 ± 1245 | 49195 ± 1479 | |

Determination of Compound 1 Stability in Plasma and PBS.

Compound 1 was stable (i.e., with a percentage loss not greater than 15%) in mouse, dog, sheep, monkey, and human plasma as well as PBS when incubated at room temperature for up to 4 hours at both 1 and 50 μg/mL.

Compound 1 was stable in minipig plasma at 1 μg/mL, whereas a slight instability (characterized by a percentage loss of 22.5%) was observed at 50 μg/mL.

The results of Compound 1 stability in plasma and in PBS samples are presented in TABLE 3.

TABLE 3

| | $C_0$ Nominal Concentration | Actual Concentration (ng/mL) | |
|---|---|---|---|
| Matrix | (ng/mL) | $C_0$ | $C_{4h}$ |
| Mouse | 1000 | 1136 | 1288 |
| | | 1036 | 1422 |
| | | 1283 | 1266 |
| Mean ± SD | | 115 ± 124 | 1325 ± 84 |
| % Difference (4 h − 0 h) | | 15.1% | |
| | 50000 | 80435 | 66779 |
| | | 67255 | 62362 |
| | | 70127 | 63006 |
| Mean ± SD | | 72606 ± 6931 | 64049 ± 2386 |
| % Difference (4 h − 0 h) | | −11.8% | |
| Dog | 1000 | 962 | 1054 |
| | | 1033 | 1126 |
| | | 1156 | 870 |
| Mean ± SD | | 1050 ± 98 | 1017 ± 132 |
| % Difference (4 h − 0 h) | | −3.2% | |
| | 50000 | 42457 | 39519 |
| | | 45231 | 48050 |
| | | 44416 | 38581 |
| Mean ± SD | | 44035 ± 1426 | 42050 ± 5217 |
| % Difference (4 h − 0 h) | | −4.5% | |

TABLE 3-continued

| | $C_0$ Nominal Concentration | Actual Concentration (ng/mL) | |
|---|---|---|---|
| Matrix | (ng/mL) | $C_0$ | $C_{4h}$ |
| Minipig | 1000 | 981 | 1021 |
| | | 997 | 1215 |
| | | 1141 | 1040 |
| Mean ± SD | | 1039 ± 88 | 1092 ± 107 |
| % Difference (4 h − 0 h) | | 5.1% | |
| | 50000 | 67014 | 54551 |
| | | 70687 | 59236 |
| | | 71484 | 48346 |
| Mean ± SD | | 69728 ± 2384 | 54044 ± 5463 |
| % Difference (4 h − 0 h) | | −22.5% | |
| Sheep | 1000 | 1199 | 1425 |
| | | 1622 | 1550 |
| | | 1664 | 1692 |
| Mean ± SD | | 1495 ± 257 | 1556 ± 133 |
| % Difference (4 h − 0 h) | | 4.1% | |
| | 50000 | 74884 | 85924 |
| | | 73441 | 89388 |
| | | 84447 | 83543 |
| Mean ± SD | | 77590 ± 5981 | 86285 ± 2939 |
| % Difference (4 h − 0 h) | | 11.2% | |
| Monkey | 1000 | 1075 | 1108 |
| | | 1240 | 1188 |
| | | 1192 | 1160 |
| Mean ± SD | | 1169 ± 85 | 1152 ± 41 |
| % Difference (4 h − 0 h) | | −1.5% | |
| | 50000 | 43353 | 46034 |
| | | 49384 | 47590 |
| | | 42860 | 49370 |
| Mean ± SD | | 45199 ± 3633 | 47664 ± 1670 |
| % Difference (4 h − 0 h) | | 5.5% | |
| Human | 1000 | 1009 | 1082 |
| | | 1005 | 1123 |
| | | 1035 | 1071 |
| Mean ± SD | | 1016 ± 17 | 1092 ± 27 |
| % Difference (4 h − 0 h) | | 7.5% | |
| | 50000 | 51417 | 50163 |
| | | 53571 | 59910 |
| | | 54627 | 48923 |
| Mean ± SD | | 53205 ± 1636 | 52999 ± 6017 |
| % Difference (4 h − 0 h) | | −0.4% | |
| PBS | 1000 | 833 | 769 |
| | | 824 | 676 |
| | | 734 | 600 |
| Mean ± SD | | 797 ± 55 | 682 ± 85 |
| % Difference (4 h − 0 h) | | −14.5% | |
| | 50000 | 49419 | 51395 |
| | | 50911 | 49815 |
| | | 50858 | 46452 |
| Mean ± SD | | 50396 ± 846 | 49221 ± 2525 |
| % Difference (4 h − 0 h) | | −2.3% | |

Determination of Compound 1 Plasma Protein Binding.

The extent of PPB has been defined according to Busher's classification: very high (PPB≥98.0%), high (85.0%≤PPB≤98.0%), and medium-to-low (PPB<85.0%).

PPB results of Compound 1 at various concentrations (1, 10, and 50 μg/mL) are summarized in TABLE 1 and fully reported in TABLE 4.

TABLE 4

| | | Concentration of Compound 1 | | | | | | |
|---|---|---|---|---|---|---|---|---|
| Experiment | Species | Nominal $C_0$ (ng/mL) | Actual $C_0$ (ng/mL) | $C_r$ (ng/mL) | $C_u$ (ng/mL) | F % | PPB % | R % |
| 1 | Minipig | 1000 | 1047 | 1441 | NQ | <4.4 [a] | >95.6 [a] | >107.8 |
| | | | 1010 | 1333 | NQ | <4.7 [a] | >95.3 [a] | >104.3 |
| | | | 1164 | 1539 | NQ | <4.1 [a] | >95.9 [a] | >103.7 |
| | Mean ± SD | | 1074 ± 80 | 1437 ± 103 | NA | <4.4 ± 0.3 [a] | >95.6 ± 0.3 [a] | >105.3 ± 2.2 |
| | | 10000 | 9553 | 12216 | 482 | 5.0 | 95.0 | 101.1 |

TABLE 4-continued

| Experiment | Species | Nominal $C_0$ (ng/mL) | Actual $C_0$ (ng/mL) | $C_r$ (ng/mL) | $C_u$ (ng/mL) | F % | PPB % | R % |
|---|---|---|---|---|---|---|---|---|
| | | | 9147 | 11904 | 501 | 5.3 | 94.7 | 102.5 |
| | | | 11182 | 13494 | 599 | 5.7 | 94.3 | 94.7 |
| | | Mean ± SD | 9961 ± 1077 | 12538 ± 843 | 527 ± 63 | 5.3 ± 0.3 | 94.7 ± 0.3 | 99.5 ± 4.2 |
| | | 50000 | 46736 | 51751 | 2946 | 7.2 | 92.8 | 87.0 |
| | | | 54997 | 63661 | NR | NC | NC | NC |
| | | | 48959 | 48394 | 3641 | 9.4 | 90.6 | 78.8 |
| | | Mean ± SD | 50231 ± 4275 | 54602 ± 8023 | 3293 [b] | 8.3 [b] | 91.7 [b] | 82.9 [b] |
| 2 | Dog | 1000 | 1153 | 1611 | NQ | <4.2 [a] | >95.8 [a] | >103.5 |
| | | | 1187 | 1390 | NQ | <4.8 [a] | >95.2 [a] | >88.6 |
| | | | 1248 | 1580 | NQ | <4.3 [a] | >95.7 [a] | >92.5 |
| | | Mean ± SD | 1196 ± 48 | 1527 ± 120 | NA | <4.4 ± 0.3 [a] | >95.6 ± 0.3 [a] | >94.9 ± 7.7 |
| | | 10000 | 8716 | 10656 | NR | NC | NC | NC |
| | | | 8039 | 10701 | 577 | 7.0 | 93.0 | 102.3 |
| | | | 4234 [#] | 11215 | NR | NC | NC | NC |
| | | Mean ± SD | 8378 [b] | 10857 ± 311 | 577 [b] | 7.0 [b] | 93.0 [b] | 102.3 [b] |
| | | 50000 | 42816 | 50194 | 2400 | 6.5 | 93.5 | 86.2 |
| | | | 38278 | 48731 | 2823 | 7.9 | 92.1 | 93.5 |
| | | | 40637 | 52325 | 1931 | 5.1 | 94.9 | 93.2 |
| | | Mean ± SD | 40577 ± 2269 | 50416 ± 1807 | 2385 ± 446 | 6.5 ± 1.4 | 93.5 ± 1.4 | 91.0 ± 4.1 |
| 3 | Human | 1000 | 1480 | 2074 | NQ | <3.1 [a] | >96.9 [a] | >109.0 |
| | | | 1670 | 2024 | NQ | <3.2 [a] | >96.8 [a] | >92.5 |
| | | | 1466 | 2216 | NQ | <2.9 [a] | >97.1 [a] | >116.4 |
| | | Mean ± SD | 1539 ± 114 | 2105 ± 100 | NA | <3.1 ± 0.2 [a] | >96.9 ± 0.2 [a] | >106.0 ± 12.2 |
| | | 10000 | 10965 | 11121 | 573 | 6.6 | 93.4 | 78.8 |
| | | | 11464 | 14447 | 663 | 5.9 | 94.1 | 97.6 |
| | | | 11833 | 13710 | 654 | 6.2 | 93.8 | 89.7 |
| | | Mean ± SD | 11421 ± 436 | 13093 ± 1747 | 630 ± 50 | 6.2 ± 0.4 | 93.8 ± 0.4 | 88.7 ± 9.5 |
| | | 50000 | 49892 | 59456 | 3060 | 6.5 | 93.5 | 93.7 |
| | | | 54867 | 60928 | 2859 | 5.9 | 94.1 | 88.1 |
| | | | 53454 | 56932 | 3102 | 6.9 | 93.1 | 84.5 |
| | | Mean ± SD | 52738 ± 2564 | 59105 ± 2021 | 3007 ± 130 | 6.4 ± 0.5 | 93.6 ± 0.5 | 88.7 ± 4.7 |
| 4 | Monkey | 1000 | 1577 | 2010 | NQ | <3.3 [a] | >96.7 [a] | >96.8 |
| | | | 1482 | 1760 | NQ | <3.8 [a] | >96.2 [a] | >89.3 |
| | | | 1603 | 1533 | NQ | <4.3 [a] | >95.7 [a] | >72.4 |
| | | Mean ± SD | 1554 ± 64 | 1768 ± 239 | NA | <3.8 ± 0.5 [a] | >96.2 ± 0.5 [a] | >86.1 ± 12.5 |
| | | 10000 | 7655 | 9163 | 339 | 4.9 | 95.1 | 90.7 |
| | | | 8718 | 10679 | 384 | 4.8 | 95.2 | 92.5 |
| | | | 8419 | 10083 | 343 | 4.4 | 95.6 | 91.5 |
| | | Mean ± SD | 8264 ± 548 | 9975 ± 764 | 355 ± 25 | 4.7 ± 0.2 | 95.3 ± 0.2 | 91.6 ± 0.9 |
| | | 50000 | 44699 | 39892 [#] | 1994 | NR | NR | NR |
| | | | 42296 | 54604 | 2033 | 4.9 | 95.1 | 98.9 |
| | | | 39204 | 51902 | 1844 | 4.7 | 95.3 | 99.9 |
| | | Mean ± SD | 42066 ± 2755 | 53253 [b] | 1957 ± 100 | 4.8 [b] | 95.2 [b] | 99.4 [b] |
| 5 | Mouse | 1000 | 1569 | 1569 | NQ | <4.4 [a] | >95.6 [a] | >72.1 |
| | | | 1378 | 1560 | NQ | <4.5 [a] | >95.5 [a] | >81.0 |
| | | | 1524 | 1455 | NQ | <5.0 [a] | >95.0 [a] | >66.2 |
| | | Mean ± SD | 1490 ± 100 | 1528 ± 63 | NA | <4.6 ± 0.3 [a] | >95.4 ± 0.3 [a] | >73.1 ± 7.5 |
| | | 10000 | 11029 | 12959 | 988 | 10.4 | 89.6 | 86.3 |
| | | | 10253 | 13494 | 747 | 7.7 | 92.3 | 94.8 |
| | | | 12758 | 15591 | 782 | 7.1 | 92.9 | 86.4 |
| | | Mean ± SD | 11346 ± 1282 | 14015 ± 1391 | 839 ± 130 | 8.4 ± 1.8 | 91.6 ± 1.8 | 89.2 ± 4.9 |
| | | 50000 | 57461 | 64540 | 4624 | 9.7 | 90.3 | 82.8 |
| | | | 60430 | 125704 [#] | 4164 | NR | NR | NR |
| | | | 58087 | 63492 | 4779 | 10.2 | 89.8 | 80.7 |
| | | Mean ± SD | 58659 ± 1565 | 64016 [b] | 4522 ± 320 | 100 [b] | 90.0 [b] | 81.8 [b] |
| 6 | Sheep | 1000 | 2221 | 2024 | NQ | <3.2 [a] | >96.8 [a] | >69.7 |
| | | | 2027 | 2585 | NQ | <2.6 [a] | >97.4 [a] | >96.1 |
| | | | 1973 | 2483 | NQ | <2.7 [a] | >97.3 [a] | >94.8 |
| | | Mean ± SD | 2364 ± 299 | NA | <2.8 ± 0.4 [a] | >97.2 ± 0.4 [a] | >97.2 ± 0.4 [a] | >86.9 ± 14.9 |
| | | 10000 | 16378 | 16595 | 610 | 4.8 | 95.2 | 77.5 |
| | | | 17745 | 20050 | 602 | 3.9 | 96.1 | 86.3 |
| | | | 17360 | 18129 | 528 | 3.8 | 96.2 | 79.1 |

TABLE 4-continued

| | | Concentration of Compound 1 | | | | | | |
|---|---|---|---|---|---|---|---|---|
| Experiment | Species | Nominal $C_0$ (ng/mL) | Actual $C_0$ (ng/mL) | $C_r$ (ng/mL) | $C_u$ (ng/mL) | F % | PPB % | R % |
| | | Mean ± SD | 17161 ± 705 | 18258 ± 1731 | 580 ± 45 | 4.2 ± 0.5 | 95.8 ± 0.5 | 81.0 ± 4.7 |
| | | 50000 | 81340 | 92345 | 2417 | 3.5 | 96.5 | 86.1 |
| | | | 77645 | 99298 | 2896 | 3.9 | 96.1 | 96.5 |
| | | | 85273 | 97221 | 3108 | 4.2 | 95.8 | 87.0 |
| | | Mean ± SD | 81419 ± 3814 | 96288 ± 3569 | 2807 ± 354 | 3.8 ± 0.4 | 96.2 ± 0.4 | 89.9 ± 5.8 |

NQ = not quantifiable,
NA = not applicable,
NR = not reportable,
NC = not calculable
# = Outlier, possibly due to a sampling error (value excluded from the mean calculation)
[a] Since Compound 1 concentration in the ultrafiltrate samples was less than the lower quantification limit (LLOQ =50 ng/mL), the fraction unbound is calculated as F % < [LLOQ/($C_0$ · R)] * 100, and PPB expressed as PPB % > 100 − F %;
[b] SD not calculated since N ≤ 2

A slight concentration dependence was observed over the concentration range investigated. The observation suggested the tendency of PPB to become non-linear with increasing Compound 1 concentration, more evidently in mouse, dog, minipig and human.

Average PPB of warfarin was ≥99.2% for all the experiments, thus validating each ultrafiltration run (see TABLE 5).

TABLE 5

| | Concentration of Warfarin | | | | | | |
|---|---|---|---|---|---|---|---|
| Experiment | Nominal $C_0$ (ng/mL) | Actual $C_0$ (ng/mL) | $C_r$ (ng/mL) | $C_u$ (ng/mL) | F % | PPB % | R % |
| 1 (PPB in Minipig) | 1265 | 1165 | 1302 | 7.52 | 0.7 | 99.3 | 86.4 |
| | | 1168 | 1356 | 6.82 | 0.6 | 99.4 | 90.2 |
| | | 1181 | 1517 | 6.73 | 0.6 | 99.4 | 100.0 |
| | Mean ± SD | 1171 ± 8.4 | 1392 ± 112 | 7.02 ± 0.4 | 0.7 ± 0.09 | 99.3 ± 0.09 | 92.2 ± 7.0 |
| 2 (PPB in Dog) | 1265 | 1187 | 1265 | 6.71 | 0.7 | 99.3 | 83.6 |
| | | 1139 | 1429 | 6.24 | 0.6 | 99.4 | 98.8 |
| | | 1139 | 1412 | 6.06 | 0.5 | 99.5 | 97.2 |
| | Mean ± SD | 1155 ± 28 | 1369 ± 90 | 6.34 ± 0.3 | 0.6 ± 0.07 | 99.4 ± 0.07 | 93.2 ± 8.4 |
| 3 (PPB in Human) | 1265 | 1115 | 1274 | 8.24 | 0.8 | 99.2 | 88.0 |
| | | 1145 | 1350 | 8.35 | 0.8 | 99.2 | 89.6 |
| | | 1141 | 1364 | 8.57 | 0.8 | 99.2 | 91.9 |
| | Mean ± SD | 1134 ± 16 | 1330 ± 49 | 8.39 ± 0.2 | 0.8 ± 0.01 | 99.2 ± 0.01 | 89.8 ± 1.9 |
| 4 (PPB in Monkey) | 1265 | 1191 | 1422 | 7.44 | 0.7 | 99.3 | 94.0 |
| | | 1155 | 1401 | 6.58 | 0.6 | 99.4 | 94.8 |
| | | 1219 | 1289 | 6.49 | 0.6 | 99.4 | 85.2 |
| | Mean ± SD | 1188 ± 32 | 1371 ± 72 | 6.84 ± 0.5 | 0.7 ± 0.03 | 99.4 ± 0.03 | 91.4 ± 5.3 |
| 5 (PPB in Mouse) | 1265 | 1178 | 1429 | 8.88 | 0.8 | 99.2 | 93.6 |
| | | 1159 | 1490 | 6.81 | 0.6 | 99.4 | 101.6 |
| | | 1165 | 1431 | 7.08 | 0.6 | 99.4 | 95.5 |
| | Mean ± SD | 1167 ± 10 | 1450 ± 35 | 7.59 ± 1.1 | 0.7 ± 0.1 | 99.3 ± 0.1 | 96.8 ± 4.3 |
| 6 (PPB in Sheep) | 1265 | 1193 | 1478 | 8.12 | 0.7 | 99.3 | 96.8 |
| | | 1160 | 1389 | 5.89 [a] | NC | NC | NC |
| | | 1193 | 1412 | 6.87 | 0.6 | 99.4 | 92.8 |
| | Mean ± SD | 1182 ± 19 | 1426 ± 46 | 6.96 ± 1.1 | 0.7 [b] | 99.3 [b] | 94.8 [b] |

[a] Sample protein contaminated (protein content >300 µg/mL). The corresponding % F, % PPB and % R are not calculated (NC) and excluded from the mean
[b] SD not calculated since N ≤ 2

No protein contamination was detected in any ultrafiltration Compound 1 samples.

Bioanalytical Results.

The matrix-matched samples were analyzed using three qualified bioanalytical LC-MS/MS methods: one for warfarin and two for Compound 1 (one for minipig and one for human, cynomolgus monkey, dog, sheep, and mouse).

Carry over was assessed throughout the study phase by injection of one or more blank samples after a high concentration standard. Carry over was more than 25% of the response at the LLOQ for Compound 1 and less than 5% for the internal standard. Carry over was more than 25% of the response at the LLOQ for warfarin and less than 5% for the internal standard. Study samples were analyzed following the expected concentration to avoid potential impact on the final results.

Compound 1 and warfarin concentrations in study samples were determined from the appropriate calibration plots within BioLims.

Samples with unexpected results were re-assayed in duplicate. In some cases, results were not reportable (NR).

Conclusions

In agreement with Busher's classification, Compound 1 binding to plasma proteins was ranked as high-to-very high (PPB>85.0%) at 1 µg/mL and high (85.0%≤PPB≤98.0%) at both 10 and 50 µg/mL. A slight concentration dependence was observed over the concentration range investigated, suggesting the tendency of PPB to become non-linear with increasing Compound 1 concentration. This trend was more evident in mouse, dog, minipig, and human.

Example 2. Tissue Distribution of Total Radioactivity in the Cynomolgus Monkey Following Single Intravenous Bolus Administration of Compound 1

The objective of this study was to assess tissue distribution, disposition, and pharmacokinetics (PK) of [$^{14}$C]-Compound 1 drug related material following a single intravenous (IV) administration to the male cynomolgus (*Macaca fascicularis*) monkeys at the target dose level of 5 mg/kg using quantitative whole-body autoradiography (QWBA). The cynomolgus monkey is representative of the distribution and excretion in a human. Three animals were placed into metabolism cages after dosing and kept up to 4, 12, and 168 h post dose, respectively.

Disposition of [$^{14}$C]-Compound 1 was investigated in one animal only (No. 103, 168 h). Total radioactivity was measured in urine, feces, and cage rinse.

Pharmacokinetic profiles were obtained in blood and plasma collected from each animal at selected timepoints post-dose up to the terminal timepoint.

Following euthanasia at 4, 12, and 168 h post dose, tissue distribution of [$^{14}$C]-Compound 1 was investigated using quantitative whole body autoradiography.

Following IV bolus administration of [$^{14}$C]-Compound 1, very limited amounts of administered radioactivity (4.2% of the dose) were excreted over 168 h post-dose. This observation indicated that most of the dose was retained in the tissues: 1.5% and 1.7% of the dose was recovered in urine and feces, respectively. Cage rinse, which relates to urinary excretion, accounted for another 0.9% of the dose.

Total radioactivity in blood and plasma was quantifiable up to terminal timepoint in all animals. Over 168 h post dose (animal 103), systemic exposure to total radioactivity, measured as area under the plasma concentration time curve (AUC) from the start of dosing to the last quantifiable time point ($T_{last}$) ($AUC_{0-t}$), was 231000 and 205000 h·ng-eq/g in blood and plasma, respectively, while maximum concentration ($C_{max}$) was 7510 ng-eq/g ($C_0$ 9260 ng-eq/g) and 11500 ng-eq/g ($C_0$ 14000 ng-eq/g), respectively. Total radioactivity showed higher partitioning into plasma than blood (blood to plasma ratio 0.6-0.8) except for 168 h where a ratio of 2.1 was observed.

Clearance (CL) was 6.69 mL/h/kg (blood) and 14.0 mL/h/kg (plasma) and was significantly lower than were hepatic and renal blood flow rates (which are approximately 2616 and 1656 mL/h/kg). Consistently, mean volume of distribution at steady state ($V_{ss}$), accounting for 2480 mL/kg (blood) and 2780 mL/kg (plasma), was greater than total body water in cynomolgus monkey (which is approximately 693 mL/kg), indicating a moderate (0.6 to 5 L/kg) volume of distribution.

In general, [$^{14}$C]-Compound 1 drug-related material was widely distributed throughout the whole body and quantifiable in all tissues up to the last timepoint sampled. The distribution pattern in tissues was comparable between selected timepoints over 168 h post-dose. Very high concentrations were observed in kidney cortex, joints (most likely connected to cartilage), and liver, suggesting potential accumulation in these tissues.

Other tissues that showed notable uptake were: salivary glands, bone surface, pancreas, hair follicles, large intestine mucosa, aortic wall, small intestine mucosa, adrenal gland, stomach mucosa, spleen, bone marrow, lymph nodes, and thymus.

Moderate brain penetration was observed (brain to blood ratio<1): total radioactivity distributed quite uniformly in relevant sub-regions (cerebellum, olfactory bulb, thalamus, caudate putamen, cerebral cortex, and substantia nigra), but the highest concentrations were measured in the lateral ventricle, most likely in the choroid plexus.

Finally, radioactivity was also measured in tissues containing melanin (e.g., hair follicles and, most importantly, the uveal tract in the eye) indicating potential binding to melanin.

Radiolabeled Test Item.

[$^{14}$C]-Compound 1 (radiolabel was given by conjugation to double $^{14}$C-labelled glycine)

Specific activity: 29.3 µCi/mg (1.08 MBq/mg)

Radiochemical Purity: 73.7%

The radiolabeled test item, supplied as powder (88.8 MBq corresponding to 81.9 mg), was dissolved in the vehicle (8.9 mL) to obtain a radioactive stock solution (SS) at a nominal concentration of 10 MBq/mL (9.2 mg/mL). Actual radioactivity concentration and radiochemical purity of SS was determined prior to use by liquid scintillation counting (LSC). SS was stored at −80° C.

Vehicle (Control).

DPBS: Dulbecco's Phosphate Buffered Saline (modified, without calcium chloride and magnesium chloride, liquid, sterile-filtered).

pH 7.1-7.5.

Osmolality: 275-304 mOs/kg.

Storage Conditions: Below 30° C. (Ambient temperature, AT), 2-8° C. when opened.

Test Item Formulation.

Target dose level: 5.0 mg/kg

Target radioactive dose: 147 µCi/kg (5.42 MBq/kg)

Dose volume: 2.0 mL/kg

Nominal concentration: 2.5 mg/mL

Nominal radioactivity concentration: 73.3 µCi/mL (2.71 MBq/mL)

Method: The final formulation was prepared the day before administration. SS was thawed at ambient temperature, heated at approximately 65° C. for 5 minutes and then allowed to cool down to room temperature under magnetic stirring. An appropriate aliquot of SS was diluted in the required volume of vehicle and kept under magnetic stirring at room temperature overnight. At the stated specific activity, no additional isotopic dilution with non-radiolabeled test item was required.

Stability of the final formulation: The heating step was assessed in advance to confirm that [$^{14}$C]-Compound 1 stability was not affected. The stability at ambient temperature was assessed over 24 hours in order to allow for formulation preparation on the day before administration.

Storage conditions of the final formulation: Ambient temperature up to 24 hours, prior to dosing.

Residual Test Item Formulation: The residual formulation was stored at −20° C.

Test System

Characterization of Test System.

Number on Study: 3 males

Age: Between 2 and 2.5 years

Body Weight: 2.40 kg, 2.24 kg, 2.29 kg

Minimum Acclimatization: At least 21 days (prior to Day 1)

Monkey was used as one of the non-rodent species required in toxicology studies by test guidelines. The cynomolgus monkey was chosen because the non-human primate blood brain barrier is more similar to that of a human than to a dog blood brain barrier.

Temperature and humidity were recorded daily during the study phases. Actual mean measurements (with ranges) were 21.3° C. and 52.7%. Average temperature and relative humidity were always within the acceptable ranges during the in life phase: 21-23° C. (20-24° C. for less than 24 hours acceptable) and 45-65% (40-70% for less than 24 hours acceptable), respectively.

Diet, Water, and Environmental Enrichment.

Diet was offered ad libitum throughout the study except for approximately 1 hour before and after dosing. A fruit, vegetable, and foraging mix supplement was also given.

Water, filtered from normal domestic water, was offered ad libitum throughout the study.

Monkeys had access to specific environmental enrichment devices in each cage. Social interaction between animal and staff was ensured for an adequate time twice a day on working days, and once a day over the weekend.

Experimental Design

Three naïve male Cynomolgus monkeys each received a single IV bolus administration of [$^{14}$C]-Compound 1 at a target dose of 5 mg/kg. Following dose administration, animals were placed into metabolic cages and the following matrices were collected as outlined in TABLE 6.

TABLE 6

| Animal No./Sex | Matrix | Animal No | Time-point (h) |
|---|---|---|---|
| 3/males | Blood | 101 | 5 min, 15 min, 30 min, 1 h, 2 h, 4 h |
| | | 102 | 5 min, 15 min, 30 min, 1 h, 2 h, 3 h, 4 h, 6 h, 8 h |
| | | 103 | 5 min, 15 min, 30 min, 1 h, 2 h, 3 h, 4 h, 6 h, 8 h, 12 h, 24 h, 168 h |
| | Tissues (carcass) | 101 | 4 h post-dose (terminal timepoint) |
| | | 102 | 12 h post-dose (terminal timepoint) |
| | | 103 | 168 h post-dose (terminal timepoint) |
| | Urine | 101/102 | Samples not available at terminal timepoint |
| | | 103 | 12 h, 24 h, 48 h, 72 h, 96 h, 120 h, 144 h, 168 h |
| | Feces | 101/102 | Samples not available at terminal timepoint |
| | | 103 | 24 h, 48 h, 72 h, 96 h, 120 h, 144 h, 168 h |

Levels of total radioactivity were determined by liquid scintillation counting (LSC) in the following matrices: blood, plasma, urine, feces, and cage rinse.

At the terminal timepoint (4 h, 12 h, and 168 h post-dose, respectively), animals were euthanized, and the tissue distribution of total radioactivity was evaluated using QWBA.

Intra-organ distribution of total radioactivity was evaluated in brain (cerebellum, olfactory bulb, thalamus, caudate putamen, cerebral cortex, and substantia nigra), eye and kidney. Sections were collected using a cryomacrotome, freeze-dried, and exposed to imaging plates. The resulting electronic whole-body autoradiograms were evaluated for the quantitative assessment of radioactivity in the tissues.

Radioactivity data in blood, plasma and tissues were subject to non-compartmental analysis for evaluation of appropriate pharmacokinetic parameters, where feasible.

Methods and Procedures

Assessment of Test Item Stability.

The stability of the test item was assessed, by measuring the radiochemical purity, under the following conditions prior to initiating in-vivo experimental activities.

An aliquot of the SS was heated at approximately 65° C. for 5 minutes to confirm that this step, during formulation preparation, would not affect $^{14}$C label stability.

The stability of the final formulation was assessed at room temperature for 4 and 24 hours.

A preliminary assessment of [$^{14}$C]-Compound 1 stability in monkey blood was also performed: a volume of monkey blank blood was spiked with an appropriate aliquot of radiolabeled SS and incubated at 37° C. for 4 and 24 hours.

As radioactivity could not be extracted using a standard approach, measurement of radiochemical purity after incubation in blood and assessment of stability in biological matrices were not possible.

Characterization of Stock Solution and Formulation.

The radioactivity concentration of the stock solution and dose formulation was determined as follows: three weighed aliquots were dispensed into glass vials, appropriately diluted with DPBS. Three weighed aliquots were then removed from each dilution, supplemented with liquid scintillant and radioassayed by LSC in order to determine the actual radioactive concentration and homogeneity of the solutions.

Dose Administration.

The dose formulation was administered intravenously, as a bolus, through the caudal vein.

Individual dose volumes were adjusted based on body weight of the animals on the day of dose administration. Doses were dispensed into pre-weighed syringes, which were weighed prior to and following dose administration. The actual dose received by each animal was calculated from dose concentration, weight of dose administered and animal weight.

Sample Collection.

Phase 1: Excretion Balance.

Following administration, urine and feces were collected quantitatively at selected times post-dose and kept refrigerated, over wet ice, during collection.

On a daily basis and/or at the end of the collection period, metabolic cages were rinsed with ethanol/water (50:50, v/v) and the wash retained for quantitative determination of radioactivity.

Cage debris were collected and pooled by animal over the entire period of collection.

Phase 2: Pharmacokinetics.

Following administration, systemic blood was removed from the cephalic vein, at each selected time point post-dose and transferred into tubes containing $K_3$EDTA as anticoagulant (actual times of bleeding were recorded). Following collection, all blood samples were thoroughly mixed and placed on wet ice. Plasma samples were prepared within two hours of blood collection.

Liquid Scintillation Counting Analysis.

Triplicate aliquots of liquid samples (e.g., dose formulations, urine, plasma and cage wash) were counted directly in liquid scintillant.

Feces were homogenized in a suitable quantity of ultrapure water (approximate ratio 1:2, w/v) using Stomacher homogenizer. Weighed quadruplicate aliquots of homogenates (0.2-0.4 g) were solubilized by addition of 1 mL of Solvable tissue solubilizer, supplemented twice with 200 µL of 30% hydrogen peroxide ($H_2O_2$) and incubated at approximately 50° C., until appropriate discoloration was achieved, prior to addition of scintillant.

Weighed triplicate aliquots of blood (100 µL) were treated as fecal homogenates.

The remaining blood was centrifuged at 2000 g for 10 min at approximately 4° C. within two hours of collection and the plasma decanted into plastic tubes. Aliquots of plasma were radio assayed by LSC. Blood pellets were discarded.

Radioactivity was determined in a Tricarb Series liquid scintillation analyzer. Quench correction was achieved during sample counting through the automatic assignment of a quench indicator (tSIE/AEC) value to the sample. This value was used to interpolate sample counting efficiency from an instrument stored quench curve generated from a series of sealed quenched standards. The interpolated efficiency value was used to automatically correct LSC data counts per minute (cpm) and obtain disintegrations per minute (dpm). A suitable scintillation fluid (Ultima Gold) was added to each sample prior to radio assaying by LSC for an appropriate time. Background counts were subtracted from quench corrected sample counts. According to the background value and count time, the limit of quantification was calculated.

Tissue Distribution.

At the last timepoint (4 h, 12 h, and 168 h post-dose, respectively) animals were euthanized and the tissue distribution of total radioactivity was evaluated using quantitative whole-body autoradiography.

Sample Collection and Embedding.

Following euthanasia, animals were frozen by immersion into a freezing mixture of hexane/solid $CO_2$. Animals were left in the freezing mixture for at least 2 hours, until completely frozen.

Frozen carcasses were embedded, left lateral side uppermost, in a block of sodium carboxymethylcellulose (approximately 2%, w/v in water).

Sectioning.

Each block was mounted in a CM3600 cryomacrotome (Leica Microsystems) maintained at approximately −20° C. After initial trimming of the block, sagittal whole body sections (40 μm) were obtained at various levels through the carcass. Sections of interest mounted on pressure sensitive tape were left to dehydrate in the cryomacrotome chamber at approximately −20° C. for approximately 60 h.

Autoradiography.

Freeze dried sections were placed against an image plate (IP), suitable for $^{14}C$, as long as 4 days. During the exposure period the IPs were placed in a copper-lead shielding box for minimizing external background signals. Following exposure, the IPs were scanned by a laser beam, using a Fuji FLA5000 phosphor imager system, and the latent image captured and stored on an electronic data file.

For each set of whole body images obtained, the system was calibrated with biological standards of known radioactivity.

Selected tissues were identified on the image and integrated, using AIDA software, to give a value for tissue concentration. Triplicate measurements were made across each selected organ/tissue, when possible, either by multiple integration on a single section or by multiple integration from a number of different sections.

Results generated from the integration were expressed as Bq/g and subsequently converted to ng-equivalents of Compound 1/g tissue (ng-eq/g), using dose formulation specific activity.

The limit of quantification (LOQ) for tissue distribution was set as 3 times the mean background levels of radioactivity (mean of seven measurements per IP).

For the purposes of quantification, the assumption was that all tissues analyzed had a similar density and quench characteristics to blood (used as calibration standards). Exceptions to this rule were bone and white fat, where correction factors of 0.48 and 0.84 were applied, respectively, to compensate for quenching of radioactivity.

Calibration Curve.

A block of frozen CMC (approximately 2%, w/v, in water) containing standards of known radioactivity was prepared on a separate occasion. A series of paper straws were fixed in the block and monkey blood containing increasing amounts of a $[^{14}C]$-Compound 1 was dispensed into the straws and frozen. The range of calibration standards was chosen to cover the extent of likely tissue concentration values (actual range 56.8-32,274 Bq/g).

Calibration lines were generated for each set of sections exposed on a single IP by selecting an area of each standard from the scanned image and assigning the corresponding radioactivity concentration previously determined by LSC.

Results

Stock Solution Analysis.

The radioactivity concentration and the radiochemical purity of the stock solution was checked prior to use. Radioactivity concentration (MBq/mL) was 9.52. Radiochemical purity was 93.2%.

Assessment of Test Item Stability.

Compound 1 was stable under the experimental conditions assessed.

Formulation Analysis.

Compound 1 Concentration: 2.33 mg/g (mg of Compound 1+$[^{14}C]$-Compound 1)

Radioactivity Concentration: 2.52 MBq/g

Formulation Specific Activity: 1.08 MBq/mg

CV: 1.9% (overall pre- and post-dose)

Difference Pre vs Post dose: 1.6%

Radiochemical Purity: 91.8% (mean pre-and post-dose)

The formulations resulted to be homogeneous prior to and across dosing (CV<5%).

The difference between pre dose and post dose concentration was within ±10%.

Administered Dose.

The actual doses of $[^{14}C]$-Compound 1 administered to male cynomolgus monkeys as single IV bolus are presented in TABLE 7.

TABLE 7

| Animal Number | Body Weight (kg) | Formulation Administered (g) | Chemical Dose[a] | | Radioactive Dose[b] | |
|---|---|---|---|---|---|---|
| | | | (mg/Animal) | (mg/kg) | (MBq/Animal) | (MBq/kg) |
| 101 | 2.29 | 4.69 | 10.9 | 4.77 | 11.8 | 5.15 |
| 102 | 2.40 | 4.83 | 11.3 | 4.69 | 12.2 | 5.06 |
| 103 | 2.24 | 4.51 | 10.5 | 4.69 | 11.3 | 5.07 |
| Mean | 2.31 | 4.68 | 10.9 | 4.72 | 11.8 | 5.09 |
| ±SD | 0.08 | 0.16 | 0.4 | 0.047 | 0.4 | 0.051 |

[a]Chemical dose concentration = 2.33 mg $[^{14}C]$-Compound 1 + Compound 1/g of formulation
[b]Radioactive dose concentration = 2.52 MBq/g of formulation Mean Actual Dose: 4.72±0.05 mg of total Compound 1/kg (mg of Compound 1+$[^{14}C]$-Compound 1)

Mean Actual Radioactive Dose: 5.09±0.05 MBq/kg

No clinical signs were observed following dosing.

Excretion.

Due to early terminal timepoints for animal 101 and 102, no excreta could be collected from these animals. Individual excretion data was obtained from animal 103 and is presented TABLE 8. Cumulative data of the same animal is also presented in TABLE 8. Cumulative excretion is also plotted in FIG. 1.

TABLE 8

| Matrix | Time (h) | Percentage of Administered Dose (%) Animal 103 | Cumulative Percentage of Administered Dose (%) |
|---|---|---|---|
| Urine | 12 | 0.1 | 0.1 |
| | 24 | 0.4 | 0.5 |
| | 48 | 0.2 | 0.7 |
| | 72 | 0.1 | 0.9 |
| | 96 | 0.2 | 1.1 |
| | 120 | 0.1 | 1.2 |
| | 144 | 0.2 | 1.4 |
| | 168 | 0.2 | 1.5 |
| | Subtotal | 1.5 | |
| Feces | 24 | 0.4 | 0.4 |
| | 48 | 0.4 | 0.9 |
| | 72 | 0.3 | 1.2 |
| | 96 | 0.2 | 1.4 |
| | 120 | 0.1 | 1.5 |
| | 144 | 0.1 | 1.7 |
| | 168 | 0.1 | 1.7 |
| | Subtotal | 1.7 | |
| Cage Rinse | 24 | 0.1 | 0.1 |
| | 48 | 0.1 | 0.3 |
| | 72 | 0.1 | 0.4 |
| | 96 | 0.1 | 0.5 |
| | 120 | 0.1 | 0.6 |
| | 144 | 0.1 | 0.8 |
| | 168 | 0.2 | 0.9 |
| | Subtotal | 0.9 | |
| TOTAL | 168 | 4.2 | 4.2 |

TABLE 9

Concentration of Total Radioactivity

| Animal ID | Time (h) | Blood Concentration (ng-eq/g) | Plasma Concentration (ng-eq/g) | Blood to Plasma Ratio |
|---|---|---|---|---|
| 101 | 0.083 | 7826 | 11097 | 0.7 |
| | 0.25 | 5497 | 8573 | 0.6 |
| | 0.5 | 4134 | 6209 | 0.7 |
| | 1 | 2913 | 4024 | 0.7 |
| | 2 | 1752 | 2297 | 0.8 |
| | 4 | 1256 | 1732 | 0.7 |
| 102 | 0.083 | 7615 | 11625 | 0.7 |
| | 0.25 | 4998 | 7792 | 0.6 |
| | 0.5 | 3818 | 5762 | 0.7 |
| | 1 | 2755 | 3783 | 0.7 |
| | 2 | 1651 | 2223 | 0.7 |
| | 3 | 1396 | 1913 | 0.7 |
| | 4 | 1299 | 1796 | 0.7 |
| | 6 | 1217 | 1700 | 0.7 |
| | 8 | 1205 | 1594 | 0.8 |
| 103 | 0.083 | 7514 | 11547 | 0.7 |
| | 0.25 | 4933 | 7783 | 0.6 |
| | 0.5 | 3931 | 5914 | 0.7 |
| | 1 | 2893 | 4166 | 0.7 |
| | 2 | 1799 | 2427 | 0.7 |
| | 3 | 1536 | 2077 | 0.7 |
| | 4 | 1409 | 1900 | 0.7 |
| | 6 | 1313 | 1881 | 0.7 |
| | 8 | 1259 | 1710 | 0.7 |
| | 12 | 1166 | 1625 | 0.7 |
| | 24 | 1187 | 1525 | 0.8 |
| | 168 | 1563 | 752 | 2.1 |

Following IV bolus administration of $[^{14}C]$-Compound 1, a very limited amount of administered radioactivity (4.2% of the dose) was excreted over 168 h post-dose, being most of the dose retained in the tissues: 1.5% and 1.7% of the dose was recovered in urine and feces, respectively. Another 0.9% of the dose was recovered in the cage rinse, which relates to urinary excretion.

Blood and Plasma Pharmacokinetics

Figure 2:
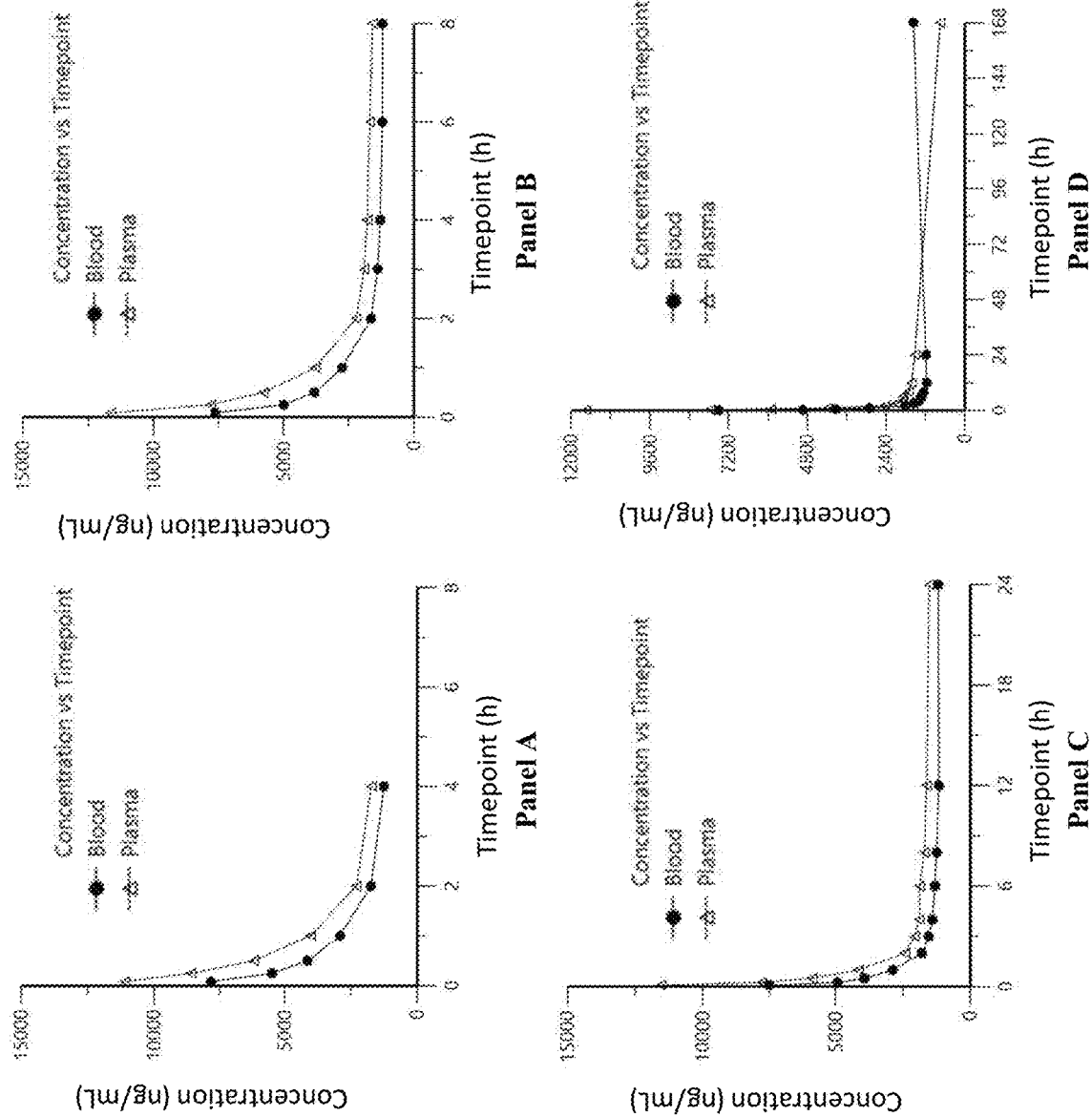
FIG. 2 illustrates individual blood and plasma profiles of total radioactivity following a single intravenous bolus of [$^{14}$C]-Compound 1 to a male cynomolgus monkeys at 5 mg/kg in Animal 101 (4 hours post dose, Panel A), Animal 102 (12 hours post dose, Panel B), Animal 103 (24 hours post-dose, Panel C) and Animal 103 (168 hours post-dose, Panel D).

Individual concentrations of radioactivity in blood and plasma at various sampling times after a single IV bolus administration of $[^{14}C]$-Compound 1 to male cynomolgus monkeys are presented in TABLE 9. Individual profiles of total radioactivity in blood and plasma are graphically shown in FIG. 2 in Animal 101 (Panel A), Animal 102 (Panel B), Animal 103 over 24 hours (Panel C) and Animal 103 over 168 hours (Panel D).

PK parameters calculated from serial concentration time profiles of total radioactivity are presented in TABLE 10.

TABLE 10

| Animal | Time (h) | Matrix | $C_0$ (ng-eq/g) | $C_{max}$ (ng-eq/g) | $T_{max}$ (h) | $T_{last}$ (h) | $AUC_{0-t}$[a] (h·ng-eq/g) | $AUC_{0-inf}$ (h·ng-eq/g) | $AUC_{Extrap}$ (%) | $T_{1/2}$ (h) | Cl (mL/h/kg) | $V_z$ (mL/kg) | $V_{ss}$ (mL/kg) |
|---|---|---|---|---|---|---|---|---|---|---|---|---|---|
| 101 | 4 | Blood | 9340 | 7830 | 0.08 | 4 | 10000 | 13400 | 25.1 | 1.85 | 374 | 1000 | 1020 |
| | | Plasma | 12600 | 11100 | 0.08 | 4 | 14000 | 17900 | 21.3 | 1.52[b] | 280 | 615 | 670 |
| 102 | 8 | Blood | 9390 | 7620 | 0.08 | 8 | 14400 | 5700 | 74.7 | 24.49[b] | 87.7 | 3100 | 2910 |
| | | Plasma | 14200 | 11600 | 0.08 | 8 | 20300 | 73800 | 72.4 | 23.24[b] | 67.8 | 2270 | 2090 |
| 103 | 24 | Blood | 9260 | 7510 | 0.08 | 24 | 34200 | 150000 | 77.2 | 67.76[b] | 33.3 | 3250 | 3210 |
| | | Plasma | 14000 | 11500 | 0.08 | 24 | 47200 | 274000 | 82.8 | 103.05[b] | 18.3 | 2710 | 2640 |
| 103 | 168 | Blood | 9260 | 7510 | 0.08 | 168 | 231000 | 747000 | 69.1 | 228.79[b] | 6.69 | 2210 | 2480 |
| | | Plasma | 14000 | 11500 | 0.08 | 168 | 205000 | 357000 | 42.7 | 140.69[b] | 14.0 | 2840 | 2780 |

Total drug-related radioactivity in blood and plasma was quantifiable up to the terminal timepoint in all animals.

In animal 103 (168 h post dose), systemic exposure to total radioactivity, measured as $AUC_{0-t}$, was 231000 and 205000 h·ng-eq/g in blood and plasma, respectively, while total radioactivity $C_{max}$ was 7510 ng-eq/g ($C_0$ 9260 ng-eq/g) and 11500 ng-eq/g ($C_0$ 14000 ng-eq/g), respectively.

CL was 6.69 mL/h/kg (blood) and 14.0 mL/h/kg (plasma) and was significantly lower than were hepatic and renal blood flow rates (which are approximately 2616 and 1656 mL/h/kg). Consistently, mean $V_{ss}$ accounting for 2480 mL/kg (blood) and 2780 mL/kg (plasma) was significantly greater than was total body water in cynomolgus monkey (which is approximately 693 mL/kg). This result indicated moderate (0.6 to 5 L/kg) distribution into tissues.

The elimination phase could not be defined because of very limited elimination over 168 h post-dose. Thus, acceptance criteria for terminal half-life $T_{1/2}$ were not fully met and total radioactivity $T_{1/2}$ could not be reliably calculated: estimates of 229 and 141 h in blood and plasma, respectively.

Within 4 h of dosing (animal 101) a $T_{1/2}$ of 1.85 h was evaluated in blood but indicated quick distribution rather than elimination.

Total radioactivity showed higher partitioning into plasma than blood (ratio 0.6-0.8) except for 168 h where a ratio of 2.1 was observed.

Tissues Distribution and Pharmacokinetics

Concentrations of radioactivity in tissues and correspondent tissue to blood ratios (T/B) obtained following single IV bolus administration of [$^{14}$C]-Compound 1 to male cynomolgus monkeys at 5 mg/kg are presented in TABLE 11.

TABLE 11

Total DRM Concentration as ng-eq/g (Tissue to blood ratio)

| Tissue/Organ | Animal 101 4 h | 102 12 h | 103 168 h |
|---|---|---|---|
| Adrenal gland_cortex | 10315 (8.2) | 16063 (10.9) | 8271 (5.0) |
| Adrenal gland_medulla | 5182 (4.1) | 7779 (5.3) | 8083 (4.9) |
| Aortic wall | 11777 (9.3) | 9211 (6.3) | 1954 (1.2) |
| Bone_inner | 1091 (0.9) | 992 (0.7) | 73.3 (0.04) |
| Bone_surface | 17582 (13.9) | 6686 (4.6) | 4995 (3.0) |
| Bone marrow | 7487 (5.9) | 13533 (9.2) | 7478 (4.6) |
| Brain_caudate | 428 (0.3) | 311 (0.2) | 484 (0.3) |
| Brain_cerebellum | 493 (0.4) | 349 (0.2) | 378 (0.2) |
| Brain_cortex | 471 (0.4) | 440 (0.3) | 424 (0.3) |
| Brain_lateral ventricle | 3763 (3.0) | 3781 (2.6) | 2868 (1.7) |
| Brain_olfactory bulb | 666 (0.5) | 849 (0.6) | 1360 (0.8) |
| Brain_putamen | 249 (0.2) | 230 (0.2) | 279 (0.2) |
| Brain_substantia nigra | 526 (0.4) | 151 (0.1) | NI |
| Brain_thalamus | 385 (0.3) | 305 (0.2) | 397 (0.2) |
| Brown fat | 2832 (2.2) | 5324 (3.6) | 2187 (1.3) |
| Eye_uveal tract (choroid + RPE) | 2416 (1.9) | 2366 (1.6) | 1286 (0.8) |
| Hair follicles | 14769 (11.7) | 15075 (10.3) | 3628 (2.2) |
| Heart_blood | 1261 (1.0) | 1468 (1.0) | 1642 (1.0) |
| Heart_myocardium | 2908 (2.3) | 4802 (3.3) | 2517 (1.5) |
| Joints (cartilage) | 59612 (47.3) | 130483 (88.9) | 47762 (29.1) |
| Kidney_cortex | 125167 (99.3) | 145490 (99.1) | 103160 (62.8) |
| Kidney_medulla | 3586 (2.8) | 3198 (2.2) | 1904 (1.2) |
| Large intestine_content | 3057 (2.4) | 3282 (2.2) | 476 (0.3) |
| Large intestine_mucosa | 12369 (9.8) | 13130 (8.9) | 2690 (1.6) |
| Large intestine_wall | 3088 (2.4) | 4023 (2.7) | 1296 (0.8) |
| Liver | 34695 (27.5) | 56919 (38.8) | 51575 (31.4) |
| Lung | 1757 (1.4) | 3243 (2.2) | 1963 (1.2) |
| Lymph nodes | 7256 (5.8) | 14028 (9.6) | 5755 (3.5) |
| Pancreas | 17587 (13.9) | 9920 (6.8) | 2595 (1.6) |
| Pituitary gland | 5581 (4.4) | 5712 (3.9) | 2850 (1.7) |
| Salivary glands_Parotid | 17854 (14.2) | 19565 (13.3) | 2790 (1.7) |
| Salivary glands_other | 15080 (12.0) | 13356 (9.1) | 2726 (1.7) |
| Skeletal muscle | 1425 (1.1) | 1509 (1.0) | 1235 (0.8) |
| Skin | 2585 (2.1) | 2049 (1.4) | 1228 (0.7) |
| Small intestine_content | 3603 (2.9) | 3520 (2.4) | 603 (0.4) |
| Small intestine_mucosa | 10504 (8.3) | 15425 (10.5) | 2698 (1.6) |
| Small intestine_wall | 3103 (2.5) | 3655 (2.5) | 1758 (1.1) |
| Spinal cord | 484 (0.4) | 401 (0.3) | 412 (0.3) |
| Spleen | 8369 (6.6) | 9236 (6.3) | 7258 (4.4) |
| Stomach_content | 1858 (0.6) | 2947 (2.0) | 128 (0.1) |
| Stomach_mucosa | 9042 (7.2) | 15960 (10.9) | 3161 (1.9) |
| Stomach_wall | 2975 (2.1) | 2905 (2.0) | 1764 (1.1) |
| Testis | 2363 (1.9) | 5181 (3.5) | 2630 (1.6) |
| Thymus | 5277 (4.2) | 7601 (5.2) | 3194 (1.9) |
| Thyroid gland | 1530 (1.2) | 1793 (1.2) | 2329 (1.4) |
| Urinary Bladder | 3663 (2.9) | 4350 (3.0) | 1452 (0.9) |
| Urine | 30379 (24.1) | 4249 (2.9) | NP |
| White fat | 1162 (0.9) | NI | NI |
| Whole blood$^a$ | 1256 | 1205 | 1563 |
| LOQ$^b$ | ≤47.1 | ≤47.1 | ≤47.1 |

Figure 3:
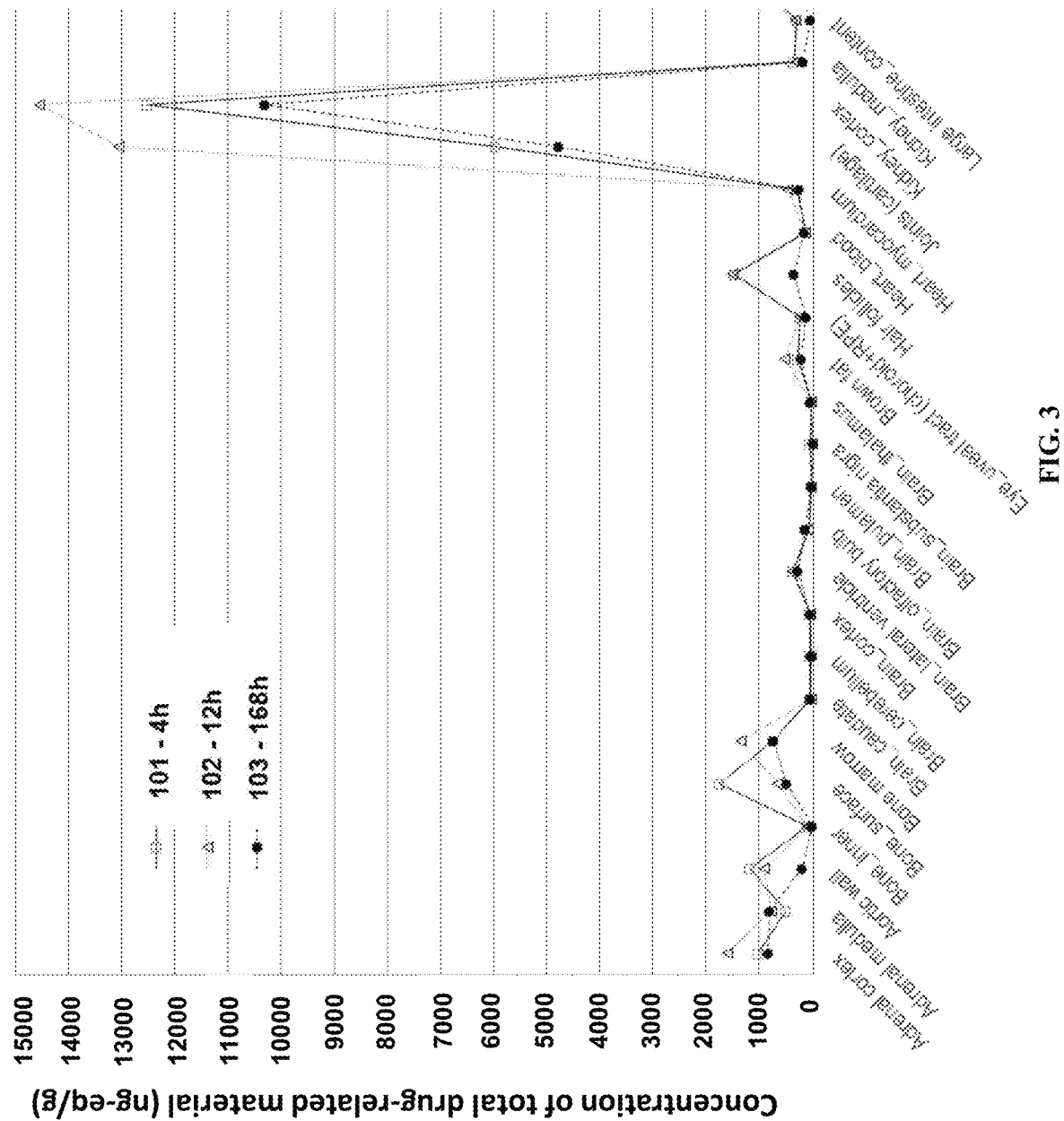
FIG. 3 illustrates concentrations of total radioactivity in representative organs and tissues at various times following a single intravenous bolus of [$^{14}$C]-Compound 1 to male cynomolgus monkeys at 5 mg/kg.
Figure 4:
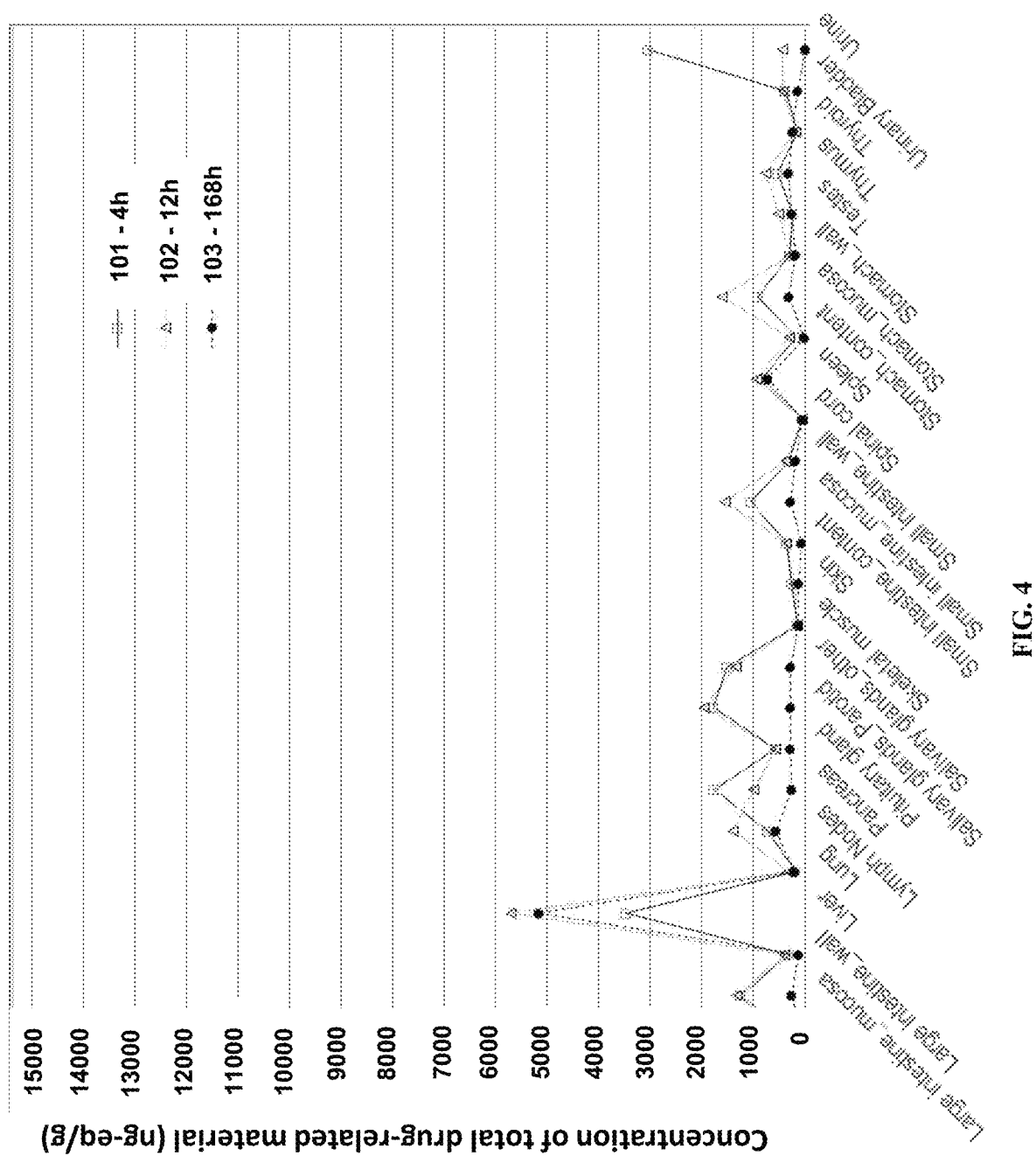
FIG. 4 illustrates concentrations of total radioactivity in representative organs and tissues at various times following a single intravenous bolus of [$^{14}$C]-Compound 1 to male cynomolgus monkeys at 5 mg/kg.
Figure 5:
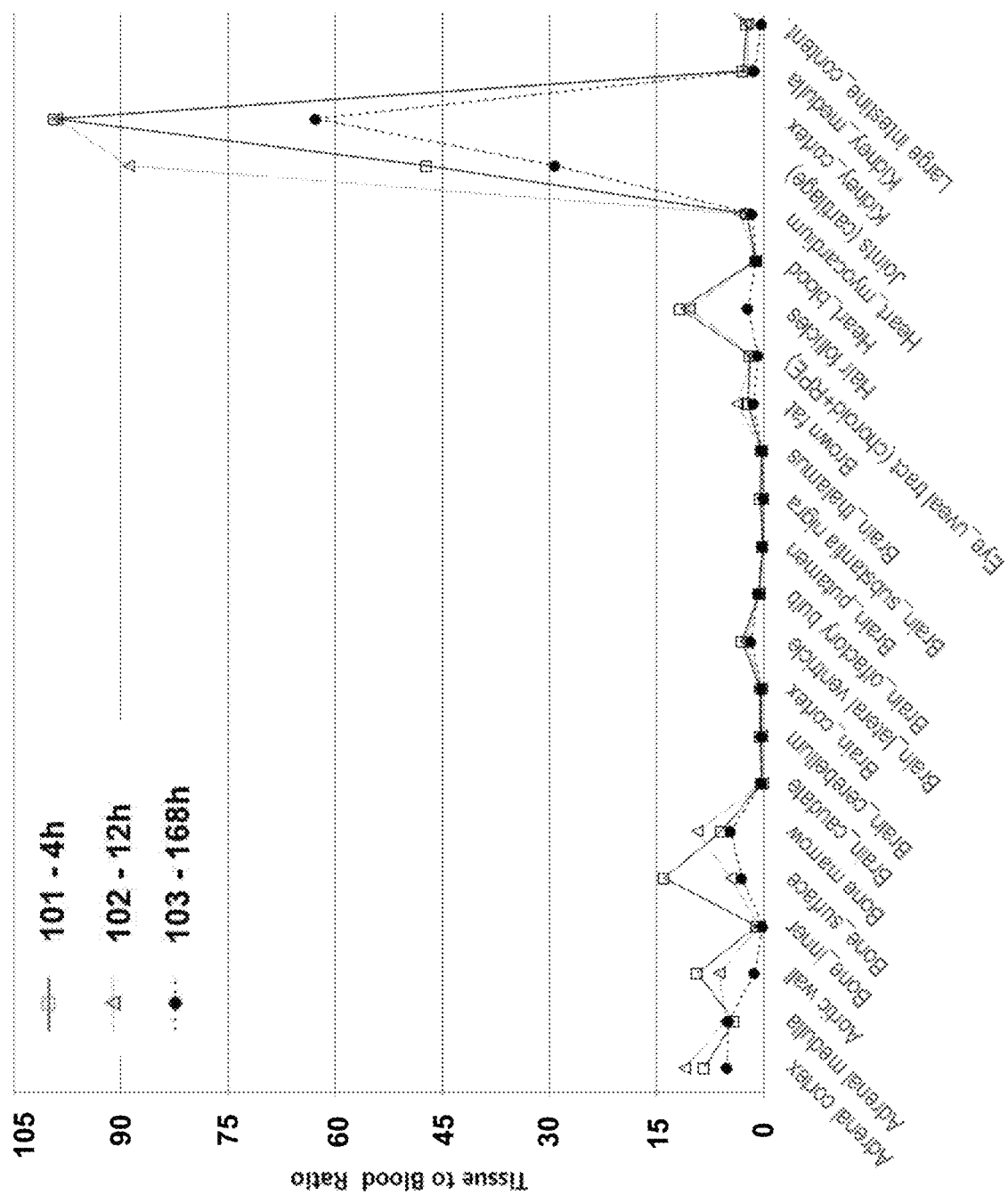
FIG. 5 illustrates tissue to blood ratios at various times following a single intravenous bolus of [$^{14}$C]-Compound 1 to male cynomolgus monkeys at 5 mg/kg.
Figure 6:
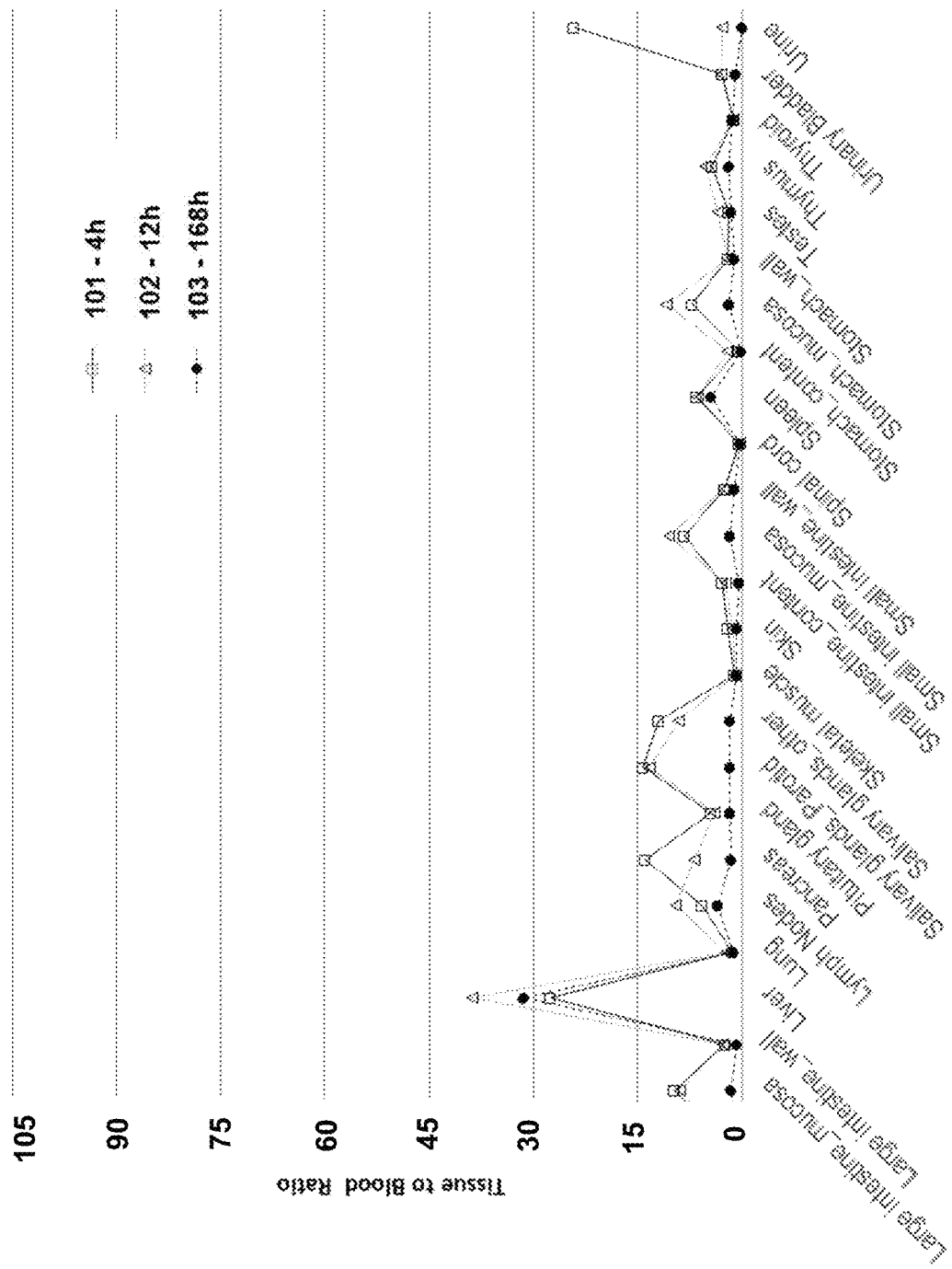
FIG. 6 illustrates tissue to blood ratios at various times following a single intravenous bolus of [$^{14}$C]-Compound 1 to male cynomolgus monkeys at 5 mg/kg.
Figure 7A:
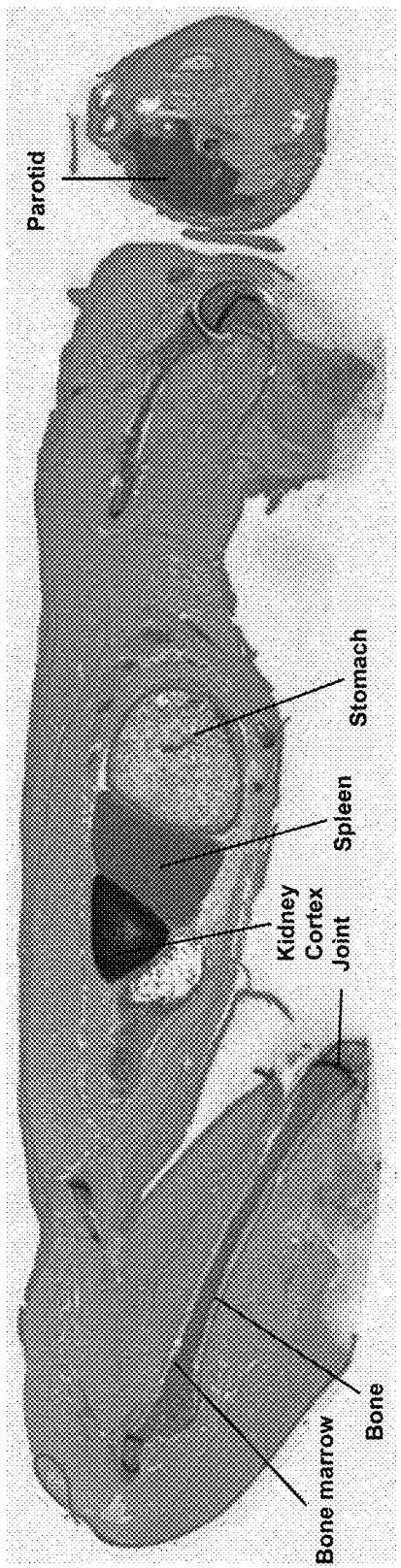
FIG. 7A and FIG. 7B are autoradiographs that depict representative tissue distribution of total radioactivity in parasagittal sections of Animal 101 following a single intravenous 5 mg/kg bolus of [$^{14}$C]-Compound 1. Any grey signal above background indicates presence of compound in tissues.
Figure 7B:
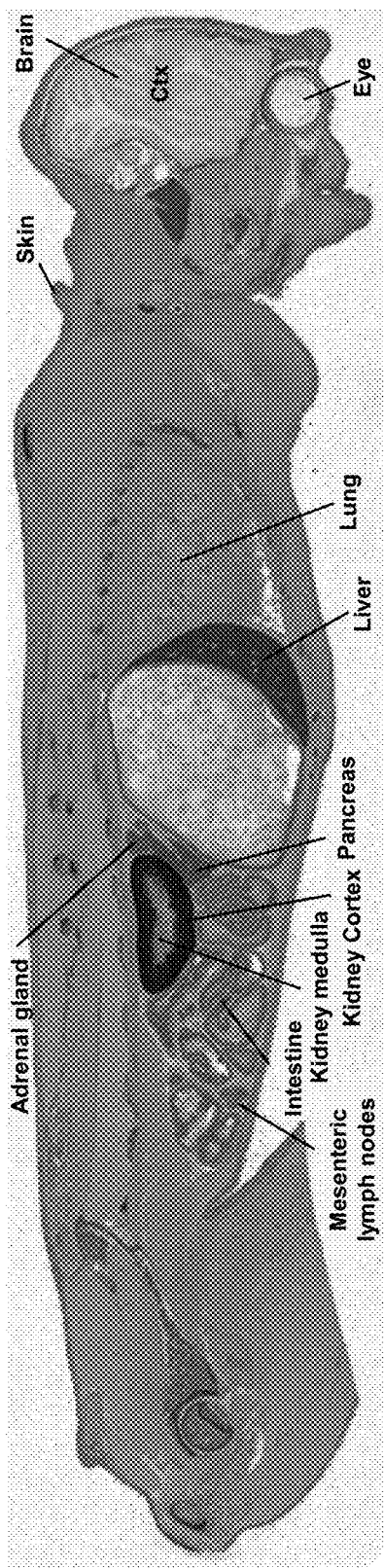
Figure 8A:
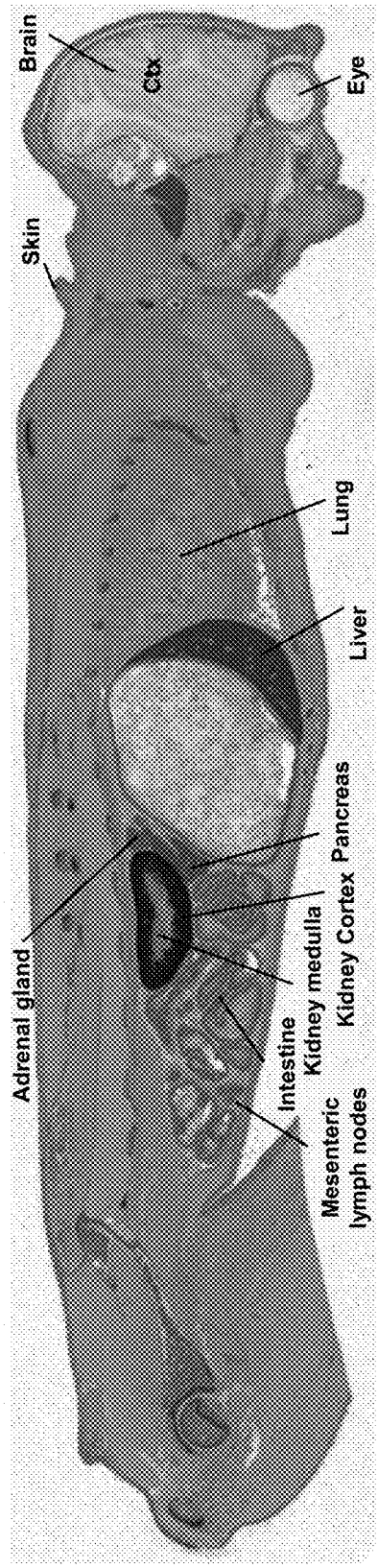
FIG. 8A and FIG. 8B are autoradiographs that depict representative tissue distribution of total radioactivity in sagittal sections of Animal 101 following a single intravenous 5 mg/kg bolus of [$^{14}$C]-Compound 1. Any grey signal above background indicates presence of compound in tissues.
Figure 8B:
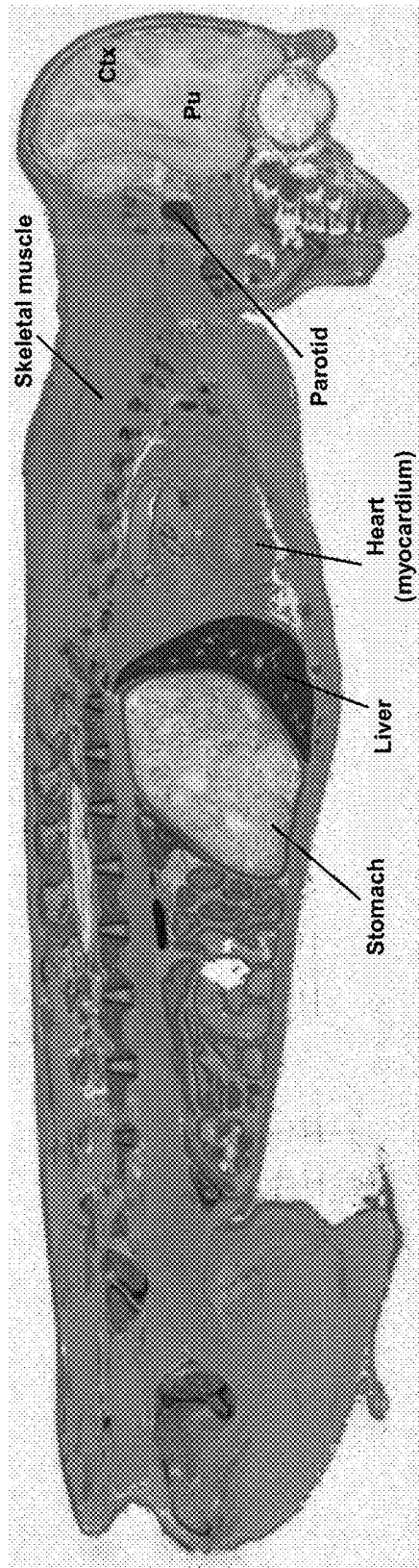
Figure 9A:
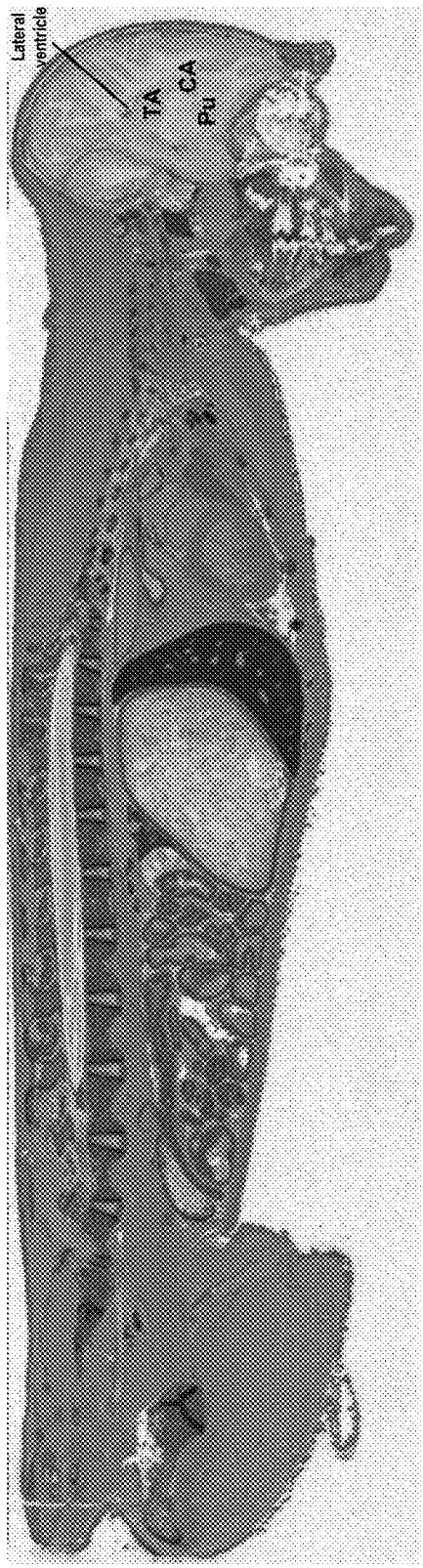
FIG. 9A and FIG. 9B are autoradiographs that depict representative tissue distribution of total radioactivity in sagittal sections of Animal 101 following a single intravenous 5 mg/kg bolus of [$^{14}$C]-Compound 1. Any grey signal above background indicates presence of compound in tissues.
Figure 9B:
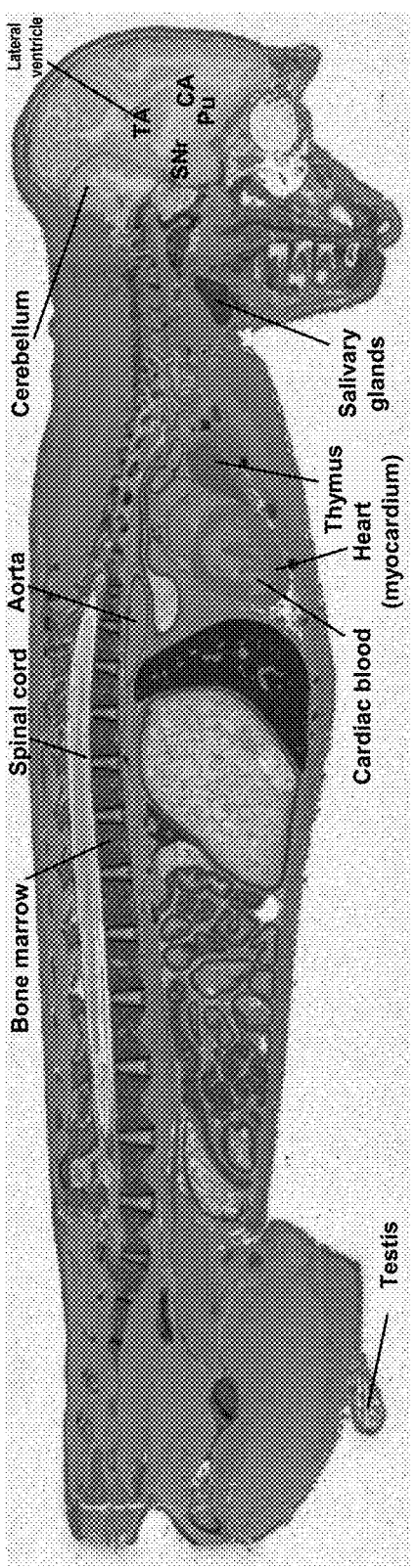
Figure 10A:
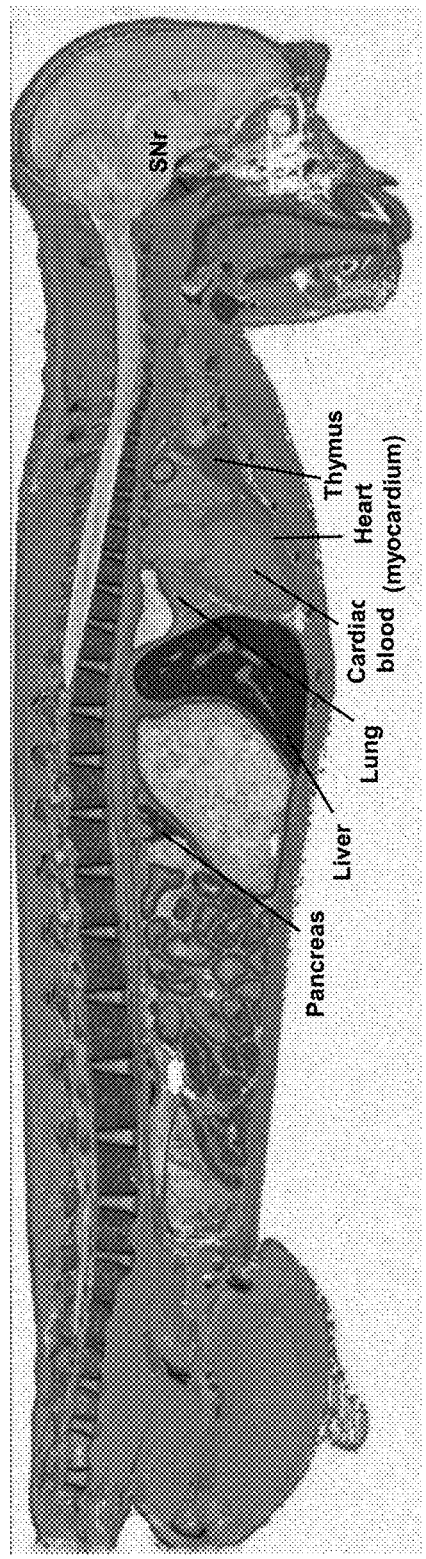
FIG. 10A and FIG. 10B are autoradiographs that depict representative tissue distribution of total radioactivity in sagittal sections of Animal 101 following a single intravenous 5 mg/kg bolus of [$^{14}$C]-Compound 1. Any grey signal above background indicates presence of compound in tissues.
Figure 10B:
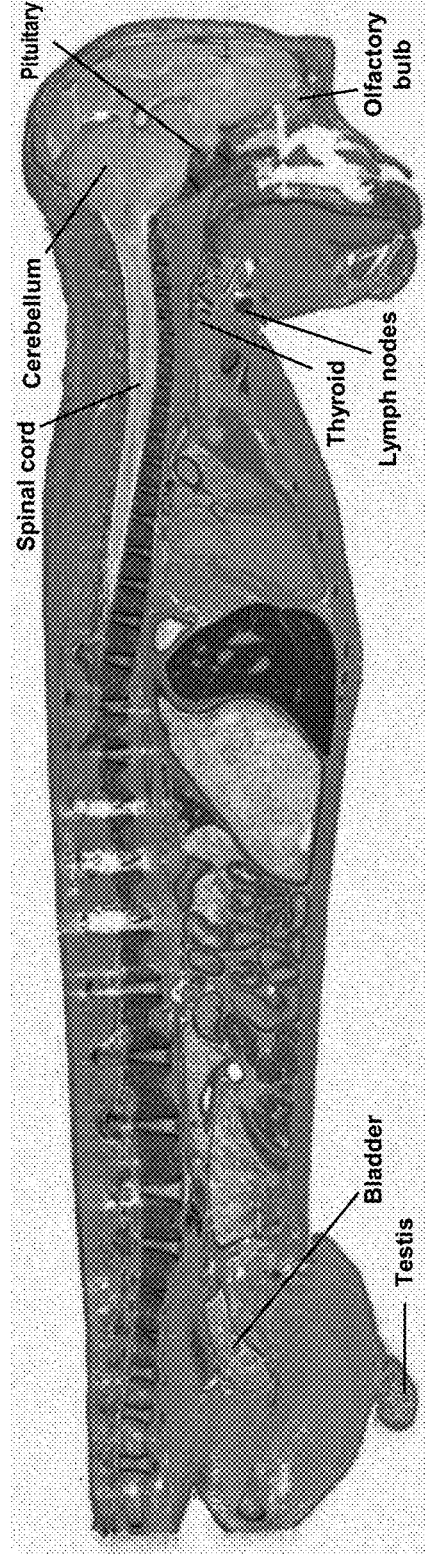

Tissue concentrations and T/B values are also graphically presented in FIG. 3-6, respectively. FIG. 3 and FIG. 4 illustrate concentrations of total radioactivity in representative organs and tissues at various times following single intravenous bolus of [$^{14}$C]-Compound 1 to male cynomolgus monkeys at 5 mg/kg. FIG. 5 and FIG. 6 illustrate tissue to blood ratios at various times following single intravenous bolus of radiocarbon-Compound 1 ([$^{14}$C]-Compound 1) to male cynomolgus monkeys at 5 mg/kg.

Figure 11:
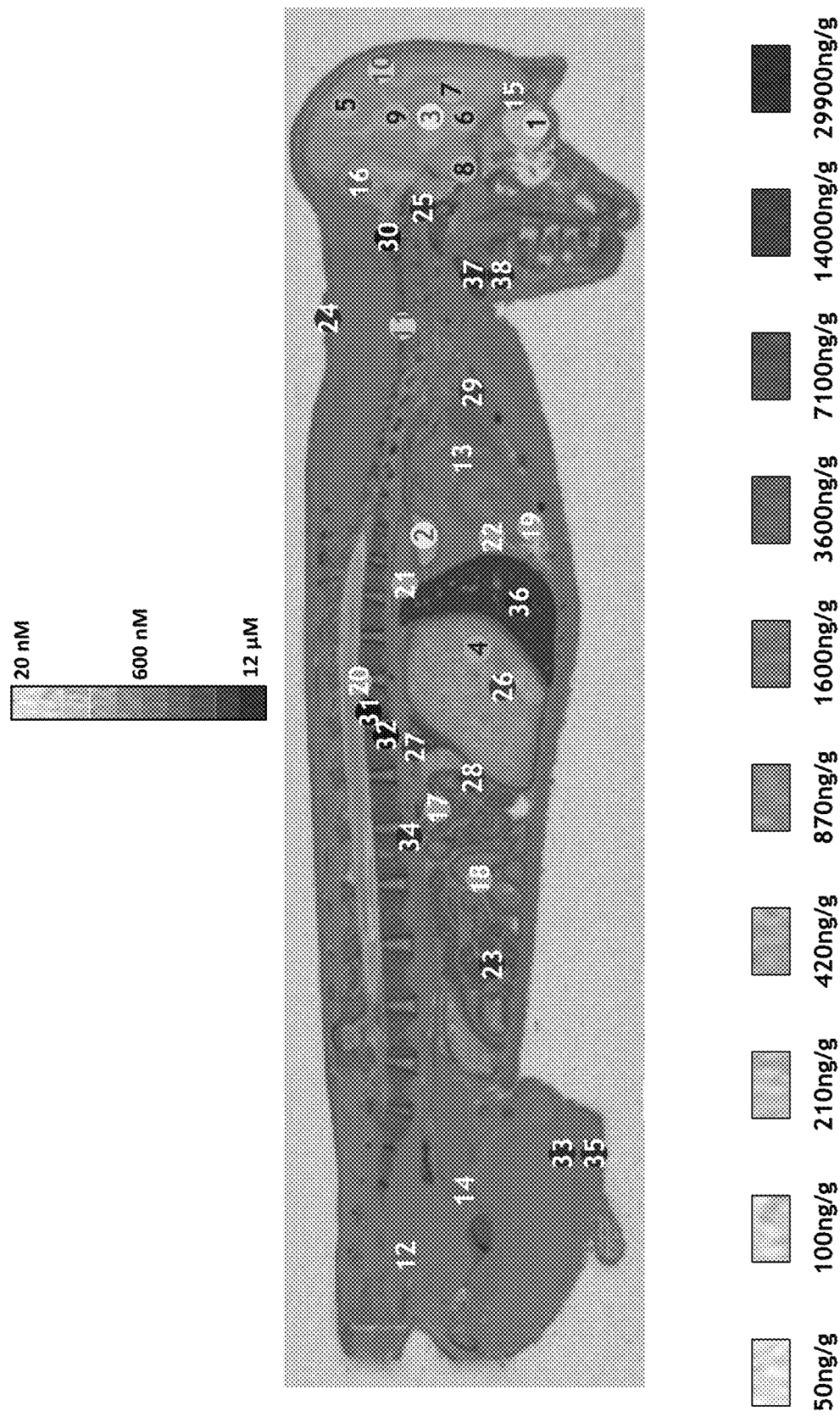
FIG. 11 is an autoradiograph that depicts representative tissue distribution of total radioactivity in a mid-sagittal section of Animal 101 following a single intravenous 5 mg/kg bolus of [$^{14}$C]-Compound 1. Any grey signal above background indicates presence of compound in tissues.

FIG. 7A, FIG. 7B, FIG. 8A, FIG. 8B, FIG. 9A, FIG. 9B, FIG. 10A, and FIG. 10B, are autoradiographs that depict representative tissue distribution of total radioactivity in midsagittal parasagittal sections of Animal 101 following a single intravenous 5 mg/kg bolus of [$^{14}$C]-Compound 1. Any grey signal above background indicates presence of compound in tissues. FIG. 11 is an autoradiograph that depicts representative tissue distribution of total radioactivity in a mid-sagittal section of Animal 101 following a single intravenous 5 mg/kg bolus of [$^{14}$C]-Compound 1. Approximate concentrations of [$^{14}$C]-Compound 1 in labelled regions of FIG. 11 are as follows: 50 ng/g: 1 (Eye); 100 ng/g: 2 (Trachea), 3 (TA); 210 ng/g: 4 (Stomach), 5 (Brain), 6 (Putamen), 7 (Caudate), 8 (Substantia Nigra), 9 (Lateral Ventricle); 420 ng/g: 10 (Cortex), 11 (Spiral cord); 870 ng/g: 12 (Skeletal muscle), 13 (Lung), 14 (Bladder), 15 (Olfactory bulb), 16 (Cerebellum); 1600 ng/g: 17 (Kidney medulla), 18 (Intestine), 19 (Heart (myocardium)), 20 (Spinal cord), 21 (Aorta), 22 (Cardiac blood); 3600 ng/g: 23 (Mesenteric lymph nodes), 24 (Skin), 25 (Pituitary); 7100 ng/g: 26

(Spleen), 27 (Adrenal gland), 28 (Pancreas), 29 (Thymus); 14000 ng/g: 30 (Parotid), 31 (Bone marrow), 32 (Cartilage); 29900 ng/g: 33 (Bone), 34 (Kidney Cortex), 35 (Cartilage (joint)), 36 (Liver), 37 (Salivary glands), 38 (Lymph nodes).

Figures 12A, 12B:
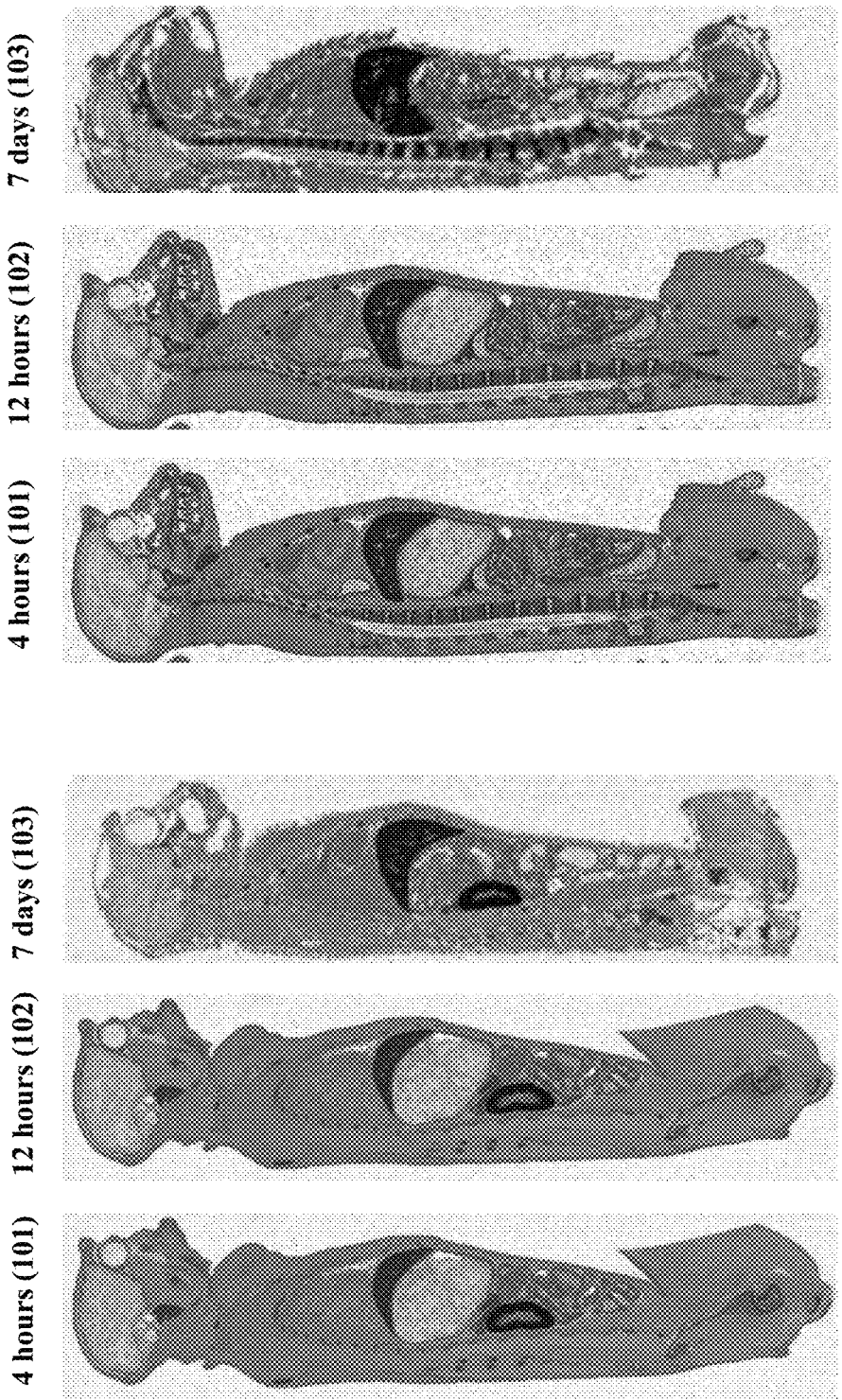
FIG. 12A and FIG. 12B are autoradiographs that depict representative tissue distribution of total radioactivity in sagittal sections of Animal 101 (4 hours post dose), Animal 102 (12 hours post dose), Animal 103 (7 days post dose) following a single intravenous 5 mg/kg bolus of [$^{14}$C]-Compound 1. Any grey signal above background indicates presence of compound in tissues.

FIG. 12A and FIG. 12B are autoradiographs that depict representative tissue distribution of total radioactivity in sagittal sections of Animal 101 (4 hours post dose), Animal 102 (12 hours post dose), Animal 103 (7 days post dose) following a single intravenous 5 mg/kg bolus of [$^{14}$C]-Compound 1. Any grey signal above background indicates presence of compound in tissues.

Figure 13:
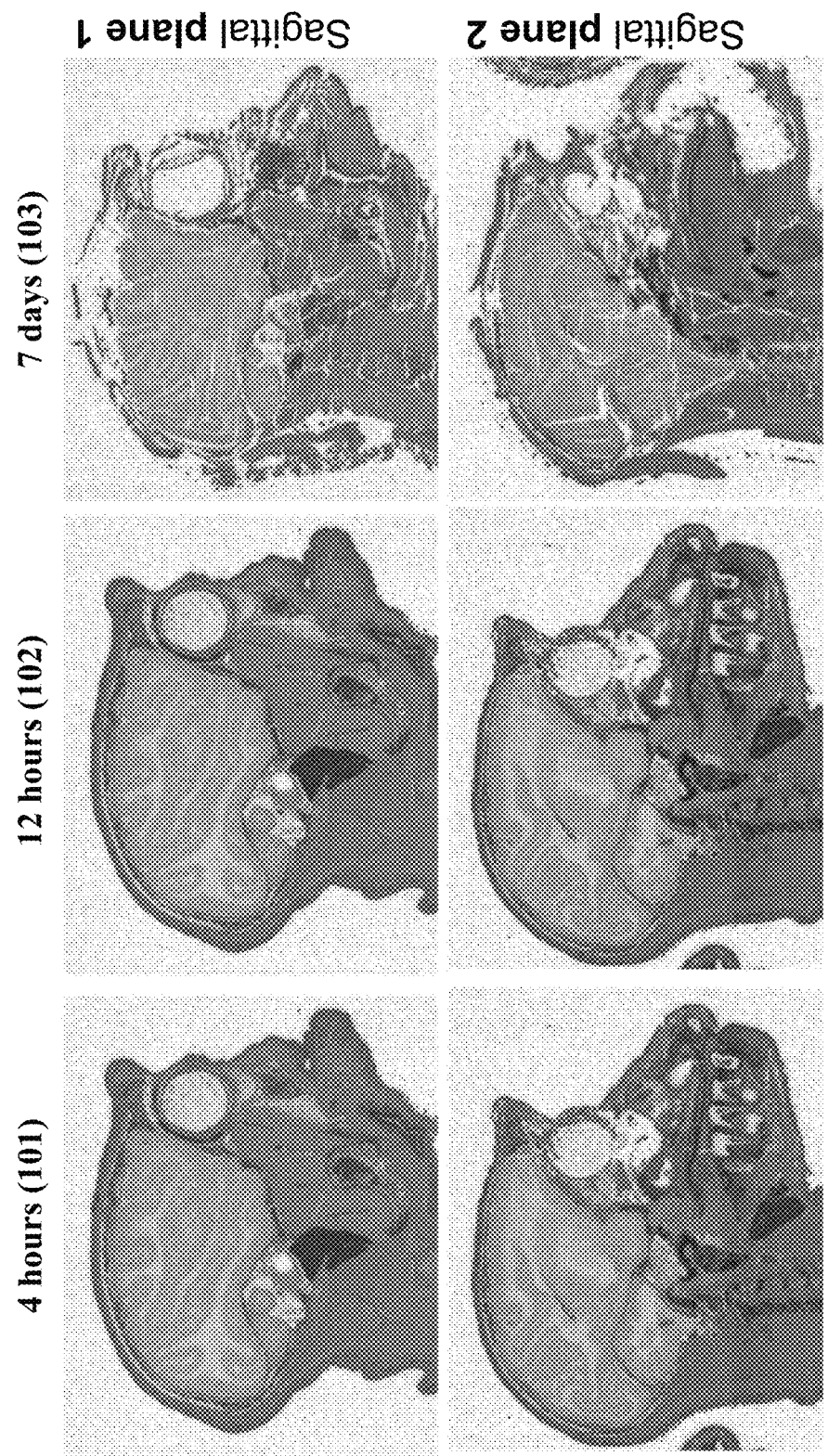
FIG. 13 are autoradiographs that depict representative cranial tissue distribution of total radioactivity in selected sagittal sections of Animal 101 (4 hours post dose), Animal 102 (12 hours post dose), Animal 103 (7 days post dose) following a single intravenous 5 mg/kg bolus of [$^{14}$C]-Compound 1. Any grey signal above background indicates presence of compound in tissues.

FIG. 13 are autoradiographs that depict representative cranial tissue distribution of total radioactivity in selected sagittal sections of Animal 101 (4 hours post dose), Animal 102 (12 hours post dose), Animal 103 (7 days post dose) following a single intravenous 5 mg/kg bolus of [$^{14}$C]-Compound 1. Any grey signal above background indicates presence of compound in tissues.

Figure 14:
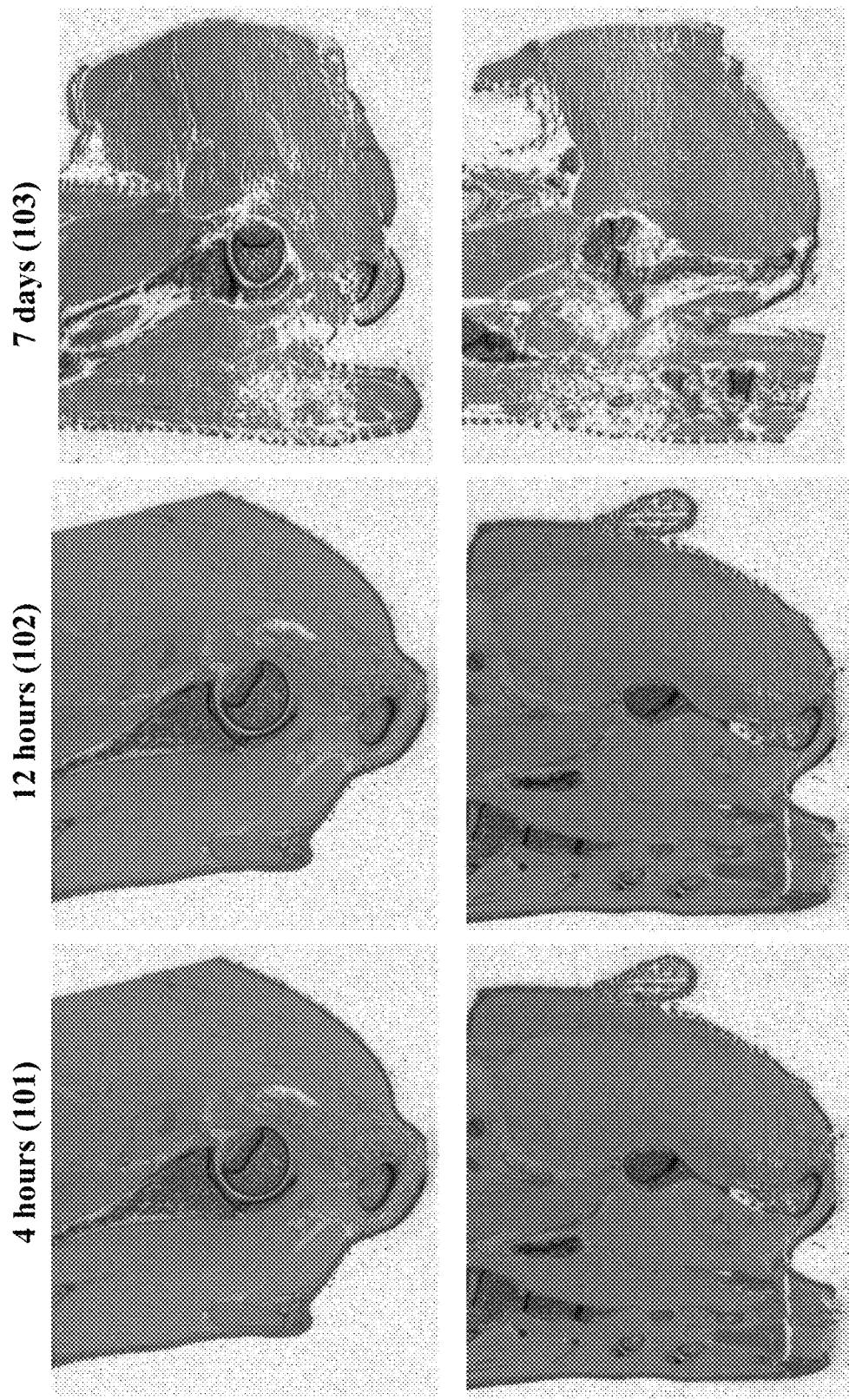
FIG. 14 are autoradiographs that depict representative pelvic-area tissue distribution of total radioactivity in selected sagittal sections of Animal 101 (4 hours post dose), Animal 102 (12 hours post dose), Animal 103 (7 days post dose) following a single intravenous 5 mg/kg bolus of [$^{14}$C]-Compound 1. Any grey signal above background indicates presence of compound in tissues.

FIG. 14 are autoradiographs that depict representative pelvic-area tissue distribution of total radioactivity in selected sagittal sections of Animal 101 (4 hours post dose), Animal 102 (12 hours post dose), Animal 103 (7 days post dose) following a single intravenous 5 mg/kg bolus of [$^{14}$C]-Compound 1. Any grey signal above background indicates presence of compound in tissues.

Within 4 hours of IV administration, radioactivity quickly and widely distributed in all tissues investigated, with the vast majority of tissues containing concentrations higher than in blood (1261 ng-eq/g).

The highest tissue concentrations at 4 hours post-dose were observed in the kidney cortex (125167 ng-eq/g, T/B 99.3), joints (likely connected with cartilage, 59612 ng-eq/g, T/B 47.3), and liver (34695 ng-eq/g, T/B 27.5).

At this timepoint, several tissues showed a T/B≥5: salivary glands (parotid T/B 14.2; others T/B 12.0), bone surface and pancreas (T/B 13.9), hair follicles (T/B 11.7), large intestine mucosa (T/B 9.8), aortic wall (T/B 9.3), small intestine mucosa (T/B 8.3), adrenal cortex (T/B 8.2), stomach mucosa (T/B 7.2), spleen (T/B 6.6), bone marrow (T/B 5.9), and lymph nodes (T/B 5.8).

At 12 h after dosing, concentrations were generally comparable to those observed at the previous timepoint. At this timepoint, kidney cortex (145490 ng-eq/g, T/B 99.1), joints (130483 ng-eq/g, T/B 88.9), and liver (56919 ng-eq/g, T/B 38.8) were still the most exposed tissues and attained the highest concentration.

At this timepoint, several tissues showed a T/B≥5: salivary glands (parotid T/B 13.3; others T/B 9.1), pancreas (T/B 6.8), adrenal cortex and stomach mucosa (T/B 10.9), small intestine mucosa (T/B 10.5), hair follicles (T/B 10.3), lymph nodes (T/B 9.6), bone marrow (T/B 9.2), large intestine mucosa (T/B 8.9), aortic wall and spleen (T/B 6.3), adrenal medulla (T/B 5.3), and thymus (T/B 5.2), compared to a cardiac blood concentration of 1468 ng-eq/g.

At 168 h post-dose, concentrations generally declined to concentrations comparable to that in blood (1642 ng-eq/g). The highest concentrations were observed in kidney cortex (103160 ng-eq/g, T/B 62.8), joints (47762 ng-eq/g, T/B 88.9), and liver (51575 ng-eq/g, T/B 31.4). The observations suggested potential accumulation in these tissues. Moreover, at this timepoint, other tissues showed notable distribution (5<T/B<3): adrenal gland, bone marrow, spleen, and lymph nodes.

[$^{14}$C]-Compound 1 showed moderate brain penetration (T/B<1) and appeared to distribute uniformly throughout the tissue and in all sub-regions analyzed (cerebellum, olfactory bulb, thalamus, caudate putamen, cerebral cortex, and substantia nigra). The highest concentrations were measured in the lateral ventricle instead: 3763, 3781, 2868 ng-eq/g at 4, 12, and 168 h post-dose, respectively. This radioactivity was most likely connected to the choroid plexus within the ventricle.

[$^{14}$C]-Compound 1 approximately equally partitioned between blood and uveal tract (choroid+retinal pigmented epithelium) in the eye (2416 ng-eq/g (T/B 1.9), 2366 ng-eq/g (T/B 1.6), 1286 ng-eq/g (T/B 0.8) at 4, 12, and 168 h post-dose, respectively). These observations indicated potential melanin binding. Consistently, high concentrations were also measured in the hair follicles.

Conclusions

Following IV bolus administration of [$^{14}$C]-Compound 1 to male Cynomolgus monkeys only 4.2% of the administered dose was excreted over 168 h post-dose: 1.5% of the dose was recovered in urine and 1.7% in feces. Cage rinse, which relates to urinary excretion, accounted for another 0.9% of the dose.

Total drug-related radioactivity in blood and plasma was quantifiable up to the terminal timepoint in all animals.

Over 168 h post dose (Animal 103), systemic exposure to total radioactivity, measured as $AUC_{0-t}$, was 231000 and 205000 h·ng-eq/g in blood and plasma, respectively, while total radioactivity $C_{max}$ was 7510 ng-eq/g ($C_0$ 9260 ng-eq/g) and 11500 ng-eq/g ($C_0$ 14000 ng-eq/g), respectively.

[$^{14}$C]-Compound 1 showed moderate (0.6 to 5 L/kg) volume of distribution and low clearance, thus the elimination half-life $T_{1/2}$ could not be reliably calculated. $T_{1/2}$ estimates were 229 and 141 h in blood and plasma, respectively.

Total radioactivity tended to partition into plasma (blood to plasma ratio 0.6-0.8) except for 168 h, where a ratio of 2.1 was observed.

In general, [$^{14}$C]-Compound 1 drug-related material was widely distributed throughout the whole body and quantifiable in all tissues up to the last timepoint sampled. The distribution pattern in tissues was comparable between selected timepoints over 168 h post-dose. Very high concentrations were observed in kidney cortex, joints (most likely connected to cartilage), and liver, suggesting potential accumulation in these tissues.

Other tissues that showed notable uptake were salivary glands, bone surface, pancreas, hair follicles, large intestine mucosa, aortic wall, small intestine mucosa, adrenal gland, stomach mucosa, spleen, bone marrow, lymph nodes, and thymus.

Moderate brain penetration was observed (brain to blood ratio<1): total radioactivity distributed quite uniformly in relevant sub-regions (cerebellum, olfactory bulb, thalamus, caudate putamen, cerebral cortex, and substantia nigra), but the highest concentrations were measured in the lateral ventricle, most likely in the choroid plexus.

Finally, radioactivity was also measured in tissues containing melanin (e.g., hair follicles and the uveal tract in the eye), indicating potential binding to melanin.

Example 3. In Vivo Pharmacokinetic and Tissue Distribution Study Following Single Intracerebroventricular Administration of Compound 1 in Male and Female C57BL6J Mouse The objective of this study was to assess the pharmacokinetics and tissue distribution of Compound 1 in male and female C57BL6J mice following single intracerebroventricular (ICV) administration at 0.6, 1, and 2 mg/kg. One-hundred male and ninety-six female naïve C57BL6J mice received Compound 1 at 0.3 mg/kg, (n=24 males and 32 females) or at 0.6 mg/kg (n=32 males and 32 females) or at 1 mg/kg (n=32 males and 32 females) or at 2 mg/kg (n=12 males).

One-hundred male and ninety-six female naïve C57BL6J mice received Compound 1 at 0.3 mg/kg, (n=24 males and 32 females) or at 0.6 mg/kg (n=32 males and 32 females) or at 1 mg/kg (n=32 males and 32 females) or at 2 mg/kg (n=12 males).

Due to severe clinical signs observed in males dosed at 2 mg/kg, the treatment was stopped after the dosing of 12 males (4 for each timepoint up to 8 hours). The dose of 2 mg/kg was replaced by a dose of 0.3 mg/kg. In the brain of animals given 2 mg/kg, the concentration at 8 hours after dosing was 3-fold higher than the concentration measured at the same timepoint in animals given 1 mg/kg and 1.7-fold higher than $C_{max}$ observed in males given 1 mg/kg.

Following a single ICV administration of Compound 1 at 0.3, 0.6, and 1 mg/kg to male and female mice, Compound 1 was quantifiable up to 648 hours after dosing (last collected PK timepoint) in the brain across doses and in the heart at 0.3 mg/kg only in both sexes and up to at least 312 hours after dosing in the spleen across doses in both sexes. The result indicated accumulation of test item in these tissues. Generally, Compound 1 was not quantifiable in plasma, intestine, liver, lung, kidney, and muscle across doses and in both sexes.

Maximum concentration occurred between 1.5 and 48 hours after dosing in brain and between 4 and 48 hours in spleen in both sexes and across dose range evaluated. Maximum concentration occurred at 24 and 48 hours after dosing in heart in females and males, respectively.

Mean composite $C_{max}$ in the female and male brain was 3930 ng/mL and 3110 ng/mL at 0.3 mg/kg, 11400 ng/mL and 6490 ng/mL at 0.6 mg/kg, and 21500 ng/mL and 15500 ng/mL at 1 mg/kg, respectively. Mean composite $AUC_{last}$ in the female and male brain was 1800000 ng·h/mL and 1440000 ng·h/mL at 0.3 mg/kg, 2360000 ng·h/mL and 2470000 ng·h/mL at 0.6 mg/kg, and 7150000 ng·h/mL and 5530000 ng·h/mL at 1 mg/kg, respectively.

Mean composite $C_{max}$ in the female and male spleen was 586 ng/mL and 756 ng/mL at 0.3 mg/kg, 984 ng/mL and 1530 ng/mL at 0.6 mg/kg, and 2270 ng/mL and 2940 ng/mL at 1 mg/kg, respectively. Mean composite $AUC_{last}$ in the female and male spleen was 96500 ng·h/mL and 48300 ng·h/mL at 0.3 mg/kg, 98300 ng·h/mL and 166000 ng·h/mL at 0.6 mg/kg, and 449000 ng·h/mL and 1010000 ng·h/mL at 1 mg/kg, respectively.

Mean composite $C_{max}$ in the female and male heart was 729 ng/mL and 416 ng/mL and mean composite $AUC_{last}$ in the female and male heart was 184000 ng·h/mL and 160000 ng·h/mL, respectively.

Following ICV administration of Compound 1, for an increase in dose from 0.3 to 1 mg/kg, the exposure (as mean composite $C_{max}$ and $AUC_{last}$) increased in brain in a proportional way as $AUC_{last}$ and slightly supra-proportionally as $C_{max}$ and in spleen in a proportional way as mean composite $C_{max}$ and supra-proportionally as mean composite AUC in both sexes.

Generally, no notable (where notable is >2-fold) gender differences in systemic exposure in brain across dose range evaluated and in heart at 0.3 mg/kg was observed, although $C_{max}$ in heart was higher in females than in males.

No notable gender differences in $C_{max}$ in spleen was observed across dose range evaluated and in AUC at 0.3 mg/kg, whilst AUC was higher in males than females at 0.6 and 1 mg/kg. This difference (as $AUC_{0-312}$) was notable at 0.6 mg/kg.

Following a single ICV administration of Compound 1 at 2 mg/kg to male mice, Compound 1 was quantifiable in the spleen and liver up to 8 hours after dosing (last collected PK timepoint), in the intestine, kidney, and lung only at 8 hours after dosing, in plasma only at 4 hour after dosing. The compound was not quantifiable in muscle and heart in both sexes.

Following a single ICV administration of Compound 1 at 0.3, 0.6, and 1 mg/kg to male and female mice, Compound 1 was not quantifiable in urine and feces across doses and in both sexes.

Test and Control Items
Test Item.
   Compound 1
   Purity: >90%
   Storage Conditions: −80° C.
Vehicle.
   DPBS: Dulbecco's Phosphate Buffered Saline (modified, without calcium chloride and magnesium chloride, liquid, sterile-filtered).
   pH 7.1-7.5.
   Osmolality: 275-304 mOs/kg.
   Storage Conditions: Below 30° C. (Ambient temperature, AT), 2-8° C. when opened.
Test Item Formulation.
   Concentrations: 1.5 mg/mL, 3 mg/mL, 5 mg/mL, and 10 mg/mL (nominal concentrations)
   Method: The test item was dissolved in the vehicle. The formulation was prepared dissolving the received amount of test item in the required amount of vehicle. A stock formulation at 10 mg/mL was prepared in advance and divided in aliquots. Each aliquot was then diluted at the different needed concentrations for each administration route. The dilutions were prepared before the first day of administration for each session of administration/route. On the day of preparation of the dilutions, the stock formulation was thawed at AT and heated at approx. 65° C. for 5 minutes, then allowed to cool to room temperature before use. After stirring the formulation was used for the dilutions. The diluted formulations were stored at AT (at least three days) in Dispensary and used according to the scheduled timepoints.
   pH Range (measured only after the first preparation): 1.5 mg/mL: 6.75; 3 mg/mL: 6.68; 5 mg/mL: 6.26; 10 mg/mL: 3.75.
   Stability of the Stock at 10 mg/mL: at least 4 weeks at −80° C. and at least 4 days at AT.
   Stability of the diluted formulations: maximum 4 days at AT for the diluted formulations.
   Residual Test Item Formulations: residual formulations were discarded at the end of the dosing.
Test System
   Mouse C57BL6J
   Number on Study: 100 male and 96 female mice
   Approximate Body Weight on Day 1: 20-25 gr
   Type of Accommodation: Solid bottom plastic cages containing sawdust litter.
   Number per Cage: 4 of the same sex, treatment group, and timepoint per cage.
   Minimum Acclimatization: At least 5 days (prior to dosing).
Diet, Water, and Environmental Enrichment.
   Diet Type: Rat and mouse maintenance diet Altromin-1324.

Water Source: Filtered from normal domestic supply.

Husbandry: Standard (as per internal Standard Operating Procedures).

Temperature Range: 20-22° C. (19-23° C. for less than 24 hours acceptable).

Relative Humidity Range: 45-65% (40-70% for less than 24 hours acceptable).

Lighting: Fluorescent lighting from approximately 06:00 to 18:00 hours daily.

Environmental Enrichment: 1 irradiated Iso-blox/5 animals, 1 fun-tunnel/cage, and 1 mouse house/cage.

Experimental Design

The study design included 100 male and 96 female naïve C57BL6J mice and four dose levels (0.3, 0.6, 1, and 2 mg/kg). Thirty-two males and 32 females received each a single ICV administration of Compound 1 at 0.6 and 1 mg/kg. Twelve males received each a single ICV administration of Compound 1 at 2 mg/kg and twenty-four males and 32 females received each a single ICV administration of Compound 1 at 0.3 mg/kg. Mice were anaesthetized with isofluorane and the skin incised in the upper part of the skull to make the bregma visible. The injection into the intracerebral ventricle was performed using a microsyringe equipped with a 27G needle. At the end of the administration, the skin was sutured. An anesthetic ointment was applied to the skin of the skull to limit the pain resulting from the incision. Dosing was performed in the presence of a veterinary to observe whether any clinical signs were noted.

For each dose level four males (three males for group 4) and four females were euthanized at the following timepoints: 1.5, 4, 8, 24 hours, 3 days, 7 days, 14 days, and 28 days post-dosing.

From each animal, blood samples were collected through the cava vein in a composite scheme and at necropsy the following tissues were collected: brain, liver, lung, kidney, heart, small intestine, spleen, and skeletal muscle.

In addition, the same animals that were euthanized at 24 hours, 3 days, 7 days, 14 days, and 28 days post-dosing were placed in metabolic cage twenty-four hours before euthanasia for collection of urine and feces in order to collect 1 pooled (n=4, with the exception of males of Group 4 for which n=3) urine and 1 pooled (n=4, with the exception of males of Group 4 for which n=3) fecal samples per timepoint/sex/dose level.

Methods and Procedures

Formulation of Test Substance.

The dose formulation was administered by volume. The dose volume administered was 5 µL/mice. Formulations were maintained at ambient room temperature up to the end of the dosing procedure. The target dose levels are detailed in TABLE 12.

TABLE 12

| Group | Sex | Animal Number | Dose* (mg/kg) | Dose* Concentration (mg/mL) | Dose Volume (µL/mice) |
|---|---|---|---|---|---|
| 1 | M | 1-32 | 0.6 | 3 | 5 |
|   | F | 33-64 |   |   |   |
| 2 | M | 65-96 | 1 | 5 | 5 |
|   | F | 97-128 |   |   |   |
| 3 | M | 129-140 | 2 | 10 | 5 |
| 4 | M | 141-160; 193-196 | 0.3 | 1.5 | 5 |
|   | F | 161-192 |   |   |   |

*Expressed in terms of the parent compound

Dose Administration.

The dose formulation was administered via ICV route. Mice were anaesthetized with isofluorane and the skin incised in the upper part of the skull to make the bregma visible. The injection into the intracerebral ventricle was performed using a microsyringe equipped with a 27G needle. At the end of the administration, the skin was sutured. An anesthetic ointment was applied to the skin of the skull to limit the pain resulting from the incision.

No dose analysis was performed in the study; therefore, the nominal doses are reported.

Sample Collection and Handling.

Plasma.

After test item administration, terminal blood samples were collected from cava vein of each animal at the following timepoints:

Day 1: 1.5 hour, 4 hours, 8 hours and 24 hours after dosing;
Day 3 corresponding to 48 hours after dosing;
Day 7 corresponding to 144 hours after dosing;
Day 14 corresponding to 312 hours after dosing; and
Day 28 corresponding to 648 hours after dosing.

Approximately 0.4-0.5 mL blood was collected into tubes containing anticoagulant ($K_3$EDTA), gently mixed and placed on crushed wet ice and then spun by centrifuge (2000 g at +4° C. for 10 minutes) as soon as practicable. The resultant plasma was separated from the erythrocyte pellet and then transferred to uniquely labelled clear polypropylene tubes and frozen immediately over solid carbon dioxide or in a freezer at nominally −80° C.

Tissues.

After test item administration, brain including cerebellum, liver, lung, kidneys (both), heart, small intestine, spleen, and skeletal muscle were collected from each animal at the following timepoints:

Day 1: 1.5 hour, 4 hours, 8 hours, and 24 hours after dosing;
Day 3 corresponding to 48 hours after dosing;
Day 7 corresponding to 144 hours after dosing;
Day 14 corresponding to 312 hours after dosing; and
Day 28 corresponding to 648 hours after dosing.

Gall bladder was removed from the liver before organ weight. Small intestine was flushed with saline solution. Quadriceps femoris muscle from both legs were collected.

Each tissue was weighed, and the weight was recorded. Tissue samples were rinsed in saline solution, transferred in polypropylene tubes or wrapped in aluminum foils and immediately frozen at −80° C.

Urine and Feces.

Urine and feces were obtained from 4 males (except for Group 4 for which urine and feces were obtained from 3 males) and 4 females placed in metabolic cages (food and water were left ad libitum) over 24 hours before euthanasia at the following timepoints:

Day 1: 24 hours after dosing;
Day 3 corresponding to 48 hours after dosing;
Day 7 corresponding to 144 hours after dosing;
Day 14 corresponding to 312 hours after dosing; and
Day 28 corresponding to 648 hours after dosing.

Urine and feces were collected in plastic tubes and frozen over solid carbon dioxide or in a freezer at −80° C. (nominal).

Storage of Samples.

All plasma samples were transported frozen and stored at nominally −80° C. until analyzed.

Sample Preparation and Analysis.

Samples were assayed for Compound 1 using a qualified method based on protein precipitation followed by LC-MS/MS analysis.

Data Handling and Analysis

All computations utilized nominal sampling timepoints and nominal doses.

Individual data points at the same nominal time were averaged and then a composite concentration-time profile was constructed for each sex at each dose level. Pharmacokinetic (PK) analysis was performed on the mean concentration-time profile and the resultant composite PK parameters were reported.

The following parameters were reported:

Nominal dose levels (expressed as mg/kg).

Compound 1 plasma and tissue concentrations (expressed as ng/mL).

Plasma and tissue PK elaboration were performed by non-compartmental pharmacokinetics analysis using Phoenix WinNonlin. The following parameters for test item, when feasible, were determined using the linear logarithmic trapezoidal rule:

$AUC_{last}$=area under the plasma concentration time curve (AUC) from the time of dosing to the last measurable concentration (expressed as ng·h/mL)

$C_{max}$=maximum observed plasma concentration (expressed as ng/mL)

$T_{max}$=time of maximum observed plasma concentration (expressed as hours)

$T_{last}$=time of last measurable plasma concentration (expressed as hours)

$t_{1/2}$=apparent terminal elimination half-life; $t_{1/2}$ data will be reported if $r^2$ was ≥0.9 (when rounded to one decimal place) and the λ period [(λz_upper−λz_lower)/t½] values will be >2.

Plasma concentrations and PK parameters are expressed in terms of Compound as parent compound. Doses and temperatures are reported as nominal. The numerical data presented in this report are computer generated.

Not quantifiable (NQ) values at early timepoints up were set to zero and included in the profiles, otherwise removed. Not quantifiable (NQ) values were treated as follows in the calculation of the composite mean concentration values:

set to zero and included in the mean calculation: where the resulting mean was below the LLQ, NQ was reported as mean value for inclusion in the composite profile, if not, the numeric mean value was reported.

if all results were NQ (or some were NA, NR, IS), NQ was reported as mean value.

For the composite PK elaboration, mean NQ values were set to zero and included in the profiles at early timepoints but otherwise removed.

$AUC_{last}$ and $C_{max}$ values were reported with three significant digits; $T_{max}$ and $T_{last}$ were displayed as the corresponding nominal times.

Results

In Life Observations.

Mortality/Morbidity.

Two females (No. 62; Group 1, 0.6 mg/kg and No. 120; Group 2, 1 mg/kg) and two males (Nos. 92 and 94; Group 2, 1 mg/kg) were found dead on Day 6. Two males (Nos. 96 and 89; Group 2, 1 mg/kg) were found dead on Day 12 and 13, respectively. Four females (Nos. 103, 106, 118, and 119; Group 2, 1 mg/kg) and two males (Nos. 136, 138; group 3, 2 mg/kg) were euthanized on Day 1 for human reasons. The animals showed hyperexcitability, locomotor ataxia, and convulsions.

One female (No. 125; Group 2; 1 mg/kg) was euthanized for human reason on Day 9. The animal showed piloerection, significant weight loss, and lack of movement. Three females (No. 58; Group 1; 0.6 mg/kg; Nos. 122 and 128; Group 2; 1 mg/kg) were euthanized for human reasons on Day 10. The animals showed piloerection, significant weight loss and lack of movement.

Seven males (Nos. 129, 130, 131, 132, 134, 135, and 140; Group 3, 2 mg/kg) showed hyperexcitability, locomotor ataxia, tremors, accelerated and jerky walking, and circular movements. These clinical signs were observed immediately after waking up from anesthesia and lasted until the time of scheduled necropsy (1.5, 4, and 8 hours, respectively). One male (No. 139; Group 3, 2 mg/kg) showed difficulty in waking up from anesthesia and reacted slowly only when stimulated. The animal showed circular movements to the left. Two males (Nos. 85 and 87; Group 2; 1 mg/kg) showed reduced locomotor activity, hunched posture, and mild piloerection. One male (No. 6, Group 1; 0.6 mg/kg) showed head tilted to the right upon awakening.

Pharmacokinetics Analysis.

Summaries of plasma pharmacokinetic parameters in C57BL6J mice are presented in TABLE 13, and tissue pharmacokinetic parameters in TABLE 14.

TABLE 13

| Dose (mg/kg) | $T_{max}$ (h) | $C_{max}$ (ng/mL) | $AUC_{last}$ (ng · h/mL) | $T_{last}$ (h) | $t_{1/2}$ (h) |
|---|---|---|---|---|---|
| Males | | | | | |
| 0.3 | NC | NC | NC | NC | NC |
| 0.6 | NC | NC | NC | NC | NC |
| 1 | NC | NC | NC | NC | NC |
| Females | | | | | |
| 0.3 | NC | NC | NC | NC | NC |
| 0.6 | NC | NC | NC | NC | NC |
| 1 | NC | NC | NC | NC | NC |

NC = Not Calculable

TABLE 14

| | Brain | | | | |
|---|---|---|---|---|---|
| | Male | | | | |
| Dose (mg/kg) | $T_{max}$ (h) | $C_{max}$ (ng/mL) | $AUC_{last}$ (ng · h/mL) | $T_{last}$ (h) | $t_{1/2}$ (h) |
| 0.3 | 1.5 | 3110 | 1440000 | 648 | 2289.43* |
| 0.6 | 4 | 6490 | 2470000 | 648 | 1989.19* |
| 1 | 24 | 15500 | 5530000 | 648 | 1072.46* |

TABLE 14-continued

|  | Female | | | | |
|---|---|---|---|---|---|
| Dose (mg/kg) | $T_{max}$ (h) | $C_{max}$ (ng/mL) | $AUC_{last}$ (ng · h/mL) | $T_{last}$ (h) | $t_{1/2}$ (h) |
| 0.3 | 48 | 3930 | 1800000 | 648 | 3085.79* |
| 0.6 | 1.5 | 11400 | 2360000 | 648 | 4810.18* |
| 1 | 8 | 21500 | 7150000 | 648 | 736.22* |

*Rsq <0.9 and or Lambda factor <2. The corresponding half-life is detailed for information only.

Spleen

|  | Male | | | | |
|---|---|---|---|---|---|
| Dose (mg/kg) | $T_{max}$ (h) | $C_{max}$ (ng/mL) | $AUC_{last}$ (ng · h/mL) | $T_{last}$ (h) | $t_{1/2}$ (h) |
| 0.3 | 4 | 756 | 48300 | 144 | 111.42* |
| 0.6 | 24 | 1530 | 166000 | 312 | 168.63* |
| 1 | 48 | 2940 | 1010000 | 648 | 406.38* |

|  | Female | | | | |
|---|---|---|---|---|---|
| Dose (mg/kg) | $T_{max}$ (h) | $C_{max}$ (ng/mL) | $AUC_{last}$ (ng · h/mL) | $T_{last}$ (h) | $t_{1/2}$ (h) |
| 0.3 | 8 | 586 | 96500 | 648 | 207.37 |
| 0.6 | 24 | 984 | 98300 | 648 | 273.73* |
| 1 | 48 | 2270 | 449000 | 312 | NC |

*Rsq <0.9 and or Lambda factor <2. The corresponding half-life is detailed for information only
NC = Not Calculable Heart

|  | Male | | | | |
|---|---|---|---|---|---|
| Dose (mg/kg) | $T_{max}$ (h) | $C_{max}$ (ng/mL) | $AUC_{last}$ (ng · h/mL) | $T_{last}$ (h) | $t_{1/2}$ (h) |
| 0.3 | 48 | 416 | 160000 | 648 | 303.18* |
| 0.6 | NC | NC | NC | NC | NC |
| 1 | NC | NC | NC | NC | NC |

|  | Female | | | | |
|---|---|---|---|---|---|
| Dose (mg/kg) | $T_{max}$ (h) | $C_{max}$ (ng/mL) | $AUC_{last}$ (ng · h/mL) | $T_{last}$ (h) | $t_{1/2}$ (h) |
| 0.3 | 24 | 729 | 184000 | 648 | NC |
| 0.6 | NC | NC | NC | NC | NC |
| 1 | NC | NC | NC | NC | NC |

*Rsq <0.9 and or Lambda factor <2. The corresponding Half-life is detailed for information only
NC = Not Calculable Liver

|  | Male | | | | |
|---|---|---|---|---|---|
| Dose (mg/kg) | $T_{max}$ (h) | $C_{max}$ (ng/mL) | $AUC_{last}$ (ng · h/mL) | $T_{last}$ (h) | $t_{1/2}$ (h) |
| 0.3 | NC | NC | NC | NC | NC |
| 0.6 | NC | NC | NC | NC | NC |
| 1 | NC | NC | NC | NC | NC |

|  | Female | | | | |
|---|---|---|---|---|---|
| Dose (mg/kg) | $T_{max}$ (h) | $C_{max}$ (ng/mL) | $AUC_{last}$ (ng · h/mL) | $T_{last}$ (h) | $t_{1/2}$ (h) |
| 0.3 | NC | NC | NC | NC | NC |
| 0.6 | NC | NC | NC | NC | NC |
| 1 | NC | NC | NC | NC | NC |

NC = Not Calculable

TABLE 14-continued

| | Kidney | | | | |
|---|---|---|---|---|---|
| | Male | | | | |
| Dose (mg/kg) | $T_{max}$ (h) | $C_{max}$ (ng/mL) | $AUC_{last}$ (ng·h/mL) | $T_{last}$ (h) | $t_{1/2}$ (h) |
| 0.3 | NC | NC | NC | NC | NC |
| 0.6 | NC | NC | NC | NC | NC |
| 1 | NC | NC | NC | NC | NC |
| | Female | | | | |
| Dose (mg/kg) | $T_{max}$ (h) | $C_{max}$ (ng/mL) | $AUC_{last}$ (ng·h/mL) | $T_{last}$ (h) | $t_{1/2}$ (h) |
| 0.3 | NC | NC | NC | NC | NC |
| 0.6 | NC | NC | NC | NC | NC |
| 1 | NC | NC | NC | NC | NC |

NC = Not Calculable

| | Intestine | | | | |
|---|---|---|---|---|---|
| | Male | | | | |
| Dose (mg/kg) | $T_{max}$ (h) | $C_{max}$ (ng/mL) | $AUC_{last}$ (ng·h/mL) | $T_{last}$ (h) | $t_{1/2}$ (h) |
| 0.3 | NC | NC | NC | NC | NC |
| 0.6 | NC | NC | NC | NC | NC |
| 1 | NC | NC | NC | NC | NC |
| | Female | | | | |
| Dose (mg/kg) | $T_{max}$ (h) | $C_{max}$ (ng/mL) | $AUC_{last}$ (ng·h/mL) | $T_{last}$ (h) | $t_{1/2}$ (h) |
| 0.3 | NC | NC | NC | NC | NC |
| 0.6 | NC | NC | NC | NC | NC |
| 1 | NC | NC | NC | NC | NC |

NC = Not Calculable

| | Lung | | | | |
|---|---|---|---|---|---|
| | Male | | | | |
| Dose (mg/kg) | $T_{max}$ (h) | $C_{max}$ (ng/mL) | $AUC_{last}$ (ng·h/mL) | $T_{last}$ (h) | $t_{1/2}$ (h) |
| 0.3 | NC | NC | NC | NC | NC |
| 0.6 | NC | NC | NC | NC | NC |
| 1 | NC | NC | NC | NC | NC |
| | Female | | | | |
| Dose (mg/kg) | $T_{max}$ (h) | $C_{max}$ (ng/mL) | $AUC_{last}$ (ng·h/mL) | $T_{last}$ (h) | $t_{1/2}$ (h) |
| 0.3 | NC | NC | NC | NC | NC |
| 0.6 | NC | NC | NC | NC | NC |
| 1 | NC | NC | NC | NC | NC |

NC = Not Calculable

TABLE 14-continued

| | | | Muscle | | |
|---|---|---|---|---|---|
| | | | Male | | |
| Dose (mg/kg) | $T_{max}$ (h) | $C_{max}$ (ng/mL) | $AUC_{last}$ (ng·h/mL) | $T_{last}$ (h) | $t_{1/2}$ (h) |
| 0.3 | NC | NC | NC | NC | NC |
| 0.6 | NC | NC | NC | NC | NC |
| 1 | NC | NC | NC | NC | NC |
| | | | Female | | |
| Dose (mg/kg) | $T_{max}$ (h) | $C_{max}$ (ng/mL) | $AUC_{last}$ (ng·h/mL) | $T_{last}$ (h) | $t_{1/2}$ (h) |
| 0.3 | NC | NC | NC | NC | NC |
| 0.6 | NC | NC | NC | NC | NC |
| 1 | NC | NC | NC | NC | NC |

NC = Not Calculable

Figure 15A:
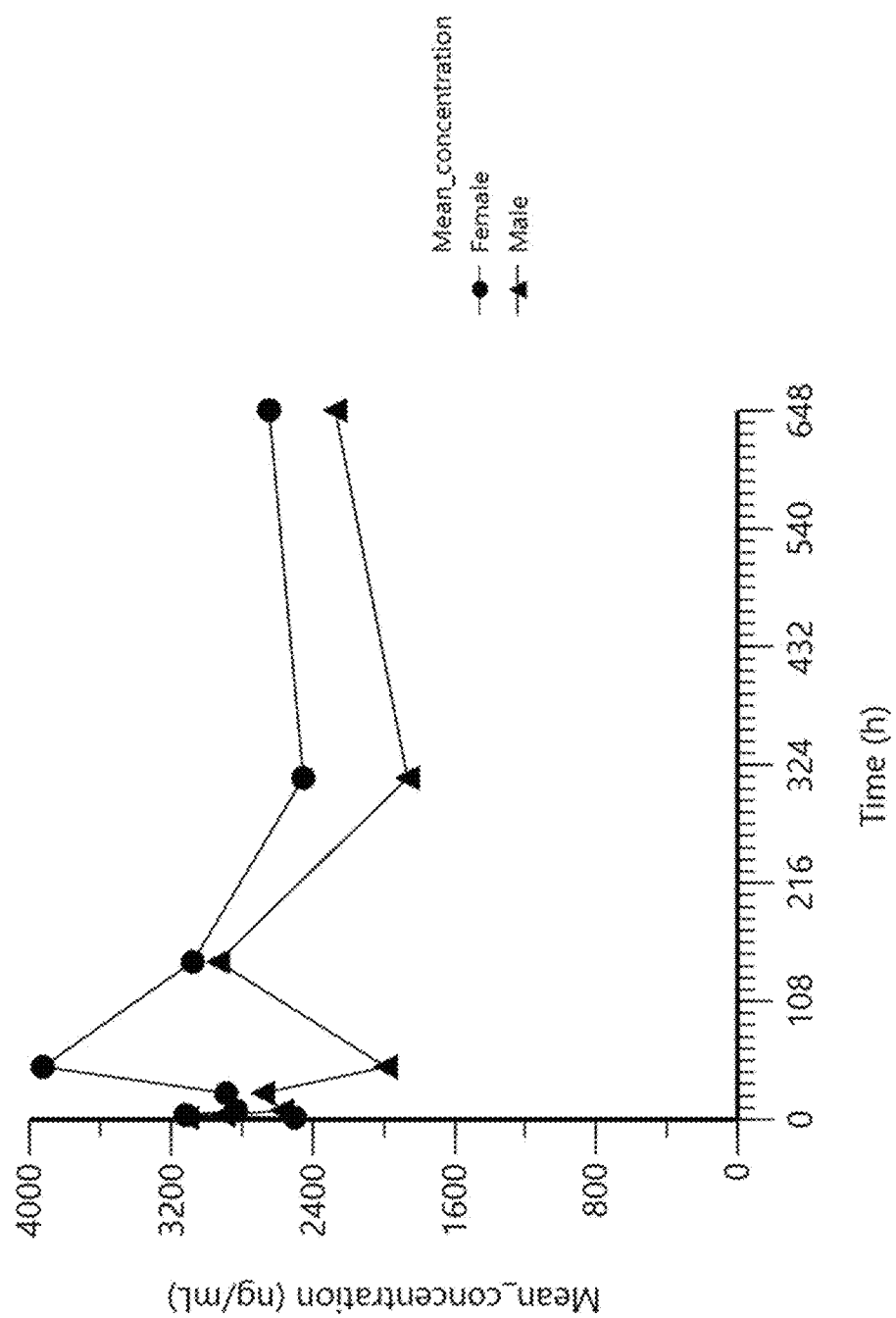
FIG. 15A illustrates a mean brain concentration vs time profile of Compound 1 in C57BL6J mice administered doses of 0.3 mg/kg.
Figure 15B:
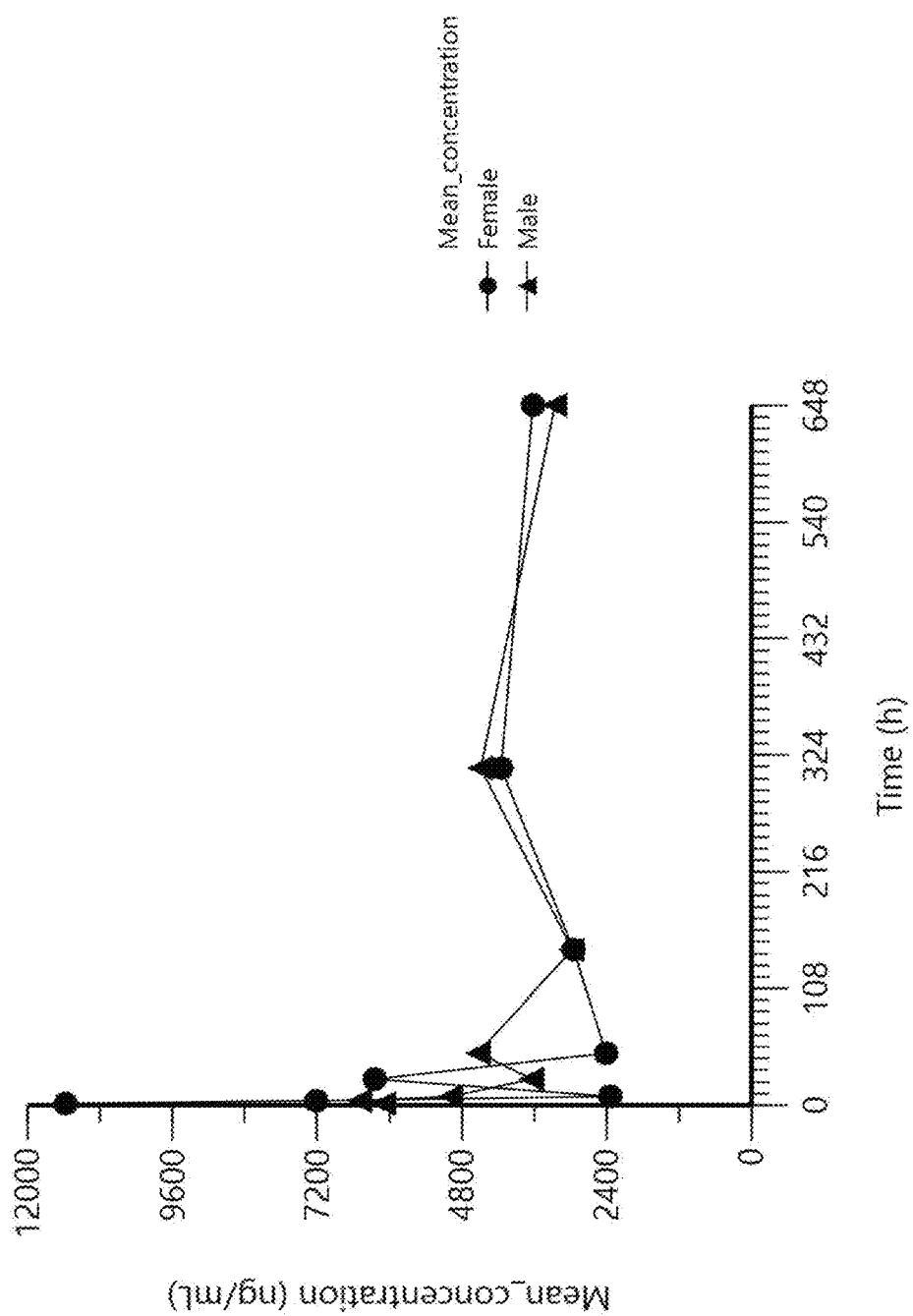
FIG. 15B illustrates mean brain concentration vs time profile of Compound 1 in mice administered doses of 0.6 mg/kg.
Figure 15C:
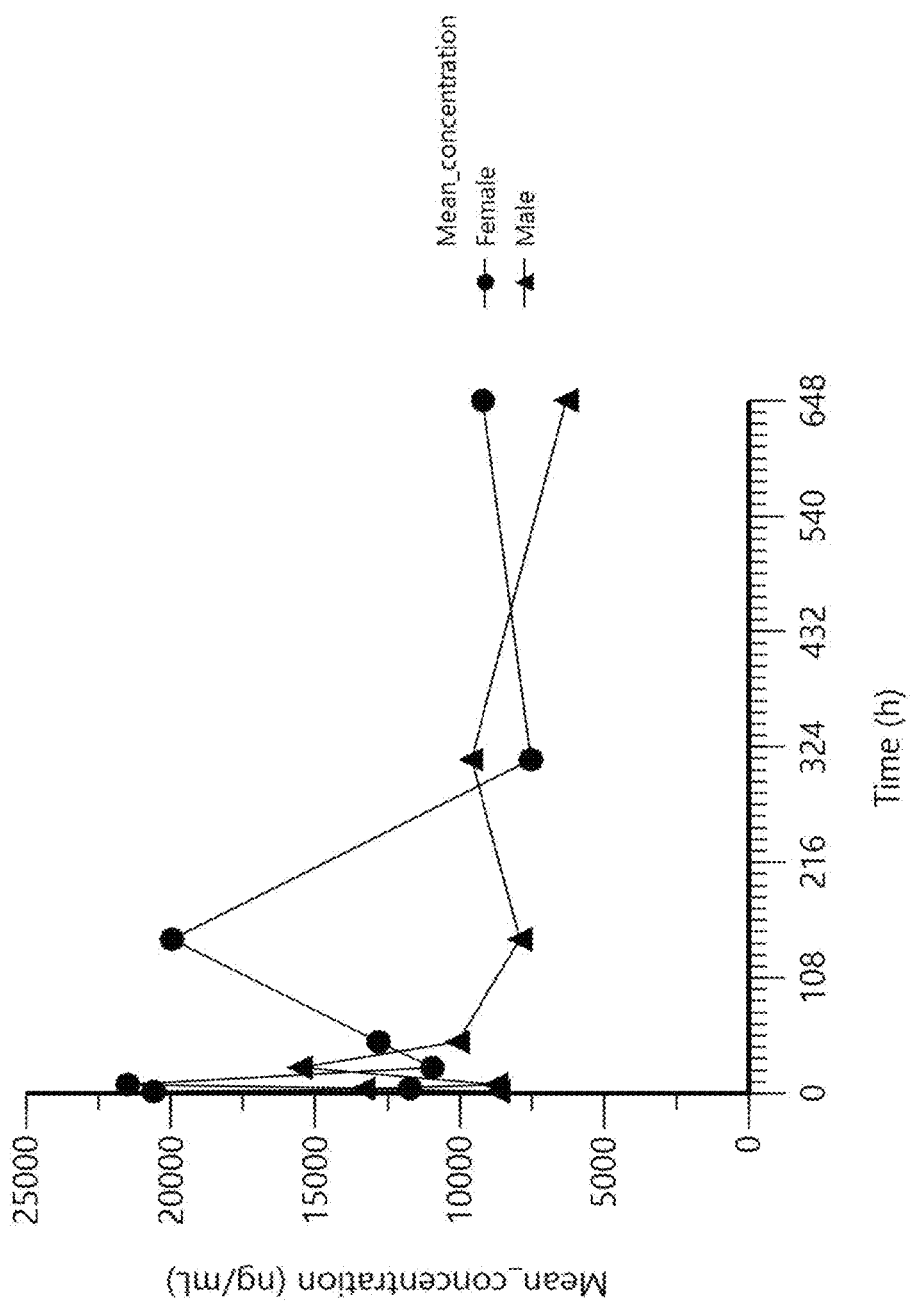
FIG. 15C illustrates mean brain concentration vs time profile of Compound 1 in C57BL6J mice administered doses of 1 mg/kg.

The mean concentrations of Compound 1 in the brain samples are shown graphically in FIG. 15A for doses of 0.3 mg/kg, FIG. 15B for doses of 0.6 mg/kg, FIG. 15C for doses of 1 mg/kg.

Figure 16A:
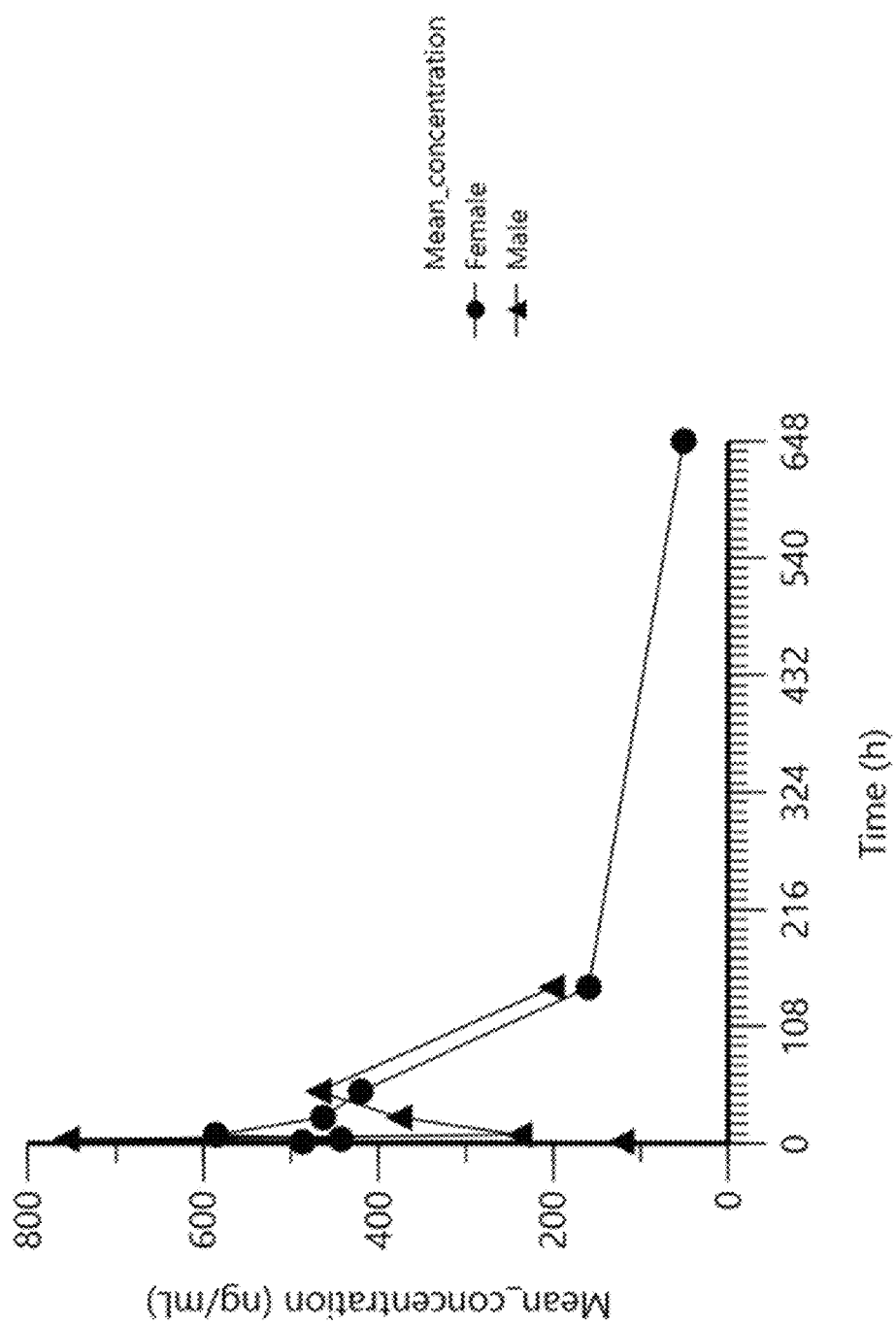
FIG. 16A illustrates mean spleen concentration vs time profile of Compound 1 in C57BL6J mice administered doses of 0.3 mg/kg.
Figure 16B:
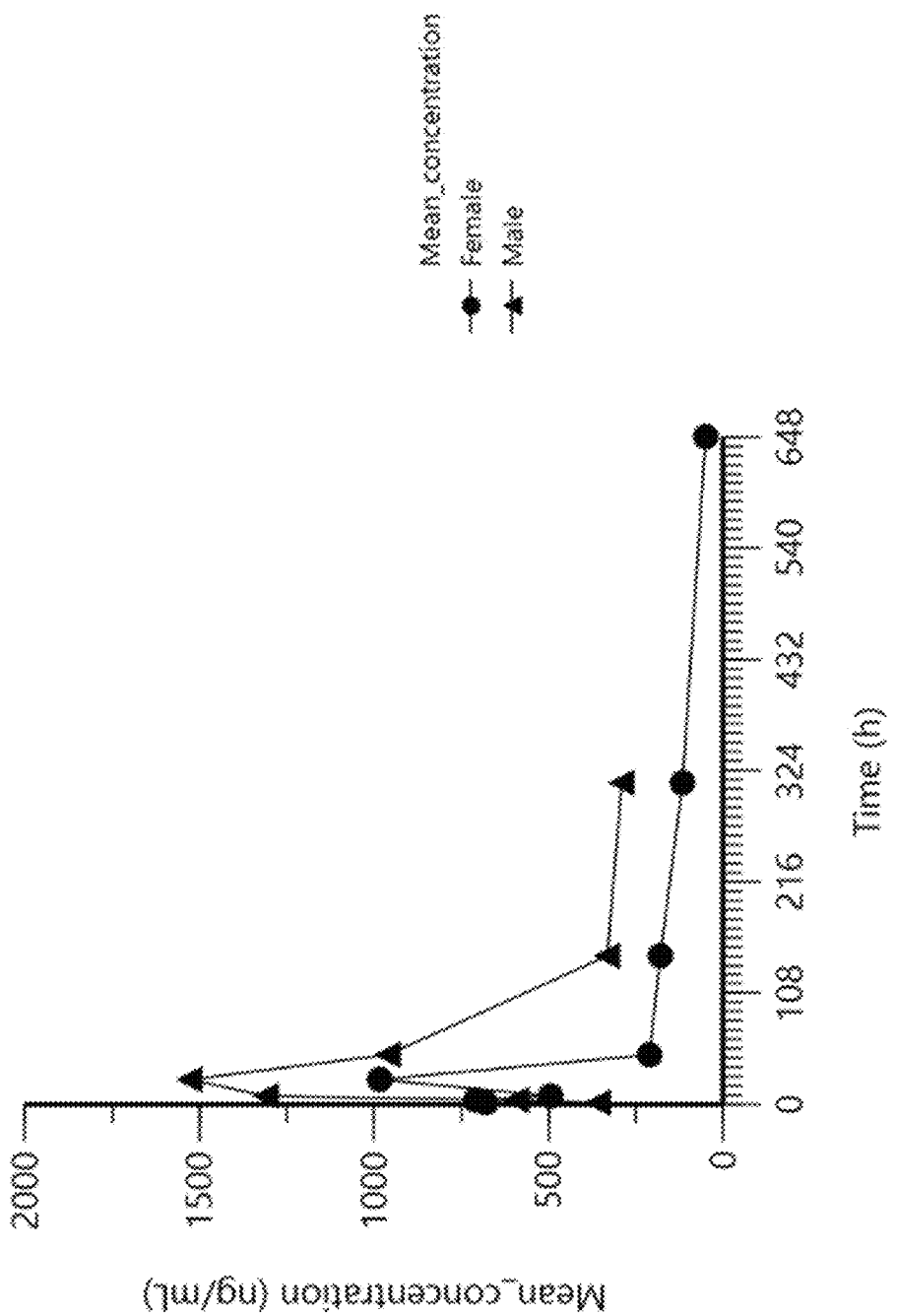
FIG. 16B illustrates mean spleen concentration vs time profile of Compound 1 in mice administered doses of 0.6 mg/kg, and FIG. 16 C illustrates mean spleen concentration vs time profile of Compound 1 in C57BL6J mice administered doses of 1 mg/kg.
Figure 16C:
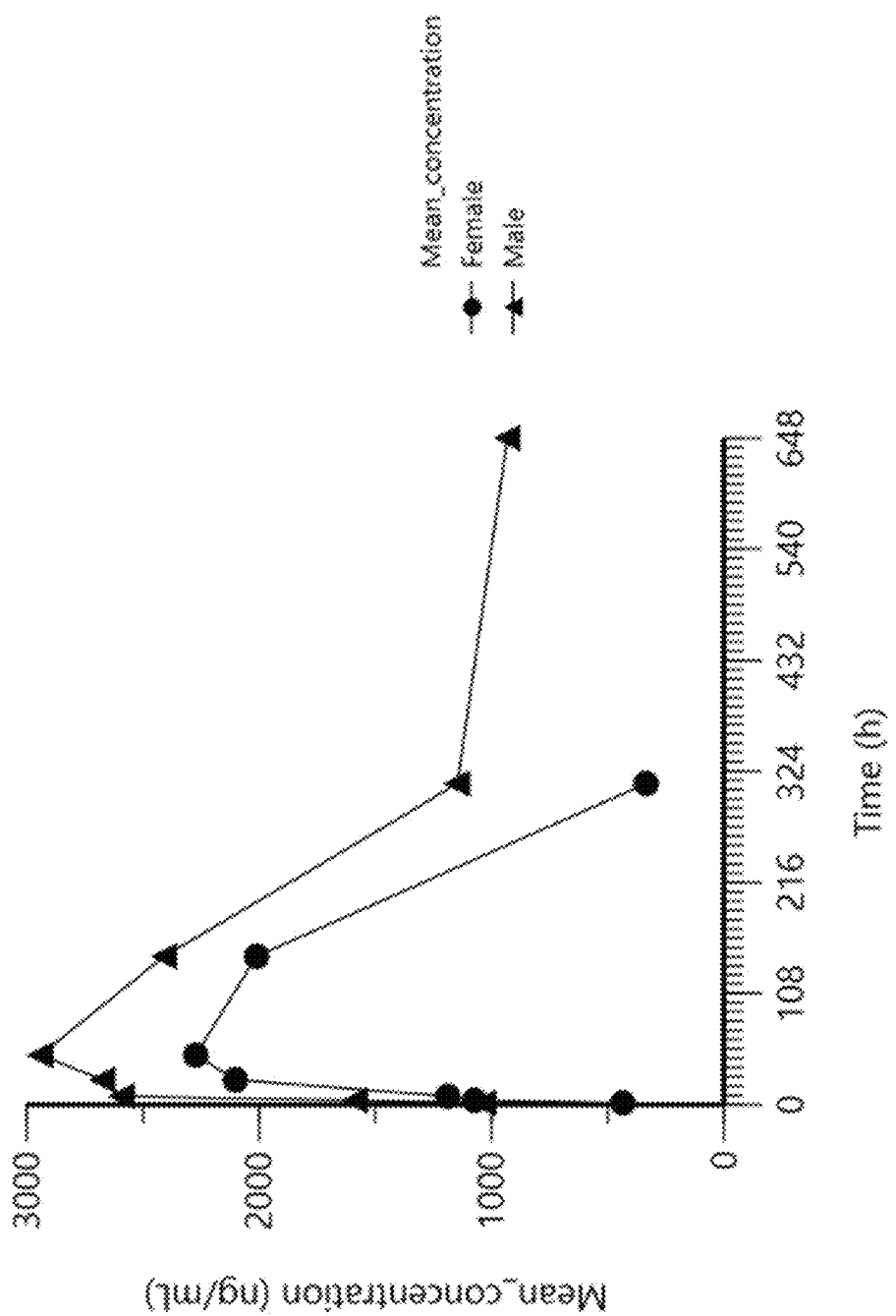

The mean concentrations of Compound 1 in the spleen samples are shown graphically in FIG. 16A for doses of 0.3 mg/kg, FIG. 16B for doses of 0.6 mg/kg, FIG. 16C for doses of 1 mg/kg.

Figure 17:
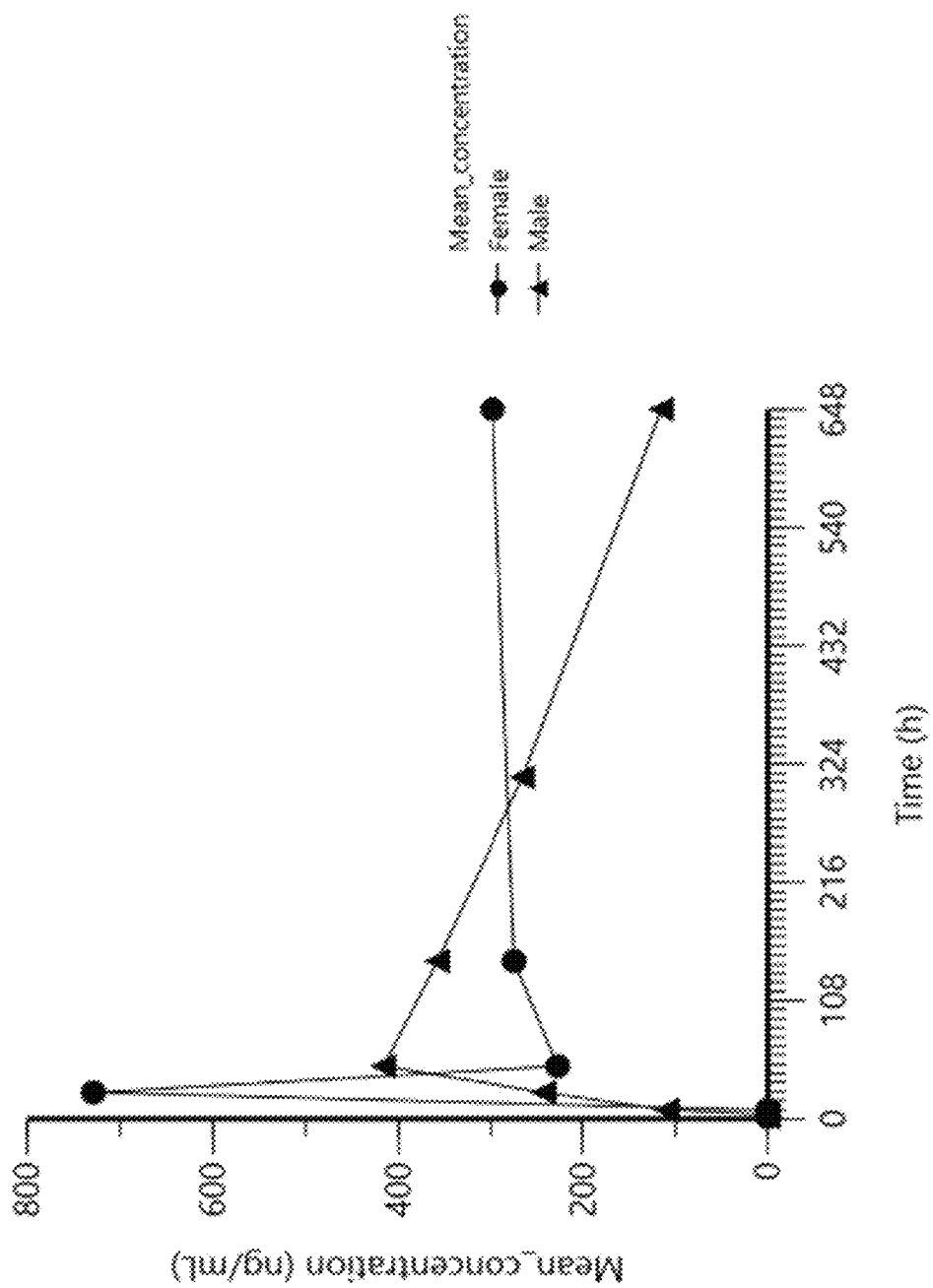
FIG. 17 illustrates mean heart concentration vs time profile of Compound 1 in C57BL6J mice administered doses of 0.3 mg/kg.

The mean concentrations of Compound 1 in the heart samples are shown graphically in FIG. 17 for doses of 0.3 mg/kg.

Summaries of plasma and tissue pharmacokinetic parameters in male and female C57BL6J mice are presented in TABLE 15.

Dose-proportionality ratios in brain and spleen is presented in TABLE 16.

TABLE 16

| | | Fold Difference in Exposure | | | |
|---|---|---|---|---|---|
| | | Male | | Female | |
| Ratio | Fold Increase in Dose | Mean $C_{max}$ | Mean $AUC_{last}$ | Mean $C_{max}$ | Mean $AUC_{last}$ |
| | | Brain | | | |
| 0.6/0.3 mg/kg | 2.0 | 2.1 | 1.7 | 2.9 | 1.3 |
| 1/0.6 mg/kg | 1.7 | 2.4 | 2.2 | 1.9 | 3.0 |
| 1/0.3 mg/kg | 3.3 | 5.0 | 3.8 | 5.5 | 4.0 |

TABLE 15

| | 0.3 mg/kg | | | | 0.6 mg/kg | | | | 1 mg/kg | | | |
|---|---|---|---|---|---|---|---|---|---|---|---|---|
| Matrix | Cmax (ng/mL) | AUClast (ng·h/mL) | Tmax (h) | Tlast (h) | Cmax (ng/mL) | AUClast (ng·h/mL) | Tmax (h) | Tlast (h) | Cmax (ng/mL) | AUClast (ng·h/mL) | Tmax (h) | Tlast (h) |
| | | | | | Males | | | | | | | |
| brain | 3110 | 1440000 | 1.5 | 648 | 6490 | 2470000 | 4 | 648 | 15500 | 5530000 | 24 | 648 |
| spleen | 756 | 48300 | 4 | 144 | 1530 | 166000 | 24 | 312 | 2940 | 1010000 | 48 | 648 |
| heart | 416 | 160000 | 48 | 648 | NA | NA | NA | NA | NA | NA | NA | NA |
| liver | NA | NA | NA | NA | NA | NA | NA | NA | NA | NA | NA | NA |
| kidney | NA | NA | NA | NA | NA | NA | NA | NA | NA | NA | NA | NA |
| intestine | NA | NA | NA | NA | NA | NA | NA | NA | NA | NA | NA | NA |
| lung | NA | NA | NA | NA | NA | NA | NA | NA | NA | NA | NA | NA |
| muscle | NA | NA | NA | NA | NA | NA | NA | NA | NA | NA | NA | NA |
| plasma | NA | NA | NA | NA | NA | NA | NA | NA | NA | NA | NA | NA |
| | | | | | Females | | | | | | | |
| brain | 3930 | 1800000 | 48 | 648 | 11400 | 2360000 | 1.5 | 648 | 21500 | 7150000 | 8 | 648 |
| spleen | 586 | 96500 | 8 | 648 | 984 | 98300 | 24 | 648 | 2270 | 449000 | 48 | 312 |
| heart | 729 | 184000 | 24 | 648 | NA | NA | NA | NA | NA | NA | NA | NA |
| liver | NA | NA | NA | NA | NA | NA | NA | NA | NA | NA | NA | NA |
| kidney | NA | NA | NA | NA | NA | NA | NA | NA | NA | NA | NA | NA |
| intestine | NA | NA | NA | NA | NA | NA | NA | NA | NA | NA | NA | NA |
| lung | NA | NA | NA | NA | NA | NA | NA | NA | NA | NA | NA | NA |

TABLE 16-continued

| | | Fold Difference in Exposure | | | |
|---|---|---|---|---|---|
| | Fold | Male | | Female | |
| Ratio | Increase in Dose | Mean $C_{max}$ | Mean $AUC_{last}$ | Mean $C_{max}$ | Mean $AUC_{last}$ |
| | | Spleen | | | |
| 0.6/0.3 mg/kg | 2.0 | 2.0 | 2.4[a] | 1.7 | 1.0 |
| 1/0.6 mg/kg | 1.7 | 1.9 | 4.0[b] | 2.3 | 6.2[b] |
| 1/0.3 mg/kg | 3.3 | 3.9 | 7.8[a] | 3.9 | 6.3[b] |

[a]AUC144
[b]AUC312

Figure 18A:
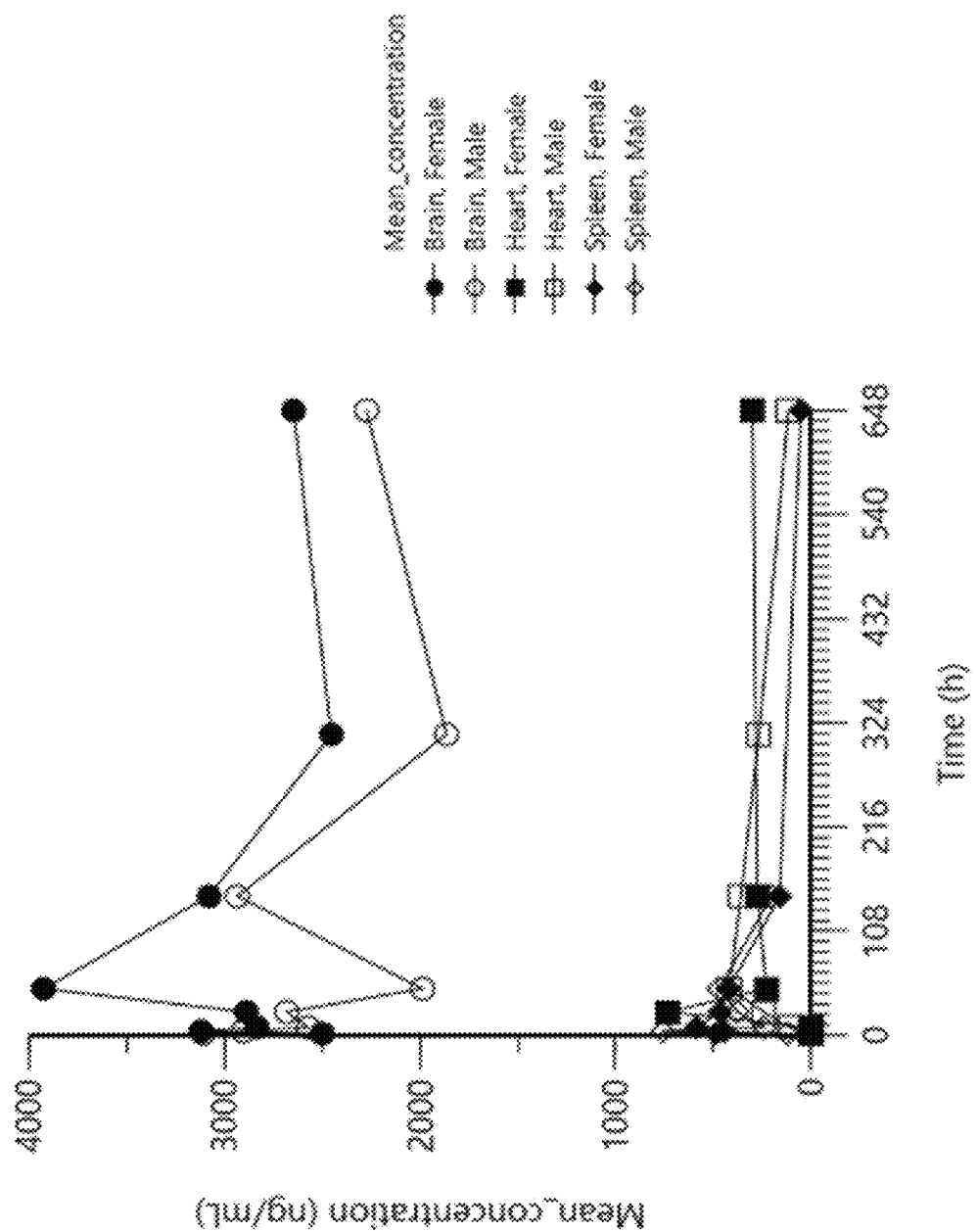
FIG. 18A illustrates mean brain, spleen, and heart concentrations vs time profile of Compound 1 in C57BL6J mice administered doses of 0.3 mg/kg.
Figure 18B:
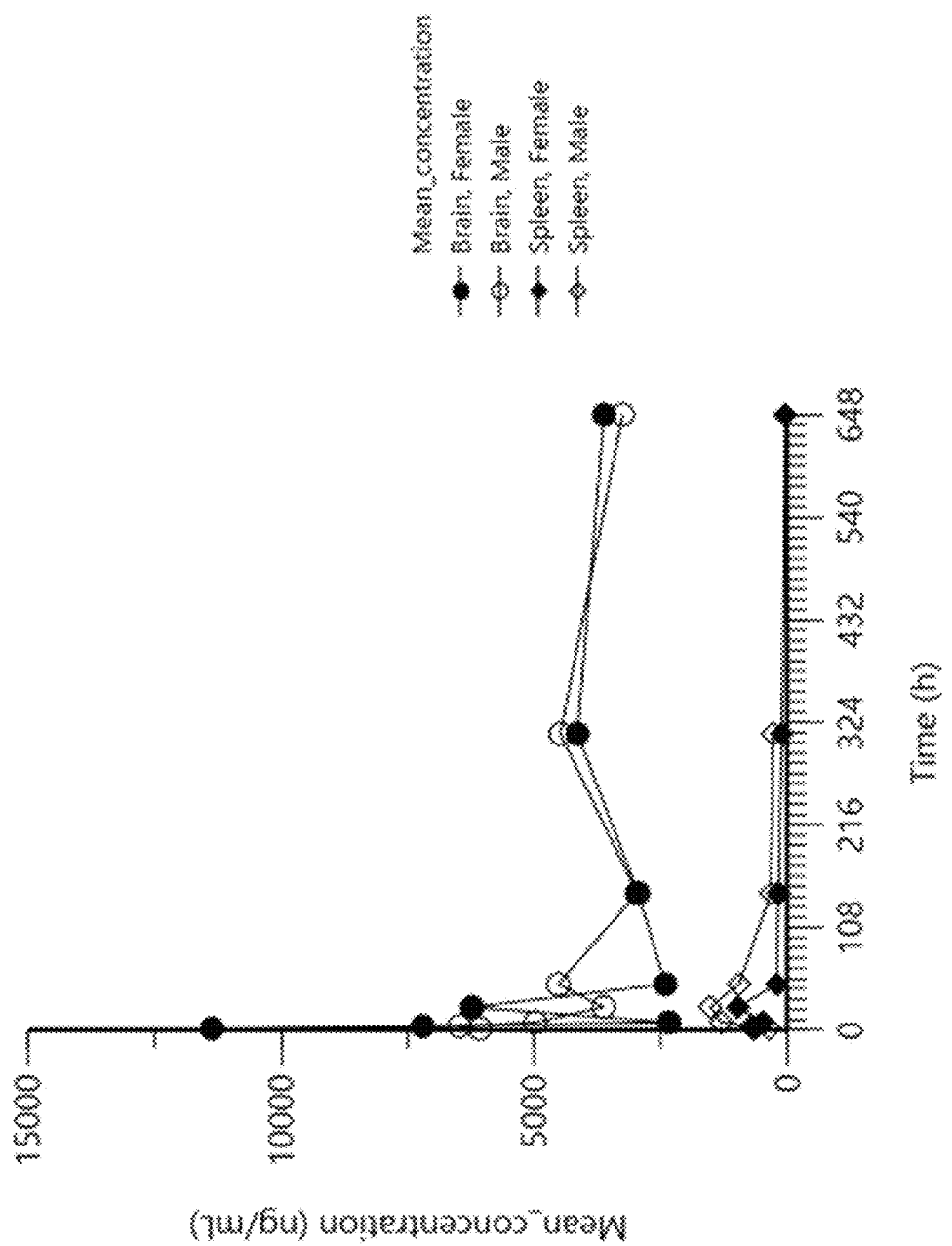
FIG. 18B illustrates mean brain, spleen, and heart concentrations vs time profile of Compound 1 in C57BL6J mice administered doses of 0.6 mg/kg.
Figure 18C:
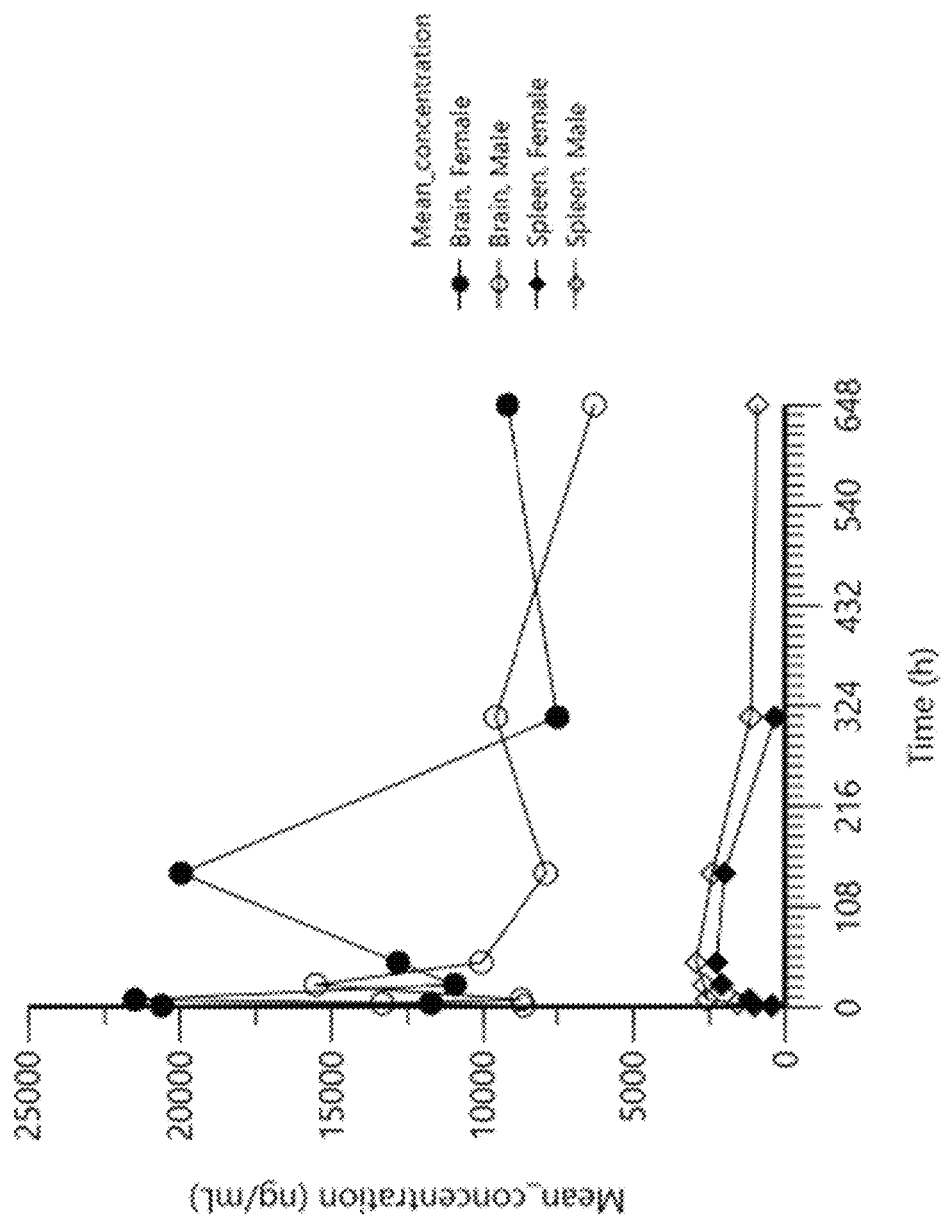
FIG. 18C illustrates mean brain, spleen, and heart concentrations vs time profile of Compound 1 in C57BL6J mice administered doses of 1 mg/kg.

Mean brain, spleen, and heart concentrations versus time profiles in male and female C57BL6J mice are presented graphically in FIG. 18A for doses of 0.3 mg/kg, FIG. 18B for doses of 0.6 mg/kg, FIG. 18C for doses of 1 mg/kg.

Summaries of urine and fecal excretion are reported in TABLE 17.

TABLE 17

| | Urine | | | | | |
|---|---|---|---|---|---|---|
| | Dose (mg/kg) | | | | | |
| Time | 0.3 | | 0.6 | | 1 | |
| (h) | Males | Females | Males | Females | Males | Females |
| 24 | NC | NC | NC | NC | NC | NC |
| 48 | NC | NC | NC | NC | NC | NC |
| 144 | NC | NC | NC | NC | NC | NC |
| 312 | NC | NC | NC | NC | NC | NC |
| 648 | NC | NC | NC | NC | NC | NC |

| | Urine | | | | | |
|---|---|---|---|---|---|---|
| | Dose (mg/kg) | | | | | |
| Time | 0.3 | | 0.6 | | 1 | |
| (h) | Males | Females | Males | Females | Males | Females |
| 24 | NC | NC | NC | NC | NC | NC |
| 48 | NC | NC | NC | NC | NC | NC |
| 144 | NC | NC | NC | NC | NC | NC |
| 312 | NC | NC | NC | NC | NC | NC |
| 648 | NC | NC | NC | NC | NC | NC |

NC = Not calculable

Discussion

Brain

Following a single ICV administration of Compound 1 at 0.3, 0.6, and 1 mg/kg to male and female mice, Compound 1 was quantifiable in the brain up to 648 hours after dosing (last collected PK timepoint) across doses and in both sexes. $T_{max}$ ranged between 1.5 and 48 hours after dosing in both sexes across dose range evaluated. Mean composite $C_{max}$ in the female and male brain was 3930 ng/mL and 3110 ng/mL at 0.3 mg/kg, 11400 ng/mL and 6490 ng/mL at 0.6 mg/kg, and 21500 ng/mL and 15500 ng/mL at 1 mg/kg, respectively. Mean composite $AUC_{last}$ in the female and male brain was 1800000 ng·h/mL and 1440000 ng·h/mL at 0.3 mg/kg, 2360000 ng·h/mL and 2470000 ng·h/mL at 0.6 mg/kg, and 7150000 ng·h/mL and 5530000 ng·h/mL at 1 mg/kg, respectively.

Following intracerebroventricular administration of Compound 1, the exposure (as mean composite $C_{max}$ and $AUC_{last}$) in brain increased with increasing dose from 0.3 to 1 mg/kg in a proportional way as $AUC_{last}$ and slightly supra-proportionally as $C_{max}$ in both sexes.

Generally, no notable (where notable is >2-fold) gender differences in systemic exposure in brain were observed across dose range evaluated.

In the brain of animals given 2 mg/kg the concentration at 8 hours after dosing was 3-fold higher than the concentration measured at the same timepoint in animals given 1 mg/kg and 1.7-fold higher than $C_{max}$ observed in males given 1 mg/kg.

Spleen

Following a single ICV administration of Compound 1 at 0.3, 0.6, and 1 mg/kg to male and female mice, Compound 1 was quantifiable in the spleen up to 648 hours after dosing (last collected PK timepoint) in females at 0.3 and 0.6 mg/kg and in males at 1 mg/kg, up to 312 hours in males at 0.6 mg/kg and in females at 1 mg/kg and up to 144 hours in males at 0.3 mg/kg. $T_{max}$ ranged between 4 and 48 hours after dosing in both sexes across the dose range evaluated. Mean composite $C_{max}$ in the female and male spleen was 586 ng/mL and 756 ng/mL at 0.3 mg/kg, 984 ng/mL and 1530 ng/mL at 0.6 mg/kg, and 2270 ng/mL and 2940 ng/mL at 1 mg/kg, respectively. Mean composite $AUC_{last}$ in the female and male spleen was 96500 ng·h/mL and 48300 ng·h/mL at 0.3 mg/kg, 98300 ng·h/mL and 166000 ng·h/mL at 0.6 mg/kg, and 449000 ng·h/mL and 1010000 ng·h/mL at 1 mg/kg, respectively.

Where calculable (in females dosed at 0.3 mg/kg/day), t½ was 208 hours.

Following intracerebroventricular administration of Compound 1, the exposure in spleen increased with increasing dose from 0.3 to 1 mg/kg in a proportional way as mean composite $C_{max}$ and supra-proportionally as mean composite AUC in both sexes.

Generally, no notable (where notable is >2-fold) gender differences in $C_{max}$ in spleen were observed across dose range evaluated and in AUC at 0.3 mg/kg, while AUC was higher in males than females at 0.6 and 1 mg/kg. This difference (as AUC0-312) was notable at 0.6 mg/kg.

Following a single intracerebroventricular administration of Compound 1 at 2 mg/kg to male mice, Compound 1 was quantifiable in the spleen up to 8 hours after dosing (last collected PK timepoint), with concentrations 1.4-fold higher than those observed at the same timepoints in males given 1 mg/kg.

Heart.

Following a single intracerebroventricular administration of Compound 1 at 0.3, 0.6, and 1 mg/kg to male and female mice, Compound 1 was quantifiable in the heart up to 648 hours after dosing (last collected PK timepoint) only at 0.3 mg/kg and up to 4 hours after dosing at 0.6 mg/kg in both sexes. $T_{max}$ occurred at 24 and 48 hours after dosing in females and males, respectively. Mean composite $C_{max}$ in the female and male heart was 729 ng/mL and 416 ng/mL. Mean composite $AUC_{last}$ in the female and male heart was 184000 ng·h/mL and 160000 ng·h/mL.

Generally, no notable (where notable is >2-fold) gender differences in systemic exposure in heart was observed, although $C_{max}$ was higher in females than in males. Following a single intracerebroventricular administration of Compound 1 at 2 mg/kg to male mice, Compound 1 was not quantifiable in the heart.

Plasma.

Following a single intracerebroventricular administration of Compound 1 at 0.3, 0.6, and 1 mg/kg to male and female mice, Compound 1 was not quantifiable in plasma at all timepoints across doses and in both sexes.

Following a single intracerebroventricular administration of Compound 1 at 2 mg/kg to male mice, Compound 1 was quantifiable in plasma only at 4 hour after dosing.
Liver.

Following a single ICV administration of Compound 1 at 0.3, 0.6, and 1 mg/kg to male and female mice, generally Compound 1 was not quantifiable in the liver across dose range and in both sexes.

Following a single ICV administration of Compound 1 at 2 mg/kg in male mice, Compound 1 was quantifiable in liver up to 8 hours after dosing (last point of tissue collection).
Kidney.

Following a single intracerebroventricular administration of Compound 1 at 0.3, 0.6, and 1 mg/kg to male and female mice, Compound 1 was not quantifiable in kidney across doses and in both sexes.

Following a single intracerebroventricular administration of Compound 1 at 2 mg/kg to male mice, Compound 1 was quantifiable in kidney only at 8 hours after dosing (last point of tissue collection).
Intestine.

Following a single intracerebroventricular administration of Compound 1 at 0.3, 0.6, and 1 mg/kg to male and female mice, generally Compound 1 was not quantifiable in the intestine across doses and in both sexes.

Following a single ICV administration of Compound 1 at 2 mg/kg to male and female mice, Compound 1 was quantifiable in the intestine only at 8 hours after dosing.
Lung.

Following a single intracerebroventricular administration of Compound 1 at 0.3, 0.6, and 1 mg/kg to male and female mice, Compound 1 was not quantifiable in the lung across dose range and in both sexes.

Following a single intracerebroventricular administration of Compound 1 at 2 mg/kg to male mice, Compound 1 was quantifiable in lung only at 8 hours after dosing (last point of tissue collection).
Muscle.

Following a single ICV administration of Compound 1 at 0.3, 0.6, and 1 mg/kg to male and female mice and at 2 mg/kg to male mice, generally Compound 1 was not quantifiable in muscle across dose range and in both sexes.
Urine.

Following a single ICV administration of Compound 1 at 0.3, 0.6, and 1 mg/kg to male and female mice, Compound 1 was not quantifiable in the urine across doses and in both sexes.
Feces.

Following a single intracerebroventricular administration of Compound 1 at 0.3, 0.6, and 1 mg/kg to male and female mice, Compound 1 was not quantifiable in the feces across doses and in both sexes.
Conclusions Following a single ICV administration of Compound 1 at 0.3, 0.6, and 1 mg/kg to male and female mice, Compound 1 was quantifiable up to 648 hours after dosing (last collected PK timepoint) in the brain across doses and in the heart only at 0.3 mg/kg in both sexes and up to at least 312 hours after dosing in the spleen across doses in both sexes. The result indicates accumulation of test item in these tissues. Generally, Compound 1 was not quantifiable in plasma, intestine, liver, lung, kidney, and muscle across doses and in both sexes.

Maximum concentration of Compound 1 occurred between 1.5 and 48 hours after dosing in brain and between 4 and 48 hours in spleen and in both sexes and across dose range evaluated and at 24 and 48 hours after dosing in heart in females and males, respectively.

Following ICV administration of Compound 1, for an increase in dose from 0.3 to 1 mg/kg the exposure (as mean composite $C_{max}$ and $AUC_{last}$) increased in brain in a proportional way as $AUC_{last}$ and slightly supra-proportionally as $C_{max}$ and in spleen in a proportional way as mean composite $C_{max}$ and supra-proportionally as mean composite AUC in both sexes.

Generally, no notable (where notable is >2-fold) gender differences in systemic exposure in brain across dose range evaluated and in heart was observed, although $C_{max}$ in heart was higher in females than in males.

No notable gender differences in $C_{max}$ in spleen was observed across dose range evaluated and in AUC at 0.3 mg/kg, while AUC was higher in males than females at 0.6 and 1 mg/kg. This difference (as $AUC_{0-312}$) was notable at 0.6 mg/kg.

Following a single ICV administration of Compound 1 at 2 mg/kg to male mice, Compound 1 was quantifiable in the spleen and liver up to 8 hours after dosing (last collected PK timepoint) and in the intestine, kidney and lung only at 8 hours after dosing, in plasma only at 4 hour after dosing. The compound was not quantifiable in muscle and heart in both sexes.

Following a single ICV administration of Compound 1 at 0.3, 0.6, and 1 mg/kg to male and female mice, Compound 1 was not quantifiable in urine and feces across doses and in both sexes.

Example 4. Knockdown of Mutant Huntington's Disease Protein by Compounds of the Disclosure This example demonstrates the ability of illustrative compounds of the disclosure to reduce selectively and potently expression of mutant Huntington's disease protein in cells without causing cytotoxicity.

A human subject-derived fibroblast cell line GM09197 was obtained from the Coriell Institute (Coriell Institute for Medical Research, Camden, N.J.). The first huntingtin allele in this cell line is a mutant huntingtin allele with 151 CAG repeats (mHTT), which is associated with development of Huntington's disease. The second huntingtin allele in this cell line contains 21 CAG repeats. In some embodiments, this level can be considered a normal or wild type huntingtin allele (wtHTT) that is not considered to cause Huntington's disease. Cells were maintained at 37° C. and 5% $CO_2$ in minimal essential media (MEM) supplemented with non-essential amino acids (Corning Inc, Corning N.Y., cat. n #10-009-CV) and 10% heat inactivated FBS (Corning Inc., Corning N.J. cat. n #35-016-CV).

Peptide nucleic acid (PNA) compounds of the disclosure were screened for toxicity and the ability to knockdown expression selectively of mHTT. Cells were plated in 24-well plates at 150,000 cells/well in supplemented MEM one day before addition of PNA. Stock solutions of PNA were heated at 80° C. for 10 min before use and were added to final concentrations of 1 μM or 5 μM in the cell cultures. Cells were incubated for 3 days in the presence or absence of PNA compound before evaluation of huntingtin knockdown and cytotoxicity.

For huntingtin knockdown assays, cells were harvested with a trypsin-EDTA solution (0.25%, Invitrogen, Carlsbad, Calif., cat. n #25200072) and lysed using M-Per buffer (Thermo Fischer Scientific, Waltham, Mass., cat. n #78503). Total protein present in the lysates were quantified using BCA assay (Pierce BCA protein Assay Kit cat. n #23225, Thermo Fischer Scientific, Waltham, Mass.). mHTT and wtHTT proteins were separated by SDS-PAGE using 4-15% gradient gels (Bio-Rad Laboratories, Hercules, Calif., cat. n #4561083) with Tris Glycine Running Buffer 0.1% SDS pH8.3 (Glycine cat. n #G8898, Sigma-Aldrich, St Louis, Mo., Tri-Base cat. n #BP152-500, Fisher Scientific, Hampton, N.H., SDS 10% solution cat. n #1610416, Bio-Rad Laboratories, Hercules, Calif.). Gels were run at 165V for 2 hours. After gel electrophoresis, proteins were transferred to a nitrocellulose membrane (Bio-Rad Laboratories, Hercules, Calif., cat. n #1620112).

A huntingtin-specific primary antibody was used to bind specifically both mHTT and wtHTT (1:2500, Abcam, Cambridge UK, cat. n #ab109115), with a beta-actin-specific primary antibody as a control (1:5000, Abcam Cambridge, UK, cat. n #ab8227). Horseradish peroxidase (HRP) conjugated anti-mouse or anti-rabbit secondary antibodies (1:10,000, Jackson ImmunoResearch Laboratories, West Grove, Pa., cat. n #315-035-0003 and 111-035-045) were used for visualizing proteins using SuperSignal West Pico Plus Chemiluminescent Substrate (Thermo Fischer Scientific, Waltham, Mass., cat. n #34577). Protein bands were quantified using iBright Analysis Software (Thermo Fischer Scientific, Waltham, Mass.). mHTT and wtHTT bands were normalized according to beta-actin expression, and mHTT and wtHTT expression inhibition was calculated as a relative value to untreated control cells.

Figure 19A:
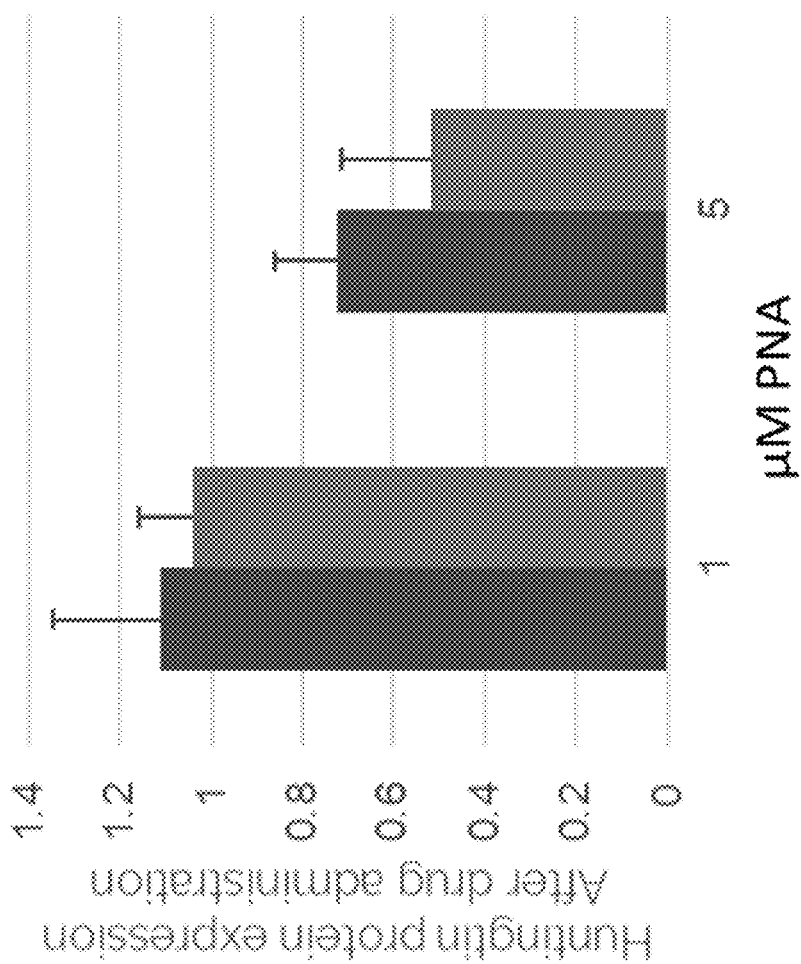
FIG. 19A shows the relative expression of wtHTT (darker bars) and mHTT (lighter bars) by GM09197 cells after treatment with Compound 2 at 1 or 5 μM.

FIG. 19A shows the relative expression of wtHTT (darker bars) and mHTT (lighter bars) after treatment with Compound 2 at 1 or 5 µM. The figure demonstrates knockdown of both mHTT and wtHTT at 5 µM, with somewhat greater knockdown of mHTT than wtHTT.

Figure 19B:
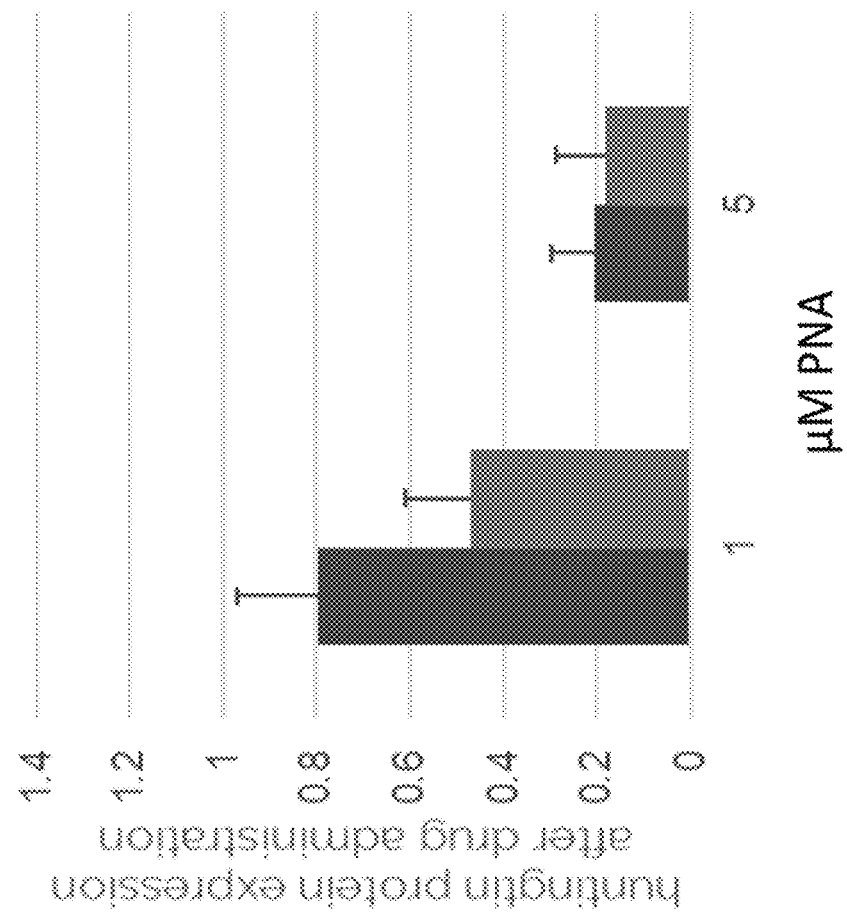
FIG. 19B shows the relative expression of wtHTT (darker bars) and mHTT (lighter bars) by GM09197 cells after treatment with Compound 3 at 1 or 5 μM.

FIG. 19B shows the relative expression of wtHTT (darker bars) and mHTT (lighter bars) after treatment with Compound 3 at 1 or 5 µM. The figure demonstrates knockdown of mHTT and wtHTT, with higher selectivity for mHTT compared to wtHTT at 1 µM. These results also show that Compound 3 exhibited greater potency than Compound 2 for mHTT knockdown in this assay.

Figure 19C:
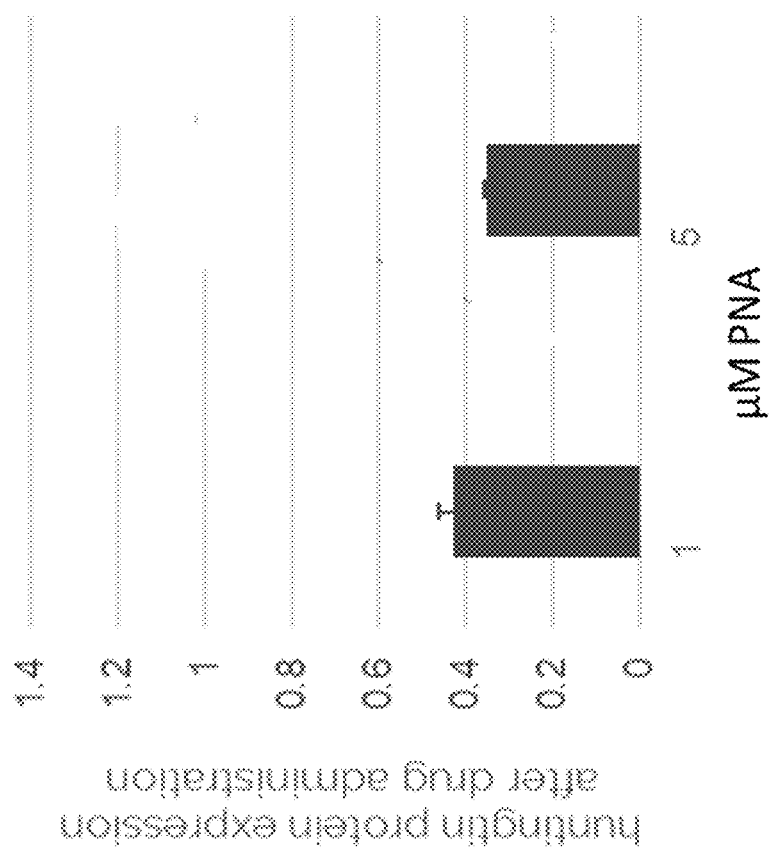
FIG. 19C shows the relative expression of wtHTT (darker bars) and mHTT (lighter bars, not visible) by GM09197 cells after treatment with Compound 4 at 1 or 5 μM. The mHTT bars are not visible as mHTT was below the limit of detection.

FIG. 19C shows the relative expression of wtHTT (darker bars) and mHTT (lighter bars, not visible) after treatment with Compound 4 at 1 or 5 µM. The mHTT bars are not visible as mHTT was below the limit of detection. These results demonstrate that Compound 4 exhibits higher potency and selectivity for knocking down mHTT compared to Compound 3 and Compound 2 in this assay.

These results demonstrate a structure-activity relationship between illustrative PNA compounds of the disclosure and potency and selectivity for modulating expression of target genes and proteins. As the PNA compounds evaluated comprise backbone modifications that alter their binding affinity for mHTT transcript, these results also show that modulating binding affinity via PNA backbone modifications can alter target selectivity and therapeutic potency.

To evaluate potential toxicity of the PNA compounds in the assay conditions, a Lactate Dehydrogenase (LDH) release cytotoxicity assay was performed using a CyQuant LDH kit (cat. n #C20300, Invitrogen, Carlsbad, Calif.).

For a maximum LDH release control, 10× Lysis Buffer was added to control wells comprising the GM09197 cells, and the plate was incubated at 37° C., 5% $CO_2$ for 50 min.

50 µL of medium from each sample and control well was transferred to designated wells in a 96-well flat bottom plate. An LDH Positive Control from the kit was also used, as were basal medium LDH activity controls, with 50 µL of culture medium±serum per basal LDH control well, and an untreated (PBS) control.

50 µL of Reaction Mixture was transferred to each sample and control well and mixed by gentle tapping. The plate was incubated at room temperature for 30 min protected from light, after which 50 µL of Stop Solution to was added to each well. Absorbance at 490 nm and 680 nm was measured. To determine LDH activity, the 680-nm absorbance value (background signal from instrument) was subtracted from the 490-nm absorbance value.

Figure 20A:
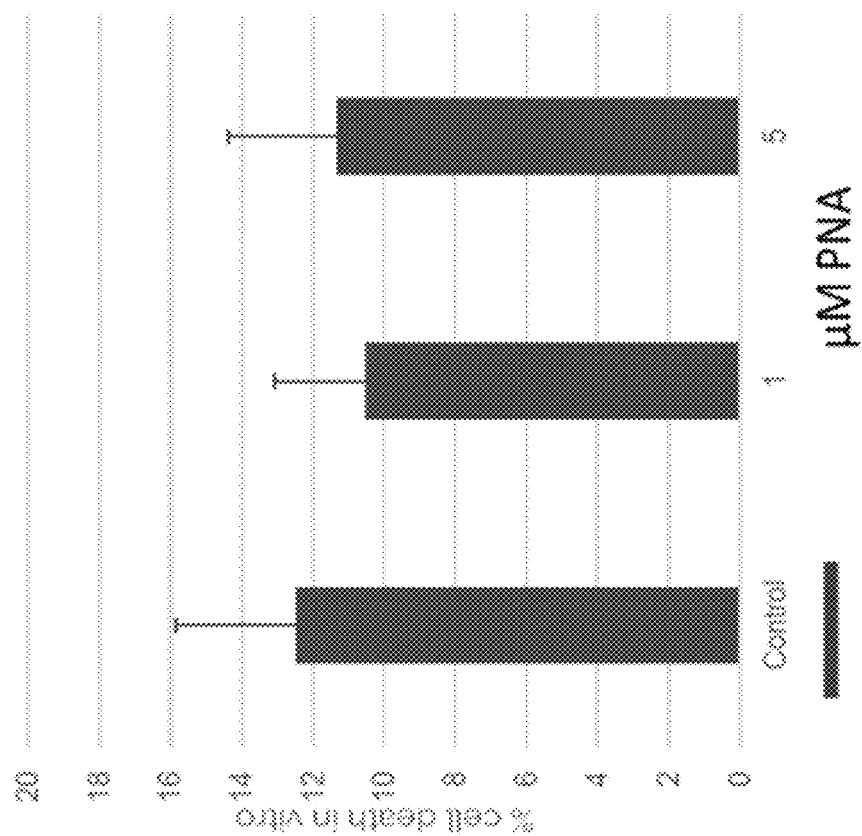
FIG. 20A shows the results of a cytotoxicity assay evaluating the percent of dead GM09197 cells present after mock-treatment (PBS, control) or treatment with Compound 2 at 1 or 5 μM.
Figure 20B:
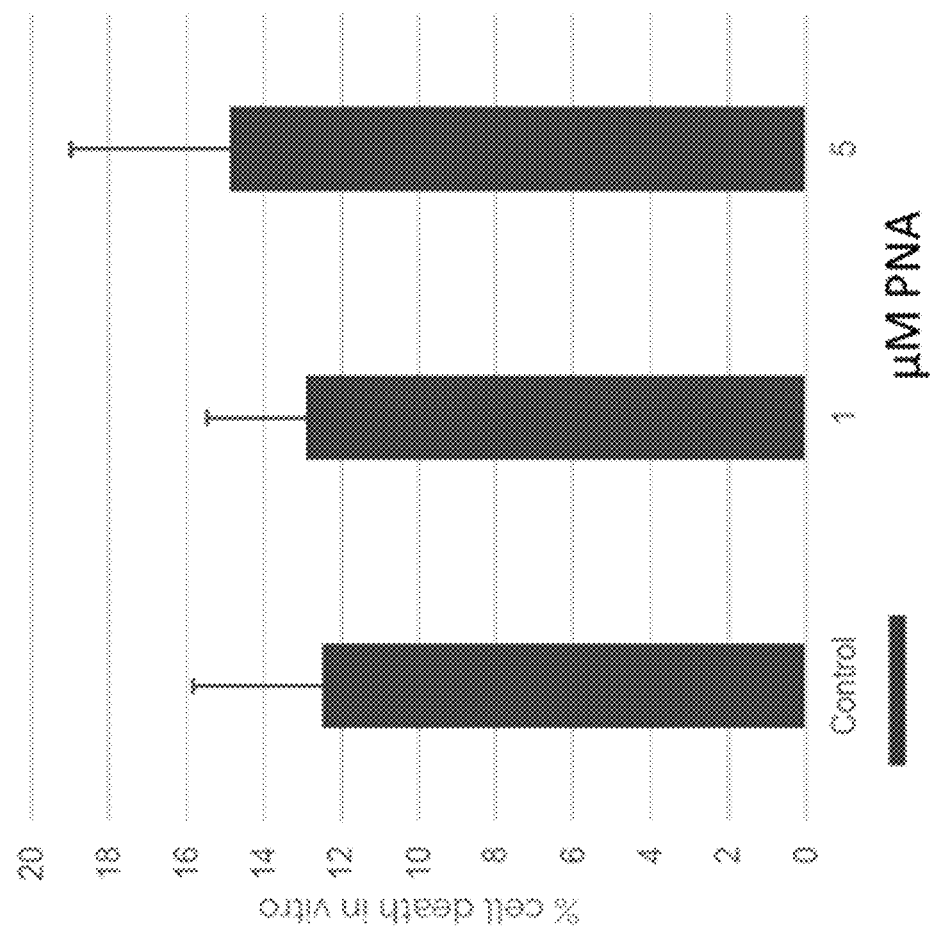
FIG. 20B shows the results of a cytotoxicity assay evaluating the percent of dead GM09197 cells present after mock-treatment (PBS, control) or treatment with Compound 3 at 1 or 5 μM.
Figure 20C:
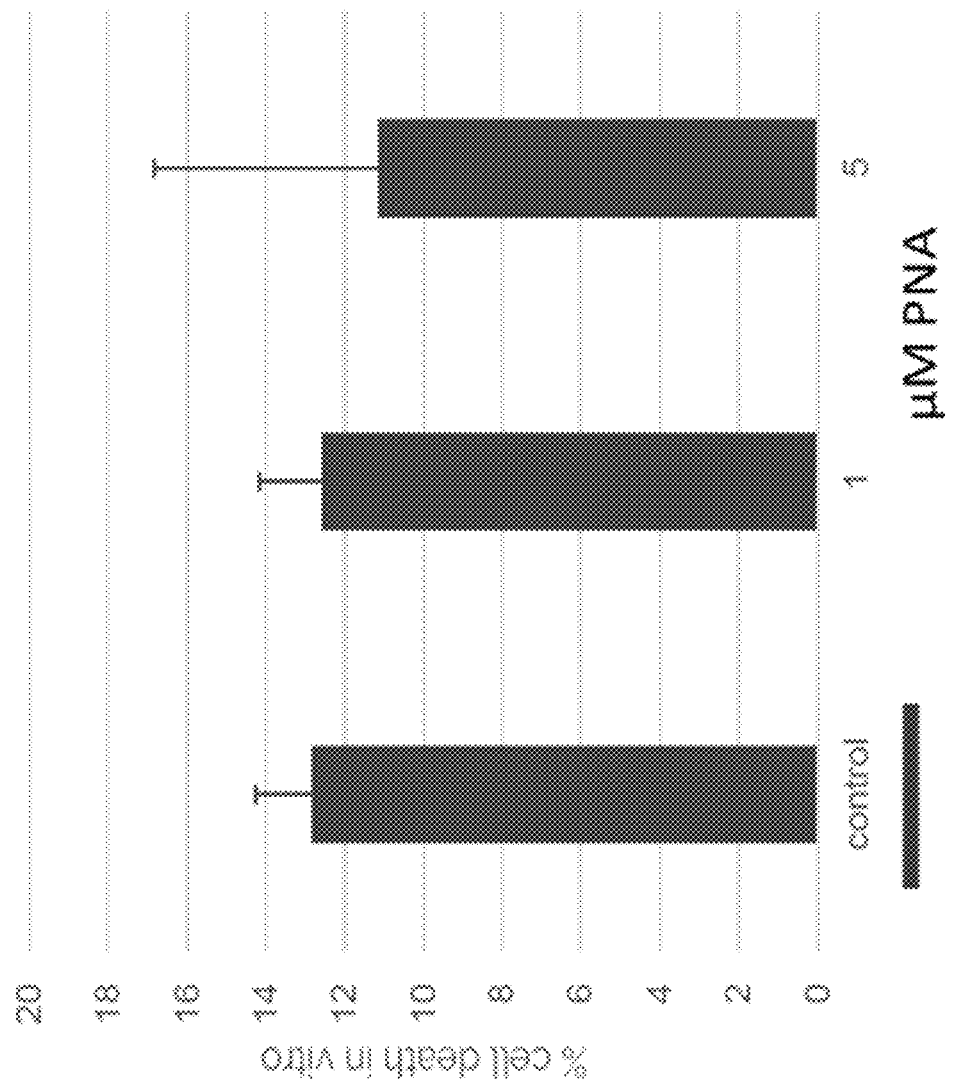
FIG. 20C shows the results of a cytotoxicity assay evaluating the percent of dead GM09197 cells present after mock-treatment (PBS, control) or treatment with Compound 4 at 1 or 5 μM.
Figure 21A:
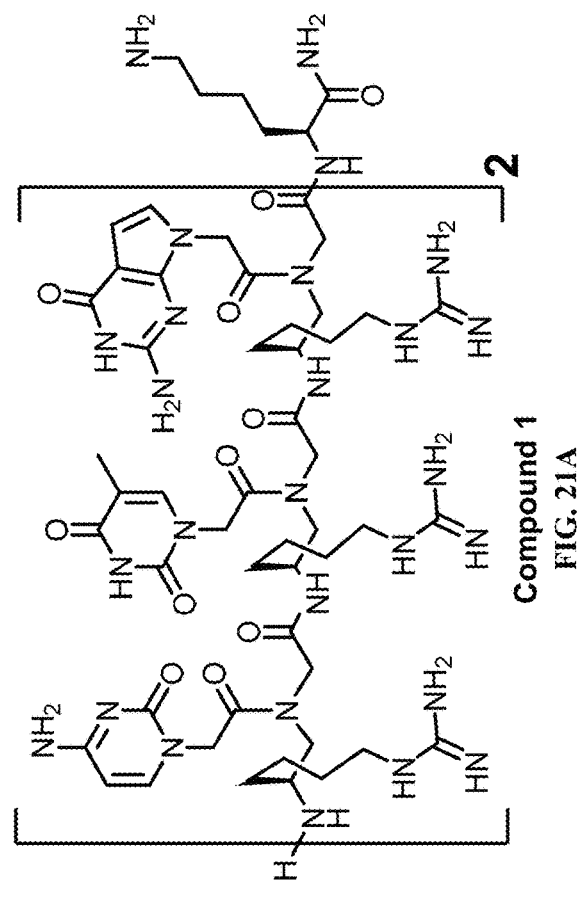
FIG. 21A depicts the structural formula of Compound 1.
Figure 21B:
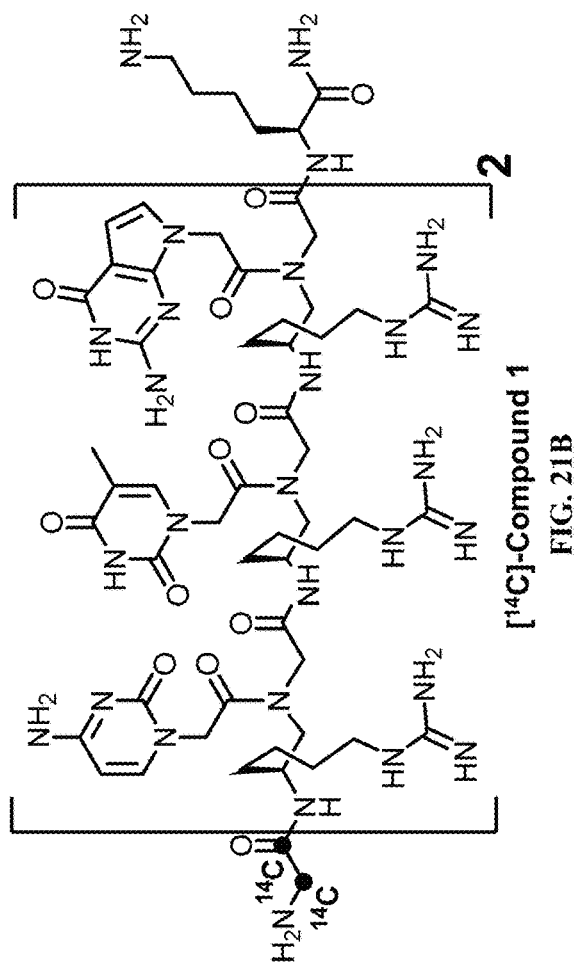
FIG. 21B depicts the structural formula of [$^{14}$C]Compound 1.
Figure 22A:
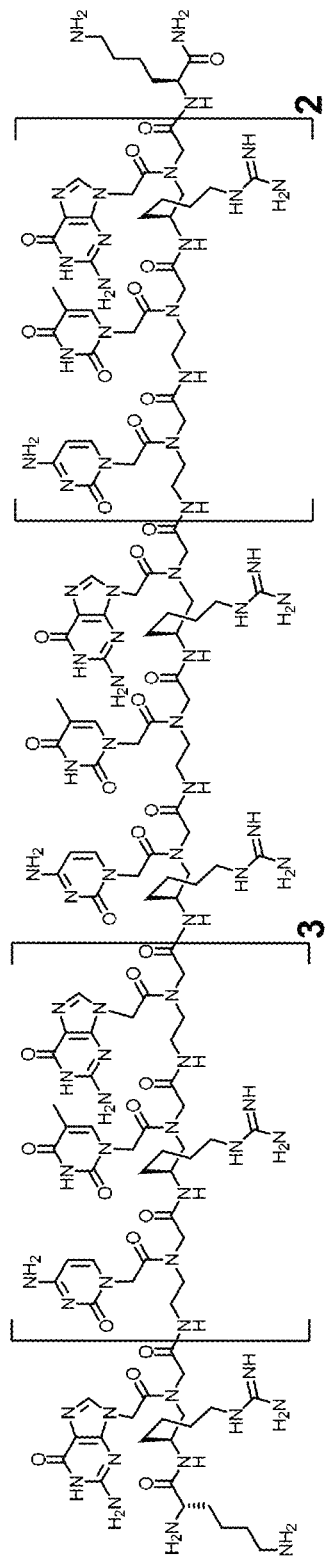
FIG. 22A depicts the structural formula of Compound 2.
Figure 22B:
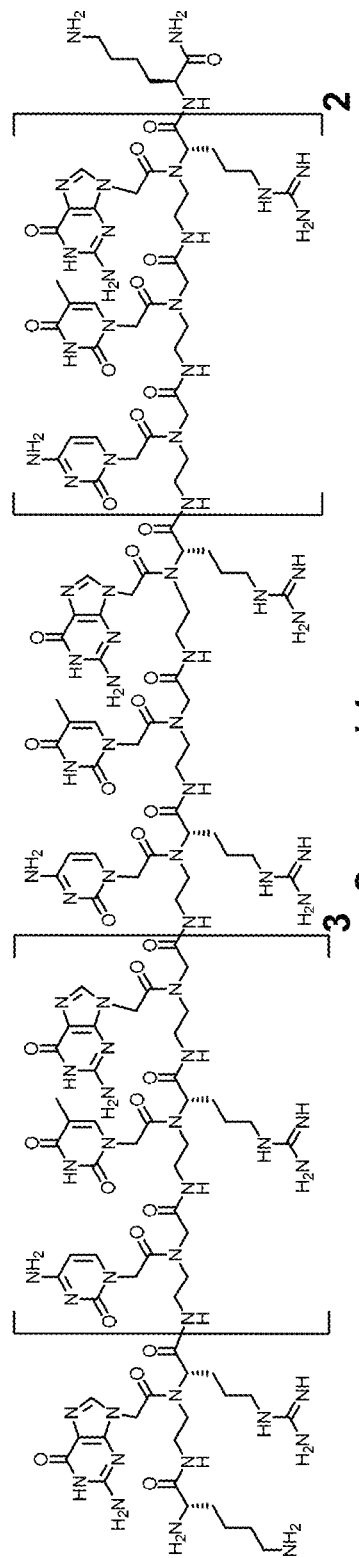
FIG. 22B depicts the structural formula of Compound 4.
Figure 23:
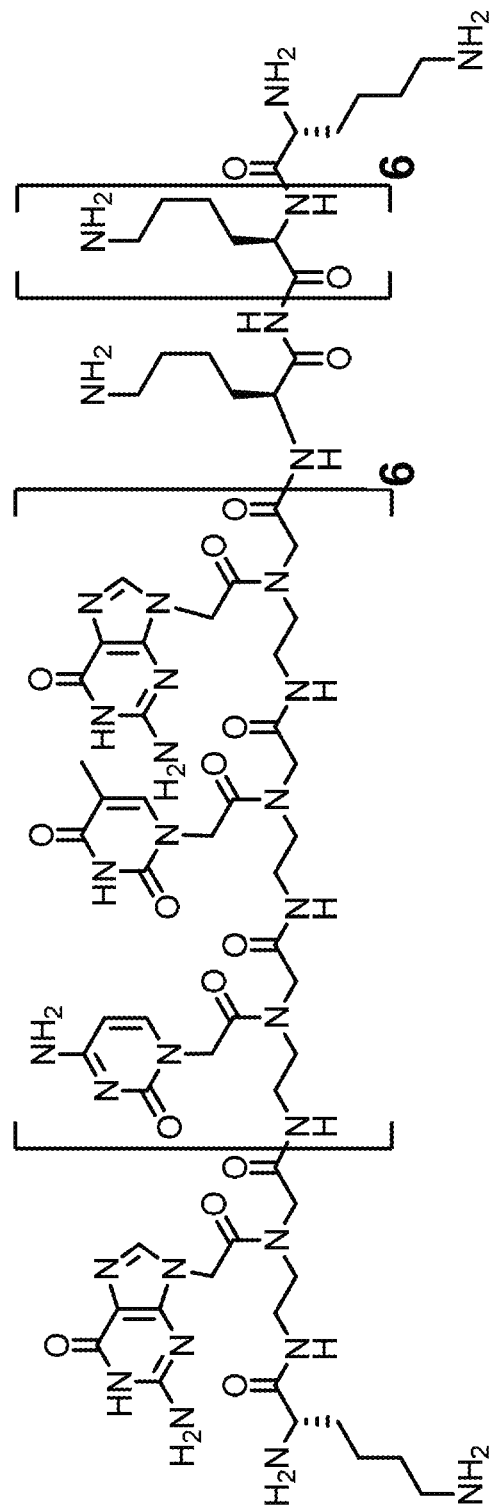
FIG. 23 depicts the structural formula of Compound 3.

The percent of dead cells detected following treatment with the PNA compounds was not significantly different than that of untreated control. The result indicates that cytotoxicity was not observed for GM09197 cells treated with PNA compounds of the disclosure Compound 2 (FIG. 20A), Compound 3 (FIG. 20B), and Compound 4 (FIG. 20C) at doses that were effective to knock down mHTT.

Example 5. In Vivo Tolerability of PNA Compounds

This example demonstrates that illustrative PNA compounds of the disclosure can be well tolerated when administered to subjects.

PNA compounds of the disclosure were administered to non-human primates intravenously via a single tail vein injection per animal. The single dose injections were well tolerated at doses of up to 5 mg/kg.

PNA compounds of the disclosure were administered via intraperitoneal injection into mice three times per week. Three times weekly doses of up to 2 mg/kg were well tolerated for up to five weeks.

EMBODIMENTS

The following non-limiting embodiments provide illustrative examples of the invention, but do not limit the scope of the invention.

Embodiment 1. A compound comprising a chain, wherein the chain comprises a series of atoms concatenated to form the chain, wherein a plurality of the atoms that are concatenated to form the chain are each independently substituted with a substituent that bears a guanidino group, wherein the chain has a pattern of one atom that is independently substituted with a substituent that bears a guanidino group, followed by five consecutive atoms that are not substituted by a substituent that bears a guanidino group, followed by a second atom that is independently substituted with a substituent that bears a guanidino group, followed by another five consecutive atoms that are not substituted by a substituent that bears a guanidino group, followed by a third atom that is independently substituted with a substituent that bears a guanidino group, wherein a first end of the chain or a second end of the chain is substituted with a peptide.

Embodiment 2. The compound of embodiment 1, wherein the pattern further comprises one atom that is independently substituted with a substituent that bears a first nucleobase, followed by five consecutive atoms that are not substituted by a substituent that bears a nucleobase, followed by a second atom that is independently substituted with a substituent that bears a second nucleobase, followed by another five consecutive atoms that are not substituted by a substituent that bears a nucleobase, followed by a third atom that is independently substituted with a substituent that bears a third nucleobase.

Embodiment 3. The compound of embodiment 1 or embodiment 2, wherein each substituent that bears a guanidino group is independently guanidinoalkylene.

Embodiment 4. The compound of embodiment 1 or embodiment 2, wherein each substituent that bears a guanidino group is 3-guanidino-prop-1-yl.

Embodiment 5. The compound of embodiment 1 or embodiment 2, wherein each substituent that bears a guanidino group is 4-guanidino-but-1-yl.

Embodiment 6. The compound of embodiment 2, wherein the substituent that bears the first nucleobase, the substituent that bears the second nucleobase, and the substituent that bears the third nucleobase are each independently purinylacyl, purinylalkylene, pyrimidinylacyl, or pyrimidinylalkylene.

Embodiment 7. The compound of embodiment 2, wherein the substituent that bears the first nucleobase, the substituent that bears the second nucleobase, and the substituent that bears the third nucleobase are each independently guaninylacyl, adeninylacyl, cytosinylacyl, thyminylacyl, or uracilylacyl.

Embodiment 8. The compound of embodiment 2, wherein the first nucleobase, the second nucleobase, and the third nucleobase form a sequence that is CTG, TGC, or GCT.

Embodiment 9. The compound of any one of embodiments 1-8, wherein the compound is a peptide nucleic acid oligomer.

Embodiment 10. The compound of any one of embodiments 1-8, wherein the compound is a gamma peptide nucleic acid oligomer.

Embodiment 11. The compound of any one of embodiments 1-8, wherein the compound is a peptide nucleic acid oligomer, and the peptide nucleic acid oligomer comprises a series of nucleobase side chains that form a sequence that is $(CTG)_n$, wherein n is 1, 2, 3, 4, 5, 6, 7, 8, 9, or 10.

Embodiment 12. The compound of any one of embodiments 1-11, wherein the compound is a peptide nucleic acid oligomer, wherein the first end of the chain is an N-terminus of the peptide nucleic acid oligomer, and the second end of the chain is a C-terminus of the peptide nucleic acid oligomer.

Embodiment 13. The compound of embodiment 12, wherein the C-terminus of the peptide nucleic acid oligomer is bound by a peptide bond to the peptide.

Embodiment 14. The compound of embodiment 12, wherein the C-terminus of the peptide nucleic acid oligomer is bound by a peptide bond to an amidated lysine residue.

Embodiment 15. The compound of any one of embodiments 12-14, wherein an N-terminus of the peptide nucleic acid oligomer is unsubstituted.

Embodiment 16. The compound of any one of embodiments 12-14, wherein an N-terminus of the peptide nucleic acid oligomer is bound by a peptide bond to a peptide.

Embodiment 17. A compound comprising a peptide nucleic acid sequence and a cell permeabilizing group attached to the peptide nucleic acid sequence, wherein if a radiolabeled analogue of the compound is subjected to an assay, wherein the assay comprises:
  (a) a first component, wherein the first component comprises:
    (i) administering a 5 mg/kg intravenous bolus dose of the radiolabeled analogue to a caudal vein of a monkey, wherein the monkey is a male Cynomolgus monkey;
    (ii) euthanizing the monkey 4 hours after the administering;
    (iii) after (ii), freezing the monkey in a mixture of hexane and solid carbon dioxide for at least two hours to provide a frozen carcass;
    (iv) embedding the frozen carcass, left lateral side uppermost, in 2% w/v aqueous sodium carboxymethylcellulose to provide an embedded carcass;
    (v) sectioning the embedded carcass into 40 µm sagittal whole body sections with a cryomacrotome;
    (vi) mounting the 40 µm sagittal whole body sections on pressure sensitive tape;
    (vii) after (vi), dehydrating the whole body sections in the cryomacrotome at about −20° C. for about 60 hours;
    (viii) after (vii), placing the whole body sections against an image plate sensitive to carbon-14 for no longer than four days;
    (ix) after (viii), scanning the image plate with a phosphor imager system; and
    (x) after (ix), determining a concentration of the radiolabeled analogue in brain tissue of the whole body sections; and
  (b) a second component, wherein the second component is analogous to the first component except that the second component uses another monkey that is euthanized 168 hours after the administering,
  wherein the radiolabeled analogue comprises an N-terminus that is substituted with a $^{14}$C-enriched glycine residue, and the radiolabeled analogue consists of a structure that differs from the compound solely in that the compound lacks the $^{14}$C-enriched glycine residue of the radiolabeled analogue,
  then in the assay, the concentration of the radiolabeled analogue in brain tissue determined in the second component is equivalent to at least about 80% of the concentration of the radiolabeled analogue in brain tissue determined in the first component.

Embodiment 18. The compound of embodiment 17, wherein the brain tissue is cortex tissue, caudate nucleus tissue, olfactory bulb tissue, putamen tissue, or thalamus tissue.

Embodiment 19. The compound of embodiment 17, wherein the brain tissue is cortex tissue, caudate nucleus tissue, olfactory bulb tissue, putamen tissue, and thalamus tissue.

Embodiment 20. The compound of embodiment 17, wherein in the assay, the concentration of the radiolabeled analogue in brain tissue determined in the second component is equivalent to at least about 100% of the concentration of the radiolabeled analogue in brain tissue determined in the first component.

Embodiment 21. The compound of embodiment 20, wherein the brain tissue of the sections is caudate nucleus tissue, olfactory bulb tissue, putamen tissue, or thalamus tissue.

Embodiment 22. The compound of embodiment 20, wherein the brain tissue of the sections is caudate nucleus tissue, olfactory bulb tissue, putamen tissue, and thalamus tissue.

Embodiment 23. The compound of embodiment 17, wherein in the assay, the concentration of the radiolabeled analogue in brain tissue determined in the second component is equivalent to at least about 150% of the concentration of the radiolabeled analogue in brain tissue determined in the first component.

Embodiment 24. The compound of embodiment 23, wherein the brain tissue of the sections is olfactory bulb tissue.

Embodiment 25. The compound of any one of embodiments 17-24, wherein the assay further comprises a third component, wherein the third component is analogous to the first component except that the second component uses another monkey that is euthanized 12 hours after the administering, wherein in the assay, the concentration of the radiolabeled analogue in brain tissue determined in the third component is equivalent to at least about 80% of the concentration of the radiolabeled analogue in brain tissue determined in the first component.

Embodiment 26. The compound of embodiment 25, wherein the brain tissue of the sections is cortex tissue, olfactory bulb tissue, putamen tissue, lateral ventricle tissue, or thalamus tissue.

Embodiment 27. The compound of embodiment 25, wherein the brain tissue of the sections is cortex tissue, olfactory bulb tissue, putamen tissue, lateral ventricle tissue, and thalamus tissue.

Embodiment 28. The compound of embodiment 25, wherein in the assay, the concentration of the radiolabeled analogue in brain tissue determined in the third component is equivalent to at least about 100% of the concentration of the radiolabeled analogue in brain tissue determined in the first component.

Embodiment 29. The compound of embodiment 28, wherein the brain tissue is olfactory bulb tissue or lateral ventricle tissue.

Embodiment 30. The compound of embodiment 28, wherein the brain tissue is olfactory bulb tissue and lateral ventricle tissue.

Embodiment 31. The compound of any one of embodiments 17-30, wherein the cell permeabilizing group is an alpha substituent of the peptide nucleic acid.

Embodiment 32. The compound of any one of embodiments 17-30, wherein the compound is a gamma peptide nucleic acid.

Embodiment 33. The compound of embodiment 32, wherein the cell permeabilizing group is a gamma substituent of the gamma peptide nucleic acid.

Embodiment 34. The compound of embodiment 33, wherein a plurality of gamma substituents of the gamma peptide nucleic acid are each independently guanidinoalkylene.

Embodiment 35. The compound of embodiment 33, wherein a plurality of gamma substituents of the gamma peptide nucleic acid are each 3-guanidino-prop-1-yl.

Embodiment 36. The compound of embodiment 33, wherein a plurality of gamma substituents of the gamma peptide nucleic acid are each 4-guanidino-but-1-yl.

Embodiment 37. The compound of any one of embodiments 17-36, wherein the peptide nucleic acid sequence is $(CTG)_n$, wherein n is 1, 2, 3, 4, 5, 6, 7, 8, 9, or 10.

Embodiment 38. The compound of any one of embodiments 17-37, wherein a C-terminus of the peptide nucleic acid is bound by a peptide bond to a peptide.

Embodiment 39. The compound of any one of embodiments 17-37, wherein a C-terminus of the peptide nucleic acid is bound by a peptide bond to an amidated lysine residue.

Embodiment 40. The compound of any one of embodiments 17-39, wherein an N-terminus of the peptide nucleic acid of the compound is unsubstituted.

Embodiment 41. A compound comprising a peptide nucleic acid sequence, wherein the peptide nucleic acid sequence comprises: (i) a series of peptide nucleic acid residues having a repeating triad of nucleobase side chains; and (ii) a cell permeabilizing group attached to the series of peptide nucleic acid residues, wherein if the compound is subjected to an assay, and the assay comprises:
(a) administering by intracerebroventricular administration a dose amount of about 0.1 mg/kg to about 2 mg/kg of the compound to mice;
(b) euthanizing the mice at a time point between about 1 hour and 28 days post intracerebroventricular administration;
(c) collecting brain tissues from the mice after the euthanizing; and
(d) using liquid chromatography-tandem mass spectrometry to determine concentrations of the brain tissues in the mice,
then in the assay, a mean maximum brain concentration is observed in the mice at a time to maximum brain concentration of about 1 hour to about 50 hours post administration and the mean maximum brain concentration of the mice is observed to be about 3000 ng/mL to about 22000 ng/mL.

Embodiment 42. The compound of embodiment 41, wherein the compound is a gamma peptide nucleic acid.

Embodiment 43. The compound of embodiment 42, wherein the cell permeabilizing group is an alpha substituent of the gamma peptide nucleic acid.

Embodiment 44. The compound of embodiment 42, wherein the cell permeabilizing group is a gamma substituent of the gamma peptide nucleic acid.

Embodiment 45. The compound of embodiment 43, wherein a plurality of gamma substituents of the gamma peptide nucleic acid are each independently guanidinoalkylene.

Embodiment 46. The compound of embodiment 43, wherein a plurality of gamma substituents of the gamma peptide nucleic acid are each 3-guanidino-prop-1-yl.

Embodiment 47. The compound of embodiment 43, wherein a plurality of gamma substituents of the gamma peptide nucleic acid are each 4-guanidino-but-1-yl.

Embodiment 48. The compound of any one of embodiments 41-47, wherein the peptide nucleic acid sequence is $(CTG)_n$, wherein n is 1, 2, 3, 4, 5, 6, 7, 8, 9, or 10.

Embodiment 49. The compound of any one of embodiments 41-48, wherein a C-terminus of the peptide nucleic acid sequence is bound by a peptide bond to a peptide.

Embodiment 50. The compound of any one of embodiments 41-48, wherein the C-terminus of the peptide nucleic acid sequence is bound by a peptide bond to an amidated lysine residue.

Embodiment 51. The compound of any one of embodiments 41-50, wherein an N-terminus of the peptide nucleic acid sequence of the compound is unsubstituted.

Embodiment 52. The compound of any one of embodiments 41-51, wherein if (1) the mice are male mice, the mean maximum brain concentration of the male mice is observed to be about 3110 ng/mL at the time to maximum brain concentration of about 1.5 hours and the dose amount of about 0.3 mg/kg, the mean maximum brain concentration of the male mice is observed to be about 6490 ng/mL at the time to maximum brain concentration of about 4 hours and the dose amount of about 0.6 mg/kg, and the mean maximum brain concentration of the male mice is observed to be about 15500 ng/mL at the time to maximum brain concentration of about 24 hours and the dose amount of about 1 mg/kg; and (2) if the mice are female mice, the mean maximum brain concentration of the female mice is observed to be about 3930 ng/mL at the time to maximum brain concentration of about 48 hours and a dose of about 0.3 mg/kg, the mean maximum brain concentration of the female mice is observed to be about 11400 ng/mL at the time to maximum brain concentration of about 1.5 hours and a dose of about 0.6 mg/kg, and the mean maximum brain concentration of the female mice is observed to be about 21500 ng/mL at the time to maximum brain concentration of about 8 hours and a dose of about 1 mg/kg.

Embodiment 53. A compound comprising a peptide nucleic acid sequence, wherein the peptide nucleic acid sequence comprises: (i) a series of peptide nucleic acid residues having a repeating triad of nucleobase side chains; and (ii) a cell permeabilizing group attached to the series of peptide nucleic acid residues, wherein if the compound is subjected to an assay, and the assay comprises:
(a) administering by intracerebroventricular administration a dose amount of about 0.1 mg/kg to about 1.5 mg/kg of the compound to mice;
(b) collecting blood samples from cava veins of the mice at a time point between about 1 hour and 28 days post intracerebroventricular administration;
(c) after the collecting the blood samples, euthanizing the mice at a time point between about 1 hour and 28 days post intracerebroventricular administration;
(d) after the euthanizing, collecting brain, intestine, liver, lung, kidney, or muscle tissues from the mice; and
(e) using liquid chromatography-tandem mass spectrometry to determine concentrations of the compound in the brain, intestine, liver, lung, kidney, or muscle tissues that were collected; and
(f) using the liquid chromatography-tandem mass spectrometry to determine concentrations of the compound in plasma from the blood samples that were collected from the mice,
then, in the assay, the compound is observed to accumulate in the brain of the mice for at most about a month after the administering and the compound is not observed at a detectable level during the month in the plasma, intestine, liver, lung, kidney, or muscle of the mice.

Embodiment 54. The compound of embodiment 53, wherein the compound is not observed at a detectable level during the month in the plasma, intestine, liver, lung, kidney, and muscle of the mice.

Embodiment 55. The compound of embodiment 53 or embodiment 54, wherein the compound is a gamma peptide nucleic acid.

Embodiment 56. The compound of embodiment 55, wherein the cell permeabilizing group is an alpha substituent of the gamma peptide nucleic acid.

Embodiment 57. The compound of embodiment 55, wherein the cell permeabilizing group is a gamma substituent of the gamma peptide nucleic acid.

Embodiment 58. The compound of embodiment 56, wherein a plurality of gamma substituents of the gamma peptide nucleic acid are each independently guanidinoalkylene.

Embodiment 59. The compound of embodiment 56, wherein a plurality of gamma substituents of the gamma peptide nucleic acid are each 3-guanidino-prop-1-yl.

Embodiment 60. The compound of embodiment 56, wherein a plurality of gamma substituents of the gamma peptide nucleic acid are each 4-guanidino-but-1-yl.

Embodiment 61. The compound of any one of embodiments 53-60, wherein the peptide nucleic acid sequence is $(CTG)_n$, wherein n is 1, 2, 3, 4, 5, 6, 7, 8, 9, or 10.

Embodiment 62. The compound of any one of embodiments 53-61, wherein a C-terminus of the peptide nucleic acid sequence is bound by a peptide bond to a peptide.

Embodiment 63. The compound of any one of embodiments 53-61, wherein the C-terminus of the peptide nucleic acid sequence is bound by a peptide bond to an amidated lysine residue.

Embodiment 64. The compound of any one of embodiments 53-63, wherein an N-terminus of the peptide nucleic acid sequence of the compound is unsubstituted.

Embodiment 65. A compound comprising a peptide nucleic acid sequence, wherein the peptide nucleic acid sequence comprises: (i) a series of peptide nucleic acid residues having a repeating triad of nucleobase side chains; and (ii) a cell permeabilizing group attached to the series of peptide nucleic acid residues, wherein if the compound is subjected to a plasma protein binding assay, and the plasma protein binding assay comprises:
(a) performing a human component of the plasma protein binding assay, wherein the human component of the plasma protein binding assay comprises (1) spiking single aliquots of human plasma with a 10 mg/mL of a first solution of the compound to obtain at least a second solution of the compound with concentrations of about 1 µg/mL to about 50 µg/mL; (2) using ultracentrifugation on the at least second solution of the compound to separate a mixture comprising the compounds that are bound to plasma proteins; (3) using liquid chromatography-tandem mass spectrometry to determine a plasma protein binding percentage in the human plasma;
(b) performing a mouse component of the plasma protein binding assay, wherein the mouse component of the plasma protein binding assay differs from the human component of the plasma protein binding assay only in that mouse plasma is used instead of the human plasma;
(c) performing a dog component of the plasma protein binding assay, wherein the dog component of the plasma protein binding assay differs from the human component of the plasma protein binding assay only in that dog plasma is used instead of the human plasma;
(d) performing a minipig component of the plasma protein binding assay, wherein the minipig component of the plasma protein binding assay differs from the human component of the plasma protein binding assay only in that minipig plasma is used instead of the human plasma;
(e) performing a sheep component of the plasma protein binding assay, wherein the sheep component of the plasma protein binding assay differs from the human component of the plasma protein binding assay only in that sheep plasma is used instead of the human plasma; and
(f) performing a monkey component of the plasma protein binding assay, wherein the monkey component of the plasma protein binding assay differs from the human component of the plasma protein binding assay only in that monkey plasma is used instead of the human plasma,
then in the plasma protein binding assay, the plasma protein binding percentage is at least about 85% in the human, mouse, dog, minipig, sheep, or monkey.

Embodiment 66. The compound of embodiment 65, wherein in the plasma protein binding assay, the plasma protein binding percentage is at least about 85% in each of the human, mouse, dog, minipig, sheep, and monkey.

Embodiment 67. The compound of embodiment 65 or embodiment 66, wherein the compound is a gamma peptide nucleic acid.

Embodiment 68. The compound of embodiment 67, wherein the cell permeabilizing group is an alpha substituent of the gamma peptide nucleic acid.

Embodiment 69. The compound of embodiment 67, wherein the cell permeabilizing group is a gamma substituent of the gamma peptide nucleic acid.

Embodiment 70. The compound of embodiment 68, wherein a plurality of gamma substituents of the gamma peptide nucleic acid are each independently guanidinoalkylene.

Embodiment 71. The compound of embodiment 68, wherein a plurality of gamma substituents of the gamma peptide nucleic acid are each 3-guanidino-prop-1-yl.

Embodiment 72. The compound of embodiment 68, wherein a plurality of gamma substituents of the gamma peptide nucleic acid are each 4-guanidino-but-1-yl.

Embodiment 73. The compound of any one of embodiments 65-72, wherein the peptide nucleic acid sequence is $(CTG)_n$, wherein n is 1, 2, 3, 4, 5, 6, 7, 8, 9, or 10.

Embodiment 74. The compound of any one of embodiments 65-73, wherein a C-terminus of the peptide nucleic acid sequence is bound by a peptide bond to a peptide.

Embodiment 75. The compound of any one of embodiments 65-73, wherein the C-terminus of the peptide nucleic acid sequence is bound by a peptide bond to an amidated lysine residue.

Embodiment 76. The compound of any one of embodiments 65-75, wherein an N-terminus of the peptide nucleic acid sequence of the compound is unsubstituted.

Embodiment 77. The compound of any one of embodiments 65-76, wherein at a concentration of about 1 μg/mL, the plasma protein binding percentage is at least about 95% in the human, mouse, dog, minipig, sheep, or monkey.

Embodiment 78. The compound of embodiment 77, wherein at the concentration of about 1 μg/mL, the plasma protein binding percentage is at least about 95% in each of the human, mouse, dog, minipig, sheep, and monkey.

Embodiment 79. A compound having the formula (I):

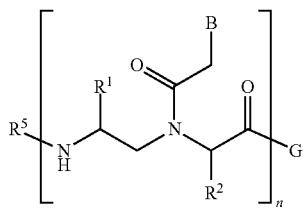

(I)

wherein:
each B is independently a nucleobase;
each $R^1$ is independently a side chain of a natural amino acid, a guanidino($C_1$-$C_4$)alkyl, or hydrogen;
each $R^2$ is independently a side chain of a natural amino acid, a guanidino($C_1$-$C_4$)alkyl, or hydrogen;
$R^5$ is a sequence comprising at least one alpha amino acid residue, beta amino acid residue, gamma amino acid residue, or a combination thereof; hydrogen; or a water solubilizing group;
n is an integer from 3-30; and
G is OH, $NH_2$, or

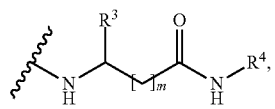

wherein:
$R^3$ is hydrogen or an amino($C_1$-$C_4$)alkyl;
$R^4$ is a sequence comprising at least one alpha amino acid residue, beta amino acid residue, gamma amino acid residue, or a combination thereof; or hydrogen; and
m is 0 or 1;
wherein the compound comprises at least one guanine-cytosine-thymine sequence;
or a pharmaceutically-acceptable salt thereof.

Embodiment 80. The compound of embodiment 79, wherein each B is independently guanine, thymine, or cytosine.

Embodiment 81. The compound of embodiment 79 or embodiment 80, wherein at least one $R^1$ is guanidino($C_1$-$C_4$)alkyl.

Embodiment 82. The compound of any one of embodiments 79-81, wherein at least one $R^2$ is guanidino($C_1$-$C_4$)alkyl.

Embodiment 83. The compound of any one of embodiments 79-82, wherein at least one $R^1$ is 4-guanidinobut-1-yl.

Embodiment 84. The compound of any one of embodiments 79-83, wherein at least one $R^1$ is 3-guanidinoprop-1-yl.

Embodiment 85. The compound of any one of embodiments 79-84, wherein at least one $R^2$ is 4-guanidinobut-1-yl.

Embodiment 86. The compound of any one of embodiments 79-85, wherein at least one $R^2$ is 3-guanidinoprop-1-yl.

Embodiment 87. The compound of any one of embodiments 79-86, wherein G is

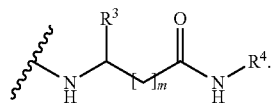

Embodiment 88. The compound of embodiment 87, wherein $R^3$ is 4-aminobut-1-yl.

Embodiment 89. The compound of embodiment 87, wherein $R^3$ is 3-aminoprop-1-yl.

Embodiment 90. The compound of any one of embodiments 87-89, wherein m is 0.

Embodiment 91. The compound of any one of embodiments 87-89, wherein m is 1.

Embodiment 92. The compound of any one of embodiments 87-91, wherein $R^4$ is hydrogen.

Embodiment 93. The compound of any one of embodiments 87-91, wherein $R^4$ is a sequence comprising at least one alpha amino acid residue.

Embodiment 94. The compound of any one of embodiments 87-91 and 93, wherein $R^4$ is

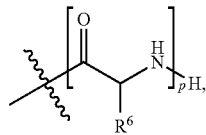

wherein
p is 1, 2, 3, 4, 5, 6, 7, 8, 9, or 10; and
each $R^6$ is independently hydrogen or an amino($C_1$-$C_4$) alkyl.

Embodiment 95. The compound of any one of embodiments 87-91, 93, and 94, wherein $R^4$ is

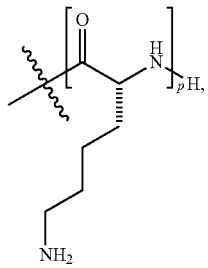

wherein
p is 1, 2, 3, 4, 5, 6, 7, 8, 9, or 10.

Embodiment 96. The compound of embodiment 95, wherein p is 3, 4, 5, 6, 7, or 8.

Embodiment 97. The compound of embodiment 95, wherein p is 7.

Embodiment 98. The compound of any one of embodiments 79-97, wherein $R^5$ is hydrogen.

Embodiment 99. The compound of any one of embodiments 79-97, wherein $R^5$ is

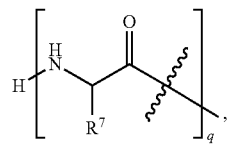

wherein
each $R^7$ is independently a side chain of a natural amino acid; and
q is 0 or 1.

Embodiment 100. The compound of any one of embodiments 79-99, wherein $R^5$ is

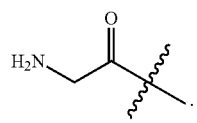

Embodiment 101. The compound of any one of embodiments 79-99, wherein $R^5$ is

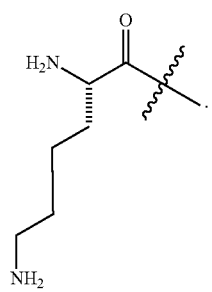

Embodiment 102. The compound of any one of embodiments 79-86, wherein $R^5$ is the water solubilizing group.

Embodiment 103. The compound of embodiment 102, wherein the water solubilizing group is a multiply-positively charged region that comprises at least six consecutive building blocks.

Embodiment 104. The compound of embodiment 103, wherein each of the consecutive building blocks independently comprises a side chain that carries a positive formal charge at neutral pH.

Embodiment 105. The compound of any one of embodiments 79-86 and 102-104, wherein, when G is OH or $NH_2$, at least one of $R^1$ and $R^2$ is a side chain of a natural amino acid or a guanidino($C_1$-$C_4$)alkyl, and $R^5$ is not hydrogen.

Embodiment 106. The compound of embodiment 79, which has the formula:

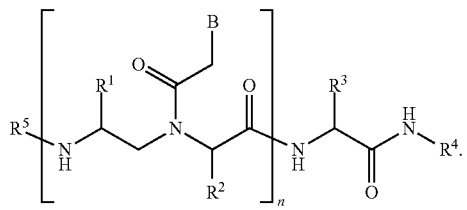

Embodiment 107. The compound of embodiment 106, wherein n is 6.

Embodiment 108. The compound of embodiment 106 or embodiment 107, wherein at least one $R^1$ is 4-guanidinobut-1-yl.

Embodiment 109. The compound of embodiment 106 or embodiment 107, wherein each $R^1$ is 4-guanidinobut-1-yl.

Embodiment 110. The compound of any one of embodiments 106-109, wherein at least one $R^2$ is hydrogen.

Embodiment 111. The compound of any one of embodiments 106-109, wherein each $R^2$ is hydrogen.

Embodiment 112. The compound of any one of embodiments 106-111, wherein $R^3$ is 4-aminobut-1-yl.

Embodiment 113. The compound of any one of embodiments 106-111, wherein $R^3$ is 3-aminoprop-1-yl.

Embodiment 114. The compound of any one of embodiments 106-113, wherein $R^4$ is hydrogen.

Embodiment 115. The compound of any one of embodiments 106-113, wherein $R^4$ is

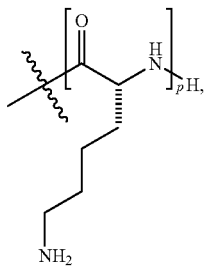

wherein p is 1, 2, 3, 4, 5, 6, 7, 8, 9, or 10.

Embodiment 116. The compound of embodiment 115, wherein p is 3, 4, 5, 6, 7, or 8.

Embodiment 117. The compound of embodiment 115, wherein p is 7.

Embodiment 118. The compound of any one of embodiments 106-117, wherein $R^5$ is hydrogen.

Embodiment 119. The compound of any one of embodiments 106-117, wherein $R^5$ is

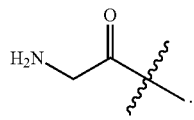

Embodiment 120. The compound of embodiment 79 or embodiment 106, which has the formula:

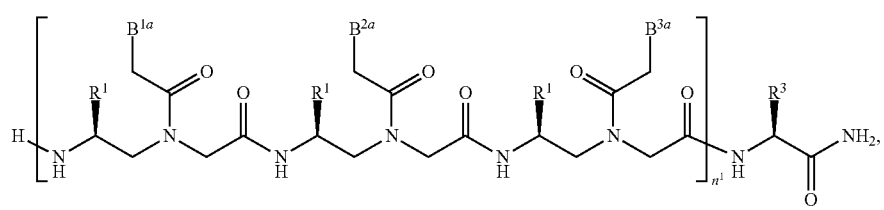

wherein:
each $B^{1a}$, $B^{2a}$ and $B^{3a}$ is independently cytosine, guanine, or thymine; and
$n^1$ is 1, 2, 3, 4, 5, 6, 7, 8, 9, or 10.

Embodiment 121. The compound of embodiment 120, wherein $n^1$ is 2.

Embodiment 122. The compound of embodiment 120 or embodiment 121, wherein each $R^1$ is 4-guanidinobut-1-yl.

Embodiment 123. The compound of embodiment 120, which has the formula:

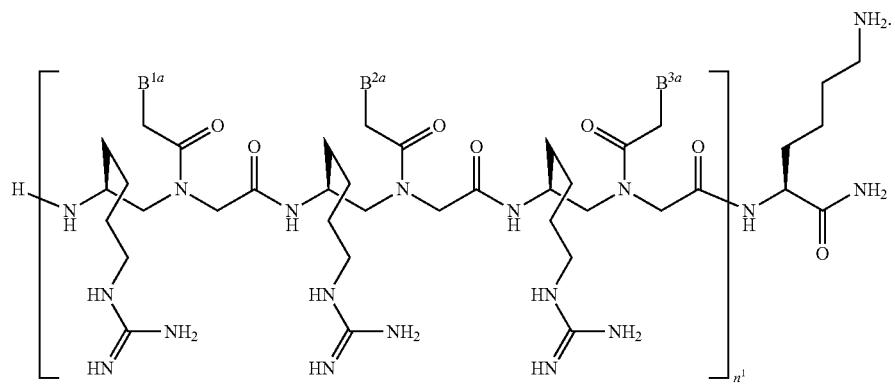

Embodiment 124. The compound of embodiment 123, wherein $B^{1a}$ is cytosine, $B^{2a}$ is thymine and $B^{3a}$ is guanine.

Embodiment 125. The compound of embodiment 123 or embodiment 124, wherein $n^1$ is 2.

Embodiment 126. The compound of embodiment 79 or embodiment 123, which has the formula:

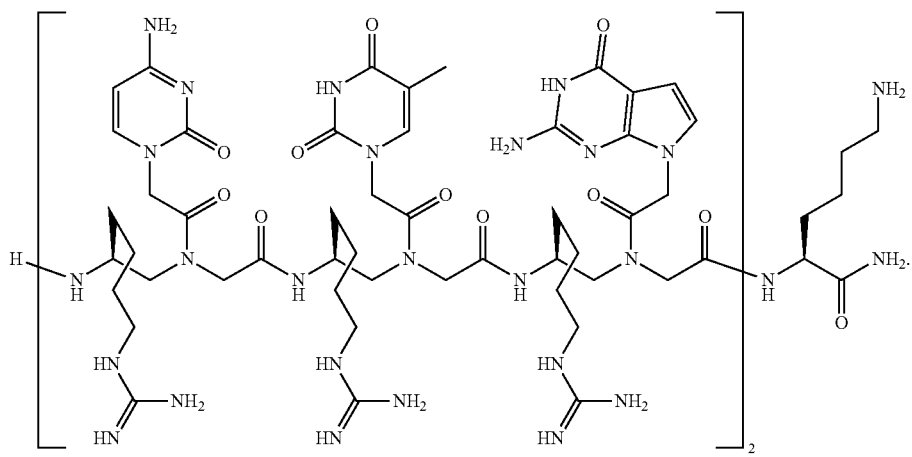

Embodiment 127. The compound of embodiment 79 or embodiment 106, which has the formula:

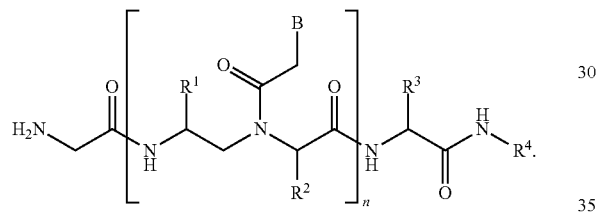

Embodiment 128. The compound of embodiment 127, wherein n is 6.

Embodiment 129. The compound of embodiment 127, which has the formula:

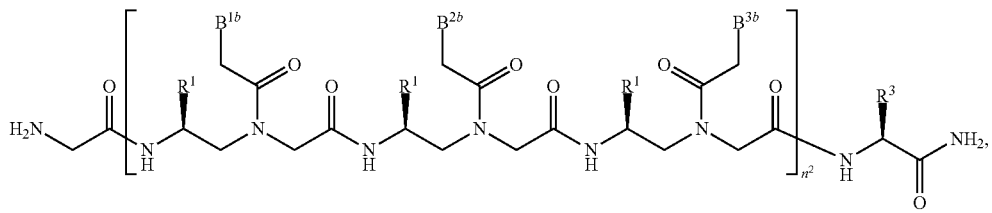

wherein:

each $B^{1b}$, $B^{2b}$ and $B^{3b}$ is independently cytosine, guanine or thymine; and $n^2$ is 1, 2, 3, 4, 5, 6, 7, 8, 9, or 10.

Embodiment 130. The compound of embodiment 129, wherein $n^2$ is 2.

Embodiment 131. The compound of embodiment 129 or embodiment 130, wherein each $R^1$ is 4-guanidinobut-1-yl.

Embodiment 132. The compound of embodiment 129, which has the formula:

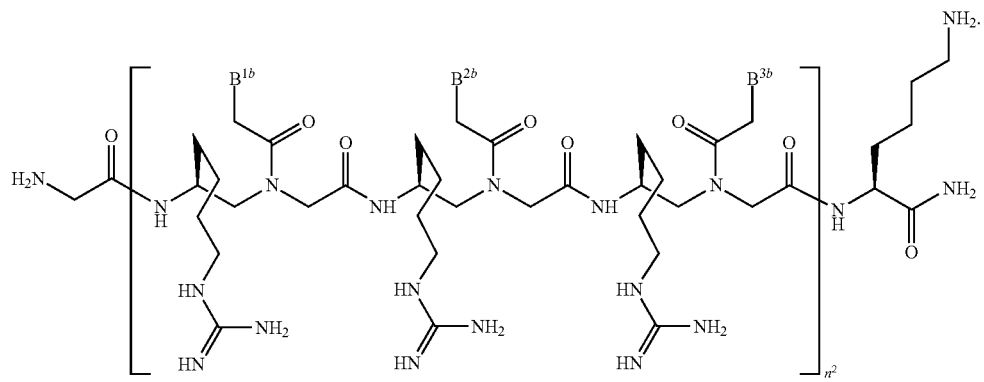

Embodiment 133. The compound of embodiment 132, wherein $B^{1b}$ is cytosine, $B^{2b}$ is thymine and $B^{3b}$ is guanine.

Embodiment 134. The compound of embodiment 132 or embodiment 133, wherein $n^2$ is 2.

Embodiment 135. The compound of embodiment 79 or embodiment 132, which has the formula:

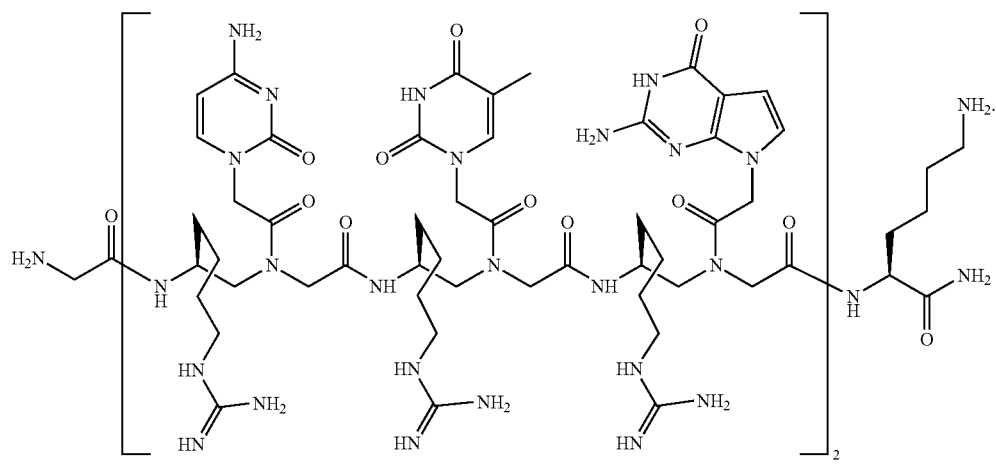

Embodiment 136. The compound of embodiment 79 or embodiment 106, which has the formula:

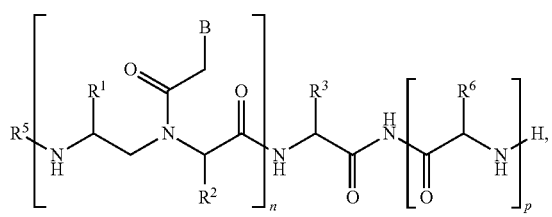

wherein p is 1, 2, 3, 4, 5, 6, 7, 8, 9, or 10; and each $R^6$ is independently hydrogen or an amino($C_1$-$C_4$) alkyl.

Embodiment 137. The compound of embodiment 136, wherein n is 10, 11, 12, 13, 14, 15, 16, 17, 18, 19, or 20.

Embodiment 138. The compound of embodiment 136, wherein n is 19.

Embodiment 139. The compound of any one of embodiments 136-138, wherein at least one $R^1$ is hydrogen.

Embodiment 140. The compound of any one of embodiments 136-139, wherein n is greater than 1, and wherein every other $R^1$ is hydrogen.

Embodiment 141. The compound of any one of embodiments 136-140, wherein at least one $R^1$ is 4-guanidinobut-1-yl.

Embodiment 142. The compound of any one of embodiments 136-140, wherein n is greater than 1, and wherein every other $R^1$ is 4-guanidinobut-1-yl.

Embodiment 143. The compound of any one of embodiments 136-142, at least one $R^2$ is hydrogen.

Embodiment 144. The compound of any one of embodiments 136-142, wherein each $R^2$ is hydrogen.

Embodiment 145. The compound of any one of embodiments 136-143, wherein at least one $R^2$ is 4-guanidinobut-1-yl.

Embodiment 146. The compound of any one of embodiments 136-143, wherein n is greater than 1, and wherein every other $R^2$ is 4-guanidinobut-1-yl.

Embodiment 147. The compound of any one of embodiments 136-146, wherein $R^3$ is 4-aminobut-1-yl.

Embodiment 148. The compound of any one of embodiments 136-146, wherein $R^3$ is 3-aminoprop-1-yl.

Embodiment 149. The compound of any one of embodiments 136-148, wherein $R^5$ is hydrogen.

Embodiment 150. The compound of any one of embodiments 136-148, wherein $R^5$ is

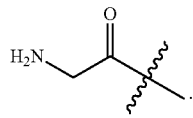

Embodiment 151. The compound of any one of embodiments 136-148, wherein $R^5$ is

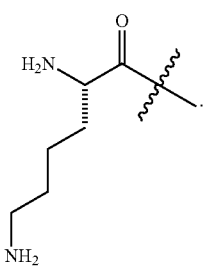

Embodiment 152. The compound of any one of embodiments 136-148, wherein $R^6$ is 4-aminobut-1-yl.

Embodiment 153. The compound of any one of embodiments 136-148, wherein $R^6$ is 3-aminoprop-1-yl.

Embodiment 154. The compound of any one of embodiments 136-148, wherein p is 7.

Embodiment 155. The compound of embodiment 115, wherein p is 3, 4, 5, 6, 7, or 8.

Embodiment 156. The compound of any one of embodiments 79, 106, and 136, which has the formula:

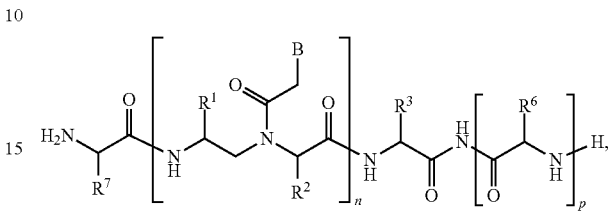

wherein $R^7$ is a side chain of a natural amino acid.

Embodiment 157. The compound of embodiment 156, wherein $R^7$ is 4-aminobut-1-yl.

Embodiment 158. The compound of embodiment 156, wherein $R^7$ is 3-aminoprop-1-yl.

Embodiment 159. The compound of embodiment 156, which has the structure

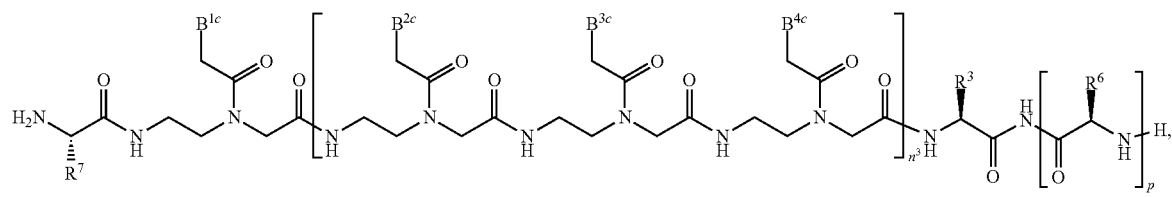

wherein:
each $B^{1c}$, $B^{2c}$, $B^{3c}$ and $B^{4c}$ is independently cytosine, guanine or thymine; and
$n^3$ is 1, 2, 3, 4, 5, 6, 7, 8, 9, or 10.

Embodiment 160. The compound of embodiment 159, wherein $B^{1c}$ is guanine.

Embodiment 161. The compound of embodiment 159 or embodiment 160, wherein $B^{2c}$ is cytosine.

Embodiment 162. The compound of any one of embodiments 159-161, wherein $B^{3c}$ is thymine.

Embodiment 163. The compound of any one of embodiments 159-162, wherein $B^{4c}$ is guanine.

Embodiment 164. The compound of any one of embodiments 159-163, wherein $n^3$ is 6.

Embodiment 165. The compound of any one of embodiments 159-164, wherein p is 7.

Embodiment 166. The compound of any one of embodiments 159-165, wherein $R^3$ is 4-aminobut-1-yl.

Embodiment 167. The compound of any one of embodiments 159-165, wherein $R^3$ is 3-aminoprop-1-yl.

Embodiment 168. The compound of any one of embodiments 159-167, wherein $R^6$ is 4-aminobut-1-yl.

Embodiment 169. The compound of any one of embodiments 159-167, wherein $R^6$ is 3-aminoprop-1-yl.

Embodiment 170. The compound of any one of embodiments 159-169, wherein $R^7$ is 4-aminobut-1-yl.

Embodiment 171. The compound of any one of embodiments 159-169, wherein $R^7$ is 3-aminoprop-1-yl.

Embodiment 172. The compound of any one of embodiments 159-163, which has the structure

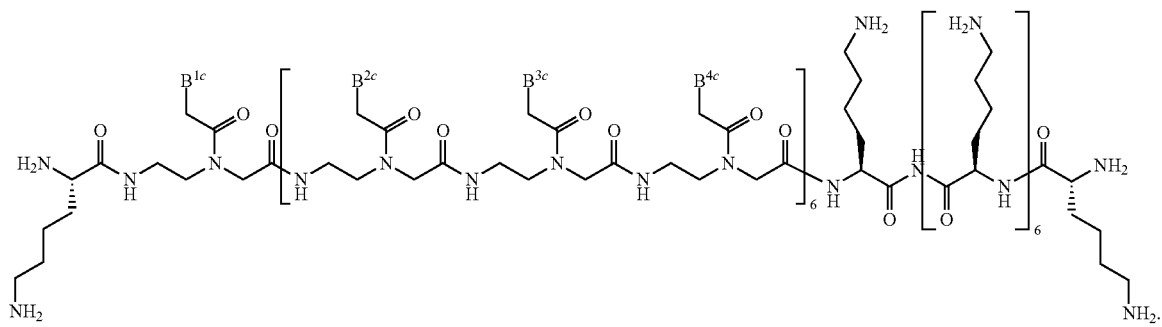

Embodiment 173. The compound of embodiment 79 or embodiment 159, which has the structure

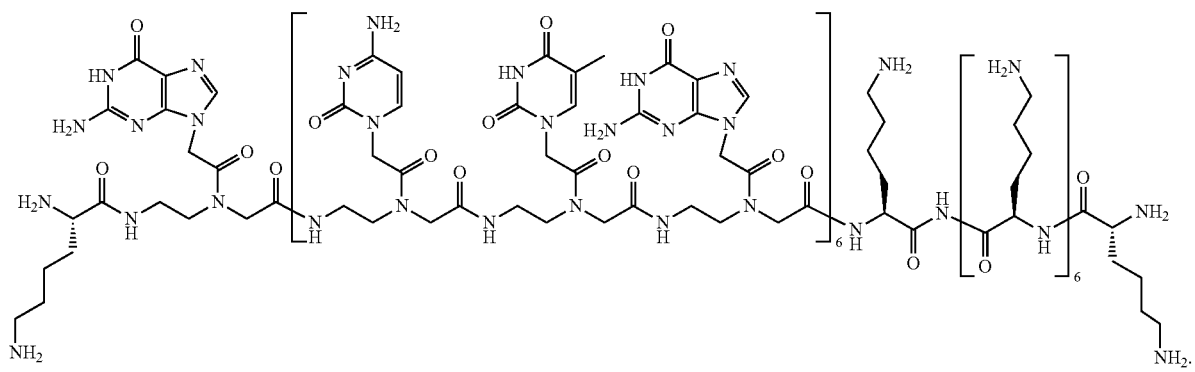

Embodiment 174. The compound of embodiment 79 or embodiment 106, which has the formula:

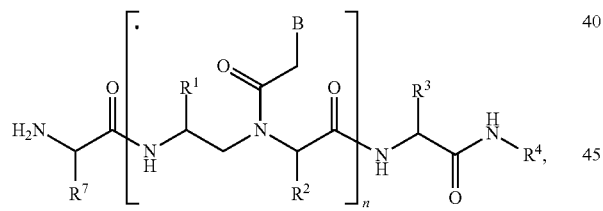

wherein $R^7$ is a side chain of a natural amino acid.

Embodiment 175. The compound of embodiment 174, wherein $R^7$ is 4-aminobut-1-yl.

Embodiment 176. The compound of embodiment 174, wherein $R^7$ is 3-aminoprop-1-yl.

Embodiment 177. The compound of any one of embodiments 79, 106, and 174, which has the structure

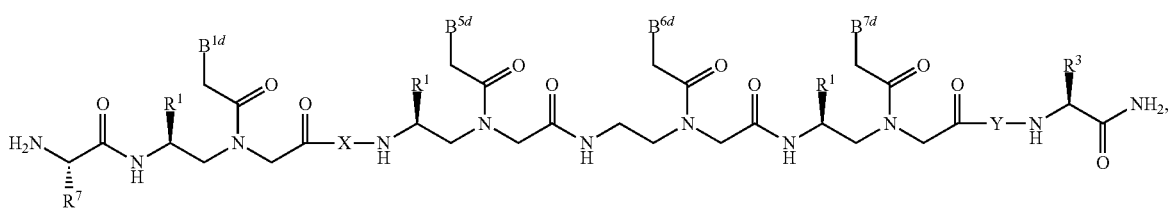

wherein:
X is

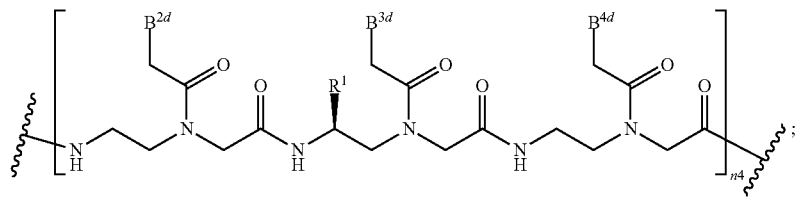

Y is

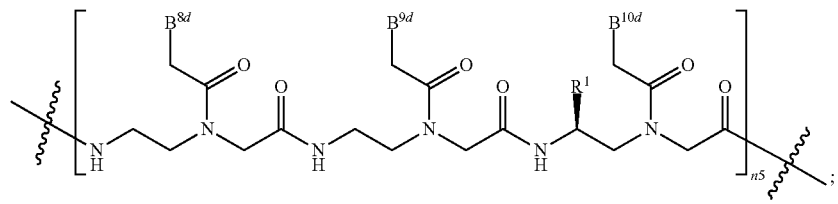

each $B^{1d}$, $B^{2d}$, $B^{3d}$, $B^{4d}$, $B^{5d}$, $B^{6d}$, $B^{7d}$, $B^{8d}$, $B^{9d}$, and $B^{10d}$ is independently cytosine, guanine or thymine;
$n^4$ is 1, 2, 3, 4, 5, 6, 7, 8, 9, or 10; and
$n^5$ is 1, 2, 3, 4, 5, 6, 7, 8, 9, or 10.

Embodiment 178. The compound of embodiment 177, wherein $B^{1d}$ is guanine.

Embodiment 179. The compound of embodiment 177 or embodiment 178, wherein $B^{2d}$ is cytosine.

Embodiment 180. The compound of any one of embodiments 177-179, wherein $B^{3d}$ is thymine.

Embodiment 181. The compound of any one of embodiments 177-180, wherein $B^{4d}$ is guanine.

Embodiment 182. The compound of any one of embodiments 177-181, wherein $B^{5d}$ is cytosine.

Embodiment 183. The compound of any one of embodiments 177-182, wherein $B^{6d}$ is thymine.

Embodiment 184. The compound of any one of embodiments 177-183, wherein $B^{7d}$ is guanine.

Embodiment 185. The compound of any one of embodiments 177-184, wherein $B^{8d}$ is cytosine.

Embodiment 186. The compound of any one of embodiments 177-185, wherein $B^{9d}$ is thymine.

Embodiment 187. The compound of any one of embodiments 177-186, wherein $B^{10d}$ is guanine.

Embodiment 188. The compound of any one of embodiments 177-187, wherein $n^4$ is 3.

Embodiment 189. The compound of any one of embodiments 177-188, wherein $n^5$ is 2.

Embodiment 190. The compound of any one of embodiments 177-189, wherein at least one $R^1$ is 4-guanidinobut-1-yl.

Embodiment 191. The compound of any one of embodiments 177-189, wherein each $R^1$ is 4-guanidinobut-1-yl.

Embodiment 192. The compound of any one of embodiments 177-191, wherein $R^3$ is 4-aminobut-1-yl.

Embodiment 193. The compound of any one of embodiments 177-191, wherein $R^3$ is 3-aminoprop-1-yl.

Embodiment 194. The compound of any one of embodiments 177-194, wherein $R^7$ is 4-aminobut-1-yl.

Embodiment 195. The compound of any one of embodiments 177-194, wherein $R^7$ is 3-aminoprop-1-yl.

Embodiment 196. The compound of any one of embodiments 177-189, which has the structure:

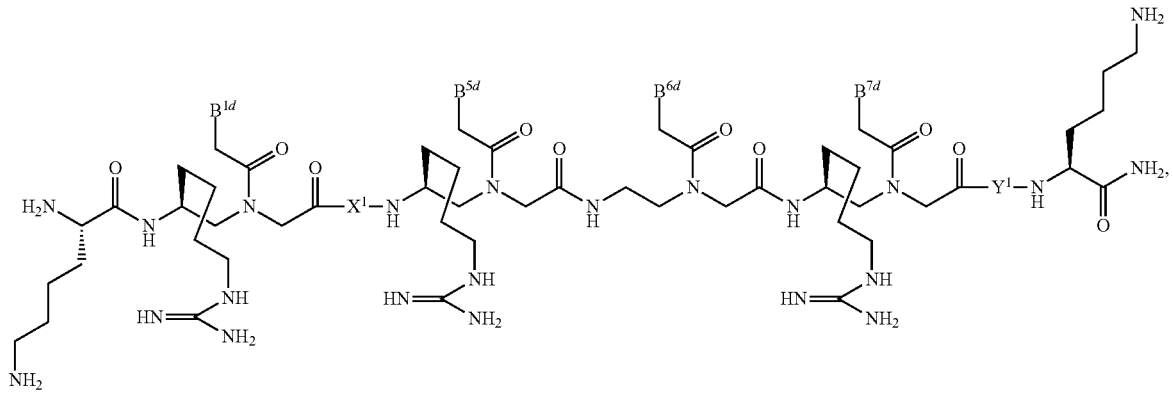

wherein:
X¹ is
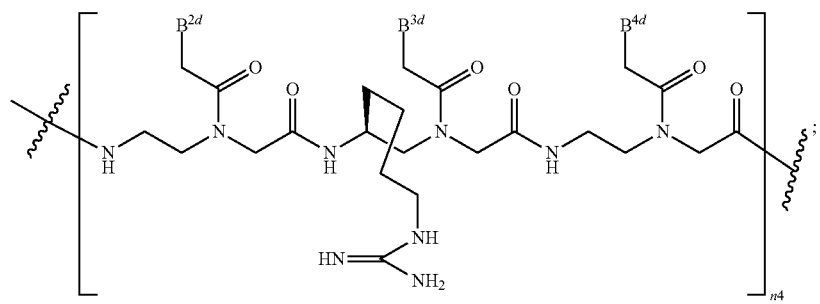
and
Y¹ is
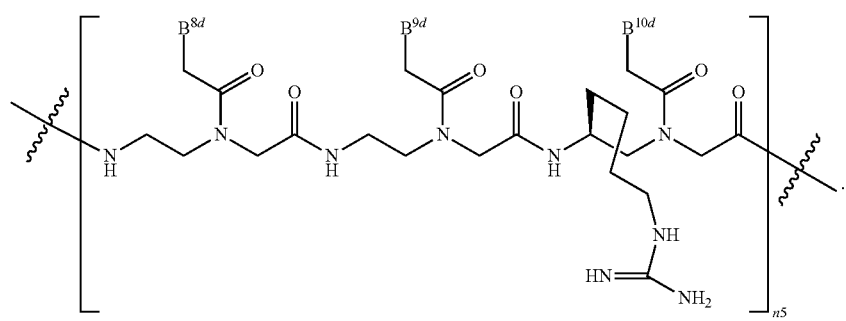
Embodiment 197. The compound of any one of embodiments 79, 106, 174, 177, and 196, which has the structure
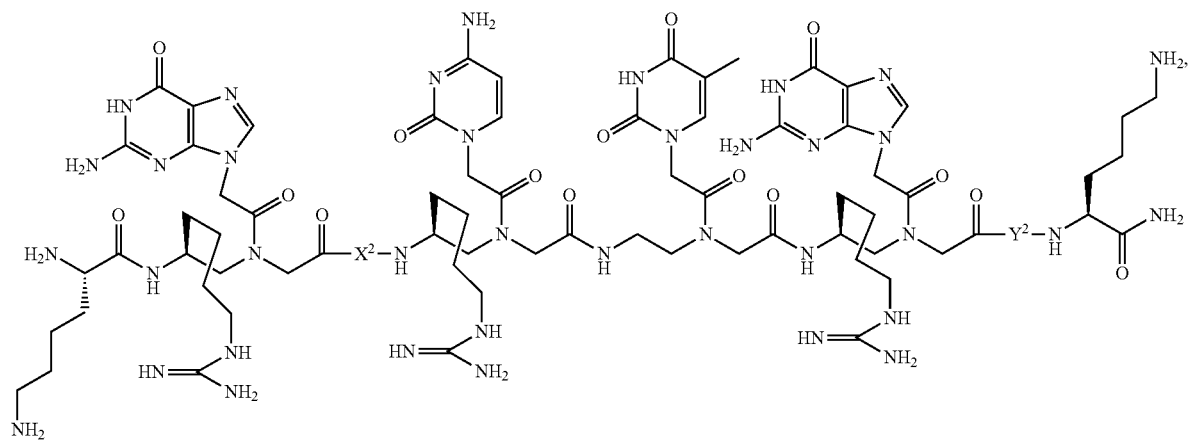

wherein:
X² is
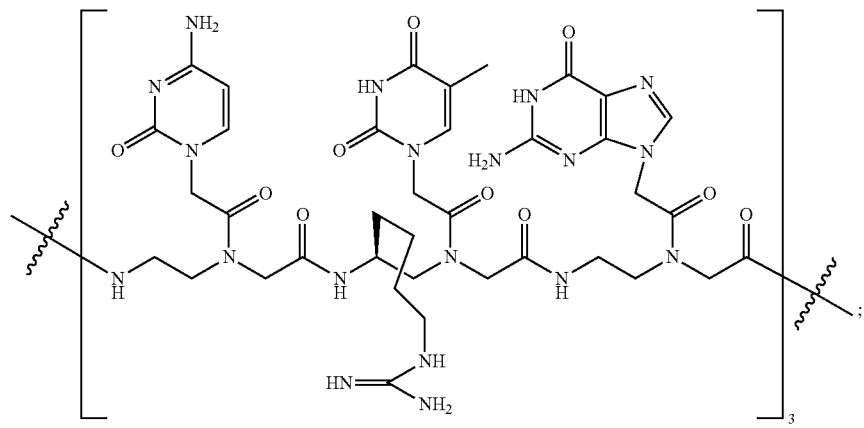
and
Y² is
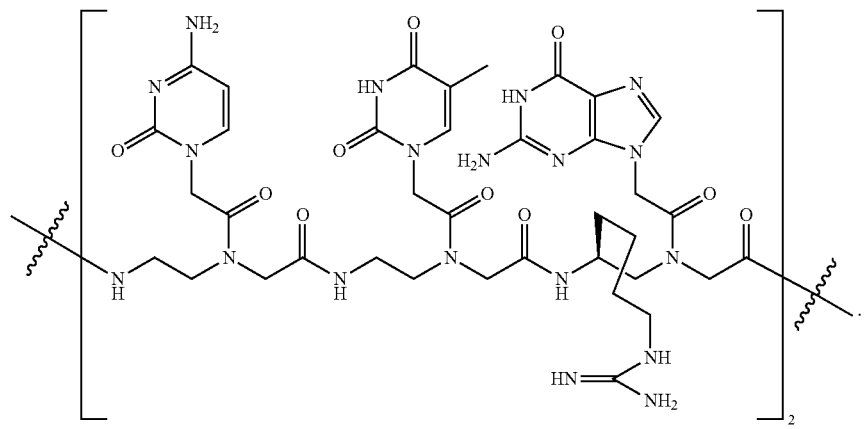
Embodiment 198. The compound of any one of embodiments 79, 106, or 174, which has the structure
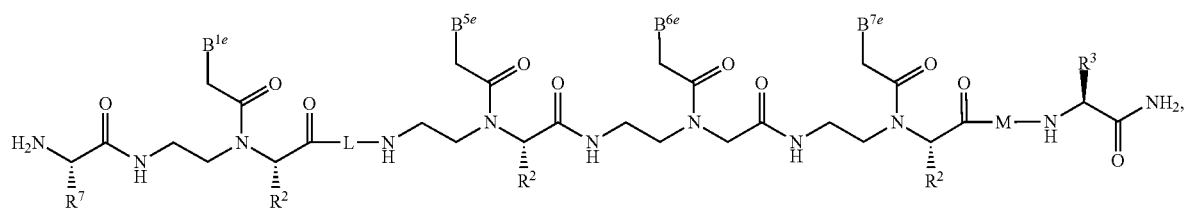

wherein:
L is

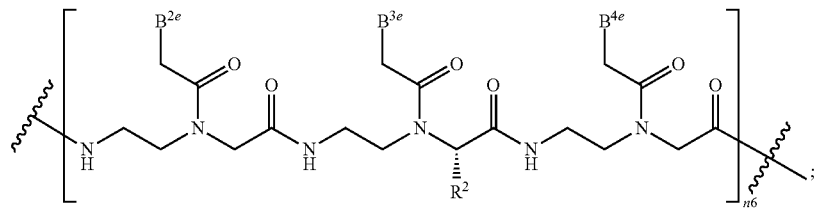

M is

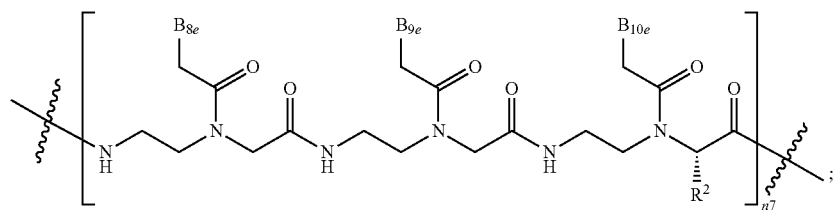

each $B^{1e}, B^{2e}, B^{3e}, B^{4e}, B^{5e}, B^{6e}, B^{7e}, B^{8e}, B^{9e}$ and $B^{10e}$ is independently cytosine, guanine or thymine;
$n^6$ is 1, 2, 3, 4, 5, 6, 7, 8, 9, or 10; and
$n^7$ is 1, 2, 3, 4, 5, 6, 7, 8, 9, or 10.

Embodiment 199. The compound of embodiment 198, wherein $B^{1e}$ is guanine.

Embodiment 200. The compound of embodiment 198 or embodiment 199, wherein $B^{2e}$ is cytosine.

Embodiment 201. The compound of any one of embodiments 198-200, wherein $B^{3e}$ is thymine.

Embodiment 202. The compound of any one of embodiments 198-201, wherein $B^{4e}$ is guanine.

Embodiment 203. The compound of any one of embodiments 198-202, wherein $B^{5e}$ is cytosine.

Embodiment 204. The compound of any one of embodiments 198-203, wherein $B^{6e}$ is thymine.

Embodiment 205. The compound of any one of embodiments 198-204, wherein $B^{7e}$ is guanine.

Embodiment 206. The compound of any one of embodiments 198-205, wherein $B^{8e}$ is cytosine.

Embodiment 207. The compound of any one of embodiments 198-206, wherein $B^{9e}$ is thymine.

Embodiment 208. The compound of any one of embodiments 198-207, wherein $B^{10e}$ is guanine.

Embodiment 209. The compound of any one of embodiments 198-208, wherein $n^6$ is 3.

Embodiment 210. The compound of any one of embodiments 198-209, wherein $n^7$ is 2.

Embodiment 211. The compound of any one of embodiments 198-210, wherein at least one $R^2$ is 3-guanidinoprop-1-yl.

Embodiment 212. The compound of any one of embodiments 198-210, wherein each $R^2$ is 3-guanidinoprop-1-yl.

Embodiment 213. The compound of any one of embodiments 198-210, wherein at least one $R^2$ is 4-guanidinobut-1-yl.

Embodiment 214. The compound of any one of embodiments 198-210, wherein each $R^2$ is 4-guanidinobut-1-yl.

Embodiment 215. The compound of any one of embodiments 198-214, wherein $R^3$ is 4-aminobut-1-yl.

Embodiment 216. The compound of any one of embodiments 198-214, wherein $R^3$ is 3-aminoprop-1-yl.

Embodiment 217. The compound of any one of embodiments 198-216, wherein $R^7$ is 4-aminobut-1-yl.

Embodiment 218. The compound of any one of embodiments 198-216, wherein $R^7$ is 3-aminoprop-1-yl.

Embodiment 219. The compound of embodiment 198, which has the structure

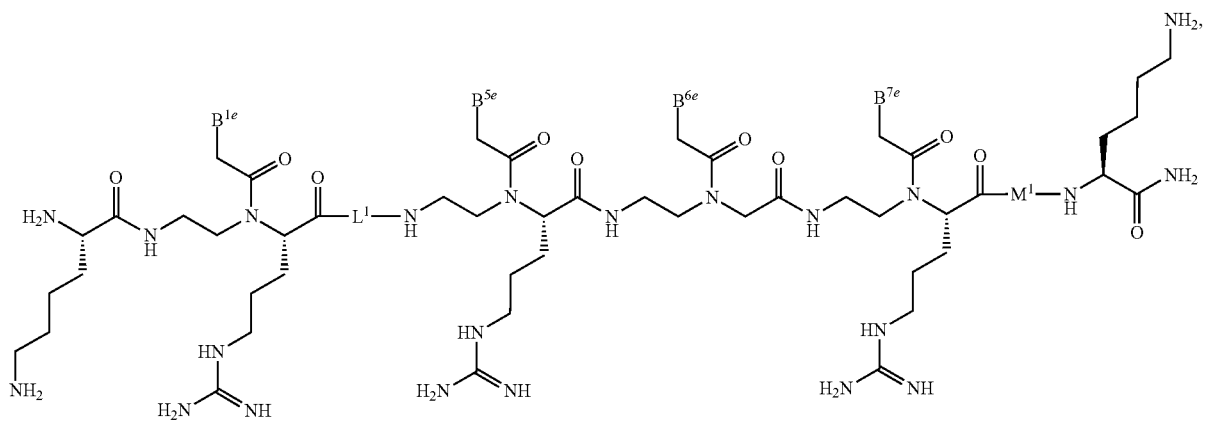
wherein:
L¹ is
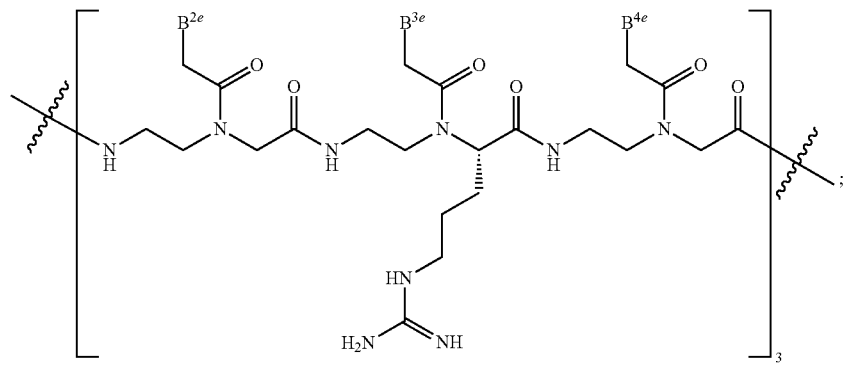
and
M¹ is
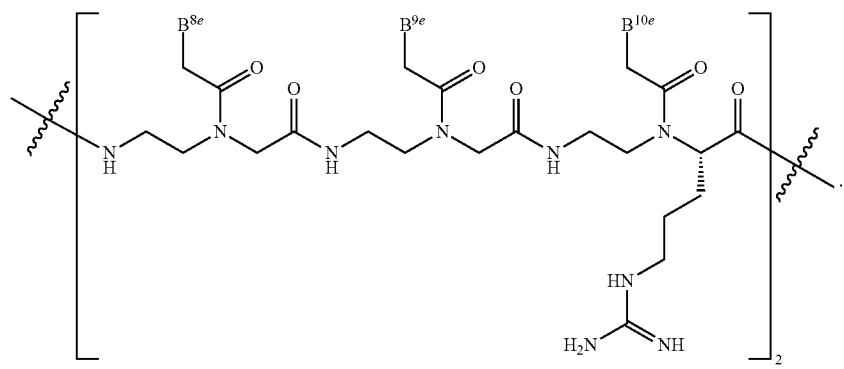
Embodiment 220. The compound of any one of embodiments 79, 106, 174, 198, and 219, which has the structure

161 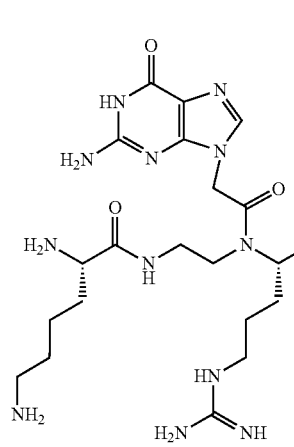 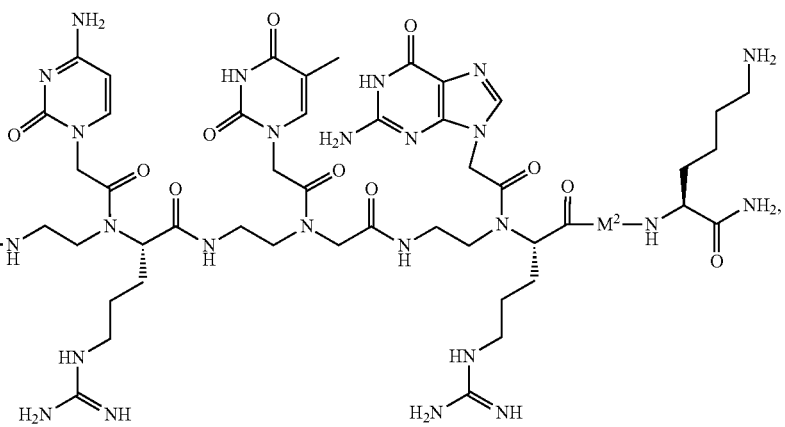 162
wherein:
$L^2$ is
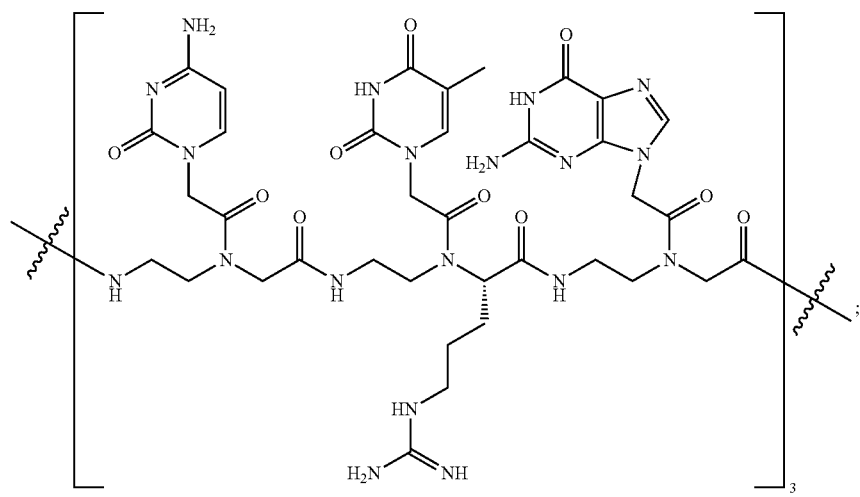
and
$M^2$ is
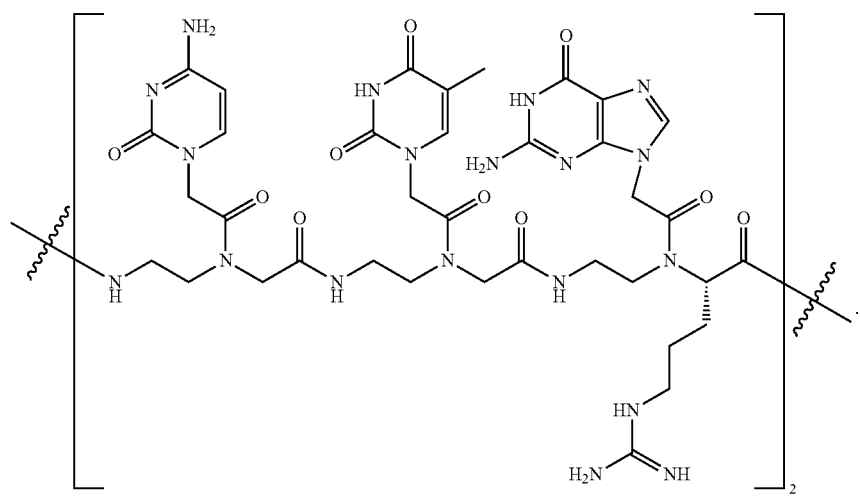

163

Embodiment 221. A method of treating a condition in a subject, the method comprising administering to the subject a therapeutically-effective amount of the compound of any one of embodiments 65-220.

Embodiment 222. The method of embodiment 221, wherein the subject is a human.

Embodiment 223. The method of embodiment 221 or embodiment 222, wherein the condition is a neurological condition.

Embodiment 224. The method of embodiment 223, wherein the neurological condition is Huntington's disease.

Embodiment 225. The method of embodiment 221 or embodiment 222, wherein the condition is a polyglutamine disease.

Embodiment 226. The method of embodiment 225, wherein the polyglutamine disease is Huntington's disease.

Embodiment 227. The method of embodiment 221 or embodiment 222, wherein the condition is a central nervous system condition.

Embodiment 228. The method of embodiment 221 or embodiment 222, wherein the condition is associated with aging.

Embodiment 229. The method of embodiment 221 or embodiment 222, wherein the condition is associated with cognitive impairment.

Embodiment 230. The method of embodiment 221 or embodiment 222, wherein the condition is associated with memory loss.

Embodiment 231. The method of embodiment 221 or embodiment 222, wherein the condition is associated with deterioration of motor skills.

Embodiment 232. The method of any one of embodiments 221-231, wherein the therapeutically-effective amount of the compound is from about 8 µg/kg to about 200 µg/kg.

Embodiment 233. The method of any one of embodiments 221-232, wherein the compound binds RNA.

Embodiment 234. The method of any one of embodiments 221-232, wherein the compound binds DNA.

Embodiment 235. The method of any one of embodiments 221-234, wherein the compound binds a CAG repeat sequence in a nucleic acid molecule.

Embodiment 236. The method of any one of embodiments 221-235, wherein the administering is intravenous administration.

Embodiment 237. The method of any one of embodiments 221-235, wherein the administering is subcutaneous administration.

Embodiment 238. The method of any one of embodiments 221-235, wherein the administering is intracerebroventricular administration.

Embodiment 239. The method of any one of embodiments 221-235, wherein the administering is oral administration.

Embodiment 240. The method of any one of embodiments 221-235, wherein the administering is intrathecal administration.

164

What is claimed is:

1. A compound having the structure:

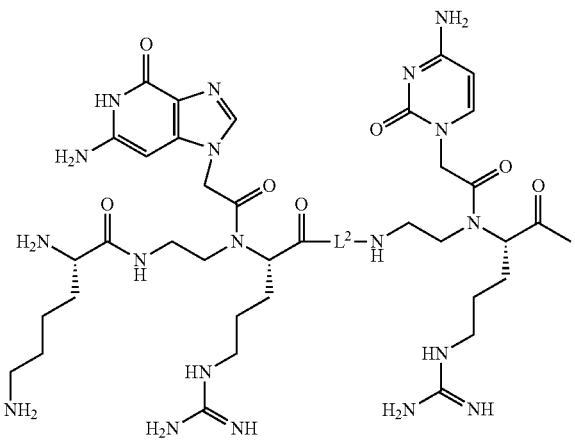

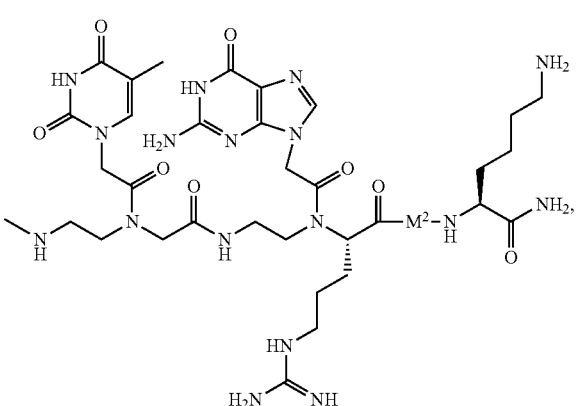

wherein:

$L^2$ is

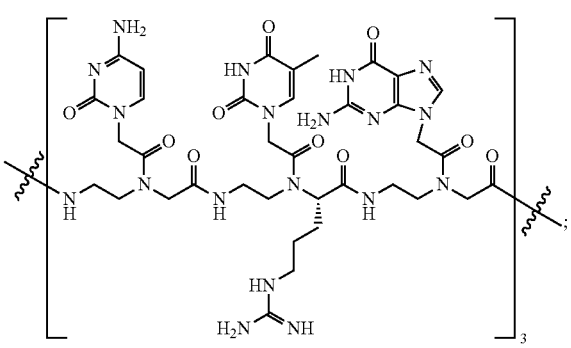

and
$M^2$ is
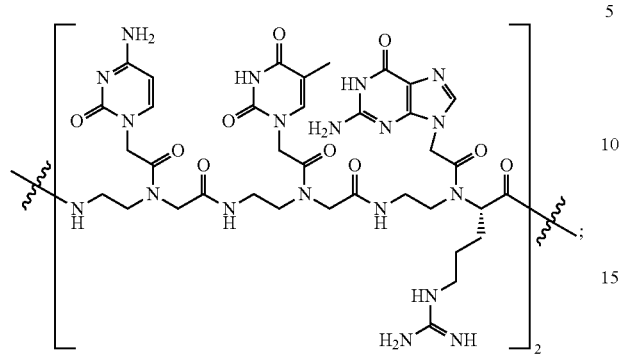
or a pharmaceutically-acceptable salt thereof.